(12) United States Patent
Kölln et al.

(10) Patent No.: US 7,553,931 B2
(45) Date of Patent: Jun. 30, 2009

(54) COMPLEMENT DEPLETION USING RECOMBINANT HUMAN C3-DERIVATIVES

(75) Inventors: Johanna Kölln, Hamburg (DE); Edzard Spillner, Hamburg (DE); Reinhard Bredehorst, Hamburg (DE)

(73) Assignee: PLS-Design GmbH, Hamburg (DE)

( * ) Notice: Subject to any disclaimer, the term of this patent is extended or adjusted under 35 U.S.C. 154(b) by 0 days.

(21) Appl. No.: 10/884,813

(22) Filed: Jul. 2, 2004

(65) Prior Publication Data

US 2005/0079585 A1    Apr. 14, 2005

Related U.S. Application Data

(60) Provisional application No. 60/484,797, filed on Jul. 3, 2003.

(51) Int. Cl.
*C07K 1/00* (2006.01)
(52) U.S. Cl. .................................................... 530/350
(58) Field of Classification Search .................. 530/350
See application file for complete search history.

(56) References Cited

OTHER PUBLICATIONS

Alper CA, Johnson AM, Birtch AG, and Moore FD (1969) Human C'3: evidence for the liver as the primary site of synthesis. Science, 163: 286-88.
Ames RS, Tometta MA, Jones CS, Tsui P. (1994) Isolation of neutralizing anti-C5a monoclonal antibodies from a filamentous phage monovalent Fab display library. J. Immunol., 152(9):4572-81.
Ames RS, Tometta MA, Jones CS, Tsui P. (1994) Isolation of neutralizing anti-C5a monoclonal antibodies from a filamentous phage monovalent Fab display library. J. Immunol., 153(2):910 (Erratum).
Ames RS, Li Y, Sarau HM, Nuthulaganti P, Foley JJ, Ellis C., Zeng Z, Su K, Jurewicz AJ, Hertzberg RP, Bergsma DJ, and Kumar C. (1996) Molecular cloning and characterization of the human fanaphylatoxin C3a receptor. J. Biol. Chem, 271: 20231-34.
Andersson, J. Ekdahl, NK and Nilsson, B. (2003) Complement Activation on a Model Biomaterial Surface-Binding of C3B Via the Alternative Pathway Amplification Loop to Plasma Proteins Absorbed to the Surface, Immunoglogy, 40 (Abstract).
Bach FH, Robson SC, Winkler H, Ferran C, Stuhlmeier KM, Wrighton CJ, and Hancock WW. (1995) Barriers to xenotransplantation. Nat. Med., 1: 869-73.
Baldwin WM, 3rd, Pruitt SK, Brauer RB, Daha MR, and Sanfilippo F. (1995) Complement in organ transplantation. Contributions to inflammation, injury, and rejection. Transplantation, 59: 797-808.
Ballow M and Cochrane CG. (1969) Two anticomplementary factors in cobra venom: hemolysis of guinea pig erythrocytes to one of them J. Immunol., 103: 944-952.
Belmont HM, Hopkins P, Edelson HS, Kaplan HB, Ludewig R, Weissmann G, and Abramson S. (1986) Complement activation during systemic lupus erythematosus. C3a and C5a anaphylatoxins circulate during Exacerbations of disease. Arthritis. Rheum., 29: 1085-89.
Biesecker G, Dihel L, Enney K and Bendele RA. (1999) Derivation of RNA aptamer inhibitors of human complement C5. Immunopharmacology, 42: 219-30.
Bohnsack JF and Cooper NR. (1988) CR2 ligands modulate human B cell activation. J. Immunol., 141: 2569-76.
Burger R. Zilow G, Bader A, Friedlein A, and Naser W. (1988) The C terminus of the anaphylatoxin C3a generated upon complement activation represents a neoantigenic determinat with diagnostic potential. J. Immunol., 141: 553-58.
Busch K, Piehler J, and Fromm H. (2000) Plant succinic semialdehyde dehydrogenase: dissection of nucleotide binding by surface plasmon resonance and fluorescence spectroscopy. Biochemistry, 39: 10110-10117.
Buyon JP, Tamerius J, Ordorica S, Young B, and Abramson SB. (1992) Activation of the alternative complement pathway accompanies disease flares in systemic lupus erythematosus during pregnancy. Arthritis Rheum., 35: 55-61.
Cheung AK, Parker CJ, and Hohnholt M. (1994) Soluble complement receptor type 1 inhibits complement activation induced by hemodialysis membranes in vitro. Kidney Int., 46: 1680-87.
Christiansen D, Milland J, Thorley BR, McKenzie IF, and Loveland BE. (1996) A functional analysis of recombinant soluble CD46 in vivo and a comparison with recombinant soluble forms of CD55 and CD35 in vitro. Eur. J. Immunol., 26: 578-85.
Chrupcala M, Pomer S, Waldherr R, Staehler G, and Kirschfink M. (1996) Effect of complement modulation with the soluble complement receptor sCR1 on survival and function of kidney xenotransplant. An experimental study with a new guinea pig to rate transplant model. Urologe A., 35: 478-84.
Cochrane CG, Muller-Eberhard HJ, and Aikin BS. (1970) Depletion of plasma complement in vivo by a protein of cobra venom: its effect on various immunologic reactions. J. Immunol., 105: 55-69.
Cooper PD. (1985) Complement and cancer: activation of the alternative pathway as a theoretical base for immunotherapy. Adv. Immun. Cancer Ther., 1: 125-66.
Cooper PD. and Sim RB. (1984) Substances that can trigger activation of the alternative pathway of complment have anti-melanoma activity in mice. Int. J. Cancer, 33: 683-87.
Couser WG, Baker PJ, and Adler S. (1985) Complement and the direct mediation of immune glomerular injury: a new perspective. Kidney Int., 28: 879-90.
Couser WG, Johnson RJ, Young BA, Yeh CG, Toth CA, and Rudolph AR. (1995) The effects of soluble recombinant complement receptor 1 on complement-mediated experimental glomerulonephritis. J. Am. Soc. Nephrol., 5: 1888-94.
Craddock PR, Fehr J, Dalmasso AP, Brighan KL, and Jacob HS. (1977) Hemodialysis leukopenia. Pulmonary vascular leukostasis resulting from complement activation by dialyzer cellophane membranes. J. Clin. Invest., 59: 879-88.

(Continued)

*Primary Examiner*—Tekchand Saidha
(74) *Attorney, Agent, or Firm*—Ballard Spahr Andrews & Ingersoll, LLP

(57) ABSTRACT

The invention provides isolated polypeptides having complement-modulating activity. Specifically, the invention resides in the provision of isolated polypeptides having complement-depleting properties, i.e. that effect an efficient consumption of complement in human serum. The current invention thus provides human C3-derivatives that are capable of forming C3-convertases exerting an extended CVF, Bb-like half-life of up several hours, compared to 1.5 minutes of the naturally occurring C3-convertases, thus escaping the physiological degradation mechanisms.

4 Claims, 18 Drawing Sheets
(10 of 18 Drawing Sheet(s) Filed in Color)

OTHER PUBLICATIONS

Dalmasso, A. P. (1997) Role of complement in xenografts redction, in Xenotransplantation: The Transplantation of Organs and Tissues Between Species, vol. 2nd ed (Cooper DK, Kemp E, Platt JL, and White DJ., eds), pp. 38-60. Springer, Berlin.

Daoudaki ME, Becherer JD, and Lambris JD. (1988) A 34 amino acid peptide of the third component of complement mediates properdin binding. J. Immunol., 140: 1577-80.

Davies A. (1996) Policing the membrane: cell surface proteins which regulate complement. Res. Immunol., 147: 82-87.

Davis AE. $3^{rd}$, and Harrison RA. (1982) Structural characterization of factor I mediated cleavage of the third component of complement. Biochemistry, 21: 5745-49.

DeBruijn MHL and Fey GH. (1985) Human complement component C3: cDNA coding sequence and derived primary structure. Proc. Natl. Acad. Sci. USA, 708-12.

Dolmer K and Sottrup-Jensen L. (1993) Disulfide bridges in human complement component C3b. FEBS Lett., 315: 85-90.

Eldering E, Huijbregts CC, Nuijens JH, Verhoeven AJ, and Hack CE. (1993) Recombinant C1 inhibitor P5/P3 variants display resistance to catalytic inactivation by stimulated neutrophils. J. Clin. Invest., 91: 1035-43.

Elsner J, Oppermann M, Czech W, Dobos G, Schopf E, Norgauer J, and Kapp A. (1994) C3a activates reative oxygen radical species production and intracellular calcium transients in human eosinophils. Eur. J. Immunol., 24: 518-22.

Eppinger MJ, Deeb GM, Bolling SF, and Ward PA. (1997) Mediators of ischemia-reperfusion injury of rat lung. Am. J. Pathol., 150: 1773-1784.

Fearon DT and Austen KF. (1975) Properdin: binding to C3b and stabilization of the C3bdependent C3-convertase. J. Exp. Med., 142: 856-863.

Fecke W, Farries TC, D'Cruz LG, Napper CM, and Harrison RA. (1998) Expression of factor I-resistant mutants of the human complement component C3 in heterologous systems.Xenotransplantation, 5: 29-34.

Fiane AE, Mollnes TE, Videm V, Hovig T, Hogasen K, Mellbye OJ, Spruce L, Moore WT, Sahu A, and Lambrs JD. (1999a) Prolongation of ex viveperfused pig xenograft survival by the complement inhibitor Compstatin. Transplant Proc., 31: 934-35.

Fiane AE, Mollnes TE, Videm V, Hovig T, Hogasen K, Mellbye OJ, Spruce L, Moore WT, Sahu A, and Lambris JD. (1999b) Compstatin, a peptide inhibitor of C3, prolongs survival of ex vivo perfused pig xenografts. Xenotransplantation, 6: 52-65.

Fishelson Z. (1991) Complement C3: a molecular mosaic-of binding sites. Mol. Immunol., 28: 545-52.

Fritzinger DC, Bredehorst R, and Vogel CW. (1994) Molecular cloning and derived primary structure of cobra venom factor. Proc. Natl. Acad. Sci. USA, 91: 12775-79.

Fritzinger DC, Petrella EC, Connelly MB, Bredehorst R, and Vogel CW. (1992) Primary structure of cobra complement component C3. J. Immunol., 149: 3554-62.

Fritzinger DC, Hew, B, Wehrhahn, D., and Vogel, CW (2003) Functional Characterization of Cobra Venom Factor/Cobra C3 Hybrid Proteins. Molecular Immunoglogy, 40 (Abstract).

Gonzalez-Rubio C, Ferreira-Cerdan A, Ponce IM, Arpa J, Fontan G, and Lopez-Trascasa M. (2001) Complement factor I deficiency associated with recurrent menigitis coinciding with menstruation. Arch. Neurol., 58: 1923-28.

Gowda DC, Petrella EC, Raj TT, Bredehorst R, and Vogel CW. (1994) Immunoreactivity and function of oligosaccharides in cobra venom factor. J. Immunol., 152: 2977-86.

Grier AH and Vogel CW. (1989) The oligosaccharide chains of cobra venom factor are required for complement activation. Mol. Immunol., 26: 563-74.

Grier AH, Schultz M, and Vogel CW. (1987) Cobra venom factor and human C3 share carbohydrate antigenicdeterminants. J. Immunol., 139: 1245-52.

Griffiths AD, Williams SC, Hartley O, Tomlinson IM, Waterhouse P, Crosby WL, Kontermann RE, Jones PT, Low NM, Allison TJ, et al. (1994) Isolation of high affinity human antibodies directly from large synthetic repertoires. Embo, J., 13: 3245-60.

Gyongyossy-Issa MI, McLeod E, and Devine DV. (1994) Complement activation in platelet concentrates is surfacedependent and modulated by the platelets. J. Lab. Clin. Med., 123: 859-68.

Hack CE, Nuijens JH, Felt-Bersma RJ, Schreuder WO, Eerenberg-Belmer AJ, Paardekooper J, Bronsveld, W. and Thijs LG. (1989) Elevated plasma levels of the anaphylatoxins C3a and C4a are associated with a fatal outcome in sepst. Am. J. Med., 86: 20-26.

Hack CE, Voerman HJ, Eisele B, Keinecke HO, Nuijens JH, Eerenberg AJ, Ogilvie, A.; Strack van Schijndel, R. J.; Delvos, U. and Thijs, L. G. (1992) Clesterase inhibitor substitution in sepsis. Lancet, 339: 378.

Heller T, Hennecke M, Baumann U, Gessner JE, zu Vilsendorf AM, Baensch M, Boulay F, Kola A, Klos A, Bautsch W, Kohl J. (1999) Selection of a C5a receptor complex disease and ischemia/reperfusion injury. J. Immunol., 163: 985-94.

Higgins PJ, Ko JL, Lobell R, Sardonini C, Alessi MK, and Yeh CG. (1997) A soluble chimeric complement inhibitory protein that possesses both decayaccelerating and factor I cofactor activities. J. Immunol., 158: 2872-81.

Hirani S, Lambris JD, and Muller-Eberhard HJ. (1986) Structural analysis of the asparagine linked oligosaccharides of human complement component C3. Biochem. J., 233: 613-16.

Homeister JW, Satoh P, and Lucchesi BR. (1992) Effects of complement activation in the isolated heart. Role of the terminal complement components. Circ. Res., 71: 303-19.

Horstick, G. (2002) Ci-esterase inhibitor in ischemia and reperfusion. Immunobiology, 205: 552-62.

Janatova J. (1986) Detection of disulphide bonds and localization of interchain linkages in the third (C3) and the fourth (C4) components of human complement. Biochem. J., 233(3): 819-25.

Kahnberg KE, Lindhe J, and Attstrom R. (1976) The role of complement in initial gingivitis. I. The effect of decomplementation by cobra venom factor. J. Periodontal Res., 11: 269-78.

Kemp E, Dieperink H, Leth P, Jensenius JC, Nielsen B, Lillevang ST, Salomon S, Steinbruchel D, Larsen S, Koch C, et al. (1994) Monoclonal antibodies to complement C3 prolong survival of discordant xenografts: guinea pig heart to rat transplantation. Transplant. Proc., 26: 1011-15.

Kemp PA, Spragg JH, Brown JC, Morgan BP, Gunn CA, and Taylor PW. (1992) Immunohistochemical determination of complement activation in joint tissues of patients with rheumatoid arthritis and osteoarthritis using neoantigerspecific monoclonal antibodies. J. Clin. Lab. Immunol., 37: 147-62.

Kilgore KS, Schmid E, Shanley TP, Flory CM, Maheswari V, Tramontini NL, Cohen H, Ward PA, Friedl HP, Warren JS. (1997) Sublytic concentrations of the membrane attack complex of complement induce endothelial interleukin-8 and monocyte chemoattractant protein-1 through nuclear factor-kappa B activation. Am. J. Pathol., 150(6): 2019-31.

Kilgore KS, Friedrichs GS, Homeister JW, and Lucchesi BR. (1994) The complement system in myocardial ischaemia/reperfusion injury. Cardiovasc. Res., 28: 437-44.

Kinoshita T, Medof ME, Silber R, and Nussenzweig V. (1985) Distribution of decayaccelerating factor in the peripheral blood of normal individuals and patients with paroxysmal nocturnal hemoglobinuria. J. Exp. Med., 162: 75-92.

Kirklin JK, Westaby S, Blackstone EH, Kirklin JW, Chenoweth DE, and Pacifico AD. (1983) Complement and the damaging effects of cardiopulmonary bypass. J. Thorac. Cardiovasc. Surg., 86: 845-57.

Kölln J, Ziegelmuller P, Klensang K, Schneider I, Bredehorst R, and Andr J. (2001) Transient expression of active Cobra Venom Factor (CVF) and CVF/C3 chimeras in mammalian cells. Biol. Chem., 382: 164.

Kölln, Spillner, E, Jörg, A, Klensang, K, and Bredehorst, R. (2004) Complement Inactivation by Recombinant Human C3 Derivatives, J. of Immunology, 173:5540-5545.

Kölln J, Matzas, M, Jänner, Nathalie, Mix, Thorsten, Klensang, K, Bredehorst, R, and Spillner, E (2004) Functional Analysis of Cobra Venom Factor/Human C3 Chimeras Transiently Expressed in Mammalian Cells, Mammalian Cells, Molecular Immunology, 41:19-28.

Konteatis ZD, Siciliano SJ, Van Riper G, Molineaux CJ, Pandya S, Fischer P, Rosen H, Mumford RA, and Springer MS. (1994) Development of C5a receptor antagonists. Differential loss of functional responses. J. Immunol., 153: 4200-05.

Lachmann PJ, Pangburn MK, and Oldroyd RG. (1982) Breakdown of C3 after complement activation. Identification of a new fragment C3g, using monoclonal antibodies. J. Exp. Med., 156: 205-16.

Laemmli UK. (1970) Cleavage of strutural proteins during the assembly of the head of bacteriophage T4. Nature, 227: 680-85.

Lambris, JD, Zhege, L, Oglesby, TJ, Atkinson, JP, Hack, CE, and Becherer, JD (1996) Dissection of CR1, Factor H, Membrane Cofactor Protein, and Factor B Binding and Functional Sites in the Third Complement Component, J. of Immunology, 156:4821-4832.

Law SK and Dodds AW. (1997) The internal thioester and the covalent binding properties of the complement proteins C3 and C4. Protein Sci., 6, 263-74.

Lennon VA, Seybold ME, Lindstrom JM, Cochrane C, and Ulevitch R. (1978) Role of complement in the pathogenesis of experimental autoimmune myasthenia gravis. J. Exp. Med., 147: 973-83.

Lens JW, van den Berg WB, van de Putte LB, Berden JH, and Lems SP. (1984) Flare-up of antigen-induced arthritis in mice after challenge with intravenous antigen: effects of pretreatment with cobra venom factor and anti-lymphocyte serum. Clin. Exp. Immunol., 57: 520-28.

Lin Y, Soares MP, Sato K, Csizmadia E, Robson SC, Smith N, and Bach FH. (2000) Longterm survival of hamster hearts in presensitized rats. J. Immunol., 164: 4883-92.

Liszewski MK and Atkinson JP. (1992) Membrane cofactor protein. Curr. Top. Microbiol. Immunol., 178: 45-60.

Lublin DM and Atkinson JP. (1989) Decayaccelerating factor: biochemistry, molecular biology, and function. Annu. Rev. Immunol., 7: 35-58.

Lupton S and Levine AJ. (1985) Mapping genetic elements of Epstein-Barr virus that facilitate extrachromosomal persistence of Epstein-Barr virus-derived plasmids in human cells. Mol. Cell. Biol., 5: 2533-42.

Makrides SC, Scesney SM, Ford PJ, Evans KS, Carson GR, and Marsh HC, Jr. (1992) Cell surface expression of the C3b/C4b receptor (CR1) protects Chinese hamster ovary cells from lysis by human complement. J. Biol. Chem., 267: 24754-261.

Medicus RG, Gotze O, and Muller-Eberhard HJ. (1976) Alternative pathway of complement: recruitment of precursor properdin by the labile C3/C5 convertase and the potentiation of the pathways. J. Exp. Med., 144: 1076-93.

Mollnes TE. (1997) Biocompatibility: complement as mediator of tissue damage and as indicator of incompatibility.Exp Clin Immunogenet, 14, 24-29.

Mollnes TE and Lachmann PJ. (1988) Regulation of complement. Scand. J. Immunol., 27: 127-142.

Moran P, Beasley H, Gorrell A, Matin E, Gribling P, Fuchs H, Gillett N, Burton LE, and Caras IW. (1992) Human recombinant soluble decay acclerating factor inhibits complement activation in vitro and in vivo. J. Immunol., 149: 1736-1743.

Morariu MA and Dalmasso AP. (1978) Experimental allergic encephalomyelitis in cobra venom factortreated and C4-deficient guinea pigs. Ann. Neurol., 4: 427-430.

Morgan, BP and Walport MJ. (1991) Complement deficiency and disease. Immunol Today, 12: 301-306.

Morgan BP, Gasque P, Singhrao SK and Piddlesden SJ. (1997) Role of complement in inflammation and injury in the nervous system. Exp. Clin. Immunogenet., 14: 19-23.

Müller-Eberhard HJ and Fjellstrom KE. (1971) Isolation of the anticomplementary protein from cobs venom and its mode of action on C3. J. Immunol., 107: 1666-72.

Newman SL, Devery Pocius JE, Ross GD, and Henson PM. (1984) Phagocytosis by human monocytederived macrophages. Independent function of receptors for C3b (CR1) and iC3b (CR3). Complement, 1: 213-27.

Oberholzer J, Yu D, Triponez F, Cretin N, Andereggen E, Mentha G, White D, Buehler L, Morel P, and Lou J. (1999) Decomplementation with cobra venom factor prolongs survival of xenografted islets in a rat to mousemodel. Immunology, 97: 173-80.

O'Keefe MC, Caporale LH, and Vogel CW. (1988) A novel cleavage product of human complement component C3 with structural and functional properties of cobra venom factor. J. Biol. Chem., 263: 12690-97.

Oran AE and Isenman DE. (1999) Identification of residues within the 727-767 segment of human complement component C3 important for its interaction with factor H and with complement receptor 1 (CR1, CD35). J. Biol. Chem., 274: 5120-30.

Pang AS and Minta JO. (1980) Inhibition of vitamin D2 induced arteriosclerosis in rats by depletion of complement with cobra venom factor. Artery, 7: 109-22.

Pangburn MK and Muiller-Eberhard HJ. (1984) The alternative pathway of complement. Springer Semin. Immunopathl., 7: 163-92.

Park KW, Tofukuji M, Metais C, Comunale ME, Dai HB, Simons M, Stahl GL, Agah Aand Sellke FW. (1999) Attenuation of endotheliumdependent dilation of pig pulmonary arterioles after cardiopulmonary bypass is preveted by monoclonal antibody to complement C5a. Anesth. Analg., 89: 42-48.

Pellas TC, Boyar W, van Oostrum J, Wasvary J, Fryer LR, Pastor G, Sills M, Braunwalder A, Yarwood DR, Kramer R, Kimble E, Hadala J, Haston W, Moreira Ludewig R, Uziel-Fusi S, Peters P, Bill K, and Wennogle LP. (1998) Novel C5a receptor antagonists regulate neutrophil functions in vitro and in vivo. J. Immunol., 160: 5616-21.

Piddlesden SJ, Jiang S, Levin JL, Vincent A, and Morgan BP. (1996) Soluble complement receptor 1 (sCR1) protects against experimental autoimmune myasthenia gravis. J. Neuroimmunol. 71: 73-177.

Piddlesden SJ, Storch MK, Hibbs M, Freeman AM, Lassmann H, and Morgan BP. (1994) Soluble recombinat complement receptor 1 inhibits inflammation and demyelination in antibody mediated demyelinating experimental allergic encephalomyelitisis. J. Immunol., 152: 5477-84.

Pinter C, Siccardi AG, Lopalco L, Longhi R, and Clivio A. (1995) HIV glycoprotein 41 and complement factor H interact with each other and share functional as well as antigenic homology. AIDS Res. Hum. Retroviruses, 11: 971-80.

Regal JF and Fraser DG. (1996) Systemic complement system depletion does not inhibit cellular accumulation in antihistamine pretreated allergic guinea pig lung. Int. Arch. Allergy Immunol., 109: 150-60.

Regal JF, Fraser DG, and Toth CA. (1993) Role of the complement system in antigeainduced bronchoconstriction and changes in blood pressure in the guinea pig. J. Pharmacol. Exp. Ther., 267: 979-88.

Rogers J, Cooper NR, Webster S, Shultz J, McGeer PL, Styren SD, Civin WH, Brachova L, Bradt B, Ward P, et al. (1992) Complement activation by betaamyloid in Alzheimer disease. Proc. Natl. Acad. Sci. USA, 89: 10016-20.

Ross GD, Newman SL, Lambris JD, Devery-Pocius JE, Cain JA, Lachmann PJ. (1983) Generation of three different fragments of bound C3 with purified factor I or serum. II. Location of binding sites in the C3 fragments for factors B and H, complement receptors, and bovine conglutinin. J. Exp. Med., 158(2): 334-52.

Ross SC and Densen P. (1984) Complement deficiency states and infection: epidemiology, pathogenesis and consequences of neisserial and other infections in an immune deficiency. Medicine (Baltimore), 63, 243-73.

Saiki RK, Gelfand DH, Stoffel S, Scharf SJ, Higuchi R, Horn GT, Mullis KB, and Erlich HA. (1988) Primer directed enzymatic amplification of DNA with a thermostable DNA polymerase. Science, 239: 487-91.

Scharfstein J, Ferreira A, Gigli I, and Nussenzweig V. (1978) Human C4-binding protein. I. Isolation and characterization. J. Exp. Med., 148: 207-22.

Schmid E, Warner RL, Crouch LD, Friedl HP, Till GO, Hugli TE, and Ward PA. (1997) Neutrophilchemotactic activity and C5a following systemic activation of complement in rats. Inflammation, 21: 325-33.

Schmidt TG, Koepke J, Frank R, and Skerra A. (1996) Molecular interaction between the Strep-tag affinity peptide and its cognate target, streptavidin. J. Mol. Biol., 255: 753-66.

Sim RB, Reboul A, Arlaud GJ, Villiers CL, and Colomb MG. (1979) Interaction of 125I labelled complement subcomponents Glr and C-ls with protease inhibitors in plasma. FEBS Lett., 97: 111-15.

Skerra A and Schmidt TG. (2000) Use of the StrepTag and streptavidin for detection and purification of recombinant proteins. Methods Enzymol., 326: 271-304.

Smyth N, Odenthal U, Merkl B, and Paulsson M. (2000) Eukaryotic expression and purification of recombinant extracellular matrix proteins carrying the Strep II tag. Methods. Mol. Biol., 139: 49-57.

Stoiber H, Schneider R, Janatova J, and Dierich MP. (1995) Human complement proteins C3b, C4b, factor H and properdin react with specific sites in gp120 and gp41, the envelope proteins of HIV-1. Immunobiology, 193: 98-113.

Strüber M, Hagl C, Hirt SW, Cremer J, Harringer W, and Haverich, A. (1999) C1-esterase inhibitor in graft failure after lung transplantation. Intensive Care Med., 25: 1315-18.

Sugita Y, Ito K, Shiozuka K, Suzuki H, Gushima H, Tomita M, and Masuho Y. (1994) Recombinant soluble CD59 inhibits reactive hemolysis with complement. Immunology, 82: 34-41.

Tack BF, Harrison RA, Janatova J, Thomas ML, and Prahl JW. (1980) Evidence for presence of an internal thiolester bondin third component of human complement. Proc. Natl. Acad. Sci. USA, 77: 5764-68.

Taniguchi S, Kobayashi T, Neethling FA, Ye Y, Niekrasz M, White DJ, and Cooper DK. (1996) Cobra venom factor stimulates anti-alpha-galactose antibody production in baboons. Implications for pig-to-human xenotransplantation. Transplantation, 62: 678-81.

Taniguchi-Sidle A and Isenman DE. (1994) Interactions of human complement component C3 with factor B and with complement receptors type 1 (CR1, CD35) ard type 3 (CR3, CD11b/CD18) involve an acidic sequence at the N-terminus of C3 alpha'-chain. J. Immunol., 153: 5285-02.

Till GO, Johnson KJ, Kunkel R, and Ward PA. (1982) Intravascular activation of complement and acute lung injury. Dependency on neutrophils and toxic oxygen metabolites. J. Clin. Invest., 69: 1126-35.

Vakeva AP, Agah A, Rollins SA, Matis LA, Li L, and Stahl GL. (1998) Myocardial infarction and apoptosis after myocardial ischemia and reperfusion: role of the terminal complement components and inhibition by anti-C5 therapy. Circulation, 97: 2259-67.

Vogel CW and Muller-Eberhard HJ. (1982) The cobra venom factor-dependent C3-convertase of human complement. A kinetic and thermodynamic analysis of a protease acting on its natural high molecular weight substrate. J. Biol. Chem., 257: 8292-99.

Vogel CW and Muller-Eberhard HJ. (1984) Cobra venom factor: improved method for purification and biochemical chara orization J. Immunol. Methods, 73: 203-20.

Vogel CW, Smith CA, and Muller-Eberhard HJ. (1984) Cobra venom factor: structural homology with the third component of human complement. J. Immunol., 133: 3235-41.

Vogel CW, Wilkie SD, and Morga AC. (1985) In vivo studies with covalent conjugates of cobra venom factor and monoclonal antibodies to human tumors. Haematol. Blood Transfus., 29: 514-17.

Vogel CW, Bredehorst R, Fritzinger DC, Grunwald T, Ziegel Muller P, and Kock MA. (1996) Structure and function of cobra venom factor, the complement-activating protein in cobra venom, In *Natural Toxins II*, Edited by B.R. Singh and A.T. Tu, 97-114.

Volanakis JE. (1995) Transcriptional regulation of complement genes. Annu. Rev. Immunol., 13: 277-305.

Wang Y, Rollins SA, Madri JA, and Matis LA. (1995) Anti C5 monoclonal antibody therapy.prevents collageninduced arthritis and ameliorates established disease. Proc. Natl. Acad. Sci. USA, 92: 8955-59.

Wang Y, Hu Q, Madri JA, Rollins SA, Chodera A, and Matis LA. (1996) Amelioration of lupuslike autoimmune disease in NZB/WF1 mice after treatment with a blocking monoclonal antibody specific for complement component C5. Proc. Natl. Acad. Sci. USA, 93: 8563-68.

Wehrhahn D. (2000) Untersuchungen zur Struktur-Funktionsbeziehunge- n von Kobra Venom Faktor-Konstruktion und rekombinante Expression von Kobra Venom Faktor/Kobra C3 Hybriden, Dissertation, Fachbereich Chemie. Universitat Hamburg, Hamburg.

Weisman HF, Bartow T, Leppo MK, Marsh HC Jr., Carson GR, Concino MF, Boyle MP, Roux KH, Weisfeldt ML, and Fearon DT. (1990) Soluble human complement receptor type 1: in vivo inhibitor of complement suppressing postischemic myocardial inflammation and necrosis. Science, 249: 146-151.

Whiss PA. (2002) Pexelizumab Alexion. Curr. Opin. Investig. Drugs, 3: 870-77.

Williams KC, Ulvestad E, and Hickey WF. (1994) Immunology of multiple sclerosis. Clin. Neurosci., 2: 229-45

Wright SD, Reddy PD, Jong MT, and Eickson BW. (1987) C3bi receptor (complement receptor type 3) recognizes a region of complement protein C3 containing sequence Arg-Gly-Asp. Proc. Natl. Acad. Sci. USA, 84: 1965-68.

Zimmerman JL., Dellinger RP, Straube RC, and Levin JL. (2000) Phase I trial of the recombinant soluble complement receptor 1 in acute lung injury and acute respiratory distress syndrome. Crit. Care Med., 28: 3149-54.

Zipfel PF, Skerka C, Caprioli J, Manuelian T, Neumann HH, Noris M, and Remuzzi G. (p01) Complement factor H and hemolytic uremic syndrome. Int. Immunopharmacol., 1: 461-68. (2001).

Chrupcale M, Pomer S, Staehler G, Waldherr R, and Kirschfink C. (1994) Prolongation of discordant renal xenograft survival by depletion of complement. Comparative effects of systemically administered cobra venom factor and soluble complement receptor type 1 in a guinea-pig to rat model. Transpl. Int., 7 Suppl 1: S650-53.

Lublin DM and Atkinson JP. (1990) Decayaccelerating factor and membrane cofactor protein. Curr. Top. Microbiol. Immunol., 153: 123-45.

Ryan US. (1986) The endothelial surface and responses to injury. Fed. Proc., 45(2): 101-8.

Wehrhahn D. (2000) Untersuchungen zur Struktur-Funktionsbeziehunge- n von Kobra Venom Faktor-Konstruktion und rekombinante Expression von Kobra Venom Faktor/Kobra C3 Hybriden, Dissertation, Fachbereich Chemie. Universitat Hamburg, Hamburg. (Abstract XP-002306770).

PCT/EP2004/00729 filed Dec. 09, 2004 International Search Report.

PCT/EP2004/00729 filed Dec. 09, 2004 Written Opinion.

Fig. 1

```
CVF   -MERMALYLVAALLIGFPGSSHGALYTLITPAVLRTDTEEQILVEAHGDSTPKQLDIFVH  59
hC3   MGPTSGPSLLLLLLTHLPLALGSPMYSIITPNILRLESEETMVLEAHDAQGDVPVTVTVH  60
        . *:  **  :* :  ..:*::***  :** ::**  :::***. .    :  : **

CVF   DFPRKQKTLFQTRVDMNPAGGMLVTPTIEIPA-KEVSTDSRQNQYVVVQVTGPQVRLEKV  118
hC3   DFPGKKLVLSSEKTVLTPATNHMGNVTFTIPANREFKSEKGRNKFVTVQATFGTQVVEKV  120
      *** *: .* . :. :.**  . : . *: *** :*..::. :*::*.**.*   :***

CVF   VLLSYQSSFLFIQTDKGIYTPGSPVLYRVFSMDHNTSKMNKTVIVEFQTPEGILVSSNSV  178
hC3   VLVSLQSGYLFIQTDKTIYTPGSTVLYRIFTVNHKLLPVGRTVMVNIENPEGIPVKQDSL  180
      **:* **.:****** ******.****:*::.*:   :.:**:*:::.**** *..:*:

CVF   DLN-----FFWPYNLPDLVSLGTWRIVAKYEHSPE-NYTAYFDVRKYVLPSFEVRLQPSE  232
hC3   SSQNQLGVLPLSWDIPELVNMGQWKIRAYYENSPQQVFSTEFEVKEYVLPSFEVIVEPTE  240
      . :     :  .:::*:**.:* *:* * **:**:   ::: *:*:********  :*:*

CVF   KFFYIDGNENFHVSITARYLYGEEVEGVAFVLFGVKIDDAKKSIPDSLTRIPIIDGDGKA  292
hC3   KFYYIYNEKGLEVTITARFLYGKKVEGTAFVIFGIQDGEQRISLPESLKRIPIEDGSGEV  300
      **:** .::.:.*:****:***::***.***:**:: .: : *:*:**.**** **.*:.

CVF   TLKRDTFRSRFPNLN--ELVGHTLYASVTVMTESGSDMVVTEQSGIHIVASPYQIHFTKT  350
hC3   VLSRKVLLDGVQNLRAEDLVGKSLYVSATVILHSGSDMVQAERSGIPIVTSPYQIHFTKT  360
       .*.*..: : . . **. :***::**.*.**: .****** :*:*** **:********

CVF   PKYFKPGMPYELTVYVTNPDGSPAAHVPVVSEAFHSMG-TTLSDGTAKLILNIPLNAQSL  409
hC3   PKYFKPGMPFDLMVFVTNPDGSPAYRVPVAVQGEDTVQSLTQGDGVAKLSINTHPSQKPL  420
      *********::*  *:********* :***.   .: ..  * .**.*** :*   . :.*

CVF   PITVRTNHGDLPRERQATKSMTAIAYQTQGGSGNYLHVAITSTEIKPGDNLPVNFNVKGN  469
hC3   SITVRTKKQELSEAEQATRTMQALPYSTVGNSNNYLHLSVLRTELRPGETLNVNFLLRMD  480
      .*****::  :*... .****:* *:: .*  *:.*.*  **:**.* *** :: :

CVF   ANSLKQIKYFTYLILNKGKIFKVGRQPRRDGQNLVTMNLHITPDLIPSFRFVAYY----Q  525
hC3   RAHEAKIRYYTYLIMNKGRLLKAGRQVREPGQDLVVLPLSITTDFIPSFRLVAYYTLIGA  540
       :*:*****:***:: .:*  **. *. **:**.*  * **.*:*****:****

CVF   VGNNEIVADSVWVDVKDTCMGTLVVKG---DNLIQMPGAAMKIKLEGDPGARVGLVAVDK  582
hC3   SGQREVVADSVWVDVKDSCVGSLVVKSGQSEDRQPVPGQQMTLKIEGDHGARVVLVAVDK  600
      *:..*:***********:*:*:****.   ::        :**  *.:****  ******

CVF   AVYVLNDKYKISQAKIWDTIEKSDFGCTAGSGQNNLGVFEDAGLALTTSTNLNTKQRSAA  642
hC3   GVFVLNKKNKLTQSKIWDVVEKADIGCTPGSGKDYAGVFSDAGLTFTSSSGQQTAQRAEL  660
      .*:***.* *: :.****.:**:* *** ***:: **** ****::*::*  **::  :

CVF   KCPQPANRRRRSSVLLLDSNASKAAEFQDQDLRKCCEDVMHENPMGYTCEKRAKYIQEGD  702
hC3   QCPQPAARRRRS-VQLTEKRMDKVGKYP-KELRKCCEDGMRENPMRFSCQRRTRFISLGE  718
      :***** *****  * *   .::  .*..::  ::******* *:**** ::*::*:::*. *:

CVF   ACKAAFLECCRYIKGVRDENQRESELFLARDDNEDGFIADSDIISRSDFPKSWLWLTKDL  762
hC3   ACKKVFLDCCNYITELRRQHARASHLGLARSNLDEDIIAEENIVSREFPESWLWNVEDL  778
      ***  .**:**.** .  :: * *.*  ***.:  :::..**:..:***:****  .:**

CVF   TEEPNSQGISSKTMSFYLRDSITTWVVLAVSFTPTKGICVAEPYEIRVMKVFFIDLQMPY  822
hC3   KEPPKN-GISTKLMNIFLKDSITTWEILAVSMSDKKGICVADPFEVTVMQDFFIDLRLPY  837
       .* *::.  ***:* *  .::::******  :::****** :***  : **. :::*****:**

CVF   SVVKNEQVEIRAILHNY-VNEDIYVRVELLYNPAFCSASTKGQRYRQQFPIKALSSRAVP  881
hC3   SVVRNEQVEIRAVLYNYRQNQELKVRVELLHNPAFCSLATTKRRHQQTVTIPPKSSLSVP  897
      ***:********:*:**  *::* ******:****** :*.**::  ::: *  :* *  :**
```

Fig. 1 (continued)

```
CVF    FVIVPLEQGLHDVEIKASVQEALWSDGVRKKLKVVPEGVQK-SIVTIVKLDPRAKGVGGT  940
hC3    YVIVPLKTGLQEVEVKAAVYHHFISDGVRKSLKVVPEGIRMNKTVAVRTLDPERLGREGV  957
       :*****: **:.**:**:*  . :  ******.*******::   .  *::  .***.   *    *.

CVF    QLEVIKARKLDDRVPDTEIETKIIIQGDPVAQIIENSIDGSKLNHLIITPSGCGEQNMIR 1000
hC3    QKEDIPPADLSDQVPDTESETRILLQGTPVAQMTEDAVDAERLKHLIVTPSGCGEQNMIG 1017
       *  *  . .*  . *.*:***** **::**  **** *:::* ..:*:***:**********

CVF    MAAPVIATYYLDTTEQWETLGINRRTEAVNQIVTGYAQQMVYKKADHSYAAFTNRASSSW 1060
hC3    MTPTVIAVHYLDETEQWEKFGLEKRQGALELIKKGYTQQLAFRQPSSAFAAFVKRAPSTW 1077
       *:..***.:*** *****.:*::::*   *::  *  .**:**:.::::..  ::***.:**.**.*:*

CVF    LTAYVVKVFAMAAKMVAGISHEIICGGVRWLILNRQQPDGAFKENAPVLSGTMQGGIQG- 1119
hC3    LTAYVVKVFSLAVNLIA-IDSQVLCGAVKWLILEKQKPDGVFQEDAPVIHQEMIGGLRNN 1136
       *********::*.:::*  *.  :::**.*:****:*:****.*:*:****:    * **::.

CVF    AEEEVYLTAFILVALLESKTICNDYVNSLDSSIKKATNYLLKKYEKLQRPYTTALTAYAL 1179
hC3    NEKDMALTAFVLISLQEAKDICEEQVNSLPGSITKAGDFLEANYMNLQRSYTVAIAGYAL 1196
       *:::  ****:*:*::  *:*  **::  ****  .**.**  ::*   :*  :***.**.*::.***

CVF    AAADQLND--DRVLMAASTGRDHWEEYNAHTHNIEGTSYALLALLKMKKFDQTGPIVRWL 1237
hC3    AQMGRLKGPLLNKFLTTAKDKNRWEDPGKQLYNVEATSYALLALLQLKDFDFVPPVVRWL 1256
       *    .:*:.    . :::::..:::**:  . .  :  *:.*.**********::*.**   .  *;:****

CVF    TDQNFYGETYGQTQATVMAFQALAEYEIQMPTHKDLNLDITIELPDREVPIRYRINYENA 1297
hC3    NEQRYYGGGYGSTQATFMVFQALAQYQKDAPDHQELNLDVSLQLPSRSSKITHRIHWESA 1316
       .:*.:**  **.**** *.*****.*.:  :  *  *::****:::**.*.    *   :**::*.*

CVF    LLARTVETKLNQDITVTASGDGKATMTILTFYNAQLQEKANVCNKFHLNVSVENIHLN-- 1355
hC3    SLLRSEETKENEGFTVTAEGKGQGTLSVVTMYHAKAKDQL-TCNKFDLKVTIKPAPETEK 1375
         * *: *** *:..:****.*.*:..*:.*::*:*:  :::  .****.*:*:::     .

CVF    -AMGAKGALMLKICTRYLGEVDSTMTIIDISMLTGFLPDAEDLTRLSKGVDRYISRYEVD 1414
hC3    RPQDAKNTMILEICTRYRGDQDATMSILDISMMTGFAPDTDDLKQLANGVDRYISKYELD 1435
         . .**.:::*:****** *: *:** *:*****:*** **:  **:.**::******:**:*

CVF    NNMAQKVAVIIYLNKVSHSEDECLHFKILKHFEVGFIQPGSVKVYSYYNLDEKCTKFYHP 1474
hC3    KAFSDRNTLIIYLDKVSHSEDDCLAFKVHQYFNVELIQPGAVKVYAYYNLEESCTRFYHP 1495
       :   ::::::  ::****:*********::**   **:   ::*:*   :****.:****.****:*.**:****

CVF    DKGTGLLNKICIGNVCRCAGETCSSLNHQERIDVPLQIEKACETNVDYVYKTKLLRIEEQ 1534
hC3    EKEDGKLNKLCRDELCRCAEENCFIQKSDDKVTLEERLDKACEPGVDYVYKTRLVKVQLS 1555
       :*     *  ***:*   .:;****  *.*     :  ::::  :   :::****.. *******;*::::  .

CVF    DGNDIYVMDVLEVIKQGTDENPRAKTHQYISQRKCQEALNLKVNDDYLIWGSRSDLLPTK 1594
hC3    NDFDEYIMAIEQTIKSGSDEVQVGQQRTFISPIKCREALKLEEKKHYLMWGLSSDFWGEK 1615
       :.  *  *:*   :  :.**.*:**  .:   :*   **:***:*;   :..****   **:   *

CVF    DKISYIITKNTWIERWPHEDECQEEEFQKLCDDFAQFSYTLTEFGCPT- 1642
hC3    PNLSYIIGKDTWVEHWPEEDECQDEENQKQCQDLGAFTESMVVFGCPN- 1663
       :.:****  *:**;*:**.****:*****;** **  *:*:..  *: :::. ****.
```

Fig. 2
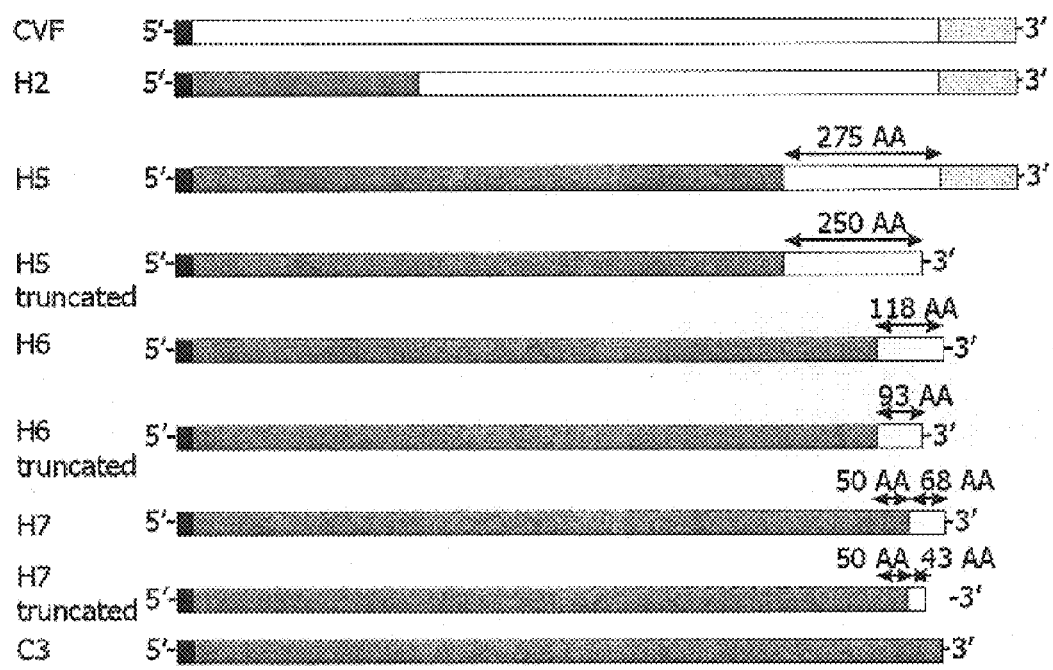

Fig. 10

```
CVF   AEEEVYLTAFILVALLESKTICNDYVNSLDSSIKKATNYLLKKYEKLQRPYTTALTAYAL 1179
hC3   NEKDMALTAFVLISLQEAKDICEEQVNSLPGSITKAGDFLEANYMNLQRSYTVAIAGYAL 1196
      *::: ****:*::* *:* **:: **** .**.** ::*   :* :***.**.*::.***

CVF   AAADQLND--DRVLMAASTGRDHWEEYNAHTHNIEGTSYALLALLKMKKFDQTGPIVRWL 1237
hC3   AQMGRLKGPLLNKFLTTAKDKNRWEDPGKQLYNVEATSYALLALLQLKDFDFVPPVVRWL 1256
      *  .:*:.    . ::::::..:::**  . : :*:*.**********:*.**  .*:****

CVF   TDQNFYGETYGQTQATVMAFQALAEYEIQMPTHKDLNLDITIELPDREVPIRYRINYENA 1297
hC3   NEQRYYGGGYGSTQATFMVFQALAQYQKDAPDHQELNLDVSLQLPSRSSKITHRIHWESA 1316
      .:*.:**  **.****.*.*****:*: : * *::****:::.**.*.  * :**:*.*

CVF   LLARTVETKLNQDITVTASGDGKATMTILTFYNAQLQEKANVCNKFHLNVSVENIHLN-- 1355
hC3   SLLRSEETKENEGFTVTAEGKGQGTLSVVTMYHAKAKDQL-TCNKFDLKVTIKPAPETEK 1375
      * *: *** *::.:****.*.*:.*:::*:*:*: :::  .****.*:*::: .

| BglII
CVF   -AMGAKGALMLKICTRYLGEVDSTMTIIDISMLTGFLPDAEDLTRLSKGVDRYISRYEVD 1414
hC3   RPQDAKNTMILEICTRYRGDQDATMSILDISMMTGFAPDTDDLKQLANGVDRYISKYELD 1435
      . **.::::*:**** *: *:**:****:****.*** **:.**.*.:**:*******.**:*

CVF   NNMAQKVAVIIYLNKVSHSEDECLHFKILKHFEVGFIQPGSVKVYSYYNLDEKCTKFYHP 1474
hC3   KAFSDRNTLIIYLDKVSHSEDDCLAFKVHQYFNVELIQPGAVKVYAYYNLEESCTRFYHP 1495
      :  ::::  ::*****:****** ** :: *:* :****:****:****:.**:****

| Bsp1407I
CVF   DKGTGLLNKICIGNVCRCAGETCSSLNHQERIDVPLQIEKACETNVDYVYKTKLLRIEEQ 1534
hC3   EKEDGKLNKLCRDELCRCAEENCFIQKSDDKVTLEERLDKACEPGVDYVYKTRLVKVQLS 1555
      :*   * ***:*   .::**** *.*   :  :::: :   :::****..*******:::: .

CVF   DGNDIYVMDVLEVIKQGTDENPRAKTHQYISQRKCQEALNLKVNDDYLIWGSRSDLLPTK 1594
hC3   NDFDEYIMAIEQTIKSGSDEVQVGQQRTFISPIKCREALKLEEKKHYLMWGLSSDFWGEK 1615
      :. * *:*  :  :.**.:**   .: :  :  :** *:****:*:  :...**:** **:    *

CVF   DKISYIITKNTWIERWPHEDECQEEEFQKLCDDFAQFSYTLTEFGCPT- 1642
hC3   PNLSYIIGKDTWVEHWPEEDECQDEENQKQCQDLGAFTESMVVFGCPN- 1663
      ::**** *:**:*:**.*****:**  ** *:*: .**:   :. ****.
```

Fig. 11
A
B

```
                         SEQUENCE LISTING

<160> NUMBER OF SEQ ID NOS: 24

<210> SEQ ID NO 1
<211> LENGTH: 5067
<212> TYPE: DNA
<213> ORGANISM: Homo sapiens
<220> FEATURE:
<221> NAME/KEY: CDS
<222> LOCATION: (61)..(5052)
<223> OTHER INFORMATION: Complement Component C3

<400> SEQUENCE: 1
ctcctcccca tcctctccct ctgtccctct gtccctctga ccctgcactg tcccagcacc       60 atg gga ccc acc tca ggt ccc agc ctg ctg ctc ctg cta cta acc cac      108
Met Gly Pro Thr Ser Gly Pro Ser Leu Leu Leu Leu Leu Leu Thr His
1               5                   10                  15 ctc ccc ctg gct ctg ggg agt ccc atg tac tct atc atc acc ccc aac      156
Leu Pro Leu Ala Leu Gly Ser Pro Met Tyr Ser Ile Ile Thr Pro Asn
                20                  25                  30 atc ttg cgg ctg gag agc gag gag acc atg gtg ctg gag gcc cac gac      204
Ile Leu Arg Leu Glu Ser Glu Glu Thr Met Val Leu Glu Ala His Asp
            35                  40                  45 gcg caa ggg gat gtt cca gtc act gtt act gtc cac gac ttc cca ggc      252
Ala Gln Gly Asp Val Pro Val Thr Val Thr Val His Asp Phe Pro Gly
        50                  55                  60 aaa aaa cta gtg ctg tcc agt gag aag act gtg ctg acc cct gcc acc      300
Lys Lys Leu Val Leu Ser Ser Glu Lys Thr Val Leu Thr Pro Ala Thr
65                  70                  75                  80 aac cac atg ggc aac gtc acc ttc acg atc cca gcc aac agg gag ttc      348
Asn His Met Gly Asn Val Thr Phe Thr Ile Pro Ala Asn Arg Glu Phe
```

-continued

|  | 85 | 90 | 95 |  |
|---|---|---|---|---|
| aag tca gaa aag ggg cgc aac aag ttc gtg acc gtg cag gcc acc ttc | | | | 396 |
| Lys Ser Glu Lys Gly Arg Asn Lys Phe Val Thr Val Gln Ala Thr Phe | | | | |
| 100 | | 105 | 110 | |

```
aag tca gaa aag ggg cgc aac aag ttc gtg acc gtg cag gcc acc ttc      396
Lys Ser Glu Lys Gly Arg Asn Lys Phe Val Thr Val Gln Ala Thr Phe
            100                 105                 110 ggg acc caa gtg gtg gag aag gtg gtg ctg gtc agc ctg cag agc ggg      444
Gly Thr Gln Val Val Glu Lys Val Val Leu Val Ser Leu Gln Ser Gly
        115                 120                 125 tac ctc ttc atc cag aca gac aag acc atc tac acc cct ggc tcc aca      492
Tyr Leu Phe Ile Gln Thr Asp Lys Thr Ile Tyr Thr Pro Gly Ser Thr
130                 135                 140 gtt ctc tat cgg atc ttc acc gtc aac cac aag ctg cta ccc gtg ggc      540
Val Leu Tyr Arg Ile Phe Thr Val Asn His Lys Leu Leu Pro Val Gly
145                 150                 155                 160 cgg acg gtc atg gtc aac att gag aac ccg gaa ggc atc ccg gtc aag      588
Arg Thr Val Met Val Asn Ile Glu Asn Pro Glu Gly Ile Pro Val Lys
                165                 170                 175 cag gac tcc ttg tct tct cag aac cag ctt ggc gtc ttg ccc ttg tct      636
Gln Asp Ser Leu Ser Ser Gln Asn Gln Leu Gly Val Leu Pro Leu Ser
            180                 185                 190 tgg gac att ccg gaa ctc gtc aac atg ggc cag tgg aag atc cga gcc      684
Trp Asp Ile Pro Glu Leu Val Asn Met Gly Gln Trp Lys Ile Arg Ala
        195                 200                 205 tac tat gaa aac tca cca cag cag gtc ttc tcc act gag ttt gag gtg      732
Tyr Tyr Glu Asn Ser Pro Gln Gln Val Phe Ser Thr Glu Phe Glu Val
210                 215                 220 aag gag tac gtg ctg ccc agt ttc gag gtc ata gtg gag cct aca gag      780
Lys Glu Tyr Val Leu Pro Ser Phe Glu Val Ile Val Glu Pro Thr Glu
225                 230                 235                 240 aaa ttc tac tac atc tat aac gag aag ggc ctg gag gtc acc atc acc      828
Lys Phe Tyr Tyr Ile Tyr Asn Glu Lys Gly Leu Glu Val Thr Ile Thr
                245                 250                 255 gcc agg ttc ctc tac ggg aag aaa gtg gag gga act gcc ttt gtc atc      876
Ala Arg Phe Leu Tyr Gly Lys Lys Val Glu Gly Thr Ala Phe Val Ile
            260                 265                 270 ttc ggg atc cag gat ggc gaa cag agg att tcc ctg cct gaa tcc ctc      924
Phe Gly Ile Gln Asp Gly Glu Gln Arg Ile Ser Leu Pro Glu Ser Leu
        275                 280                 285 aag cgc att ccg att gag gat ggc tcg ggg gag gtt gtg ctg agc cgg      972
Lys Arg Ile Pro Ile Glu Asp Gly Ser Gly Glu Val Val Leu Ser Arg
290                 295                 300 aag gta ctg ctg gac ggg gtg cag aac ctc cga gca gaa gac ctg gtg     1020
Lys Val Leu Leu Asp Gly Val Gln Asn Leu Arg Ala Glu Asp Leu Val
305                 310                 315                 320 ggg aag tct ttg tac gtg tct gcc acc gtc atc ttg cac tca ggc agt     1068
Gly Lys Ser Leu Tyr Val Ser Ala Thr Val Ile Leu His Ser Gly Ser
                325                 330                 335 gac atg gtg cag gca gag cgc agc ggg atc ccc atc gtg acc tct ccc     1116
Asp Met Val Gln Ala Glu Arg Ser Gly Ile Pro Ile Val Thr Ser Pro
            340                 345                 350 tac cag atc cac ttc acc aag aca ccc aag tac ttc aaa cca gga atg     1164
Tyr Gln Ile His Phe Thr Lys Thr Pro Lys Tyr Phe Lys Pro Gly Met
        355                 360                 365 ccc ttt gac ctc atg gtg ttc gtg acg aac cct gat ggc tct cca gcc     1212
Pro Phe Asp Leu Met Val Phe Val Thr Asn Pro Asp Gly Ser Pro Ala
370                 375                 380 tac cga gtc ccc gtg gca gtc cag ggc gag gac act gtg cag tct cta     1260
Tyr Arg Val Pro Val Ala Val Gln Gly Glu Asp Thr Val Gln Ser Leu
385                 390                 395                 400 acc cag gga gat ggc gtg gcc aaa ctc agc atc aac aca cac ccc agc     1308
```

```
                Thr Gln Gly Asp Gly Val Ala Lys Leu Ser Ile Asn Thr His Pro Ser
                            405                 410                 415 cag aag ccc ttg agc atc acg gtg cgc acg aag aag cag gag ctc tcg          1356
Gln Lys Pro Leu Ser Ile Thr Val Arg Thr Lys Lys Gln Glu Leu Ser
            420                 425                 430 gag gca gag cag gct acc agg acc atg cag gct ctg ccc tac agc acc          1404
Glu Ala Glu Gln Ala Thr Arg Thr Met Gln Ala Leu Pro Tyr Ser Thr
        435                 440                 445 gtg ggc aac tcc aac aat tac ctg cat ctc tca gtg cta cgt aca gag          1452
Val Gly Asn Ser Asn Asn Tyr Leu His Leu Ser Val Leu Arg Thr Glu
    450                 455                 460 ctc aga ccc ggg gag acc ctc aac gtc aac ttc ctc ctg cga atg gac          1500
Leu Arg Pro Gly Glu Thr Leu Asn Val Asn Phe Leu Leu Arg Met Asp
465                 470                 475                 480 cgc gcc cac gag gcc aag atc cgc tac tac acc tac ctg atc atg aac          1548
Arg Ala His Glu Ala Lys Ile Arg Tyr Tyr Thr Tyr Leu Ile Met Asn
                485                 490                 495 aag ggc agg ctg ttg aag gcg gga cgc cag gtg cga gag ccc ggc cag          1596
Lys Gly Arg Leu Leu Lys Ala Gly Arg Gln Val Arg Glu Pro Gly Gln
            500                 505                 510 gac ctg gtg gtg ctg ccc ctg tcc atc acc acc gac ttc atc cct tcc          1644
Asp Leu Val Val Leu Pro Leu Ser Ile Thr Thr Asp Phe Ile Pro Ser
        515                 520                 525 ttc cgc ctg gtg gcg tac tac acg ctg atc ggt gcc agc ggc cag agg          1692
Phe Arg Leu Val Ala Tyr Tyr Thr Leu Ile Gly Ala Ser Gly Gln Arg
    530                 535                 540 gag gtg gtg gcc gac tcc gtg tgg gtg gac gtc aag gac tcc tgc gtg          1740
Glu Val Val Ala Asp Ser Val Trp Val Asp Val Lys Asp Ser Cys Val
545                 550                 555                 560 ggc tcg ctg gtg gta aaa agc ggc cag tca gaa gac cgg cag cct gta          1788
Gly Ser Leu Val Val Lys Ser Gly Gln Ser Glu Asp Arg Gln Pro Val
                565                 570                 575 cct ggg cag cag atg acc ctg aag ata gag ggt gac cac ggg gcc cgg          1836
Pro Gly Gln Gln Met Thr Leu Lys Ile Glu Gly Asp His Gly Ala Arg
            580                 585                 590 gtg gta ctg gtg gcc gtg gac aag ggc gtg ttc gtg ctg aat aag aag          1884
Val Val Leu Val Ala Val Asp Lys Gly Val Phe Val Leu Asn Lys Lys
        595                 600                 605 aac aaa ctg acg cag agt aag atc tgg gac gtg gtg gag aag gca gac          1932
Asn Lys Leu Thr Gln Ser Lys Ile Trp Asp Val Val Glu Lys Ala Asp
    610                 615                 620 atc ggc tgc acc ccg ggc agt ggg aag gat tac gcc ggt gtc ttc tcc          1980
Ile Gly Cys Thr Pro Gly Ser Gly Lys Asp Tyr Ala Gly Val Phe Ser
625                 630                 635                 640 gac gca ggg ctg acc ttc acg agc agc agt ggc cag cag acc gcc cag          2028
Asp Ala Gly Leu Thr Phe Thr Ser Ser Ser Gly Gln Gln Thr Ala Gln
                645                 650                 655 agg gca gaa ctt cag tgc ccg cag cca gcc gcc cgc cga cgc cgt tcc          2076
Arg Ala Glu Leu Gln Cys Pro Gln Pro Ala Ala Arg Arg Arg Arg Ser
            660                 665                 670 gtg cag ctc acg gag aag cga atg gac aaa gtc ggc aag tac ccc aag          2124
Val Gln Leu Thr Glu Lys Arg Met Asp Lys Val Gly Lys Tyr Pro Lys
        675                 680                 685 gag ctg cgc aag tgc tgc gag gac ggc atg cgg gag aac ccc atg agg          2172
Glu Leu Arg Lys Cys Cys Glu Asp Gly Met Arg Glu Asn Pro Met Arg
    690                 695                 700 ttc tcg tgc cag cgc cgg acc cgt ttc atc tcc ctg ggc gag gcg tgc          2220
Phe Ser Cys Gln Arg Arg Thr Arg Phe Ile Ser Leu Gly Glu Ala Cys
705                 710                 715                 720
```

| | | |
|---|---|---|
| aag aag gtc ttc ctg gac tgc tgc aac tac atc aca gag ctg cgg cgg<br>Lys Lys Val Phe Leu Asp Cys Cys Asn Tyr Ile Thr Glu Leu Arg Arg<br>                725                             730                      735 | | 2268 |
| cag cac gcg cgg gcc agc cac ctg ggc ctg gcc agg agt aac ctg gat<br>Gln His Ala Arg Ala Ser His Leu Gly Leu Ala Arg Ser Asn Leu Asp<br>            740                                745                          750 | | 2316 |
| gag gac atc att gca gaa gag aac atc gtt tcc cga agt gag ttc cca<br>Glu Asp Ile Ile Ala Glu Glu Asn Ile Val Ser Arg Ser Glu Phe Pro<br>            755                              760                         765 | | 2364 |
| gag agc tgg ctg tgg aac gtt gag gac ttg aaa gag cca ccg aaa aat<br>Glu Ser Trp Leu Trp Asn Val Glu Asp Leu Lys Glu Pro Pro Lys Asn<br>770                          775                             780 | | 2412 |
| gga atc tct acg aag ctc atg aat ata ttt ttg aaa gac tcc atc acc<br>Gly Ile Ser Thr Lys Leu Met Asn Ile Phe Leu Lys Asp Ser Ile Thr<br>785                          790                             795                         800 | | 2460 |
| acg tgg gag att ctg gct gtc agc atg tcg gac aag aaa ggg atc tgt<br>Thr Trp Glu Ile Leu Ala Val Ser Met Ser Asp Lys Lys Gly Ile Cys<br>                      805                             810                         815 | | 2508 |
| gtg gca gac ccc ttc gag gtc aca gta atg cag gac ttc ttc atc gac<br>Val Ala Asp Pro Phe Glu Val Thr Val Met Gln Asp Phe Phe Ile Asp<br>            820                                825                          830 | | 2556 |
| ctg cgg cta ccc tac tct gtt gtt cga aac gag cag gtg gaa atc cga<br>Leu Arg Leu Pro Tyr Ser Val Val Arg Asn Glu Gln Val Glu Ile Arg<br>                835                             840                         845 | | 2604 |
| gcc gtt ctc tac aat tac cgg cag aac caa gag ctc aag gtg agg gtg<br>Ala Val Leu Tyr Asn Tyr Arg Gln Asn Gln Glu Leu Lys Val Arg Val<br>            850                              855                         860 | | 2652 |
| gaa cta ctc cac aat cca gcc ttc tgc agc ctg gcc acc acc aag agg<br>Glu Leu Leu His Asn Pro Ala Phe Cys Ser Leu Ala Thr Thr Lys Arg<br>865                          870                             875                         880 | | 2700 |
| cgt cac cag cag acc gta acc atc ccc ccc aag tcc tcg ttg tcc gtt<br>Arg His Gln Gln Thr Val Thr Ile Pro Pro Lys Ser Ser Leu Ser Val<br>                      885                             890                         895 | | 2748 |
| cca tat gtc atc gtg ccg cta aag acc ggc ctg cag gaa gtg gaa gtc<br>Pro Tyr Val Ile Val Pro Leu Lys Thr Gly Leu Gln Glu Val Glu Val<br>            900                              905                         910 | | 2796 |
| aag gct gcc gtc tac cat cat ttc atc agt gac ggt gtc agg aag tcc<br>Lys Ala Ala Val Tyr His His Phe Ile Ser Asp Gly Val Arg Lys Ser<br>            915                              920                         925 | | 2844 |
| ctg aag gtc gtg ccg gaa gga atc aga atg aac aaa act gtg gct gtt<br>Leu Lys Val Val Pro Glu Gly Ile Arg Met Asn Lys Thr Val Ala Val<br>930                          935                             940 | | 2892 |
| cgc acc ctg gat cca gaa cgc ctg ggc cgt gaa gga gtg cag aaa gag<br>Arg Thr Leu Asp Pro Glu Arg Leu Gly Arg Glu Gly Val Gln Lys Glu<br>945                          950                          955                         960 | | 2940 |
| gac atc cca cct gca gac ctc agt gac caa gtc ccg gac acc gag tct<br>Asp Ile Pro Pro Ala Asp Leu Ser Asp Gln Val Pro Asp Thr Glu Ser<br>                      965                             970                         975 | | 2988 |
| gag acc aga att ctc ctg caa ggg acc cca gtg gcc cag atg aca gag<br>Glu Thr Arg Ile Leu Leu Gln Gly Thr Pro Val Ala Gln Met Thr Glu<br>            980                              985                         990 | | 3036 |
| gat gcc gtc gac gcg gaa cgg ctg  aag cac ctc att gtg  acc ccc tcg<br>Asp Ala Val Asp Ala Glu Arg Leu  Lys His Leu Ile Val  Thr Pro Ser<br>            995                              1000                       1005 | | 3084 |
| ggc tgc  ggg gaa cag aac atg  atc ggc atg acg ccc  acg gtc atc<br>Gly Cys  Gly Glu Gln Asn Met  Ile Gly Met Thr Pro  Thr Val Ile<br>          1010                            1015                       1020 | | 3129 |
| gct gtg  cat tac ctg gat gaa  acg gag cag tgg gag  aag ttc ggc<br>Ala Val  His Tyr Leu Asp Glu  Thr Glu Gln Trp Glu  Lys Phe Gly<br>          1025                            1030                       1035 | | 3174 |

-continued

| | | |
|---|---|---|
| cta gag aag cgg cag ggg gcc ttg gag ctc atc aag aag ggg tac<br>Leu Glu Lys Arg Gln Gly Ala Leu Glu Leu Ile Lys Lys Gly Tyr<br>1040                        1045                      1050 | 3219 |
| acc cag cag ctg gcc ttc aga caa ccc agc tct gcc ttt gcg gcc<br>Thr Gln Gln Leu Ala Phe Arg Gln Pro Ser Ser Ala Phe Ala Ala<br>1055                        1060                      1065 | 3264 |
| ttc gtg aaa cgg gca ccc agc acc tgg ctg acc gcc tac gtg gtc<br>Phe Val Lys Arg Ala Pro Ser Thr Trp Leu Thr Ala Tyr Val Val<br>1070                        1075                      1080 | 3309 |
| aag gtc ttc tct ctg gct gtc aac ctc atc gcc atc gac tcc caa<br>Lys Val Phe Ser Leu Ala Val Asn Leu Ile Ala Ile Asp Ser Gln<br>1085                        1090                      1095 | 3354 |
| gtc ctc tgc ggg gct gtt aaa tgg ctg atc ctg gag aag cag aag<br>Val Leu Cys Gly Ala Val Lys Trp Leu Ile Leu Glu Lys Gln Lys<br>1100                        1105                      1110 | 3399 |
| ccc gac ggg gtc ttc cag gag gat gcg ccc gtg ata cac caa gaa<br>Pro Asp Gly Val Phe Gln Glu Asp Ala Pro Val Ile His Gln Glu<br>1115                        1120                      1125 | 3444 |
| atg att ggt gga tta cgg aac aac aac gag aaa gac atg gcc ctc<br>Met Ile Gly Gly Leu Arg Asn Asn Asn Glu Lys Asp Met Ala Leu<br>1130                        1135                      1140 | 3489 |
| acg gcc ttt gtt ctc atc tcg ctg cag gag gct aaa gat att tgc<br>Thr Ala Phe Val Leu Ile Ser Leu Gln Glu Ala Lys Asp Ile Cys<br>1145                        1150                      1155 | 3534 |
| gag gag cag gtc aac agc ctg cca ggc agc atc act aaa gca gga<br>Glu Glu Gln Val Asn Ser Leu Pro Gly Ser Ile Thr Lys Ala Gly<br>1160                        1165                      1170 | 3579 |
| gac ttc ctt gaa gcc aac tac atg aac cta cag aga tcc tac act<br>Asp Phe Leu Glu Ala Asn Tyr Met Asn Leu Gln Arg Ser Tyr Thr<br>1175                        1180                      1185 | 3624 |
| gtg gcc att gct ggc tat gct ctg gcc cag atg ggc agg ctg aag<br>Val Ala Ile Ala Gly Tyr Ala Leu Ala Gln Met Gly Arg Leu Lys<br>1190                        1195                      1200 | 3669 |
| ggg cct ctt ctt aac aaa ttt ctg acc aca gcc aaa gat aag aac<br>Gly Pro Leu Leu Asn Lys Phe Leu Thr Thr Ala Lys Asp Lys Asn<br>1205                        1210                      1215 | 3714 |
| cgc tgg gag gac cct ggt aag cag ctc tac aac gtg gag gcc aca<br>Arg Trp Glu Asp Pro Gly Lys Gln Leu Tyr Asn Val Glu Ala Thr<br>1220                        1225                      1230 | 3759 |
| tcc tat gcc ctc ttg gcc cta ctg cag cta aaa gac ttt gac ttt<br>Ser Tyr Ala Leu Leu Ala Leu Leu Gln Leu Lys Asp Phe Asp Phe<br>1235                        1240                      1245 | 3804 |
| gtg cct ccc gtc gtg cgt tgg ctc aat gaa cag aga tac tac ggt<br>Val Pro Pro Val Val Arg Trp Leu Asn Glu Gln Arg Tyr Tyr Gly<br>1250                        1255                      1260 | 3849 |
| ggt ggc tat ggc tct acc cag gcc acc ttc atg gtg ttc caa gcc<br>Gly Gly Tyr Gly Ser Thr Gln Ala Thr Phe Met Val Phe Gln Ala<br>1265                        1270                      1275 | 3894 |
| ttg gct caa tac caa aag gac gcc cct gac cac cag gaa ctg aac<br>Leu Ala Gln Tyr Gln Lys Asp Ala Pro Asp His Gln Glu Leu Asn<br>1280                        1285                      1290 | 3939 |
| ctt gat gtg tcc ctc caa ctg ccc agc cgc agc tcc aag atc acc<br>Leu Asp Val Ser Leu Gln Leu Pro Ser Arg Ser Ser Lys Ile Thr<br>1295                        1300                      1305 | 3984 |
| cac cgt atc cac tgg gaa tct gcc agc ctc ctg cga tca gaa gag<br>His Arg Ile His Trp Glu Ser Ala Ser Leu Leu Arg Ser Glu Glu<br>1310                        1315                      1320 | 4029 |
| acc aag gaa aat gag ggt ttc aca gtc aca gct gaa gga aaa ggc<br>Thr Lys Glu Asn Glu Gly Phe Thr Val Thr Ala Glu Gly Lys Gly | 4074 |

-continued

|                                                                                                 |      |
|-------------------------------------------------------------------------------------------------|------|
| caa ggc acc ttg tcg gtg gtg aca atg tac cat gct aag gcc aaa<br>Gln Gly Thr Leu Ser Val Val Thr Met Tyr His Ala Lys Ala Lys<br>      1340                    1345                    1350 | 4119 |
| gat caa ctc acc tgt aat aaa ttc gac ctc aag gtc acc ata aaa<br>Asp Gln Leu Thr Cys Asn Lys Phe Asp Leu Lys Val Thr Ile Lys<br>      1355                    1360                    1365 | 4164 |
| cca gca ccg gaa aca gaa aag agg cct cag gat gcc aag aac act<br>Pro Ala Pro Glu Thr Glu Lys Arg Pro Gln Asp Ala Lys Asn Thr<br>      1370                    1375                    1380 | 4209 |
| atg atc ctt gag atc tgt acc agg tac cgg gga gac cag gat gcc<br>Met Ile Leu Glu Ile Cys Thr Arg Tyr Arg Gly Asp Gln Asp Ala<br>      1385                    1390                    1395 | 4254 |
| act atg tct ata ttg gac ata tcc atg atg act ggc ttt gct cca<br>Thr Met Ser Ile Leu Asp Ile Ser Met Met Thr Gly Phe Ala Pro<br>      1400                    1405                    1410 | 4299 |
| gac aca gat gac ctg aag cag ctg gcc aat ggt gtt gac aga tac<br>Asp Thr Asp Asp Leu Lys Gln Leu Ala Asn Gly Val Asp Arg Tyr<br>      1415                    1420                    1425 | 4344 |
| atc tcc aag tat gag ctg gac aaa gcc ttc tcc gat agg aac acc<br>Ile Ser Lys Tyr Glu Leu Asp Lys Ala Phe Ser Asp Arg Asn Thr<br>      1430                    1435                    1440 | 4389 |
| ctc atc atc tac ctg gac aag gtc tca cac tct gag gat gac tgt<br>Leu Ile Ile Tyr Leu Asp Lys Val Ser His Ser Glu Asp Asp Cys<br>      1445                    1450                    1455 | 4434 |
| cta gct ttc aaa gtt cac caa tac ttt aat gta gag ctt atc cag<br>Leu Ala Phe Lys Val His Gln Tyr Phe Asn Val Glu Leu Ile Gln<br>      1460                    1465                    1470 | 4479 |
| cct gga gca gtc aag gtc tac gcc tat tac aac ctg gag gaa agc<br>Pro Gly Ala Val Lys Val Tyr Ala Tyr Tyr Asn Leu Glu Glu Ser<br>      1475                    1480                    1485 | 4524 |
| tgt acc cgg ttc tac cat ccg gaa aag gag gat gga aag ctg aac<br>Cys Thr Arg Phe Tyr His Pro Glu Lys Glu Asp Gly Lys Leu Asn<br>      1490                    1495                    1500 | 4569 |
| aag ctc tgc cgt gat gaa ctg tgc cgc tgt gct gag gag aat tgc<br>Lys Leu Cys Arg Asp Glu Leu Cys Arg Cys Ala Glu Glu Asn Cys<br>      1505                    1510                    1515 | 4614 |
| ttc ata caa aag tcg gat gac aag gtc acc ctg gaa gaa cgg ctg<br>Phe Ile Gln Lys Ser Asp Asp Lys Val Thr Leu Glu Glu Arg Leu<br>      1520                    1525                    1530 | 4659 |
| gac aag gcc tgt gag cca gga gtg gac tat gtg tac aag acc cga<br>Asp Lys Ala Cys Glu Pro Gly Val Asp Tyr Val Tyr Lys Thr Arg<br>      1535                    1540                    1545 | 4704 |
| ctg gtc aag gtt cag ctg tcc aat gac ttt gac gag tac atc atg<br>Leu Val Lys Val Gln Leu Ser Asn Asp Phe Asp Glu Tyr Ile Met<br>      1550                    1555                    1560 | 4749 |
| gcc att gag cag acc atc aag tca ggc tcg gat gag gtg cag gtt<br>Ala Ile Glu Gln Thr Ile Lys Ser Gly Ser Asp Glu Val Gln Val<br>      1565                    1570                    1575 | 4794 |
| gga cag cag cgc acg ttc atc agc ccc atc aag tgc aga gaa gcc<br>Gly Gln Gln Arg Thr Phe Ile Ser Pro Ile Lys Cys Arg Glu Ala<br>      1580                    1585                    1590 | 4839 |
| ctg aag ctg gag gag aag aaa cac tac ctc atg tgg ggt ctc tcc<br>Leu Lys Leu Glu Glu Lys Lys His Tyr Leu Met Trp Gly Leu Ser<br>      1595                    1600                    1605 | 4884 |
| tcc gat ttc tgg gga gag aag ccc aac ctc agc tac atc atc ggg<br>Ser Asp Phe Trp Gly Glu Lys Pro Asn Leu Ser Tyr Ile Ile Gly<br>      1610                    1615                    1620 | 4929 |
| aag gac act tgg gtg gag cac tgg cct gag gag gac gaa tgc caa | 4974 |

```
Lys Asp Thr Trp Val Glu His Trp Pro Glu Glu Asp Glu Cys Gln
1625                1630                1635 gac gaa gag aac cag aaa caa tgc cag gac ctc ggc gcc ttc acc     5019
Asp Glu Glu Asn Gln Lys Gln Cys Gln Asp Leu Gly Ala Phe Thr
1640                1645                1650 gag agc atg gtt gtc ttt ggg tgc ccc aac tga ccacaccccc attcc    5067
Glu Ser Met Val Val Phe Gly Cys Pro Asn
1655                1660

<210> SEQ ID NO 2
<211> LENGTH: 1663
<212> TYPE: PRT
<213> ORGANISM: Homo sapiens

<400> SEQUENCE: 2

Met Gly Pro Thr Ser Gly Pro Ser Leu Leu Leu Leu Leu Thr His
1               5                   10                  15

Leu Pro Leu Ala Leu Gly Ser Pro Met Tyr Ser Ile Ile Thr Pro Asn
                20                  25                  30

Ile Leu Arg Leu Glu Ser Glu Glu Thr Met Val Leu Glu Ala His Asp
            35                  40                  45

Ala Gln Gly Asp Val Pro Val Thr Val Thr Val His Asp Phe Pro Gly
        50                  55                  60

Lys Lys Leu Val Leu Ser Ser Glu Lys Thr Val Leu Thr Pro Ala Thr
65                  70                  75                  80

Asn His Met Gly Asn Val Thr Phe Thr Ile Pro Ala Asn Arg Glu Phe
                85                  90                  95

Lys Ser Glu Lys Gly Arg Asn Lys Phe Val Thr Val Gln Ala Thr Phe
            100                 105                 110

Gly Thr Gln Val Val Glu Lys Val Val Leu Val Ser Leu Gln Ser Gly
        115                 120                 125

Tyr Leu Phe Ile Gln Thr Asp Lys Thr Ile Tyr Thr Pro Gly Ser Thr
    130                 135                 140

Val Leu Tyr Arg Ile Phe Thr Val Asn His Lys Leu Leu Pro Val Gly
145                 150                 155                 160

Arg Thr Val Met Val Asn Ile Glu Asn Pro Glu Gly Ile Pro Val Lys
                165                 170                 175

Gln Asp Ser Leu Ser Ser Gln Asn Gln Leu Gly Val Leu Pro Leu Ser
            180                 185                 190

Trp Asp Ile Pro Glu Leu Val Asn Met Gly Gln Trp Lys Ile Arg Ala
        195                 200                 205

Tyr Tyr Glu Asn Ser Pro Gln Gln Val Phe Ser Thr Glu Phe Glu Val
    210                 215                 220

Lys Glu Tyr Val Leu Pro Ser Phe Glu Val Ile Val Glu Pro Thr Glu
225                 230                 235                 240

Lys Phe Tyr Tyr Ile Tyr Asn Glu Lys Gly Leu Glu Val Thr Ile Thr
                245                 250                 255

Ala Arg Phe Leu Tyr Gly Lys Lys Val Glu Gly Thr Ala Phe Val Ile
            260                 265                 270

Phe Gly Ile Gln Asp Gly Glu Gln Arg Ile Ser Leu Pro Glu Ser Leu
        275                 280                 285

Lys Arg Ile Pro Ile Glu Asp Gly Ser Gly Glu Val Val Leu Ser Arg
    290                 295                 300

Lys Val Leu Leu Asp Gly Val Gln Asn Leu Arg Ala Glu Asp Leu Val
305                 310                 315                 320
```

```
Gly Lys Ser Leu Tyr Val Ser Ala Thr Val Ile Leu His Ser Gly Ser
                325                 330                 335

Asp Met Val Gln Ala Glu Arg Ser Gly Ile Pro Ile Val Thr Ser Pro
                340                 345                 350

Tyr Gln Ile His Phe Thr Lys Thr Pro Lys Tyr Phe Lys Pro Gly Met
                355                 360                 365

Pro Phe Asp Leu Met Val Phe Val Thr Asn Pro Asp Gly Ser Pro Ala
            370                 375                 380

Tyr Arg Val Pro Val Ala Val Gln Gly Glu Asp Thr Val Gln Ser Leu
385                 390                 395                 400

Thr Gln Gly Asp Gly Val Ala Lys Leu Ser Ile Asn Thr His Pro Ser
                405                 410                 415

Gln Lys Pro Leu Ser Ile Thr Val Arg Thr Lys Lys Gln Glu Leu Ser
                420                 425                 430

Glu Ala Glu Gln Ala Thr Arg Thr Met Gln Ala Leu Pro Tyr Ser Thr
                435                 440                 445

Val Gly Asn Ser Asn Asn Tyr Leu His Leu Ser Val Leu Arg Thr Glu
                450                 455                 460

Leu Arg Pro Gly Glu Thr Leu Asn Val Asn Phe Leu Leu Arg Met Asp
465                 470                 475                 480

Arg Ala His Glu Ala Lys Ile Arg Tyr Tyr Thr Tyr Leu Ile Met Asn
                485                 490                 495

Lys Gly Arg Leu Leu Lys Ala Gly Arg Gln Val Arg Glu Pro Gly Gln
                500                 505                 510

Asp Leu Val Val Leu Pro Leu Ser Ile Thr Thr Asp Phe Ile Pro Ser
                515                 520                 525

Phe Arg Leu Val Ala Tyr Tyr Thr Leu Ile Gly Ala Ser Gly Gln Arg
530                 535                 540

Glu Val Val Ala Asp Ser Val Trp Val Asp Val Lys Asp Ser Cys Val
545                 550                 555                 560

Gly Ser Leu Val Val Lys Ser Gly Gln Ser Glu Asp Arg Gln Pro Val
                565                 570                 575

Pro Gly Gln Gln Met Thr Leu Lys Ile Glu Gly Asp His Gly Ala Arg
                580                 585                 590

Val Val Leu Val Ala Val Asp Lys Gly Val Phe Val Leu Asn Lys Lys
                595                 600                 605

Asn Lys Leu Thr Gln Ser Lys Ile Trp Asp Val Val Glu Lys Ala Asp
                610                 615                 620

Ile Gly Cys Thr Pro Gly Ser Gly Lys Asp Tyr Ala Gly Val Phe Ser
625                 630                 635                 640

Asp Ala Gly Leu Thr Phe Thr Ser Ser Ser Gly Gln Gln Thr Ala Gln
                645                 650                 655

Arg Ala Glu Leu Gln Cys Pro Gln Pro Ala Ala Arg Arg Arg Arg Ser
                660                 665                 670

Val Gln Leu Thr Glu Lys Arg Met Asp Lys Val Gly Lys Tyr Pro Lys
                675                 680                 685

Glu Leu Arg Lys Cys Cys Glu Asp Gly Met Arg Glu Asn Pro Met Arg
                690                 695                 700

Phe Ser Cys Gln Arg Arg Thr Arg Phe Ile Ser Leu Gly Glu Ala Cys
705                 710                 715                 720

Lys Lys Val Phe Leu Asp Cys Cys Asn Tyr Ile Thr Glu Leu Arg Arg
                725                 730                 735

Gln His Ala Arg Ala Ser His Leu Gly Leu Ala Arg Ser Asn Leu Asp
```

-continued

```
                740                 745                 750
Glu Asp Ile Ile Ala Glu Glu Asn Ile Val Ser Arg Ser Glu Phe Pro
        755                 760                 765
Glu Ser Trp Leu Trp Asn Val Glu Asp Leu Lys Glu Pro Pro Lys Asn
770                 775                 780
Gly Ile Ser Thr Lys Leu Met Asn Ile Phe Leu Lys Asp Ser Ile Thr
785                 790                 795                 800
Thr Trp Glu Ile Leu Ala Val Ser Met Ser Asp Lys Lys Gly Ile Cys
                805                 810                 815
Val Ala Asp Pro Phe Glu Val Thr Val Met Gln Asp Phe Phe Ile Asp
        820                 825                 830
Leu Arg Leu Pro Tyr Ser Val Val Arg Asn Glu Gln Val Glu Ile Arg
        835                 840                 845
Ala Val Leu Tyr Asn Tyr Arg Gln Asn Gln Glu Leu Lys Val Arg Val
        850                 855                 860
Glu Leu Leu His Asn Pro Ala Phe Cys Ser Leu Ala Thr Thr Lys Arg
865                 870                 875                 880
Arg His Gln Gln Thr Val Thr Ile Pro Pro Lys Ser Ser Leu Ser Val
                885                 890                 895
Pro Tyr Val Ile Val Pro Leu Lys Thr Gly Leu Gln Glu Val Glu Val
                900                 905                 910
Lys Ala Ala Val Tyr His His Phe Ile Ser Asp Gly Val Arg Lys Ser
                915                 920                 925
Leu Lys Val Val Pro Glu Gly Ile Arg Met Asn Lys Thr Val Ala Val
        930                 935                 940
Arg Thr Leu Asp Pro Glu Arg Leu Gly Arg Glu Gly Val Gln Lys Glu
945                 950                 955                 960
Asp Ile Pro Pro Ala Asp Leu Ser Asp Gln Val Pro Asp Thr Glu Ser
                965                 970                 975
Glu Thr Arg Ile Leu Leu Gln Gly Thr Pro Val Ala Gln Met Thr Glu
                980                 985                 990
Asp Ala Val Asp Ala Glu Arg Leu  Lys His Leu Ile Val  Thr Pro Ser
        995                 1000                1005
Gly Cys Gly Glu Gln Asn Met  Ile Gly Met Thr Pro  Thr Val Ile
        1010                1015                1020
Ala Val His Tyr Leu Asp Glu  Thr Glu Gln Trp Glu  Lys Phe Gly
        1025                1030                1035
Leu Glu Lys Arg Gln Gly Ala  Leu Glu Leu Ile Lys  Lys Gly Tyr
        1040                1045                1050
Thr Gln Gln Leu Ala Phe Arg  Gln Pro Ser Ser Ala  Phe Ala Ala
        1055                1060                1065
Phe Val Lys Arg Ala Pro Ser  Thr Trp Leu Thr Ala  Tyr Val Val
        1070                1075                1080
Lys Val Phe Ser Leu Ala Val  Asn Leu Ile Ala Ile  Asp Ser Gln
        1085                1090                1095
Val Leu Cys Gly Ala Val Lys  Trp Leu Ile Leu Glu  Lys Gln Lys
        1100                1105                1110
Pro Asp Gly Val Phe Gln Glu  Asp Ala Pro Val Ile  His Gln Glu
        1115                1120                1125
Met Ile Gly Gly Leu Arg Asn  Asn Asn Glu Lys Asp  Met Ala Leu
        1130                1135                1140
Thr Ala Phe Val Leu Ile Ser  Leu Gln Glu Ala Lys  Asp Ile Cys
        1145                1150                1155
```

-continued

```
Glu Glu Gln Val Asn Ser Leu Pro Gly Ser Ile Thr Lys Ala Gly
    1160                1165                1170

Asp Phe Leu Glu Ala Asn Tyr Met Asn Leu Gln Arg Ser Tyr Thr
    1175                1180                1185

Val Ala Ile Ala Gly Tyr Ala Leu Ala Gln Met Gly Arg Leu Lys
    1190                1195                1200

Gly Pro Leu Leu Asn Lys Phe Leu Thr Thr Ala Lys Asp Lys Asn
    1205                1210                1215

Arg Trp Glu Asp Pro Gly Lys Gln Leu Tyr Asn Val Glu Ala Thr
    1220                1225                1230

Ser Tyr Ala Leu Leu Ala Leu Leu Gln Leu Lys Asp Phe Asp Phe
    1235                1240                1245

Val Pro Pro Val Val Arg Trp Leu Asn Glu Gln Arg Tyr Tyr Gly
    1250                1255                1260

Gly Gly Tyr Gly Ser Thr Gln Ala Thr Phe Met Val Phe Gln Ala
    1265                1270                1275

Leu Ala Gln Tyr Gln Lys Asp Ala Pro Asp His Gln Glu Leu Asn
    1280                1285                1290

Leu Asp Val Ser Leu Gln Leu Pro Ser Arg Ser Ser Lys Ile Thr
    1295                1300                1305

His Arg Ile His Trp Glu Ser Ala Ser Leu Leu Arg Ser Glu Glu
    1310                1315                1320

Thr Lys Glu Asn Glu Gly Phe Thr Val Thr Ala Glu Gly Lys Gly
    1325                1330                1335

Gln Gly Thr Leu Ser Val Val Thr Met Tyr His Ala Lys Ala Lys
    1340                1345                1350

Asp Gln Leu Thr Cys Asn Lys Phe Asp Leu Lys Val Thr Ile Lys
    1355                1360                1365

Pro Ala Pro Glu Thr Glu Lys Arg Pro Gln Asp Ala Lys Asn Thr
    1370                1375                1380

Met Ile Leu Glu Ile Cys Thr Arg Tyr Arg Gly Asp Gln Asp Ala
    1385                1390                1395

Thr Met Ser Ile Leu Asp Ile Ser Met Met Thr Gly Phe Ala Pro
    1400                1405                1410

Asp Thr Asp Asp Leu Lys Gln Leu Ala Asn Gly Val Asp Arg Tyr
    1415                1420                1425

Ile Ser Lys Tyr Glu Leu Asp Lys Ala Phe Ser Asp Arg Asn Thr
    1430                1435                1440

Leu Ile Ile Tyr Leu Asp Lys Val Ser His Ser Glu Asp Asp Cys
    1445                1450                1455

Leu Ala Phe Lys Val His Gln Tyr Phe Asn Val Glu Leu Ile Gln
    1460                1465                1470

Pro Gly Ala Val Lys Val Tyr Ala Tyr Tyr Asn Leu Glu Glu Ser
    1475                1480                1485

Cys Thr Arg Phe Tyr His Pro Glu Lys Glu Asp Gly Lys Leu Asn
    1490                1495                1500

Lys Leu Cys Arg Asp Glu Leu Cys Arg Cys Ala Glu Glu Asn Cys
    1505                1510                1515

Phe Ile Gln Lys Ser Asp Asp Lys Val Thr Leu Glu Glu Arg Leu
    1520                1525                1530

Asp Lys Ala Cys Glu Pro Gly Val Asp Tyr Val Tyr Lys Thr Arg
    1535                1540                1545
```

```
Leu Val Lys Val Gln Leu Ser Asn Asp Phe Asp Glu Tyr Ile Met
    1550                1555                1560

Ala Ile Glu Gln Thr Ile Lys Ser Gly Ser Asp Glu Val Gln Val
    1565                1570                1575

Gly Gln Gln Arg Thr Phe Ile Ser Pro Ile Lys Cys Arg Glu Ala
    1580                1585                1590

Leu Lys Leu Glu Glu Lys Lys His Tyr Leu Met Trp Gly Leu Ser
    1595                1600                1605

Ser Asp Phe Trp Gly Glu Lys Pro Asn Leu Ser Tyr Ile Ile Gly
    1610                1615                1620

Lys Asp Thr Trp Val Glu His Trp Pro Glu Glu Asp Glu Cys Gln
    1625                1630                1635

Asp Glu Glu Asn Gln Lys Gln Cys Gln Asp Leu Gly Ala Phe Thr
    1640                1645                1650

Glu Ser Met Val Val Phe Gly Cys Pro Asn
    1655                1660

<210> SEQ ID NO 3
<211> LENGTH: 5928
<212> TYPE: DNA
<213> ORGANISM: Naja naja
<220> FEATURE:
<221> NAME/KEY: CDS
<222> LOCATION: (4)..(4932)
<223> OTHER INFORMATION: Cobra Venom Factor (CVF)

<400> SEQUENCE: 3 ccc atg gag agg atg gct ctc tat ctg gtg gct gct cta ttg att ggt      48
    Met Glu Arg Met Ala Leu Tyr Leu Val Ala Ala Leu Leu Ile Gly
    1               5                   10                  15 ttt cca ggg tct tct cat ggg gct ctc tac acc ctc atc acc cct gct      96
Phe Pro Gly Ser Ser His Gly Ala Leu Tyr Thr Leu Ile Thr Pro Ala
                20                  25                  30 gtt ttg cga aca gac aca gaa gag caa att ttg gtg gag gcc cat gga     144
Val Leu Arg Thr Asp Thr Glu Glu Gln Ile Leu Val Glu Ala His Gly
            35                  40                  45 gac agt act cca aaa cag ctt gac atc ttt gtt cat gat ttt cca cgg     192
Asp Ser Thr Pro Lys Gln Leu Asp Ile Phe Val His Asp Phe Pro Arg
        50                  55                  60 aag cag aaa acc ttg ttc caa acc aga gta gat atg aat cca gca gga     240
Lys Gln Lys Thr Leu Phe Gln Thr Arg Val Asp Met Asn Pro Ala Gly
    65                  70                  75 ggc atg ctt gtc act cca act ata gag att cca gca aaa gaa gtg agt     288
Gly Met Leu Val Thr Pro Thr Ile Glu Ile Pro Ala Lys Glu Val Ser
80                  85                  90                  95 acg gac tcc agg caa aat caa tat gtg gtt gtg caa gta act ggt cct     336
Thr Asp Ser Arg Gln Asn Gln Tyr Val Val Val Gln Val Thr Gly Pro
                100                 105                 110 caa gtg aga ttg gaa aag gtg gtt ctc ctt tct tac cag agt agc ttt     384
Gln Val Arg Leu Glu Lys Val Val Leu Leu Ser Tyr Gln Ser Ser Phe
            115                 120                 125 ctg ttt atc cag aca gat aaa ggc atc tat aca cca ggg tct cca gta     432
Leu Phe Ile Gln Thr Asp Lys Gly Ile Tyr Thr Pro Gly Ser Pro Val
        130                 135                 140 ctc tat cgt gtt ttt tct atg gat cac aac aca agc aag atg aac aaa     480
Leu Tyr Arg Val Phe Ser Met Asp His Asn Thr Ser Lys Met Asn Lys
    145                 150                 155 act gtg att gtt gag ttt cag act cca gaa ggc att ctt gtc agt tct     528
Thr Val Ile Val Glu Phe Gln Thr Pro Glu Gly Ile Leu Val Ser Ser
160                 165                 170                 175
```

```
aat tca gtt gac cta aac ttc ttc tgg cct tac aat tta cca gac ctt      576
Asn Ser Val Asp Leu Asn Phe Phe Trp Pro Tyr Asn Leu Pro Asp Leu
            180                 185                 190 gtc agt ttg ggg act tgg agg att gtg gcc aaa tat gaa cat tcc cca      624
Val Ser Leu Gly Thr Trp Arg Ile Val Ala Lys Tyr Glu His Ser Pro
        195                 200                 205 gag aat tat act gca tat ttt gat gtc agg aaa tat gtg ttg cca agc      672
Glu Asn Tyr Thr Ala Tyr Phe Asp Val Arg Lys Tyr Val Leu Pro Ser
    210                 215                 220 ttt gaa gtc cgt ctg caa cca tca gag aag ttt ttt tac att gac ggc      720
Phe Glu Val Arg Leu Gln Pro Ser Glu Lys Phe Phe Tyr Ile Asp Gly
225                 230                 235 aat gaa aat ttc cac gtg tct atc act gca agg tac ttg tat gga gag      768
Asn Glu Asn Phe His Val Ser Ile Thr Ala Arg Tyr Leu Tyr Gly Glu
240                 245                 250                 255 gaa gtg gaa ggt gtg gcc ttt gtc ctc ttt gga gtg aaa ata gat gat      816
Glu Val Glu Gly Val Ala Phe Val Leu Phe Gly Val Lys Ile Asp Asp
                260                 265                 270 gct aaa aag agt att cca gac tca ctc acg aga att ccg att att gat      864
Ala Lys Lys Ser Ile Pro Asp Ser Leu Thr Arg Ile Pro Ile Ile Asp
            275                 280                 285 gga gat ggg aaa gca aca cta aaa aga gat aca ttc cgt tct cga ttt      912
Gly Asp Gly Lys Ala Thr Leu Lys Arg Asp Thr Phe Arg Ser Arg Phe
        290                 295                 300 cca aat ctc aat gag ctt gtt ggg cat act ctg tat gca tct gta aca      960
Pro Asn Leu Asn Glu Leu Val Gly His Thr Leu Tyr Ala Ser Val Thr
    305                 310                 315 gtc atg aca gaa tca ggc agt gat atg gta gtg act gag caa agc ggc     1008
Val Met Thr Glu Ser Gly Ser Asp Met Val Val Thr Glu Gln Ser Gly
320                 325                 330                 335 att cat att gtg gca tct ccc tat cag atc cac ttc aca aaa acc ccc     1056
Ile His Ile Val Ala Ser Pro Tyr Gln Ile His Phe Thr Lys Thr Pro
                340                 345                 350 aaa tat ttc aag cca gga atg cca tat gaa ctg acg gtg tat gtt acc     1104
Lys Tyr Phe Lys Pro Gly Met Pro Tyr Glu Leu Thr Val Tyr Val Thr
            355                 360                 365 aac cct gat ggc tca cca gct gcc cat gtg cca gtg gta tca gag gcc     1152
Asn Pro Asp Gly Ser Pro Ala Ala His Val Pro Val Val Ser Glu Ala
        370                 375                 380 ttt cat tct atg gga acc act ttg agt gat ggg act gct aag ctc atc     1200
Phe His Ser Met Gly Thr Thr Leu Ser Asp Gly Thr Ala Lys Leu Ile
    385                 390                 395 ctg aac ata cca ttg aat gct caa agc cta cca atc act gtt aga act     1248
Leu Asn Ile Pro Leu Asn Ala Gln Ser Leu Pro Ile Thr Val Arg Thr
400                 405                 410                 415 aac cat gga gac ctc cca aga gaa cgc cag gca aca aag tcc atg aca     1296
Asn His Gly Asp Leu Pro Arg Glu Arg Gln Ala Thr Lys Ser Met Thr
                420                 425                 430 gcc ata gcc tac caa acc cag gga gga tct gga aac tat ctt cat gta     1344
Ala Ile Ala Tyr Gln Thr Gln Gly Gly Ser Gly Asn Tyr Leu His Val
            435                 440                 445 gcc att aca tct aca gag att aag ccc gga gat aac tta cct gtc aat     1392
Ala Ile Thr Ser Thr Glu Ile Lys Pro Gly Asp Asn Leu Pro Val Asn
        450                 455                 460 ttc aat gtg aag ggc aat gca aat tca ctg aag cag atc aaa tat ttc     1440
Phe Asn Val Lys Gly Asn Ala Asn Ser Leu Lys Gln Ile Lys Tyr Phe
    465                 470                 475 aca tac ctc ata ttg aat aaa ggg aag att ttc aag gtt ggc agg caa     1488
Thr Tyr Leu Ile Leu Asn Lys Gly Lys Ile Phe Lys Val Gly Arg Gln
```

```
                480               485               490               495 ccc agg aga gat ggg cag aat ctg gtg acc atg aat ctg cat atc act    1536
Pro Arg Arg Asp Gly Gln Asn Leu Val Thr Met Asn Leu His Ile Thr
                500               505               510 cca gat ctc atc cct tcc ttc cgg ttt gtg gct tac tac caa gtg gga    1584
Pro Asp Leu Ile Pro Ser Phe Arg Phe Val Ala Tyr Tyr Gln Val Gly
        515               520               525 aac aac gaa att gtg gct gat tct gtc tgg gtg gat gtg aag gat acc    1632
Asn Asn Glu Ile Val Ala Asp Ser Val Trp Val Asp Val Lys Asp Thr
        530               535               540 tgc atg gga acg ttg gtt gtg aaa gga gac aat cta ata caa atg cca    1680
Cys Met Gly Thr Leu Val Val Lys Gly Asp Asn Leu Ile Gln Met Pro
    545               550               555 gga gct gca atg aaa atc aaa ttg gaa ggg gat cca ggt gct cgg gtt    1728
Gly Ala Ala Met Lys Ile Lys Leu Glu Gly Asp Pro Gly Ala Arg Val
560               565               570               575 ggt ctt gtg gct gtg gac aaa gca gta tat gtt ctc aat gat aaa tat    1776
Gly Leu Val Ala Val Asp Lys Ala Val Tyr Val Leu Asn Asp Lys Tyr
                580               585               590 aag att agc caa gct aag ata tgg gac aca ata gaa aag agt gac ttt    1824
Lys Ile Ser Gln Ala Lys Ile Trp Asp Thr Ile Glu Lys Ser Asp Phe
        595               600               605 ggc tgt aca gct ggc agt ggc cag aat aat ctg ggt gtg ttt gaa gat    1872
Gly Cys Thr Ala Gly Ser Gly Gln Asn Asn Leu Gly Val Phe Glu Asp
        610               615               620 gct gga ctg gct ctg aca acc agc act aat ctc aac acc aaa cag aga    1920
Ala Gly Leu Ala Leu Thr Thr Ser Thr Asn Leu Asn Thr Lys Gln Arg
    625               630               635 tca gct gca aag tgt cct cag cct gca aat cgg agg cgt cgc agt tct    1968
Ser Ala Ala Lys Cys Pro Gln Pro Ala Asn Arg Arg Arg Arg Ser Ser
640               645               650               655 gtt ttg ctg ctt gac agc aac gca agc aaa gcg gca gaa ttt cag gat    2016
Val Leu Leu Leu Asp Ser Asn Ala Ser Lys Ala Ala Glu Phe Gln Asp
                660               665               670 caa gac ctg cgt aaa tgc tgt gaa gat gtc atg cat gag aac ccc atg    2064
Gln Asp Leu Arg Lys Cys Cys Glu Asp Val Met His Glu Asn Pro Met
        675               680               685 ggg tac act tgt gaa aag cgt gca aaa tac atc cag gag gga gat gct    2112
Gly Tyr Thr Cys Glu Lys Arg Ala Lys Tyr Ile Gln Glu Gly Asp Ala
        690               695               700 tgt aag gct gcc ttc ctt gaa tgc tgt cgc tac atc aag ggg gtc cga    2160
Cys Lys Ala Ala Phe Leu Glu Cys Cys Arg Tyr Ile Lys Gly Val Arg
705               710               715 gat gaa aac caa cgg gag agc gag ttg ttt ctg gca aga gat gat aat    2208
Asp Glu Asn Gln Arg Glu Ser Glu Leu Phe Leu Ala Arg Asp Asp Asn
720               725               730               735 gaa gat ggt ttc ata gca gat agt gat atc atc tca agg tct gat ttc    2256
Glu Asp Gly Phe Ile Ala Asp Ser Asp Ile Ile Ser Arg Ser Asp Phe
                740               745               750 ccc aag agt tgg ttg tgg cta aca aag gac ttg acc gag gag cct aac    2304
Pro Lys Ser Trp Leu Trp Leu Thr Lys Asp Leu Thr Glu Glu Pro Asn
        755               760               765 agt caa ggg att tca agc aag aca atg tct ttt tat ctg agg gat tcc    2352
Ser Gln Gly Ile Ser Ser Lys Thr Met Ser Phe Tyr Leu Arg Asp Ser
        770               775               780 atc aca acc tgg gtg gtg ctg gct gta agc ttt aca ccc acc aaa ggg    2400
Ile Thr Thr Trp Val Val Leu Ala Val Ser Phe Thr Pro Thr Lys Gly
    785               790               795 atc tgt gtg gct gaa cct tat gaa ata aga gtc atg aaa gtc ttc ttc    2448
```

```
Ile Cys Val Ala Glu Pro Tyr Glu Ile Arg Val Met Lys Val Phe Phe
800                 805                 810                 815 att gat ctt caa atg cca tat tca gta gtg aag aat gag cag gtg gag    2496
Ile Asp Leu Gln Met Pro Tyr Ser Val Val Lys Asn Glu Gln Val Glu
                820                 825                 830 att cga gct att ctg cac aac tac gtt aac gag gat att tat gtg cga    2544
Ile Arg Ala Ile Leu His Asn Tyr Val Asn Glu Asp Ile Tyr Val Arg
            835                 840                 845 gtg gaa ctg tta tac aac cca gcc ttc tgc agt gct tcc aca aaa gga    2592
Val Glu Leu Leu Tyr Asn Pro Ala Phe Cys Ser Ala Ser Thr Lys Gly
        850                 855                 860 caa aga tac cga cag cag ttc cca att aaa gcc ctg tcc tcc aga gca    2640
Gln Arg Tyr Arg Gln Gln Phe Pro Ile Lys Ala Leu Ser Ser Arg Ala
    865                 870                 875 gta ccg ttt gtg ata gtc cca tta gag caa gga ttg cat gat gtt gag    2688
Val Pro Phe Val Ile Val Pro Leu Glu Gln Gly Leu His Asp Val Glu
880                 885                 890                 895 att aaa gca agt gtc cag gaa gcg ttg tgg tca gac ggt gtg agg aag    2736
Ile Lys Ala Ser Val Gln Glu Ala Leu Trp Ser Asp Gly Val Arg Lys
                900                 905                 910 aaa ctg aaa gtt gta cct gaa ggg gta cag aaa tcc att gtg act att    2784
Lys Leu Lys Val Val Pro Glu Gly Val Gln Lys Ser Ile Val Thr Ile
            915                 920                 925 gtt aaa ctg gac cca agg gca aaa gga gtt ggt gga aca cag cta gaa    2832
Val Lys Leu Asp Pro Arg Ala Lys Gly Val Gly Gly Thr Gln Leu Glu
        930                 935                 940 gtg atc aaa gcc cgc aaa tta gat gac aga gtg cct gac aca gaa att    2880
Val Ile Lys Ala Arg Lys Leu Asp Asp Arg Val Pro Asp Thr Glu Ile
    945                 950                 955 gaa acc aag att atc atc caa ggt gac cct gtg gct cag att att gaa    2928
Glu Thr Lys Ile Ile Ile Gln Gly Asp Pro Val Ala Gln Ile Ile Glu
960                 965                 970                 975 aac tca att gat gga agt aaa ctc aac cat ctc att atc act cct tct    2976
Asn Ser Ile Asp Gly Ser Lys Leu Asn His Leu Ile Ile Thr Pro Ser
                980                 985                 990 ggc tgt ggg gag caa aat atg atc cgc atg gcc gca cca gtt att gcc    3024
Gly Cys Gly Glu Gln Asn Met Ile Arg Met Ala Ala Pro Val Ile Ala
            995                 1000                1005 acc tac tac ctg gac acc aca gag cag tgg gag act ctc ggc ata       3069
Thr Tyr Tyr Leu Asp Thr Thr Glu Gln Trp Glu Thr Leu Gly Ile
        1010                1015                1020 aat cgc agg act gaa gct gtc aat cag atc gtg act ggt tat gcc       3114
Asn Arg Arg Thr Glu Ala Val Asn Gln Ile Val Thr Gly Tyr Ala
    1025                1030                1035 cag cag atg gtg tac aag aaa gca gat cat tcc tat gca gca ttt       3159
Gln Gln Met Val Tyr Lys Lys Ala Asp His Ser Tyr Ala Ala Phe
    1040                1045                1050 aca aac cgt gca tct agt tct tgg cta aca gca tat gtc gta aaa       3204
Thr Asn Arg Ala Ser Ser Ser Trp Leu Thr Ala Tyr Val Val Lys
    1055                1060                1065 gtc ttt gcc atg gct gcc aaa atg gta gca ggc att agt cat gaa       3249
Val Phe Ala Met Ala Ala Lys Met Val Ala Gly Ile Ser His Glu
    1070                1075                1080 atc att tgt gga ggt gtg agg tgg ctg att ctg aac agg caa caa       3294
Ile Ile Cys Gly Gly Val Arg Trp Leu Ile Leu Asn Arg Gln Gln
    1085                1090                1095 cca gat gga gcg ttc aaa gaa aat gcc cct gta ctt tct gga aca       3339
Pro Asp Gly Ala Phe Lys Glu Asn Ala Pro Val Leu Ser Gly Thr
    1100                1105                1110
```

-continued

| | | | | | | | | | | | | | | |
|---|---|---|---|---|---|---|---|---|---|---|---|---|---|---|
| atg | cag | gga | gga | att | caa | ggt | gct | gaa | gaa | gaa | gta | tat | tta | aca | 3384 |
| Met | Gln | Gly | Gly | Ile | Gln | Gly | Ala | Glu | Glu | Glu | Val | Tyr | Leu | Thr | |
| | | 1115 | | | | | 1120 | | | | | 1125 | | | | gct ttc att ctg gtt gcg ttg ttg gaa tcc aaa aca atc tgc aat   3429
Ala Phe Ile Leu Val Ala Leu Leu Glu Ser Lys Thr Ile Cys Asn
         1130                1135                1140 gac tat gtc aat agt cta gac agc agc atc aag aag gcc aca aat   3474
Asp Tyr Val Asn Ser Leu Asp Ser Ser Ile Lys Lys Ala Thr Asn
         1145                1150                1155 tat tta ctc aaa aag tat gag aaa ctg caa agg cct tac act aca   3519
Tyr Leu Leu Lys Lys Tyr Glu Lys Leu Gln Arg Pro Tyr Thr Thr
         1160                1165                1170 gcc ctc aca gcc tat gct ttg gct gct gca gac caa ctc aat gat   3564
Ala Leu Thr Ala Tyr Ala Leu Ala Ala Ala Asp Gln Leu Asn Asp
         1175                1180                1185 gac agg gta ctc atg gca gca tca aca gga agg gat cat tgg gaa   3609
Asp Arg Val Leu Met Ala Ala Ser Thr Gly Arg Asp His Trp Glu
         1190                1195                1200 gaa tac aat gct cac acc cac aac att gaa ggc act tcc tat gcc   3654
Glu Tyr Asn Ala His Thr His Asn Ile Glu Gly Thr Ser Tyr Ala
         1205                1210                1215 ttg ttg gcc ctg ctg aaa atg aag aaa ttt gat caa act ggt ccc   3699
Leu Leu Ala Leu Leu Lys Met Lys Lys Phe Asp Gln Thr Gly Pro
         1220                1225                1230 ata gtc aga tgg ctg aca gat cag aat ttt tat ggg gaa aca tat   3744
Ile Val Arg Trp Leu Thr Asp Gln Asn Phe Tyr Gly Glu Thr Tyr
         1235                1240                1245 gga caa acc caa gca aca gtt atg gca ttt caa gct ctt gct gaa   3789
Gly Gln Thr Gln Ala Thr Val Met Ala Phe Gln Ala Leu Ala Glu
         1250                1255                1260 tat gag att cag atg cct acc cat aag gac tta aac tta gat att   3834
Tyr Glu Ile Gln Met Pro Thr His Lys Asp Leu Asn Leu Asp Ile
         1265                1270                1275 act att gaa ctg cca gat cga gaa gta cct ata agg tac aga att   3879
Thr Ile Glu Leu Pro Asp Arg Glu Val Pro Ile Arg Tyr Arg Ile
         1280                1285                1290 aat tat gaa aat gct ctc ctg gct cgg aca gta gag acc aaa ctc   3924
Asn Tyr Glu Asn Ala Leu Leu Ala Arg Thr Val Glu Thr Lys Leu
         1295                1300                1305 aac caa gac atc act gtg aca gca tca ggt gat gga aaa gca aca   3969
Asn Gln Asp Ile Thr Val Thr Ala Ser Gly Asp Gly Lys Ala Thr
         1310                1315                1320 atg acc att ttg aca ttc tat aac gca cag ttg cag gag aag gca   4014
Met Thr Ile Leu Thr Phe Tyr Asn Ala Gln Leu Gln Glu Lys Ala
         1325                1330                1335 aat gtt tgc aat aaa ttt cat ctt aat gtt tct gtt gaa aac atc   4059
Asn Val Cys Asn Lys Phe His Leu Asn Val Ser Val Glu Asn Ile
         1340                1345                1350 cac ttg aat gca atg gga gcc aag gga gcc ctc atg ctc aag atc   4104
His Leu Asn Ala Met Gly Ala Lys Gly Ala Leu Met Leu Lys Ile
         1355                1360                1365 tgc aca agg tat ctg gga gaa gtt gat tct aca atg aca ata att   4149
Cys Thr Arg Tyr Leu Gly Glu Val Asp Ser Thr Met Thr Ile Ile
         1370                1375                1380 gat att tct atg ctg act ggt ttt ctc cct gat gct gaa gac ctt   4194
Asp Ile Ser Met Leu Thr Gly Phe Leu Pro Asp Ala Glu Asp Leu
         1385                1390                1395 aca agg ctt tct aaa gga gtg gac aga tac atc tcc aga tat gaa   4239
Thr Arg Leu Ser Lys Gly Val Asp Arg Tyr Ile Ser Arg Tyr Glu
         1400                1405                1410

-continued

| | | | | | | | | | | | | | |
|---|---|---|---|---|---|---|---|---|---|---|---|---|---|
| gtt | gac | aat | aat | atg | gct | cag | aaa | gta | gct | gtt | atc | att | tac tta |
| Val | Asp | Asn | Asn | Met | Ala | Gln | Lys | Val | Ala | Val | Ile | Ile | Tyr Leu |
| | | | 1415 | | | | 1420 | | | | | 1425 | |

```
gtt gac aat aat atg gct cag aaa gta gct gtt atc att tac tta       4284
Val Asp Asn Asn Met Ala Gln Lys Val Ala Val Ile Ile Tyr Leu
            1415                1420                    1425 aac aag gtc tcc cac tct gaa gat gaa tgc ctg cac ttt aag att       4329
Asn Lys Val Ser His Ser Glu Asp Glu Cys Leu His Phe Lys Ile
        1430                1435                1440 ctc aag cat ttt gaa gtt ggc ttc att cag cca gga tca gtc aag       4374
Leu Lys His Phe Glu Val Gly Phe Ile Gln Pro Gly Ser Val Lys
        1445                1450                1455 gtg tac agc tac tac aat cta gat gaa aaa tgt acc aag ttc tac       4419
Val Tyr Ser Tyr Tyr Asn Leu Asp Glu Lys Cys Thr Lys Phe Tyr
        1460                1465                1470 cat cca gat aaa gga aca ggc ctt ctc aat aag ata tgt att ggt       4464
His Pro Asp Lys Gly Thr Gly Leu Leu Asn Lys Ile Cys Ile Gly
        1475                1480                1485 aac gtt tgc cga tgt gca gga gaa acc tgt tcc tcg ctc aac cat       4509
Asn Val Cys Arg Cys Ala Gly Glu Thr Cys Ser Ser Leu Asn His
        1490                1495                1500 cag gaa agg att gat gtt cca tta caa att gaa aaa gcc tgc gag       4554
Gln Glu Arg Ile Asp Val Pro Leu Gln Ile Glu Lys Ala Cys Glu
        1505                1510                1515 acg aat gtg gat tat gtc tac aaa acc aag ctg ctt cga ata gaa       4599
Thr Asn Val Asp Tyr Val Tyr Lys Thr Lys Leu Leu Arg Ile Glu
        1520                1525                1530 gaa caa gat ggt aat gat atc tat gtc atg gat gtt tta gaa gtt       4644
Glu Gln Asp Gly Asn Asp Ile Tyr Val Met Asp Val Leu Glu Val
        1535                1540                1545 att aaa caa ggt act gac gaa aat cca cga gca aag acc cac cag       4689
Ile Lys Gln Gly Thr Asp Glu Asn Pro Arg Ala Lys Thr His Gln
        1550                1555                1560 tac ata agt caa agg aaa tgc cag gag gct ctg aat ctg aag gtg       4734
Tyr Ile Ser Gln Arg Lys Cys Gln Glu Ala Leu Asn Leu Lys Val
        1565                1570                1575 aat gat gat tat ctg atc tgg ggt tcc agg agt gac ctg ttg ccc       4779
Asn Asp Asp Tyr Leu Ile Trp Gly Ser Arg Ser Asp Leu Leu Pro
        1580                1585                1590 acg aaa gat aaa att tcc tac atc att aca aag aac aca tgg att       4824
Thr Lys Asp Lys Ile Ser Tyr Ile Ile Thr Lys Asn Thr Trp Ile
        1595                1600                1605 gag aga tgg cca cat gaa gac gaa tgt cag gaa gaa gaa ttc caa       4869
Glu Arg Trp Pro His Glu Asp Glu Cys Gln Glu Glu Glu Phe Gln
        1610                1615                1620 aag ttg tgt gat gac ttt gct cag ttt agc tac aca ttg act gag       4914
Lys Leu Cys Asp Asp Phe Ala Gln Phe Ser Tyr Thr Leu Thr Glu
        1625                1630                1635 ttt ggc tgc cct act taa aagttcagaa gaatcaatga taggaaggaa          4962
Phe Gly Cys Pro Thr
        1640 attctcagaa gacagatttt tgagccaatg catatatgtt actttgcctc ttgatctttt   5022 agttttatgt caatttgctc tgttattttc ccttaaattg tttatacata aaataaataa   5082 tcgatttctt actttgatat gttcttgatt tttaataaac aatggtgatt catgattatt   5142 tttttcttct tctgatccat ccaatatttg aagtgctctg aacagagcac ttatggagta   5202 atgttttagt gatggatgaa taagttggtg agtcaatatt atcaggccct atatactctt   5262 atggaagatc gatttgtacc caagaaaaca tagattgaaa tgtgttactt tgaaaacaga   5322 ggtttcagtt gtatatgttt acacttggat acaatcttaa ctcttaataa acactgatct   5382
```

-continued

```
cagaacattt aacagctgct atttaataat gacaaaatat tctttgactg cacccacaga    5442
aaacattgca ttacattaga atgggtttta tcagatgact aagtctgcta gacttgccat    5502
ctgtcaaaat gtgcctcttc cccagctcca actttaagga tagtaactaa tagatgttct    5562
ctcattggct cctgacagag gtgtggtagc cactgagttt ccctggatga cactagaagc    5622
tggcagcaca ctgcagcctg gtggaggggc ctcttttgct atcccatgag cttctattca    5682
tcctcttatc tgttgggatg gggatgggac gtctctgatt ttccaggtat acaggtgatc    5742
tcatttacta acatcaccac taacttcaag gattggttga ggggttatgc caatgtgatt    5802
gaaggtttca cccatgtgaa tctattctcc aatcccaatg ctgtatctat gctgctcatt    5862
tctgcttgta aaatggtat aaaaagaata aacactgccc aggcagtcag acatctttgg     5922
acactg                                                               5928
```

<210> SEQ ID NO 4
<211> LENGTH: 1642
<212> TYPE: PRT
<213> ORGANISM: Naja naja

<400> SEQUENCE: 4

```
Met Glu Arg Met Ala Leu Tyr Leu Val Ala Leu Leu Ile Gly Phe
 1               5                  10                  15

Pro Gly Ser Ser His Gly Ala Leu Tyr Thr Leu Ile Thr Pro Ala Val
             20                  25                  30

Leu Arg Thr Asp Thr Glu Glu Gln Ile Leu Val Glu Ala His Gly Asp
         35                  40                  45

Ser Thr Pro Lys Gln Leu Asp Ile Phe Val His Asp Phe Pro Arg Lys
     50                  55                  60

Gln Lys Thr Leu Phe Gln Thr Arg Val Asp Met Asn Pro Ala Gly Gly
 65                  70                  75                  80

Met Leu Val Thr Pro Thr Ile Glu Ile Pro Ala Lys Glu Val Ser Thr
                 85                  90                  95

Asp Ser Arg Gln Asn Gln Tyr Val Val Val Gln Val Thr Gly Pro Gln
            100                 105                 110

Val Arg Leu Glu Lys Val Val Leu Leu Ser Tyr Gln Ser Ser Phe Leu
        115                 120                 125

Phe Ile Gln Thr Asp Lys Gly Ile Tyr Thr Pro Gly Ser Pro Val Leu
    130                 135                 140

Tyr Arg Val Phe Ser Met Asp His Asn Thr Ser Lys Met Asn Lys Thr
145                 150                 155                 160

Val Ile Val Glu Phe Gln Thr Pro Glu Gly Ile Leu Val Ser Ser Asn
                165                 170                 175

Ser Val Asp Leu Asn Phe Phe Trp Pro Tyr Asn Leu Pro Asp Leu Val
            180                 185                 190

Ser Leu Gly Thr Trp Arg Ile Val Ala Lys Tyr Glu His Ser Pro Glu
        195                 200                 205

Asn Tyr Thr Ala Tyr Phe Asp Val Arg Lys Tyr Val Leu Pro Ser Phe
    210                 215                 220

Glu Val Arg Leu Gln Pro Ser Glu Lys Phe Phe Tyr Ile Asp Gly Asn
225                 230                 235                 240

Glu Asn Phe His Val Ser Ile Thr Ala Arg Tyr Leu Tyr Gly Glu Glu
                245                 250                 255

Val Glu Gly Val Ala Phe Val Leu Phe Gly Val Lys Ile Asp Asp Ala
            260                 265                 270
```

-continued

```
Lys Lys Ser Ile Pro Asp Ser Leu Thr Arg Ile Pro Ile Asp Gly
            275                 280                 285

Asp Gly Lys Ala Thr Leu Lys Arg Asp Thr Phe Arg Ser Arg Phe Pro
        290                 295                 300

Asn Leu Asn Glu Leu Val Gly His Thr Leu Tyr Ala Ser Val Thr Val
305                 310                 315                 320

Met Thr Glu Ser Gly Ser Asp Met Val Thr Glu Gln Ser Gly Ile
                325                 330                 335

His Ile Val Ala Ser Pro Tyr Gln Ile His Phe Thr Lys Thr Pro Lys
            340                 345                 350

Tyr Phe Lys Pro Gly Met Pro Tyr Glu Leu Thr Val Tyr Val Thr Asn
        355                 360                 365

Pro Asp Gly Ser Pro Ala Ala His Val Pro Val Val Ser Glu Ala Phe
    370                 375                 380

His Ser Met Gly Thr Thr Leu Ser Asp Gly Thr Ala Lys Leu Ile Leu
385                 390                 395                 400

Asn Ile Pro Leu Asn Ala Gln Ser Leu Pro Ile Thr Val Arg Thr Asn
                405                 410                 415

His Gly Asp Leu Pro Arg Glu Arg Gln Ala Thr Lys Ser Met Thr Ala
            420                 425                 430

Ile Ala Tyr Gln Thr Gln Gly Gly Ser Gly Asn Tyr Leu His Val Ala
        435                 440                 445

Ile Thr Ser Thr Glu Ile Lys Pro Gly Asp Asn Leu Pro Val Asn Phe
    450                 455                 460

Asn Val Lys Gly Asn Ala Asn Ser Leu Lys Gln Ile Lys Tyr Phe Thr
465                 470                 475                 480

Tyr Leu Ile Leu Asn Lys Gly Lys Ile Phe Lys Val Gly Arg Gln Pro
                485                 490                 495

Arg Arg Asp Gly Gln Asn Leu Val Thr Met Asn Leu His Ile Thr Pro
            500                 505                 510

Asp Leu Ile Pro Ser Phe Arg Phe Val Ala Tyr Tyr Gln Val Gly Asn
        515                 520                 525

Asn Glu Ile Val Ala Asp Ser Val Trp Val Asp Val Lys Asp Thr Cys
    530                 535                 540

Met Gly Thr Leu Val Val Lys Gly Asp Asn Leu Ile Gln Met Pro Gly
545                 550                 555                 560

Ala Ala Met Lys Ile Lys Leu Glu Gly Asp Pro Gly Ala Arg Val Gly
                565                 570                 575

Leu Val Ala Val Asp Lys Ala Val Tyr Val Leu Asn Asp Lys Tyr Lys
            580                 585                 590

Ile Ser Gln Ala Lys Ile Trp Asp Thr Ile Glu Lys Ser Asp Phe Gly
        595                 600                 605

Cys Thr Ala Gly Ser Gly Gln Asn Asn Leu Gly Val Phe Glu Asp Ala
    610                 615                 620

Gly Leu Ala Leu Thr Thr Ser Thr Asn Leu Asn Thr Lys Gln Arg Ser
625                 630                 635                 640

Ala Ala Lys Cys Pro Gln Pro Ala Asn Arg Arg Arg Arg Ser Ser Val
                645                 650                 655

Leu Leu Leu Asp Ser Asn Ala Ser Lys Ala Ala Glu Phe Gln Asp Gln
            660                 665                 670

Asp Leu Arg Lys Cys Cys Glu Asp Val Met His Glu Asn Pro Met Gly
        675                 680                 685

Tyr Thr Cys Glu Lys Arg Ala Lys Tyr Ile Gln Glu Gly Asp Ala Cys
```

-continued

```
            690                 695                 700
Lys Ala Ala Phe Leu Glu Cys Cys Arg Tyr Ile Lys Gly Val Arg Asp
705                 710                 715                 720

Glu Asn Gln Arg Glu Ser Glu Leu Phe Leu Ala Arg Asp Asp Asn Glu
                725                 730                 735

Asp Gly Phe Ile Ala Asp Ser Asp Ile Ile Ser Arg Ser Asp Phe Pro
                740                 745                 750

Lys Ser Trp Leu Trp Leu Thr Lys Asp Leu Thr Glu Pro Asn Ser
                755                 760                 765

Gln Gly Ile Ser Ser Lys Thr Met Ser Phe Tyr Leu Arg Asp Ser Ile
770                 775                 780

Thr Thr Trp Val Val Leu Ala Val Ser Phe Thr Pro Thr Lys Gly Ile
785                 790                 795                 800

Cys Val Ala Glu Pro Tyr Glu Ile Arg Val Met Lys Val Phe Phe Ile
                805                 810                 815

Asp Leu Gln Met Pro Tyr Ser Val Val Lys Asn Glu Gln Val Glu Ile
                820                 825                 830

Arg Ala Ile Leu His Asn Tyr Val Asn Glu Asp Ile Tyr Val Arg Val
                835                 840                 845

Glu Leu Leu Tyr Asn Pro Ala Phe Cys Ser Ala Ser Thr Lys Gly Gln
850                 855                 860

Arg Tyr Arg Gln Gln Phe Pro Ile Lys Ala Leu Ser Ser Arg Ala Val
865                 870                 875                 880

Pro Phe Val Ile Val Pro Leu Glu Gln Gly Leu His Asp Val Glu Ile
                885                 890                 895

Lys Ala Ser Val Gln Glu Ala Leu Trp Ser Asp Gly Val Arg Lys Lys
                900                 905                 910

Leu Lys Val Val Pro Glu Gly Val Gln Lys Ser Ile Val Thr Ile Val
                915                 920                 925

Lys Leu Asp Pro Arg Ala Lys Gly Val Gly Gly Thr Gln Leu Glu Val
                930                 935                 940

Ile Lys Ala Arg Lys Leu Asp Asp Arg Val Pro Asp Thr Glu Ile Glu
945                 950                 955                 960

Thr Lys Ile Ile Ile Gln Gly Asp Pro Val Ala Gln Ile Ile Glu Asn
                965                 970                 975

Ser Ile Asp Gly Ser Lys Leu Asn His Leu Ile Ile Thr Pro Ser Gly
                980                 985                 990

Cys Gly Glu Gln Asn Met Ile Arg Met Ala Ala Pro Val Ile Ala Thr
                995                1000                1005

Tyr Tyr Leu Asp Thr Thr Glu Gln Trp Glu Thr Leu Gly Ile Asn
        1010                1015                1020

Arg Arg Thr Glu Ala Val Asn Gln Ile Val Thr Gly Tyr Ala Gln
        1025                1030                1035

Gln Met Val Tyr Lys Lys Ala Asp His Ser Tyr Ala Ala Phe Thr
        1040                1045                1050

Asn Arg Ala Ser Ser Ser Trp Leu Thr Ala Tyr Val Val Lys Val
        1055                1060                1065

Phe Ala Met Ala Ala Lys Met Val Ala Gly Ile Ser His Glu Ile
        1070                1075                1080

Ile Cys Gly Gly Val Arg Trp Leu Ile Leu Asn Arg Gln Gln Pro
        1085                1090                1095

Asp Gly Ala Phe Lys Glu Asn Ala Pro Val Leu Ser Gly Thr Met
        1100                1105                1110
```

```
Gln Gly Gly Ile Gln Gly Ala Glu Glu Val Tyr Leu Thr Ala
    1115                1120                1125

Phe Ile Leu Val Ala Leu Leu Glu Ser Lys Thr Ile Cys Asn Asp
1130                1135                1140

Tyr Val Asn Ser Leu Asp Ser Ser Ile Lys Lys Ala Thr Asn Tyr
    1145                1150                1155

Leu Leu Lys Lys Tyr Glu Lys Leu Gln Arg Pro Tyr Thr Thr Ala
    1160                1165                1170

Leu Thr Ala Tyr Ala Leu Ala Ala Ala Asp Gln Leu Asn Asp Asp
    1175                1180                1185

Arg Val Leu Met Ala Ala Ser Thr Gly Arg Asp His Trp Glu Glu
    1190                1195                1200

Tyr Asn Ala His Thr His Asn Ile Glu Gly Thr Ser Tyr Ala Leu
    1205                1210                1215

Leu Ala Leu Leu Lys Met Lys Lys Phe Asp Gln Thr Gly Pro Ile
    1220                1225                1230

Val Arg Trp Leu Thr Asp Gln Asn Phe Tyr Gly Glu Thr Tyr Gly
    1235                1240                1245

Gln Thr Gln Ala Thr Val Met Ala Phe Gln Ala Leu Ala Glu Tyr
    1250                1255                1260

Glu Ile Gln Met Pro Thr His Lys Asp Leu Asn Leu Asp Ile Thr
    1265                1270                1275

Ile Glu Leu Pro Asp Arg Glu Val Pro Ile Arg Tyr Arg Ile Asn
    1280                1285                1290

Tyr Glu Asn Ala Leu Leu Ala Arg Thr Val Glu Thr Lys Leu Asn
    1295                1300                1305

Gln Asp Ile Thr Val Thr Ala Ser Gly Asp Gly Lys Ala Thr Met
    1310                1315                1320

Thr Ile Leu Thr Phe Tyr Asn Ala Gln Leu Gln Glu Lys Ala Asn
    1325                1330                1335

Val Cys Asn Lys Phe His Leu Asn Val Ser Val Glu Asn Ile His
    1340                1345                1350

Leu Asn Ala Met Gly Ala Lys Gly Ala Leu Met Leu Lys Ile Cys
    1355                1360                1365

Thr Arg Tyr Leu Gly Glu Val Asp Ser Thr Met Thr Ile Ile Asp
    1370                1375                1380

Ile Ser Met Leu Thr Gly Phe Leu Pro Asp Ala Glu Asp Leu Thr
    1385                1390                1395

Arg Leu Ser Lys Gly Val Asp Arg Tyr Ile Ser Arg Tyr Glu Val
    1400                1405                1410

Asp Asn Asn Met Ala Gln Lys Val Ala Val Ile Ile Tyr Leu Asn
    1415                1420                1425

Lys Val Ser His Ser Glu Asp Glu Cys Leu His Phe Lys Ile Leu
    1430                1435                1440

Lys His Phe Glu Val Gly Phe Ile Gln Pro Gly Ser Val Lys Val
    1445                1450                1455

Tyr Ser Tyr Tyr Asn Leu Asp Glu Lys Cys Thr Lys Phe Tyr His
    1460                1465                1470

Pro Asp Lys Gly Thr Gly Leu Leu Asn Lys Ile Cys Ile Gly Asn
    1475                1480                1485

Val Cys Arg Cys Ala Gly Glu Thr Cys Ser Ser Leu Asn His Gln
    1490                1495                1500
```

-continued

```
Glu Arg Ile Asp Val Pro Leu Gln Ile Glu Lys Ala Cys Glu Thr
    1505                1510                1515

Asn Val Asp Tyr Val Tyr Lys Thr Lys Leu Leu Arg Ile Glu Glu
    1520                1525                1530

Gln Asp Gly Asn Asp Ile Tyr Val Met Asp Val Leu Glu Val Ile
    1535                1540                1545

Lys Gln Gly Thr Asp Glu Asn Pro Arg Ala Lys Thr His Gln Tyr
    1550                1555                1560

Ile Ser Gln Arg Lys Cys Gln Glu Ala Leu Asn Leu Lys Val Asn
    1565                1570                1575

Asp Asp Tyr Leu Ile Trp Gly Ser Arg Ser Asp Leu Leu Pro Thr
    1580                1585                1590

Lys Asp Lys Ile Ser Tyr Ile Ile Thr Lys Asn Thr Trp Ile Glu
    1595                1600                1605

Arg Trp Pro His Glu Asp Glu Cys Gln Glu Glu Glu Phe Gln Lys
    1610                1615                1620

Leu Cys Asp Asp Phe Ala Gln Phe Ser Tyr Thr Leu Thr Glu Phe
    1625                1630                1635

Gly Cys Pro Thr
    1640
```

<210> SEQ ID NO 5
<211> LENGTH: 4992
<212> TYPE: DNA
<213> ORGANISM: Artificial Sequence
<220> FEATURE:
<223> OTHER INFORMATION: Recombinant Human C3
<220> FEATURE:
<221> NAME/KEY: CDS
<222> LOCATION: (1)..(4992)
<223> OTHER INFORMATION: Construct H6

<400> SEQUENCE: 5

```
atg gga ccc acc tca ggt ccc agc ctg ctg ctc ctg cta cta acc cac        48
Met Gly Pro Thr Ser Gly Pro Ser Leu Leu Leu Leu Leu Leu Thr His
1               5                   10                  15 ctc ccc ctg gct ctg ggg agt ccc atg tac tct atc atc acc ccc aac        96
Leu Pro Leu Ala Leu Gly Ser Pro Met Tyr Ser Ile Ile Thr Pro Asn
            20                  25                  30 atc ttg cgg ctg gag agc gag gag acc atg gtg ctg gag gcc cac gac       144
Ile Leu Arg Leu Glu Ser Glu Glu Thr Met Val Leu Glu Ala His Asp
        35                  40                  45 gcg caa ggg gat gtt cca gtc act gtt act gtc cac gac ttc cca ggc       192
Ala Gln Gly Asp Val Pro Val Thr Val Thr Val His Asp Phe Pro Gly
    50                  55                  60 aaa aaa cta gtg ctg tcc agt gag aag act gtg ctg acc cct gcc acc       240
Lys Lys Leu Val Leu Ser Ser Glu Lys Thr Val Leu Thr Pro Ala Thr
65                  70                  75                  80 aac cac atg ggc aac gtc acc ttc acg atc cca gcc aac agg gag ttc       288
Asn His Met Gly Asn Val Thr Phe Thr Ile Pro Ala Asn Arg Glu Phe
                85                  90                  95 aag tca gaa aag ggg cgc aac aag ttc gtg acc gtg cag gcc acc ttc       336
Lys Ser Glu Lys Gly Arg Asn Lys Phe Val Thr Val Gln Ala Thr Phe
            100                 105                 110 ggg acc caa gtg gtg gag aag gtg gtg ctg gtc agc ctg cag agc ggg       384
Gly Thr Gln Val Val Glu Lys Val Val Leu Val Ser Leu Gln Ser Gly
        115                 120                 125 tac ctc ttc atc cag aca gac aag acc atc tac acc cct ggc tcc aca       432
Tyr Leu Phe Ile Gln Thr Asp Lys Thr Ile Tyr Thr Pro Gly Ser Thr
    130                 135                 140
```

-continued

| | |
|---|---|
| gtt ctc tat cgg atc ttc acc gtc aac cac aag ctg cta ccc gtg ggc<br>Val Leu Tyr Arg Ile Phe Thr Val Asn His Lys Leu Leu Pro Val Gly<br>145                    150                        155                    160 | 480 |
| cgg acg gtc atg gtc aac att gag aac ccg gaa ggc atc ccg gtc aag<br>Arg Thr Val Met Val Asn Ile Glu Asn Pro Glu Gly Ile Pro Val Lys<br>                 165                        170                        175 | 528 |
| cag gac tcc ttg tct tct cag aac cag ctt ggc gtc ttg ccc ttg tct<br>Gln Asp Ser Leu Ser Ser Gln Asn Gln Leu Gly Val Leu Pro Leu Ser<br>       180                        185                        190 | 576 |
| tgg gac att ccg gaa ctc gtc aac atg ggc cag tgg aag atc cga gcc<br>Trp Asp Ile Pro Glu Leu Val Asn Met Gly Gln Trp Lys Ile Arg Ala<br>                 195                        200                        205 | 624 |
| tac tat gaa aac tca cca cag cag gtc ttc tcc act gag ttt gag gtg<br>Tyr Tyr Glu Asn Ser Pro Gln Gln Val Phe Ser Thr Glu Phe Glu Val<br>210                    215                        220 | 672 |
| aag gag tac gtg ctg ccc agt ttc gag gtc ata gtg gag cct aca gag<br>Lys Glu Tyr Val Leu Pro Ser Phe Glu Val Ile Val Glu Pro Thr Glu<br>225                    230                        235                    240 | 720 |
| aaa ttc tac tac atc tat aac gag aag ggc ctg gag gtc acc atc acc<br>Lys Phe Tyr Tyr Ile Tyr Asn Glu Lys Gly Leu Glu Val Thr Ile Thr<br>                 245                        250                        255 | 768 |
| gcc agg ttc ctc tac ggg aag aaa gtg gag gga act gcc ttt gtc atc<br>Ala Arg Phe Leu Tyr Gly Lys Lys Val Glu Gly Thr Ala Phe Val Ile<br>       260                        265                        270 | 816 |
| ttc ggg atc cag gat ggc gaa cag agg att tcc ctg cct gaa tcc ctc<br>Phe Gly Ile Gln Asp Gly Glu Gln Arg Ile Ser Leu Pro Glu Ser Leu<br>                 275                        280                        285 | 864 |
| aag cgc att ccg att gag gat ggc tcg ggg gag gtt gtg ctg agc cgg<br>Lys Arg Ile Pro Ile Glu Asp Gly Ser Gly Glu Val Val Leu Ser Arg<br>290                    295                        300 | 912 |
| aag gta ctg ctg gac ggg gtg cag aac ctc cga gca gaa gac ctg gtg<br>Lys Val Leu Leu Asp Gly Val Gln Asn Leu Arg Ala Glu Asp Leu Val<br>305                    310                        315                    320 | 960 |
| ggg aag tct ttg tac gtg tct gcc acc gtc atc ttg cac tca ggc agt<br>Gly Lys Ser Leu Tyr Val Ser Ala Thr Val Ile Leu His Ser Gly Ser<br>                 325                        330                        335 | 1008 |
| gac atg gtg cag gca gag cgc agc ggg atc ccc atc gtg acc tct ccc<br>Asp Met Val Gln Ala Glu Arg Ser Gly Ile Pro Ile Val Thr Ser Pro<br>       340                        345                        350 | 1056 |
| tac cag atc cac ttc acc aag aca ccc aag tac ttc aaa cca gga atg<br>Tyr Gln Ile His Phe Thr Lys Thr Pro Lys Tyr Phe Lys Pro Gly Met<br>                 355                        360                        365 | 1104 |
| ccc ttt gac ctc atg gtg ttc gtg acg aac cct gat ggc tct cca gcc<br>Pro Phe Asp Leu Met Val Phe Val Thr Asn Pro Asp Gly Ser Pro Ala<br>370                    375                        380 | 1152 |
| tac cga gtc ccc gtg gca gtc cag ggc gag gac act gtg cag tct cta<br>Tyr Arg Val Pro Val Ala Val Gln Gly Glu Asp Thr Val Gln Ser Leu<br>385                    390                        395                    400 | 1200 |
| acc cag gga gat ggc gtg gcc aaa ctc agc atc aac aca cac ccc agc<br>Thr Gln Gly Asp Gly Val Ala Lys Leu Ser Ile Asn Thr His Pro Ser<br>                 405                        410                        415 | 1248 |
| cag aag ccc ttg agc atc acg gtg cgc acg aag aag cag gag ctc tcg<br>Gln Lys Pro Leu Ser Ile Thr Val Arg Thr Lys Lys Gln Glu Leu Ser<br>       420                        425                        430 | 1296 |
| gag gca gag cag gct acc agg acc atg cag gct ctg ccc tac agc acc<br>Glu Ala Glu Gln Ala Thr Arg Thr Met Gln Ala Leu Pro Tyr Ser Thr<br>                 435                        440                        445 | 1344 |
| gtg ggc aac tcc aac aat tac ctg cat ctc tca gtg cta cgt aca gag<br>Val Gly Asn Ser Asn Asn Tyr Leu His Leu Ser Val Leu Arg Thr Glu | 1392 |

```
                450               455               460
ctc aga ccc ggg gag acc ctc aac gtc aac ttc ctc ctg cga atg gac    1440
Leu Arg Pro Gly Glu Thr Leu Asn Val Asn Phe Leu Leu Arg Met Asp
465                 470                 475                 480 cgc gcc cac gag gcc aag atc cgc tac tac acc tac ctg atc atg aac    1488
Arg Ala His Glu Ala Lys Ile Arg Tyr Tyr Thr Tyr Leu Ile Met Asn
                485                 490                 495 aag ggc agg ctg ttg aag gcg gga cgc cag gtg cga gag ccc ggc cag    1536
Lys Gly Arg Leu Leu Lys Ala Gly Arg Gln Val Arg Glu Pro Gly Gln
            500                 505                 510 gac ctg gtg gtg ctg ccc ctg tcc atc acc acc gac ttc atc cct tcc    1584
Asp Leu Val Val Leu Pro Leu Ser Ile Thr Thr Asp Phe Ile Pro Ser
        515                 520                 525 ttc cgc ctg gtg gcg tac tac acg ctg atc ggt gcc agc ggc cag agg    1632
Phe Arg Leu Val Ala Tyr Tyr Thr Leu Ile Gly Ala Ser Gly Gln Arg
    530                 535                 540 gag gtg gtg gcc gac tcc gtg tgg gtg gac gtc aag gac tcc tgc gtg    1680
Glu Val Val Ala Asp Ser Val Trp Val Asp Val Lys Asp Ser Cys Val
545                 550                 555                 560 ggc tcg ctg gtg gta aaa agc ggc cag tca gaa gac cgg cag cct gta    1728
Gly Ser Leu Val Val Lys Ser Gly Gln Ser Glu Asp Arg Gln Pro Val
                565                 570                 575 cct ggg cag cag atg acc ctg aag ata gag ggt gac cac ggg gcc cgg    1776
Pro Gly Gln Gln Met Thr Leu Lys Ile Glu Gly Asp His Gly Ala Arg
            580                 585                 590 gtg gta ctg gtg gcc gtg gac aag ggc gtg ttc gtg ctg aat aag aag    1824
Val Val Leu Val Ala Val Asp Lys Gly Val Phe Val Leu Asn Lys Lys
        595                 600                 605 aac aaa ctg acg cag agt aag atc tgg gac gtg gtg gag aag gca gac    1872
Asn Lys Leu Thr Gln Ser Lys Ile Trp Asp Val Val Glu Lys Ala Asp
    610                 615                 620 atc ggc tgc acc ccg ggc agt ggg aag gat tac gcc ggt gtc ttc tcc    1920
Ile Gly Cys Thr Pro Gly Ser Gly Lys Asp Tyr Ala Gly Val Phe Ser
625                 630                 635                 640 gac gca ggg ctg acc ttc acg agc agc agt ggc cag cag acc gcc cag    1968
Asp Ala Gly Leu Thr Phe Thr Ser Ser Ser Gly Gln Gln Thr Ala Gln
                645                 650                 655 agg gca gaa ctt cag tgc ccg cag cca gcc gcc cgc cga cgc cgt tcc    2016
Arg Ala Glu Leu Gln Cys Pro Gln Pro Ala Ala Arg Arg Arg Arg Ser
            660                 665                 670 gtg cag ctc acg gag aag cga atg gac aaa gtc ggc aag tac ccc aag    2064
Val Gln Leu Thr Glu Lys Arg Met Asp Lys Val Gly Lys Tyr Pro Lys
        675                 680                 685 gag ctg cgc aag tgc tgc gag gac ggc atg cgg gag aac ccc atg agg    2112
Glu Leu Arg Lys Cys Cys Glu Asp Gly Met Arg Glu Asn Pro Met Arg
    690                 695                 700 ttc tcg tgc cag cgc cgg acc cgt ttc atc tcc ctg ggc gag gcg tgc    2160
Phe Ser Cys Gln Arg Arg Thr Arg Phe Ile Ser Leu Gly Glu Ala Cys
705                 710                 715                 720 aag aag gtc ttc ctg gac tgc tgc aac tac atc aca gag ctg cgg cgg    2208
Lys Lys Val Phe Leu Asp Cys Cys Asn Tyr Ile Thr Glu Leu Arg Arg
                725                 730                 735 cag cac gcg cgg gcc agc cac ctg ggc ctg gcc agg agt aac ctg gat    2256
Gln His Ala Arg Ala Ser His Leu Gly Leu Ala Arg Ser Asn Leu Asp
            740                 745                 750 gag gac atc att gca gaa gag aac atc gtt tcc cga agt gag ttc cca    2304
Glu Asp Ile Ile Ala Glu Glu Asn Ile Val Ser Arg Ser Glu Phe Pro
        755                 760                 765 gag agc tgg ctg tgg aac gtt gag gac ttg aaa gag cca ccg aaa aat    2352
```

```
                Glu Ser Trp Leu Trp Asn Val Glu Asp Leu Lys Glu Pro Pro Lys Asn
                    770                 775                 780 gga atc tct acg aag ctc atg aat ata ttt ttg aaa gac tcc atc acc              2400
Gly Ile Ser Thr Lys Leu Met Asn Ile Phe Leu Lys Asp Ser Ile Thr
785                 790                 795                 800 acg tgg gag att ctg gct gtc agc atg tcg gac aag aaa ggg atc tgt              2448
Thr Trp Glu Ile Leu Ala Val Ser Met Ser Asp Lys Lys Gly Ile Cys
                    805                 810                 815 gtg gca gac ccc ttc gag gtc aca gta atg cag gac ttc ttc atc gac              2496
Val Ala Asp Pro Phe Glu Val Thr Val Met Gln Asp Phe Phe Ile Asp
                820                 825                 830 ctg cgg cta ccc tac tct gtt gtt cga aac gag cag gtg gaa atc cga              2544
Leu Arg Leu Pro Tyr Ser Val Val Arg Asn Glu Gln Val Glu Ile Arg
            835                 840                 845 gcc gtt ctc tac aat tac cgg cag aac caa gag ctc aag gtg agg gtg              2592
Ala Val Leu Tyr Asn Tyr Arg Gln Asn Gln Glu Leu Lys Val Arg Val
        850                 855                 860 gaa cta ctc cac aat cca gcc ttc tgc agc ctg gcc acc acc aag agg              2640
Glu Leu Leu His Asn Pro Ala Phe Cys Ser Leu Ala Thr Thr Lys Arg
865                 870                 875                 880 cgt cac cag cag acc gta acc atc ccc ccc aag tcc tcg ttg tcc gtt              2688
Arg His Gln Gln Thr Val Thr Ile Pro Pro Lys Ser Ser Leu Ser Val
                    885                 890                 895 cca tat gtc atc gtg ccg cta aag acc ggc ctg cag gaa gtg gaa gtc              2736
Pro Tyr Val Ile Val Pro Leu Lys Thr Gly Leu Gln Glu Val Glu Val
                900                 905                 910 aag gct gcc gtc tac cat cat ttc atc agt gac ggt gtc agg aag tcc              2784
Lys Ala Ala Val Tyr His His Phe Ile Ser Asp Gly Val Arg Lys Ser
            915                 920                 925 ctg aag gtc gtg ccg gaa gga atc aga atg aac aaa act gtg gct gtt              2832
Leu Lys Val Val Pro Glu Gly Ile Arg Met Asn Lys Thr Val Ala Val
        930                 935                 940 cgc acc ctg gat cca gaa cgc ctg ggc cgt gaa gga gtg cag aaa gag              2880
Arg Thr Leu Asp Pro Glu Arg Leu Gly Arg Glu Gly Val Gln Lys Glu
945                 950                 955                 960 gac atc cca cct gca gac ctc agt gac caa gtc ccg gac acc gag tct              2928
Asp Ile Pro Pro Ala Asp Leu Ser Asp Gln Val Pro Asp Thr Glu Ser
                    965                 970                 975 gag acc aga att ctc ctg caa ggg acc cca gtg gcc cag atg aca gag              2976
Glu Thr Arg Ile Leu Leu Gln Gly Thr Pro Val Ala Gln Met Thr Glu
                980                 985                 990 gat gcc gtc gac gcg gaa cgg ctg  aag cac ctc att gtg  acc ccc tcg            3024
Asp Ala Val Asp Ala Glu Arg Leu  Lys His Leu Ile Val  Thr Pro Ser
                995                  1000                1005 ggc tgc  ggg gaa cag aac atg  atc ggc atg acg ccc  acg gtc atc               3069
Gly Cys  Gly Glu Gln Asn Met  Ile Gly Met Thr Pro  Thr Val Ile
         1010                 1015                 1020 gct gtg  cat tac ctg gat gaa  acg gag cag tgg gag  aag ttc ggc               3114
Ala Val  His Tyr Leu Asp Glu  Thr Glu Gln Trp Glu  Lys Phe Gly
         1025                 1030                 1035 cta gag  aag cgg cag ggg gcc  ttg gag ctc atc aag  aag ggg tac               3159
Leu Glu  Lys Arg Gln Gly Ala  Leu Glu Leu Ile Lys  Lys Gly Tyr
         1040                 1045                 1050 acc cag  cag ctg gcc ttc aga  caa ccc agc tct gcc  ttt gcg gcc               3204
Thr Gln  Gln Leu Ala Phe Arg  Gln Pro Ser Ser Ala  Phe Ala Ala
         1055                 1060                 1065 ttc gtg  aaa cgg gca ccc agc  acc tgg ctg acc gcc  tac gtg gtc               3249
Phe Val  Lys Arg Ala Pro Ser  Thr Trp Leu Thr Ala  Tyr Val Val
         1070                 1075                 1080
```

```
                                                              -continued aag gtc ttc tct ctg gct gtc aac ctc atc gcc atc gac tcc caa      3294
Lys Val Phe Ser Leu Ala Val Asn Leu Ile Ala Ile Asp Ser Gln
    1085                1090                1095 gtc ctc tgc ggg gct gtt aaa tgg ctg atc ctg gag aag cag aag      3339
Val Leu Cys Gly Ala Val Lys Trp Leu Ile Leu Glu Lys Gln Lys
1100                1105                1110 ccc gac ggg gtc ttc cag gag gat gcg ccc gtg ata cac caa gaa      3384
Pro Asp Gly Val Phe Gln Glu Asp Ala Pro Val Ile His Gln Glu
    1115                1120                1125 atg att ggt gga tta cgg aac aac aac gag aaa gac atg gcc ctc      3429
Met Ile Gly Gly Leu Arg Asn Asn Asn Glu Lys Asp Met Ala Leu
    1130                1135                1140 acg gcc ttt gtt ctc atc tcg ctg cag gag gct aaa gat att tgc      3474
Thr Ala Phe Val Leu Ile Ser Leu Gln Glu Ala Lys Asp Ile Cys
    1145                1150                1155 gag gag cag gtc aac agc ctg cca ggc agc atc act aaa gca gga      3519
Glu Glu Gln Val Asn Ser Leu Pro Gly Ser Ile Thr Lys Ala Gly
    1160                1165                1170 gac ttc ctt gaa gcc aac tac atg aac cta cag aga tcc tac act      3564
Asp Phe Leu Glu Ala Asn Tyr Met Asn Leu Gln Arg Ser Tyr Thr
    1175                1180                1185 gtg gcc att gct ggc tat gct ctg gcc cag atg ggc agg ctg aag      3609
Val Ala Ile Ala Gly Tyr Ala Leu Ala Gln Met Gly Arg Leu Lys
    1190                1195                1200 ggg cct ctt ctt aac aaa ttt ctg acc aca gcc aaa gat aag aac      3654
Gly Pro Leu Leu Asn Lys Phe Leu Thr Thr Ala Lys Asp Lys Asn
    1205                1210                1215 cgc tgg gag gac cct ggt aag cag ctc tac aac gtg gag gcc aca      3699
Arg Trp Glu Asp Pro Gly Lys Gln Leu Tyr Asn Val Glu Ala Thr
    1220                1225                1230 tcc tat gcc ctc ttg gcc cta ctg cag cta aaa gac ttt gac ttt      3744
Ser Tyr Ala Leu Leu Ala Leu Leu Gln Leu Lys Asp Phe Asp Phe
    1235                1240                1245 gtg cct ccc gtc gtg cgt tgg ctc aat gaa cag aga tac tac ggt      3789
Val Pro Pro Val Val Arg Trp Leu Asn Glu Gln Arg Tyr Tyr Gly
    1250                1255                1260 ggt ggc tat ggc tct acc cag gcc acc ttc atg gtg ttc caa gcc      3834
Gly Gly Tyr Gly Ser Thr Gln Ala Thr Phe Met Val Phe Gln Ala
    1265                1270                1275 ttg gct caa tac caa aag gac gcc cct gac cac cag gaa ctg aac      3879
Leu Ala Gln Tyr Gln Lys Asp Ala Pro Asp His Gln Glu Leu Asn
    1280                1285                1290 ctt gat gtg tcc ctc caa ctg ccc agc cgc agc tcc aag atc acc      3924
Leu Asp Val Ser Leu Gln Leu Pro Ser Arg Ser Ser Lys Ile Thr
    1295                1300                1305 cac cgt atc cac tgg gaa tct gcc agc ctc ctg cga tca gaa gag      3969
His Arg Ile His Trp Glu Ser Ala Ser Leu Leu Arg Ser Glu Glu
    1310                1315                1320 acc aag gaa aat gag ggt ttc aca gtc aca gct gaa gga aaa ggc      4014
Thr Lys Glu Asn Glu Gly Phe Thr Val Thr Ala Glu Gly Lys Gly
    1325                1330                1335 caa ggc acc ttg tcg gtg gtg aca atg tac cat gct aag gcc aaa      4059
Gln Gly Thr Leu Ser Val Val Thr Met Tyr His Ala Lys Ala Lys
    1340                1345                1350 gat caa ctc acc tgt aat aaa ttc gac ctc aag gtc acc ata aaa      4104
Asp Gln Leu Thr Cys Asn Lys Phe Asp Leu Lys Val Thr Ile Lys
    1355                1360                1365 cca gca ccg gaa aca gaa aag agg cct cag gat gcc aag aac act      4149
Pro Ala Pro Glu Thr Glu Lys Arg Pro Gln Asp Ala Lys Asn Thr
    1370                1375                1380
```

-continued

```
atg atc ctt gag atc tgt acc agg tac cgg gga gac cag gat gcc      4194
Met Ile Leu Glu Ile Cys Thr Arg Tyr Arg Gly Asp Gln Asp Ala
    1385                1390                1395 act atg tct ata ttg gac ata tcc atg atg act ggc ttt gct cca      4239
Thr Met Ser Ile Leu Asp Ile Ser Met Met Thr Gly Phe Ala Pro
1400                1405                1410 gac aca gat gac ctg aag cag ctg gcc aat ggt gtt gac aga tac      4284
Asp Thr Asp Asp Leu Lys Gln Leu Ala Asn Gly Val Asp Arg Tyr
    1415                1420                1425 atc tcc aag tat gag ctg gac aaa gcc ttc tcc gat agg aac acc      4329
Ile Ser Lys Tyr Glu Leu Asp Lys Ala Phe Ser Asp Arg Asn Thr
1430                1435                1440 ctc atc atc tac ctg gac aag gtc tca cac tct gag gat gac tgt      4374
Leu Ile Ile Tyr Leu Asp Lys Val Ser His Ser Glu Asp Asp Cys
    1445                1450                1455 cta gct ttc aaa gtt cac caa tac ttt aat gta gag ctt atc cag      4419
Leu Ala Phe Lys Val His Gln Tyr Phe Asn Val Glu Leu Ile Gln
1460                1465                1470 cct gga gca gtc aag gtc tac gcc tat tac aac ctg gag gaa agc      4464
Pro Gly Ala Val Lys Val Tyr Ala Tyr Tyr Asn Leu Glu Glu Ser
    1475                1480                1485 tgt acc cgg ttc tac cat ccg gaa aag gag gat gga aag ctg aac      4509
Cys Thr Arg Phe Tyr His Pro Glu Lys Glu Asp Gly Lys Leu Asn
1490                1495                1500 aag ctc tgc cgt gat gaa ctg tgc cgc tgt gct gag gag aat tgc      4554
Lys Leu Cys Arg Asp Glu Leu Cys Arg Cys Ala Glu Glu Asn Cys
    1505                1510                1515 ttc ata caa aag tcg gat gac aag gtc acc ctg gaa gaa cgg ctg      4599
Phe Ile Gln Lys Ser Asp Asp Lys Val Thr Leu Glu Glu Arg Leu
1520                1525                1530 gac aag gcc tgt gag cca gga gtg gac tat gtg tac aaa acc aag      4644
Asp Lys Ala Cys Glu Pro Gly Val Asp Tyr Val Tyr Lys Thr Lys
    1535                1540                1545 ctg ctt cga ata gaa gaa caa gat ggt aat gat atc tat gtc atg      4689
Leu Leu Arg Ile Glu Glu Gln Asp Gly Asn Asp Ile Tyr Val Met
1550                1555                1560 gat gtt tta gaa gtt att aaa caa ggt act gac gaa aat cca cga      4734
Asp Val Leu Glu Val Ile Lys Gln Gly Thr Asp Glu Asn Pro Arg
    1565                1570                1575 gca aag acc cac cag tac ata agt caa agg aaa tgc cag gag gct      4779
Ala Lys Thr His Gln Tyr Ile Ser Gln Arg Lys Cys Gln Glu Ala
1580                1585                1590 ctg aat ctg aag gtg aat gat gat tat ctg atc tgg ggt tcc agg      4824
Leu Asn Leu Lys Val Asn Asp Asp Tyr Leu Ile Trp Gly Ser Arg
    1595                1600                1605 agt gac ctg ttg ccc acg aaa gat aaa att tcc tac atc att aca      4869
Ser Asp Leu Leu Pro Thr Lys Asp Lys Ile Ser Tyr Ile Ile Thr
1610                1615                1620 aag aac aca tgg att gag aga tgg cca cat gaa gac gaa tgt cag      4914
Lys Asn Thr Trp Ile Glu Arg Trp Pro His Glu Asp Glu Cys Gln
    1625                1630                1635 gaa gaa gaa ttc caa aag ttg tgt gat gac ttt gct cag ttt agc      4959
Glu Glu Glu Phe Gln Lys Leu Cys Asp Asp Phe Ala Gln Phe Ser
1640                1645                1650 tac aca ttg act gag ttt ggc tgc cct act taa                      4992
Tyr Thr Leu Thr Glu Phe Gly Cys Pro Thr
    1655                1660
```

<210> SEQ ID NO 6

```
<211> LENGTH: 1663
<212> TYPE: PRT
<213> ORGANISM: Artificial Sequence
<220> FEATURE:
<223> OTHER INFORMATION: Recombinant Human C3

<400> SEQUENCE: 6
```

| | | | | | | | | | | | | | | | |
|---|---|---|---|---|---|---|---|---|---|---|---|---|---|---|---|
| Met | Gly | Pro | Thr | Ser | Gly | Pro | Ser | Leu | Leu | Leu | Leu | Leu | Thr | His | |
| 1 | | | | 5 | | | | | 10 | | | | | 15 | |
| Leu | Pro | Leu | Ala | Leu | Gly | Ser | Pro | Met | Tyr | Ser | Ile | Ile | Thr | Pro | Asn |
| | | | 20 | | | | | 25 | | | | | 30 | | |
| Ile | Leu | Arg | Leu | Glu | Ser | Glu | Glu | Thr | Met | Val | Leu | Glu | Ala | His | Asp |
| | | 35 | | | | | 40 | | | | | 45 | | | |
| Ala | Gln | Gly | Asp | Val | Pro | Val | Thr | Val | Thr | Val | His | Asp | Phe | Pro | Gly |
| | 50 | | | | | 55 | | | | | 60 | | | | |
| Lys | Lys | Leu | Val | Leu | Ser | Ser | Glu | Lys | Thr | Val | Leu | Thr | Pro | Ala | Thr |
| 65 | | | | | 70 | | | | | 75 | | | | | 80 |
| Asn | His | Met | Gly | Asn | Val | Thr | Phe | Thr | Ile | Pro | Ala | Asn | Arg | Glu | Phe |
| | | | | 85 | | | | | 90 | | | | | 95 | |
| Lys | Ser | Glu | Lys | Gly | Arg | Asn | Lys | Phe | Val | Thr | Val | Gln | Ala | Thr | Phe |
| | | | 100 | | | | | 105 | | | | | 110 | | |
| Gly | Thr | Gln | Val | Val | Glu | Lys | Val | Leu | Val | Ser | Leu | Gln | Ser | Gly | |
| | | 115 | | | | | 120 | | | | | 125 | | | |
| Tyr | Leu | Phe | Ile | Gln | Thr | Asp | Lys | Thr | Ile | Tyr | Thr | Pro | Gly | Ser | Thr |
| | 130 | | | | | 135 | | | | | 140 | | | | |
| Val | Leu | Tyr | Arg | Ile | Phe | Thr | Val | Asn | His | Lys | Leu | Leu | Pro | Val | Gly |
| 145 | | | | | 150 | | | | | 155 | | | | | 160 |
| Arg | Thr | Val | Met | Val | Asn | Ile | Glu | Asn | Pro | Glu | Gly | Ile | Pro | Val | Lys |
| | | | | 165 | | | | | 170 | | | | | 175 | |
| Gln | Asp | Ser | Leu | Ser | Ser | Gln | Asn | Gln | Leu | Gly | Val | Leu | Pro | Leu | Ser |
| | | | 180 | | | | | 185 | | | | | 190 | | |
| Trp | Asp | Ile | Pro | Glu | Leu | Val | Asn | Met | Gly | Gln | Trp | Lys | Ile | Arg | Ala |
| | | 195 | | | | | 200 | | | | | 205 | | | |
| Tyr | Tyr | Glu | Asn | Ser | Pro | Gln | Gln | Val | Phe | Ser | Thr | Glu | Phe | Glu | Val |
| | 210 | | | | | 215 | | | | | 220 | | | | |
| Lys | Glu | Tyr | Val | Leu | Pro | Ser | Phe | Glu | Val | Ile | Val | Glu | Pro | Thr | Glu |
| 225 | | | | | 230 | | | | | 235 | | | | | 240 |
| Lys | Phe | Tyr | Tyr | Ile | Tyr | Asn | Glu | Lys | Gly | Leu | Glu | Val | Thr | Ile | Thr |
| | | | | 245 | | | | | 250 | | | | | 255 | |
| Ala | Arg | Phe | Leu | Tyr | Gly | Lys | Lys | Val | Glu | Gly | Thr | Ala | Phe | Val | Ile |
| | | | 260 | | | | | 265 | | | | | 270 | | |
| Phe | Gly | Ile | Gln | Asp | Gly | Glu | Gln | Arg | Ile | Ser | Leu | Pro | Glu | Ser | Leu |
| | | 275 | | | | | 280 | | | | | 285 | | | |
| Lys | Arg | Ile | Pro | Ile | Glu | Asp | Gly | Ser | Gly | Glu | Val | Val | Leu | Ser | Arg |
| | 290 | | | | | 295 | | | | | 300 | | | | |
| Lys | Val | Leu | Leu | Asp | Gly | Val | Gln | Asn | Leu | Arg | Ala | Glu | Asp | Leu | Val |
| 305 | | | | | 310 | | | | | 315 | | | | | 320 |
| Gly | Lys | Ser | Leu | Tyr | Val | Ser | Ala | Thr | Val | Ile | Leu | His | Ser | Gly | Ser |
| | | | | 325 | | | | | 330 | | | | | 335 | |
| Asp | Met | Val | Gln | Ala | Glu | Arg | Ser | Gly | Ile | Pro | Ile | Val | Thr | Ser | Pro |
| | | | 340 | | | | | 345 | | | | | 350 | | |
| Tyr | Gln | Ile | His | Phe | Thr | Lys | Thr | Pro | Lys | Tyr | Phe | Lys | Pro | Gly | Met |
| | | 355 | | | | | 360 | | | | | 365 | | | |
| Pro | Phe | Asp | Leu | Met | Val | Phe | Val | Thr | Asn | Pro | Asp | Gly | Ser | Pro | Ala |
| | 370 | | | | | 375 | | | | | 380 | | | | |

-continued

```
Tyr Arg Val Pro Val Ala Val Gln Gly Glu Asp Thr Val Gln Ser Leu
385                 390                 395                 400

Thr Gln Gly Asp Gly Val Ala Lys Leu Ser Ile Asn Thr His Pro Ser
            405                 410                 415

Gln Lys Pro Leu Ser Ile Thr Val Arg Thr Lys Lys Gln Glu Leu Ser
                420                 425                 430

Glu Ala Glu Gln Ala Thr Arg Thr Met Gln Ala Leu Pro Tyr Ser Thr
            435                 440                 445

Val Gly Asn Ser Asn Asn Tyr Leu His Leu Ser Val Leu Arg Thr Glu
    450                 455                 460

Leu Arg Pro Gly Glu Thr Leu Asn Val Asn Phe Leu Leu Arg Met Asp
465                 470                 475                 480

Arg Ala His Glu Ala Lys Ile Arg Tyr Tyr Thr Tyr Leu Ile Met Asn
                485                 490                 495

Lys Gly Arg Leu Leu Lys Ala Gly Arg Gln Val Arg Glu Pro Gly Gln
                500                 505                 510

Asp Leu Val Val Leu Pro Leu Ser Ile Thr Thr Asp Phe Ile Pro Ser
            515                 520                 525

Phe Arg Leu Val Ala Tyr Tyr Thr Leu Ile Gly Ala Ser Gly Gln Arg
530                 535                 540

Glu Val Val Ala Asp Ser Val Trp Val Asp Val Lys Asp Ser Cys Val
545                 550                 555                 560

Gly Ser Leu Val Val Lys Ser Gly Gln Ser Glu Asp Arg Gln Pro Val
                565                 570                 575

Pro Gly Gln Gln Met Thr Leu Lys Ile Glu Gly Asp His Gly Ala Arg
            580                 585                 590

Val Val Leu Val Ala Val Asp Lys Gly Val Phe Val Leu Asn Lys Lys
    595                 600                 605

Asn Lys Leu Thr Gln Ser Lys Ile Trp Asp Val Val Glu Lys Ala Asp
    610                 615                 620

Ile Gly Cys Thr Pro Gly Ser Gly Lys Asp Tyr Ala Gly Val Phe Ser
625                 630                 635                 640

Asp Ala Gly Leu Thr Phe Thr Ser Ser Ser Gly Gln Gln Thr Ala Gln
            645                 650                 655

Arg Ala Glu Leu Gln Cys Pro Gln Pro Ala Ala Arg Arg Arg Arg Ser
            660                 665                 670

Val Gln Leu Thr Glu Lys Arg Met Asp Lys Val Gly Lys Tyr Pro Lys
            675                 680                 685

Glu Leu Arg Lys Cys Cys Glu Asp Gly Met Arg Glu Asn Pro Met Arg
690                 695                 700

Phe Ser Cys Gln Arg Arg Thr Arg Phe Ile Ser Leu Gly Glu Ala Cys
705                 710                 715                 720

Lys Lys Val Phe Leu Asp Cys Cys Asn Tyr Ile Thr Glu Leu Arg Arg
                725                 730                 735

Gln His Ala Arg Ala Ser His Leu Gly Leu Ala Arg Ser Asn Leu Asp
            740                 745                 750

Glu Asp Ile Ile Ala Glu Glu Asn Ile Val Ser Arg Ser Glu Phe Pro
            755                 760                 765

Glu Ser Trp Leu Trp Asn Val Glu Asp Leu Lys Glu Pro Pro Lys Asn
            770                 775                 780

Gly Ile Ser Thr Lys Leu Met Asn Ile Phe Leu Lys Asp Ser Ile Thr
785                 790                 795                 800
```

```
-continued

Thr Trp Glu Ile Leu Ala Val Ser Met Ser Asp Lys Gly Ile Cys
            805                 810                 815

Val Ala Asp Pro Phe Glu Val Thr Val Met Gln Asp Phe Phe Ile Asp
            820                 825                 830

Leu Arg Leu Pro Tyr Ser Val Val Arg Asn Glu Gln Val Glu Ile Arg
            835                 840                 845

Ala Val Leu Tyr Asn Tyr Arg Gln Asn Gln Glu Leu Lys Val Arg Val
        850                 855                 860

Glu Leu Leu His Asn Pro Ala Phe Cys Ser Leu Ala Thr Thr Lys Arg
865                 870                 875                 880

Arg His Gln Gln Thr Val Thr Ile Pro Pro Lys Ser Ser Leu Ser Val
                885                 890                 895

Pro Tyr Val Ile Val Pro Leu Lys Thr Gly Leu Gln Glu Val Glu Val
                900                 905                 910

Lys Ala Ala Val Tyr His His Phe Ile Ser Asp Gly Val Arg Lys Ser
                915                 920                 925

Leu Lys Val Val Pro Glu Gly Ile Arg Met Asn Lys Thr Val Ala Val
        930                 935                 940

Arg Thr Leu Asp Pro Glu Arg Leu Gly Arg Gly Val Gln Lys Glu
945                 950                 955                 960

Asp Ile Pro Pro Ala Asp Leu Ser Asp Gln Val Pro Asp Thr Glu Ser
                965                 970                 975

Glu Thr Arg Ile Leu Leu Gln Gly Thr Pro Val Ala Gln Met Thr Glu
                980                 985                 990

Asp Ala Val Asp Ala Glu Arg Leu Lys His Leu Ile Val Thr Pro Ser
            995                 1000                1005

Gly Cys Gly Glu Gln Asn Met Ile Gly Met Thr Pro Thr Val Ile
        1010                1015                1020

Ala Val His Tyr Leu Asp Glu Thr Glu Gln Trp Glu Lys Phe Gly
        1025                1030                1035

Leu Glu Lys Arg Gln Gly Ala Leu Glu Leu Ile Lys Lys Gly Tyr
        1040                1045                1050

Thr Gln Gln Leu Ala Phe Arg Gln Pro Ser Ser Ala Phe Ala Ala
        1055                1060                1065

Phe Val Lys Arg Ala Pro Ser Thr Trp Leu Thr Ala Tyr Val Val
        1070                1075                1080

Lys Val Phe Ser Leu Ala Val Asn Leu Ile Ala Ile Asp Ser Gln
        1085                1090                1095

Val Leu Cys Gly Ala Val Lys Trp Leu Ile Leu Glu Lys Gln Lys
        1100                1105                1110

Pro Asp Gly Val Phe Gln Glu Asp Ala Pro Val Ile His Gln Glu
        1115                1120                1125

Met Ile Gly Gly Leu Arg Asn Asn Asn Glu Lys Asp Met Ala Leu
        1130                1135                1140

Thr Ala Phe Val Leu Ile Ser Leu Gln Glu Ala Lys Asp Ile Cys
        1145                1150                1155

Glu Glu Gln Val Asn Ser Leu Pro Gly Ser Ile Thr Lys Ala Gly
        1160                1165                1170

Asp Phe Leu Glu Ala Asn Tyr Met Asn Leu Gln Arg Ser Tyr Thr
        1175                1180                1185

Val Ala Ile Ala Gly Tyr Ala Leu Ala Gln Met Gly Arg Leu Lys
        1190                1195                1200

Gly Pro Leu Leu Asn Lys Phe Leu Thr Thr Ala Lys Asp Lys Asn
```

-continued

```
            1205                1210                1215
Arg Trp Glu Asp Pro Gly Lys Gln Leu Tyr Asn Val Glu Ala Thr
    1220                1225                1230
Ser Tyr Ala Leu Leu Ala Leu Leu Gln Leu Lys Asp Phe Asp Phe
    1235                1240                1245
Val Pro Pro Val Val Arg Trp Leu Asn Glu Gln Arg Tyr Tyr Gly
    1250                1255                1260
Gly Gly Tyr Gly Ser Thr Gln Ala Thr Phe Met Val Phe Gln Ala
    1265                1270                1275
Leu Ala Gln Tyr Gln Lys Asp Ala Pro Asp His Gln Glu Leu Asn
    1280                1285                1290
Leu Asp Val Ser Leu Gln Leu Pro Ser Arg Ser Ser Lys Ile Thr
    1295                1300                1305
His Arg Ile His Trp Glu Ser Ala Ser Leu Leu Arg Ser Glu Glu
    1310                1315                1320
Thr Lys Glu Asn Glu Gly Phe Thr Val Thr Ala Glu Gly Lys Gly
    1325                1330                1335
Gln Gly Thr Leu Ser Val Val Thr Met Tyr His Ala Lys Ala Lys
    1340                1345                1350
Asp Gln Leu Thr Cys Asn Lys Phe Asp Leu Lys Val Thr Ile Lys
    1355                1360                1365
Pro Ala Pro Glu Thr Glu Lys Arg Pro Gln Asp Ala Lys Asn Thr
    1370                1375                1380
Met Ile Leu Glu Ile Cys Thr Arg Tyr Arg Gly Asp Gln Asp Ala
    1385                1390                1395
Thr Met Ser Ile Leu Asp Ile Ser Met Met Thr Gly Phe Ala Pro
    1400                1405                1410
Asp Thr Asp Asp Leu Lys Gln Leu Ala Asn Gly Val Asp Arg Tyr
    1415                1420                1425
Ile Ser Lys Tyr Glu Leu Asp Lys Ala Phe Ser Asp Arg Asn Thr
    1430                1435                1440
Leu Ile Ile Tyr Leu Asp Lys Val Ser His Ser Glu Asp Asp Cys
    1445                1450                1455
Leu Ala Phe Lys Val His Gln Tyr Phe Asn Val Glu Leu Ile Gln
    1460                1465                1470
Pro Gly Ala Val Lys Val Tyr Ala Tyr Tyr Asn Leu Glu Glu Ser
    1475                1480                1485
Cys Thr Arg Phe Tyr His Pro Glu Lys Glu Asp Gly Lys Leu Asn
    1490                1495                1500
Lys Leu Cys Arg Asp Glu Leu Cys Arg Cys Ala Glu Glu Asn Cys
    1505                1510                1515
Phe Ile Gln Lys Ser Asp Asp Lys Val Thr Leu Glu Glu Arg Leu
    1520                1525                1530
Asp Lys Ala Cys Glu Pro Gly Val Asp Tyr Val Tyr Lys Thr Lys
    1535                1540                1545
Leu Leu Arg Ile Glu Glu Gln Asp Gly Asn Asp Ile Tyr Val Met
    1550                1555                1560
Asp Val Leu Glu Val Ile Lys Gln Gly Thr Asp Glu Asn Pro Arg
    1565                1570                1575
Ala Lys Thr His Gln Tyr Ile Ser Gln Arg Lys Cys Gln Glu Ala
    1580                1585                1590
Leu Asn Leu Lys Val Asn Asp Asp Tyr Leu Ile Trp Gly Ser Arg
    1595                1600                1605
```

```
Ser Asp Leu Leu Pro Thr Lys Asp Lys Ile Ser Tyr Ile Ile Thr
    1610            1615                1620

Lys Asn Thr Trp Ile Glu Arg Trp Pro His Glu Asp Glu Cys Gln
1625            1630                1635

Glu Glu Glu Phe Gln Lys Leu Cys Asp Asp Phe Ala Gln Phe Ser
    1640            1645                1650

Tyr Thr Leu Thr Glu Phe Gly Cys Pro Thr
    1655            1660

<210> SEQ ID NO 7
<211> LENGTH: 4914
<212> TYPE: DNA
<213> ORGANISM: Artificial Sequence
<220> FEATURE:
<223> OTHER INFORMATION: Hybrid protein
<220> FEATURE:
<221> NAME/KEY: CDS
<222> LOCATION: (1)..(4914)
<223> OTHER INFORMATION: Construct H6 truncated

<400> SEQUENCE: 7 atg gga ccc acc tca ggt ccc agc ctg ctg ctc ctg cta cta acc cac       48
Met Gly Pro Thr Ser Gly Pro Ser Leu Leu Leu Leu Leu Leu Thr His
1               5                   10                  15 ctc ccc ctg gct ctg ggg agt ccc atg tac tct atc atc acc ccc aac       96
Leu Pro Leu Ala Leu Gly Ser Pro Met Tyr Ser Ile Ile Thr Pro Asn
            20                  25                  30 atc ttg cgg ctg gag agc gag gag acc atg gtg ctg gag gcc cac gac       144
Ile Leu Arg Leu Glu Ser Glu Glu Thr Met Val Leu Glu Ala His Asp
        35                  40                  45 gcg caa ggg gat gtt cca gtc act gtt act gtc cac gac ttc cca ggc       192
Ala Gln Gly Asp Val Pro Val Thr Val Thr Val His Asp Phe Pro Gly
    50                  55                  60 aaa aaa cta gtg ctg tcc agt gag aag act gtg ctg acc cct gcc acc       240
Lys Lys Leu Val Leu Ser Ser Glu Lys Thr Val Leu Thr Pro Ala Thr
65                  70                  75                  80 aac cac atg ggc aac gtc acc ttc acg atc cca gcc aac agg gag ttc       288
Asn His Met Gly Asn Val Thr Phe Thr Ile Pro Ala Asn Arg Glu Phe
                85                  90                  95 aag tca gaa aag ggg cgc aac aag ttc gtg acc gtg cag gcc acc ttc       336
Lys Ser Glu Lys Gly Arg Asn Lys Phe Val Thr Val Gln Ala Thr Phe
            100                 105                 110 ggg acc caa gtg gtg gag aag gtg gtg ctg gtc agc ctg cag agc ggg       384
Gly Thr Gln Val Val Glu Lys Val Val Leu Val Ser Leu Gln Ser Gly
        115                 120                 125 tac ctc ttc atc cag aca gac aag acc atc tac acc cct ggc tcc aca       432
Tyr Leu Phe Ile Gln Thr Asp Lys Thr Ile Tyr Thr Pro Gly Ser Thr
    130                 135                 140 gtt ctc tat cgg atc ttc acc gtc aac cac aag ctg cta ccc gtg ggc       480
Val Leu Tyr Arg Ile Phe Thr Val Asn His Lys Leu Leu Pro Val Gly
145                 150                 155                 160 cgg acg gtc atg gtc aac att gag aac ccg gaa ggc atc ccg gtc aag       528
Arg Thr Val Met Val Asn Ile Glu Asn Pro Glu Gly Ile Pro Val Lys
                165                 170                 175 cag gac tcc ttg tct tct cag aac cag ctt ggc gtc ttg ccc ttg tct       576
Gln Asp Ser Leu Ser Ser Gln Asn Gln Leu Gly Val Leu Pro Leu Ser
            180                 185                 190 tgg gac att ccg gaa ctc gtc aac atg ggc cag tgg aag atc cga gcc       624
Trp Asp Ile Pro Glu Leu Val Asn Met Gly Gln Trp Lys Ile Arg Ala
        195                 200                 205
```

-continued

| | | |
|---|---|---|
| tac tat gaa aac tca cca cag cag gtc ttc tcc act gag ttt gag gtg<br>Tyr Tyr Glu Asn Ser Pro Gln Gln Val Phe Ser Thr Glu Phe Glu Val<br>210                        215                        220 | 672 |
| aag gag tac gtg ctg ccc agt ttc gag gtc ata gtg gag cct aca gag<br>Lys Glu Tyr Val Leu Pro Ser Phe Glu Val Ile Val Glu Pro Thr Glu<br>225                      230                      235                      240 | 720 |
| aaa ttc tac tac atc tat aac gag aag ggc ctg gag gtc acc atc acc<br>Lys Phe Tyr Tyr Ile Tyr Asn Glu Lys Gly Leu Glu Val Thr Ile Thr<br>                  245                      250                      255 | 768 |
| gcc agg ttc ctc tac ggg aag aaa gtg gag gga act gcc ttt gtc atc<br>Ala Arg Phe Leu Tyr Gly Lys Lys Val Glu Gly Thr Ala Phe Val Ile<br>260                        265                      270 | 816 |
| ttc ggg atc cag gat ggc gaa cag agg att tcc ctg cct gaa tcc ctc<br>Phe Gly Ile Gln Asp Gly Glu Gln Arg Ile Ser Leu Pro Glu Ser Leu<br>                  275                      280                      285 | 864 |
| aag cgc att ccg att gag gat ggc tcg ggg gag gtt gtg ctg agc cgg<br>Lys Arg Ile Pro Ile Glu Asp Gly Ser Gly Glu Val Val Leu Ser Arg<br>290                        295                      300 | 912 |
| aag gta ctg ctg gac ggg gtg cag aac ctc cga gca gaa gac ctg gtg<br>Lys Val Leu Leu Asp Gly Val Gln Asn Leu Arg Ala Glu Asp Leu Val<br>305                      310                      315                      320 | 960 |
| ggg aag tct ttg tac gtg tct gcc acc gtc atc ttg cac tca ggc agt<br>Gly Lys Ser Leu Tyr Val Ser Ala Thr Val Ile Leu His Ser Gly Ser<br>                  325                      330                      335 | 1008 |
| gac atg gtg cag gca gag cgc agc ggg atc ccc atc gtg acc tct ccc<br>Asp Met Val Gln Ala Glu Arg Ser Gly Ile Pro Ile Val Thr Ser Pro<br>                  340                      345                      350 | 1056 |
| tac cag atc cac ttc acc aag aca ccc aag tac ttc aaa cca gga atg<br>Tyr Gln Ile His Phe Thr Lys Thr Pro Lys Tyr Phe Lys Pro Gly Met<br>                  355                      360                      365 | 1104 |
| ccc ttt gac ctc atg gtg ttc gtg acg aac cct gat ggc tct cca gcc<br>Pro Phe Asp Leu Met Val Phe Val Thr Asn Pro Asp Gly Ser Pro Ala<br>370                        375                      380 | 1152 |
| tac cga gtc ccc gtg gca gtc cag ggc gag gac act gtg cag tct cta<br>Tyr Arg Val Pro Val Ala Val Gln Gly Glu Asp Thr Val Gln Ser Leu<br>385                      390                      395                      400 | 1200 |
| acc cag gga gat ggc gtg gcc aaa ctc agc atc aac aca cac ccc agc<br>Thr Gln Gly Asp Gly Val Ala Lys Leu Ser Ile Asn Thr His Pro Ser<br>                  405                      410                      415 | 1248 |
| cag aag ccc ttg agc atc acg gtg cgc acg aag aag cag gag ctc tcg<br>Gln Lys Pro Leu Ser Ile Thr Val Arg Thr Lys Lys Gln Glu Leu Ser<br>                  420                      425                      430 | 1296 |
| gag gca gag cag gct acc agg acc atg cag gct ctg ccc tac agc acc<br>Glu Ala Glu Gln Ala Thr Arg Thr Met Gln Ala Leu Pro Tyr Ser Thr<br>435                        440                      445 | 1344 |
| gtg ggc aac tcc aac aat tac ctg cat ctc tca gtg cta cgt aca gag<br>Val Gly Asn Ser Asn Asn Tyr Leu His Leu Ser Val Leu Arg Thr Glu<br>450                        455                      460 | 1392 |
| ctc aga ccc ggg gag acc ctc aac gtc aac ttc ctc ctg cga atg gac<br>Leu Arg Pro Gly Glu Thr Leu Asn Val Asn Phe Leu Leu Arg Met Asp<br>465                      470                      475                      480 | 1440 |
| cgc gcc cac gag gcc aag atc cgc tac tac acc tac ctg atc atg aac<br>Arg Ala His Glu Ala Lys Ile Arg Tyr Tyr Thr Tyr Leu Ile Met Asn<br>                  485                      490                      495 | 1488 |
| aag ggc agg ctg ttg aag gcg gga cgc cag gtg cga gag ccc ggc cag<br>Lys Gly Arg Leu Leu Lys Ala Gly Arg Gln Val Arg Glu Pro Gly Gln<br>                  500                      505                      510 | 1536 |
| gac ctg gtg gtg ctg ccc ctg tcc atc acc acc gac ttc atc cct tcc<br>Asp Leu Val Val Leu Pro Leu Ser Ile Thr Thr Asp Phe Ile Pro Ser<br>515                        520                      525 | 1584 |

```
ttc cgc ctg gtg gcg tac tac acg ctg atc ggt gcc agc ggc cag agg      1632
Phe Arg Leu Val Ala Tyr Tyr Thr Leu Ile Gly Ala Ser Gly Gln Arg
530                 535                 540 gag gtg gtg gcc gac tcc gtg tgg gtg gac gtc aag gac tcc tgc gtg      1680
Glu Val Val Ala Asp Ser Val Trp Val Asp Val Lys Asp Ser Cys Val
545                 550                 555                 560 ggc tcg ctg gtg gta aaa agc ggc cag tca gaa gac cgg cag cct gta      1728
Gly Ser Leu Val Val Lys Ser Gly Gln Ser Glu Asp Arg Gln Pro Val
                565                 570                 575 cct ggg cag cag atg acc ctg aag ata gag ggt gac cac ggg gcc cgg      1776
Pro Gly Gln Gln Met Thr Leu Lys Ile Glu Gly Asp His Gly Ala Arg
            580                 585                 590 gtg gta ctg gtg gcc gtg gac aag ggc gtg ttc gtg ctg aat aag aag      1824
Val Val Leu Val Ala Val Asp Lys Gly Val Phe Val Leu Asn Lys Lys
        595                 600                 605 aac aaa ctg acg cag agt aag atc tgg gac gtg gtg gag aag gca gac      1872
Asn Lys Leu Thr Gln Ser Lys Ile Trp Asp Val Val Glu Lys Ala Asp
610                 615                 620 atc ggc tgc acc ccg ggc agt ggg aag gat tac gcc ggt gtc ttc tcc      1920
Ile Gly Cys Thr Pro Gly Ser Gly Lys Asp Tyr Ala Gly Val Phe Ser
625                 630                 635                 640 gac gca ggg ctg acc ttc acg agc agc agt ggc cag cag acc gcc cag      1968
Asp Ala Gly Leu Thr Phe Thr Ser Ser Ser Gly Gln Gln Thr Ala Gln
                645                 650                 655 agg gca gaa ctt cag tgc ccg cag cca gcc gcc cgc cga cgc cgt tcc      2016
Arg Ala Glu Leu Gln Cys Pro Gln Pro Ala Ala Arg Arg Arg Arg Ser
            660                 665                 670 gtg cag ctc acg gag aag cga atg gac aaa gtc ggc aag tac ccc aag      2064
Val Gln Leu Thr Glu Lys Arg Met Asp Lys Val Gly Lys Tyr Pro Lys
        675                 680                 685 gag ctg cgc aag tgc tgc gag gac ggc atg cgg gag aac ccc atg agg      2112
Glu Leu Arg Lys Cys Cys Glu Asp Gly Met Arg Glu Asn Pro Met Arg
690                 695                 700 ttc tcg tgc cag cgc cgg acc cgt ttc atc tcc ctg ggc gag gcg tgc      2160
Phe Ser Cys Gln Arg Arg Thr Arg Phe Ile Ser Leu Gly Glu Ala Cys
705                 710                 715                 720 aag aag gtc ttc ctg gac tgc tgc aac tac atc aca gag ctg cgg cgg      2208
Lys Lys Val Phe Leu Asp Cys Cys Asn Tyr Ile Thr Glu Leu Arg Arg
                725                 730                 735 cag cac gcg cgg gcc agc cac ctg ggc ctg gcc agg agt aac ctg gat      2256
Gln His Ala Arg Ala Ser His Leu Gly Leu Ala Arg Ser Asn Leu Asp
            740                 745                 750 gag gac atc att gca gaa gag aac atc gtt tcc cga agt gag ttc cca      2304
Glu Asp Ile Ile Ala Glu Glu Asn Ile Val Ser Arg Ser Glu Phe Pro
        755                 760                 765 gag agc tgg ctg tgg aac gtt gag gac ttg aaa gag cca ccg aaa aat      2352
Glu Ser Trp Leu Trp Asn Val Glu Asp Leu Lys Glu Pro Pro Lys Asn
770                 775                 780 gga atc tct acg aag ctc atg aat ata ttt ttg aaa gac tcc atc acc      2400
Gly Ile Ser Thr Lys Leu Met Asn Ile Phe Leu Lys Asp Ser Ile Thr
785                 790                 795                 800 acg tgg gag att ctg gct gtc agc atg tcg gac aag aaa ggg atc tgt      2448
Thr Trp Glu Ile Leu Ala Val Ser Met Ser Asp Lys Lys Gly Ile Cys
                805                 810                 815 gtg gca gac ccc ttc gag gtc aca gta atg cag gac ttc ttc atc gac      2496
Val Ala Asp Pro Phe Glu Val Thr Val Met Gln Asp Phe Phe Ile Asp
            820                 825                 830 ctg cgg cta ccc tac tct gtt gtt cga aac gag cag gtg gaa atc cga      2544
Leu Arg Leu Pro Tyr Ser Val Val Arg Asn Glu Gln Val Glu Ile Arg
```

-continued

```
                   835                 840                 845
gcc gtt ctc tac aat tac cgg cag aac caa gag ctc aag gtg agg gtg    2592
Ala Val Leu Tyr Asn Tyr Arg Gln Asn Gln Glu Leu Lys Val Arg Val
        850                 855                 860 gaa cta ctc cac aat cca gcc ttc tgc agc ctg gcc acc acc aag agg    2640
Glu Leu Leu His Asn Pro Ala Phe Cys Ser Leu Ala Thr Thr Lys Arg
865                 870                 875                 880 cgt cac cag cag acc gta acc atc ccc ccc aag tcc tcg ttg tcc gtt    2688
Arg His Gln Gln Thr Val Thr Ile Pro Pro Lys Ser Ser Leu Ser Val
                885                 890                 895 cca tat gtc atc gtg ccg cta aag acc ggc ctg cag gaa gtg gaa gtc    2736
Pro Tyr Val Ile Val Pro Leu Lys Thr Gly Leu Gln Glu Val Glu Val
            900                 905                 910 aag gct gcc gtc tac cat cat ttc atc agt gac ggt gtc agg aag tcc    2784
Lys Ala Ala Val Tyr His His Phe Ile Ser Asp Gly Val Arg Lys Ser
        915                 920                 925 ctg aag gtc gtg ccg gaa gga atc aga atg aac aaa act gtg gct gtt    2832
Leu Lys Val Val Pro Glu Gly Ile Arg Met Asn Lys Thr Val Ala Val
    930                 935                 940 cgc acc ctg gat cca gaa cgc ctg ggc cgt gaa gga gtg cag aaa gag    2880
Arg Thr Leu Asp Pro Glu Arg Leu Gly Arg Glu Gly Val Gln Lys Glu
945                 950                 955                 960 gac atc cca cct gca gac ctc agt gac caa gtc ccg gac acc gag tct    2928
Asp Ile Pro Pro Ala Asp Leu Ser Asp Gln Val Pro Asp Thr Glu Ser
                965                 970                 975 gag acc aga att ctc ctg caa ggg acc cca gtg gcc cag atg aca gag    2976
Glu Thr Arg Ile Leu Leu Gln Gly Thr Pro Val Ala Gln Met Thr Glu
            980                 985                 990 gat gcc gtc gac gcg gaa cgg ctg  aag cac ctc att gtg  acc ccc tcg    3024
Asp Ala Val Asp Ala Glu Arg Leu  Lys His Leu Ile Val  Thr Pro Ser
        995                 1000                1005 ggc tgc ggg gaa cag aac atg  atc ggc atg acg ccc  acg gtc atc          3069
Gly Cys Gly Glu Gln Asn Met  Ile Gly Met Thr Pro  Thr Val Ile
    1010                1015                1020 gct gtg cat tac ctg gat gaa  acg gag cag tgg gag  aag ttc ggc          3114
Ala Val His Tyr Leu Asp Glu  Thr Glu Gln Trp Glu  Lys Phe Gly
    1025                1030                1035 cta gag aag cgg cag ggg gcc  ttg gag ctc atc aag  aag ggg tac          3159
Leu Glu Lys Arg Gln Gly Ala  Leu Glu Leu Ile Lys  Lys Gly Tyr
    1040                1045                1050 acc cag cag ctg gcc ttc aga  caa ccc agc tct gcc  ttt gcg gcc          3204
Thr Gln Gln Leu Ala Phe Arg  Gln Pro Ser Ser Ala  Phe Ala Ala
    1055                1060                1065 ttc gtg aaa cgg gca ccc agc  acc tgg ctg acc gcc  tac gtg gtc          3249
Phe Val Lys Arg Ala Pro Ser  Thr Trp Leu Thr Ala  Tyr Val Val
    1070                1075                1080 aag gtc ttc tct ctg gct gtc  aac ctc atc gcc atc  gac tcc caa          3294
Lys Val Phe Ser Leu Ala Val  Asn Leu Ile Ala Ile  Asp Ser Gln
    1085                1090                1095 gtc ctc tgc ggg gct gtt aaa  tgg ctg atc ctg gag  aag cag aag          3339
Val Leu Cys Gly Ala Val Lys  Trp Leu Ile Leu Glu  Lys Gln Lys
    1100                1105                1110 ccc gac ggg gtc ttc cag gag  gat gcg ccc gtg ata  cac caa gaa          3384
Pro Asp Gly Val Phe Gln Glu  Asp Ala Pro Val Ile  His Gln Glu
    1115                1120                1125 atg att ggt gga tta cgg aac  aac aac gag aaa gac  atg gcc ctc          3429
Met Ile Gly Gly Leu Arg Asn  Asn Asn Glu Lys Asp  Met Ala Leu
    1130                1135                1140 acg gcc ttt gtt ctc atc tcg  ctg cag gag gct aaa  gat att tgc          3474
```

```
                Thr Ala Phe Val Leu Ile Ser Leu Gln Glu Ala Lys Asp Ile Cys
                    1145                1150                1155 gag gag cag gtc aac agc ctg cca ggc agc atc act aaa gca gga           3519
Glu Glu Gln Val Asn Ser Leu Pro Gly Ser Ile Thr Lys Ala Gly
    1160                1165                1170 gac ttc ctt gaa gcc aac tac atg aac cta cag aga tcc tac act           3564
Asp Phe Leu Glu Ala Asn Tyr Met Asn Leu Gln Arg Ser Tyr Thr
    1175                1180                1185 gtg gcc att gct ggc tat gct ctg gcc cag atg ggc agg ctg aag           3609
Val Ala Ile Ala Gly Tyr Ala Leu Ala Gln Met Gly Arg Leu Lys
    1190                1195                1200 ggg cct ctt ctt aac aaa ttt ctg acc aca gcc aaa gat aag aac           3654
Gly Pro Leu Leu Asn Lys Phe Leu Thr Thr Ala Lys Asp Lys Asn
    1205                1210                1215 cgc tgg gag gac cct ggt aag cag ctc tac aac gtg gag gcc aca           3699
Arg Trp Glu Asp Pro Gly Lys Gln Leu Tyr Asn Val Glu Ala Thr
    1220                1225                1230 tcc tat gcc ctc ttg gcc cta ctg cag cta aaa gac ttt gac ttt           3744
Ser Tyr Ala Leu Leu Ala Leu Leu Gln Leu Lys Asp Phe Asp Phe
    1235                1240                1245 gtg cct ccc gtc gtg cgt tgg ctc aat gaa cag aga tac tac ggt           3789
Val Pro Pro Val Val Arg Trp Leu Asn Glu Gln Arg Tyr Tyr Gly
    1250                1255                1260 ggt ggc tat ggc tct acc cag gcc acc ttc atg gtg ttc caa gcc           3834
Gly Gly Tyr Gly Ser Thr Gln Ala Thr Phe Met Val Phe Gln Ala
    1265                1270                1275 ttg gct caa tac caa aag gac gcc cct gac cac cag gaa ctg aac           3879
Leu Ala Gln Tyr Gln Lys Asp Ala Pro Asp His Gln Glu Leu Asn
    1280                1285                1290 ctt gat gtg tcc ctc caa ctg ccc agc cgc agc tcc aag atc acc           3924
Leu Asp Val Ser Leu Gln Leu Pro Ser Arg Ser Ser Lys Ile Thr
    1295                1300                1305 cac cgt atc cac tgg gaa tct gcc agc ctc ctg cga tca gaa gag           3969
His Arg Ile His Trp Glu Ser Ala Ser Leu Leu Arg Ser Glu Glu
    1310                1315                1320 acc aag gaa aat gag ggt ttc aca gtc aca gct gaa gga aaa ggc           4014
Thr Lys Glu Asn Glu Gly Phe Thr Val Thr Ala Glu Gly Lys Gly
    1325                1330                1335 caa ggc acc ttg tcg gtg gtg aca atg tac cat gct aag gcc aaa           4059
Gln Gly Thr Leu Ser Val Val Thr Met Tyr His Ala Lys Ala Lys
    1340                1345                1350 gat caa ctc acc tgt aat aaa ttc gac ctc aag gtc acc ata aaa           4104
Asp Gln Leu Thr Cys Asn Lys Phe Asp Leu Lys Val Thr Ile Lys
    1355                1360                1365 cca gca ccg gaa aca gaa aag agg cct cag gat gcc aag aac act           4149
Pro Ala Pro Glu Thr Glu Lys Arg Pro Gln Asp Ala Lys Asn Thr
    1370                1375                1380 atg atc ctt gag atc tgt acc agg tac cgg gga gac cag gat gcc           4194
Met Ile Leu Glu Ile Cys Thr Arg Tyr Arg Gly Asp Gln Asp Ala
    1385                1390                1395 act atg tct ata ttg gac ata tcc atg atg act ggc ttt gct cca           4239
Thr Met Ser Ile Leu Asp Ile Ser Met Met Thr Gly Phe Ala Pro
    1400                1405                1410 gac aca gat gac ctg aag cag ctg gcc aat ggt gtt gac aga tac           4284
Asp Thr Asp Asp Leu Lys Gln Leu Ala Asn Gly Val Asp Arg Tyr
    1415                1420                1425 atc tcc aag tat gag ctg gac aaa gcc ttc tcc gat agg aac acc           4329
Ile Ser Lys Tyr Glu Leu Asp Lys Ala Phe Ser Asp Arg Asn Thr
    1430                1435                1440
```

```
ctc atc atc tac ctg gac aag gtc tca cac tct gag gat gac tgt    4374
Leu Ile Ile Tyr Leu Asp Lys Val Ser His Ser Glu Asp Asp Cys
    1445                1450                1455 cta gct ttc aaa gtt cac caa tac ttt aat gta gag ctt atc cag    4419
Leu Ala Phe Lys Val His Gln Tyr Phe Asn Val Glu Leu Ile Gln
1460                1465                1470 cct gga gca gtc aag gtc tac gcc tat tac aac ctg gag gaa agc    4464
Pro Gly Ala Val Lys Val Tyr Ala Tyr Tyr Asn Leu Glu Glu Ser
    1475                1480                1485 tgt acc cgg ttc tac cat ccg gaa aag gag gat gga aag ctg aac    4509
Cys Thr Arg Phe Tyr His Pro Glu Lys Glu Asp Gly Lys Leu Asn
    1490                1495                1500 aag ctc tgc cgt gat gaa ctg tgc cgc tgt gct gag gag aat tgc    4554
Lys Leu Cys Arg Asp Glu Leu Cys Arg Cys Ala Glu Glu Asn Cys
1505                1510                1515 ttc ata caa aag tcg gat gac aag gtc acc ctg gaa gaa cgg ctg    4599
Phe Ile Gln Lys Ser Asp Asp Lys Val Thr Leu Glu Glu Arg Leu
    1520                1525                1530 gac aag gcc tgt gag cca gga gtg gac tat gtg tac aaa acc aag    4644
Asp Lys Ala Cys Glu Pro Gly Val Asp Tyr Val Tyr Lys Thr Lys
    1535                1540                1545 ctg ctt cga ata gaa gaa caa gat ggt aat gat atc tat gtc atg    4689
Leu Leu Arg Ile Glu Glu Gln Asp Gly Asn Asp Ile Tyr Val Met
1550                1555                1560 gat gtt tta gaa gtt att aaa caa ggt act gac gaa aat cca cga    4734
Asp Val Leu Glu Val Ile Lys Gln Gly Thr Asp Glu Asn Pro Arg
    1565                1570                1575 gca aag acc cac cag tac ata agt caa agg aaa tgc cag gag gct    4779
Ala Lys Thr His Gln Tyr Ile Ser Gln Arg Lys Cys Gln Glu Ala
    1580                1585                1590 ctg aat ctg aag gtg aat gat gat tat ctg atc tgg ggt tcc agg    4824
Leu Asn Leu Lys Val Asn Asp Asp Tyr Leu Ile Trp Gly Ser Arg
1595                1600                1605 agt gac ctg ttg ccc acg aaa gat aaa att tcc tac atc att aca    4869
Ser Asp Leu Leu Pro Thr Lys Asp Lys Ile Ser Tyr Ile Ile Thr
    1610                1615                1620 aag aac aca tgg att gag aga tgg cca cat gaa gac gaa tgt cag    4914
Lys Asn Thr Trp Ile Glu Arg Trp Pro His Glu Asp Glu Cys Gln
    1625                1630                1635
```

<210> SEQ ID NO 8
<211> LENGTH: 1638
<212> TYPE: PRT
<213> ORGANISM: Artificial Sequence
<220> FEATURE:
<223> OTHER INFORMATION: Hybrid protein

<400> SEQUENCE: 8

```
Met Gly Pro Thr Ser Gly Pro Ser Leu Leu Leu Leu Leu Thr His
1               5                   10                  15

Leu Pro Leu Ala Leu Gly Ser Pro Met Tyr Ser Ile Ile Thr Pro Asn
                20                  25                  30

Ile Leu Arg Leu Glu Ser Glu Glu Thr Met Val Leu Glu Ala His Asp
            35                  40                  45

Ala Gln Gly Asp Val Pro Val Thr Val Thr Val His Asp Phe Pro Gly
        50                  55                  60

Lys Lys Leu Val Leu Ser Ser Glu Lys Thr Val Leu Thr Pro Ala Thr
65                  70                  75                  80

Asn His Met Gly Asn Val Thr Phe Thr Ile Pro Ala Asn Arg Glu Phe
                85                  90                  95
```

-continued

```
Lys Ser Glu Lys Gly Arg Asn Lys Phe Val Thr Val Gln Ala Thr Phe
            100                 105                 110
Gly Thr Gln Val Val Glu Lys Val Leu Val Ser Leu Gln Ser Gly
            115                 120                 125
Tyr Leu Phe Ile Gln Thr Asp Lys Thr Ile Tyr Thr Pro Gly Ser Thr
            130                 135                 140
Val Leu Tyr Arg Ile Phe Thr Val Asn His Lys Leu Leu Pro Val Gly
145                 150                 155                 160
Arg Thr Val Met Val Asn Ile Glu Asn Pro Glu Gly Ile Pro Val Lys
                    165                 170                 175
Gln Asp Ser Leu Ser Ser Gln Asn Gln Leu Gly Val Leu Pro Leu Ser
            180                 185                 190
Trp Asp Ile Pro Glu Leu Val Asn Met Gly Gln Trp Lys Ile Arg Ala
            195                 200                 205
Tyr Tyr Glu Asn Ser Pro Gln Gln Val Phe Ser Thr Glu Phe Glu Val
            210                 215                 220
Lys Glu Tyr Val Leu Pro Ser Phe Glu Val Ile Val Glu Pro Thr Glu
225                 230                 235                 240
Lys Phe Tyr Tyr Ile Tyr Asn Glu Lys Gly Leu Glu Val Thr Ile Thr
                    245                 250                 255
Ala Arg Phe Leu Tyr Gly Lys Lys Val Glu Gly Thr Ala Phe Val Ile
            260                 265                 270
Phe Gly Ile Gln Asp Gly Glu Gln Arg Ile Ser Leu Pro Glu Ser Leu
            275                 280                 285
Lys Arg Ile Pro Ile Glu Asp Gly Ser Gly Glu Val Val Leu Ser Arg
            290                 295                 300
Lys Val Leu Leu Asp Gly Val Gln Asn Leu Arg Ala Glu Asp Leu Val
305                 310                 315                 320
Gly Lys Ser Leu Tyr Val Ser Ala Thr Val Ile Leu His Ser Gly Ser
                    325                 330                 335
Asp Met Val Gln Ala Glu Arg Ser Gly Ile Pro Ile Val Thr Ser Pro
            340                 345                 350
Tyr Gln Ile His Phe Thr Lys Thr Pro Lys Tyr Phe Lys Pro Gly Met
            355                 360                 365
Pro Phe Asp Leu Met Val Phe Val Thr Asn Pro Asp Gly Ser Pro Ala
            370                 375                 380
Tyr Arg Val Pro Val Ala Val Gln Gly Glu Asp Thr Val Gln Ser Leu
385                 390                 395                 400
Thr Gln Gly Asp Gly Val Ala Lys Leu Ser Ile Asn Thr His Pro Ser
                    405                 410                 415
Gln Lys Pro Leu Ser Ile Thr Val Arg Thr Lys Lys Gln Glu Leu Ser
            420                 425                 430
Glu Ala Glu Gln Ala Thr Arg Thr Met Gln Ala Leu Pro Tyr Ser Thr
            435                 440                 445
Val Gly Asn Ser Asn Asn Tyr Leu His Leu Ser Val Leu Arg Thr Glu
            450                 455                 460
Leu Arg Pro Gly Glu Thr Leu Asn Val Asn Phe Leu Leu Arg Met Asp
465                 470                 475                 480
Arg Ala His Glu Ala Lys Ile Arg Tyr Tyr Thr Tyr Leu Ile Met Asn
                    485                 490                 495
Lys Gly Arg Leu Leu Lys Ala Gly Arg Gln Val Arg Glu Pro Gly Gln
            500                 505                 510
```

-continued

```
Asp Leu Val Val Leu Pro Leu Ser Ile Thr Thr Asp Phe Ile Pro Ser
    515                 520                 525

Phe Arg Leu Val Ala Tyr Tyr Thr Leu Ile Gly Ala Ser Gly Gln Arg
530                 535                 540

Glu Val Val Ala Asp Ser Val Trp Val Asp Val Lys Asp Ser Cys Val
545                 550                 555                 560

Gly Ser Leu Val Val Lys Ser Gly Gln Ser Glu Asp Arg Gln Pro Val
                565                 570                 575

Pro Gly Gln Gln Met Thr Leu Lys Ile Glu Gly Asp His Gly Ala Arg
                580                 585                 590

Val Val Leu Val Ala Val Asp Lys Gly Val Phe Val Leu Asn Lys Lys
            595                 600                 605

Asn Lys Leu Thr Gln Ser Lys Ile Trp Asp Val Glu Lys Ala Asp
    610                 615                 620

Ile Gly Cys Thr Pro Gly Ser Gly Lys Asp Tyr Ala Gly Val Phe Ser
625                 630                 635                 640

Asp Ala Gly Leu Thr Phe Thr Ser Ser Gly Gln Gln Thr Ala Gln
                645                 650                 655

Arg Ala Glu Leu Gln Cys Pro Gln Pro Ala Ala Arg Arg Arg Ser
                660                 665                 670

Val Gln Leu Thr Glu Lys Arg Met Asp Lys Val Gly Lys Tyr Pro Lys
                675                 680                 685

Glu Leu Arg Lys Cys Cys Glu Asp Gly Met Arg Glu Asn Pro Met Arg
            690                 695                 700

Phe Ser Cys Gln Arg Arg Thr Arg Phe Ile Ser Leu Gly Glu Ala Cys
705                 710                 715                 720

Lys Lys Val Phe Leu Asp Cys Cys Asn Tyr Ile Thr Glu Leu Arg Arg
                725                 730                 735

Gln His Ala Arg Ala Ser His Leu Gly Leu Ala Arg Ser Asn Leu Asp
                740                 745                 750

Glu Asp Ile Ile Ala Glu Glu Asn Ile Val Ser Arg Ser Glu Phe Pro
            755                 760                 765

Glu Ser Trp Leu Trp Asn Val Glu Asp Leu Lys Glu Pro Pro Lys Asn
770                 775                 780

Gly Ile Ser Thr Lys Leu Met Asn Ile Phe Leu Lys Asp Ser Ile Thr
785                 790                 795                 800

Thr Trp Glu Ile Leu Ala Val Ser Met Ser Asp Lys Lys Gly Ile Cys
                805                 810                 815

Val Ala Asp Pro Phe Glu Val Thr Val Met Gln Asp Phe Phe Ile Asp
                820                 825                 830

Leu Arg Leu Pro Tyr Ser Val Val Arg Asn Glu Gln Val Glu Ile Arg
                835                 840                 845

Ala Val Leu Tyr Asn Tyr Arg Gln Asn Gln Glu Leu Lys Val Arg Val
850                 855                 860

Glu Leu Leu His Asn Pro Ala Phe Cys Ser Leu Ala Thr Thr Lys Arg
865                 870                 875                 880

Arg His Gln Gln Thr Val Thr Ile Pro Pro Lys Ser Ser Leu Ser Val
                885                 890                 895

Pro Tyr Val Ile Val Pro Leu Lys Thr Gly Leu Gln Glu Val Glu Val
                900                 905                 910

Lys Ala Ala Val Tyr His His Phe Ile Ser Asp Gly Val Arg Lys Ser
            915                 920                 925

Leu Lys Val Val Pro Glu Gly Ile Arg Met Asn Lys Thr Val Ala Val
```

-continued

```
            930                935                940
Arg Thr Leu Asp Pro Glu Arg Leu Gly Arg Glu Gly Val Gln Lys Glu
945                950                955                960

Asp Ile Pro Pro Ala Asp Leu Ser Asp Gln Val Pro Asp Thr Glu Ser
                965                970                975

Glu Thr Arg Ile Leu Leu Gln Gly Thr Pro Val Ala Gln Met Thr Glu
            980                985                990

Asp Ala Val Asp Ala Glu Arg Leu Lys His Leu Ile Val Thr Pro Ser
            995                1000                1005

Gly Cys Gly Glu Gln Asn Met Ile Gly Met Thr Pro Thr Val Ile
    1010                1015                1020

Ala Val His Tyr Leu Asp Glu Thr Glu Gln Trp Glu Lys Phe Gly
    1025                1030                1035

Leu Glu Lys Arg Gln Gly Ala Leu Glu Leu Ile Lys Lys Gly Tyr
    1040                1045                1050

Thr Gln Gln Leu Ala Phe Arg Gln Pro Ser Ser Ala Phe Ala Ala
    1055                1060                1065

Phe Val Lys Arg Ala Pro Ser Thr Trp Leu Thr Ala Tyr Val Val
    1070                1075                1080

Lys Val Phe Ser Leu Ala Val Asn Leu Ile Ala Ile Asp Ser Gln
    1085                1090                1095

Val Leu Cys Gly Ala Val Lys Trp Leu Ile Leu Glu Lys Gln Lys
    1100                1105                1110

Pro Asp Gly Val Phe Gln Glu Asp Ala Pro Val Ile His Gln Glu
    1115                1120                1125

Met Ile Gly Gly Leu Arg Asn Asn Asn Glu Lys Asp Met Ala Leu
    1130                1135                1140

Thr Ala Phe Val Leu Ile Ser Leu Gln Glu Ala Lys Asp Ile Cys
    1145                1150                1155

Glu Glu Gln Val Asn Ser Leu Pro Gly Ser Ile Thr Lys Ala Gly
    1160                1165                1170

Asp Phe Leu Glu Ala Asn Tyr Met Asn Leu Gln Arg Ser Tyr Thr
    1175                1180                1185

Val Ala Ile Ala Gly Tyr Ala Leu Ala Gln Met Gly Arg Leu Lys
    1190                1195                1200

Gly Pro Leu Leu Asn Lys Phe Leu Thr Thr Ala Lys Asp Lys Asn
    1205                1210                1215

Arg Trp Glu Asp Pro Gly Lys Gln Leu Tyr Asn Val Glu Ala Thr
    1220                1225                1230

Ser Tyr Ala Leu Leu Ala Leu Leu Gln Leu Lys Asp Phe Asp Phe
    1235                1240                1245

Val Pro Pro Val Val Arg Trp Leu Asn Glu Gln Arg Tyr Tyr Gly
    1250                1255                1260

Gly Gly Tyr Gly Ser Thr Gln Ala Thr Phe Met Val Phe Gln Ala
    1265                1270                1275

Leu Ala Gln Tyr Gln Lys Asp Ala Pro Asp His Gln Glu Leu Asn
    1280                1285                1290

Leu Asp Val Ser Leu Gln Leu Pro Ser Arg Ser Ser Lys Ile Thr
    1295                1300                1305

His Arg Ile His Trp Glu Ser Ala Ser Leu Leu Arg Ser Glu Glu
    1310                1315                1320

Thr Lys Glu Asn Glu Gly Phe Thr Val Thr Ala Glu Gly Lys Gly
    1325                1330                1335
```

-continued

```
Gln Gly Thr Leu Ser Val Val Thr Met Tyr His Ala Lys Ala Lys
        1340                1345                1350

Asp Gln Leu Thr Cys Asn Lys Phe Asp Leu Lys Val Thr Ile Lys
        1355                1360                1365

Pro Ala Pro Glu Thr Glu Lys Arg Pro Gln Asp Ala Lys Asn Thr
        1370                1375                1380

Met Ile Leu Glu Ile Cys Thr Arg Tyr Arg Gly Asp Gln Asp Ala
        1385                1390                1395

Thr Met Ser Ile Leu Asp Ile Ser Met Met Thr Gly Phe Ala Pro
        1400                1405                1410

Asp Thr Asp Asp Leu Lys Gln Leu Ala Asn Gly Val Asp Arg Tyr
        1415                1420                1425

Ile Ser Lys Tyr Glu Leu Asp Lys Ala Phe Ser Asp Arg Asn Thr
        1430                1435                1440

Leu Ile Ile Tyr Leu Asp Lys Val Ser His Ser Glu Asp Asp Cys
        1445                1450                1455

Leu Ala Phe Lys Val His Gln Tyr Phe Asn Val Glu Leu Ile Gln
        1460                1465                1470

Pro Gly Ala Val Lys Val Tyr Ala Tyr Tyr Asn Leu Glu Glu Ser
        1475                1480                1485

Cys Thr Arg Phe Tyr His Pro Glu Lys Glu Asp Gly Lys Leu Asn
        1490                1495                1500

Lys Leu Cys Arg Asp Glu Leu Cys Arg Cys Ala Glu Glu Asn Cys
        1505                1510                1515

Phe Ile Gln Lys Ser Asp Asp Lys Val Thr Leu Glu Glu Arg Leu
        1520                1525                1530

Asp Lys Ala Cys Glu Pro Gly Val Asp Tyr Val Tyr Lys Thr Lys
        1535                1540                1545

Leu Leu Arg Ile Glu Glu Gln Asp Gly Asn Asp Ile Tyr Val Met
        1550                1555                1560

Asp Val Leu Glu Val Ile Lys Gln Gly Thr Asp Glu Asn Pro Arg
        1565                1570                1575

Ala Lys Thr His Gln Tyr Ile Ser Gln Arg Lys Cys Gln Glu Ala
        1580                1585                1590

Leu Asn Leu Lys Val Asn Asp Asp Tyr Leu Ile Trp Gly Ser Arg
        1595                1600                1605

Ser Asp Leu Leu Pro Thr Lys Asp Lys Ile Ser Tyr Ile Ile Thr
        1610                1615                1620

Lys Asn Thr Trp Ile Glu Arg Trp Pro His Glu Asp Glu Cys Gln
        1625                1630                1635
```

<210> SEQ ID NO 9
<211> LENGTH: 4992
<212> TYPE: DNA
<213> ORGANISM: Artificial Sequence
<220> FEATURE:
<223> OTHER INFORMATION: Recombinant Human C3
<220> FEATURE:
<221> NAME/KEY: CDS
<222> LOCATION: (1)..(4992)
<223> OTHER INFORMATION: Construct H5

<400> SEQUENCE: 9

```
atg gga ccc acc tca ggt ccc agc ctg ctg ctc ctg cta cta acc cac      48
Met Gly Pro Thr Ser Gly Pro Ser Leu Leu Leu Leu Leu Leu Thr His
1               5                   10                  15
```

```
ctc ccc ctg gct ctg ggg agt ccc atg tac tct atc atc acc ccc aac      96
Leu Pro Leu Ala Leu Gly Ser Pro Met Tyr Ser Ile Ile Thr Pro Asn
        20                  25                  30 atc ttg cgg ctg gag agc gag gag acc atg gtg ctg gag gcc cac gac     144
Ile Leu Arg Leu Glu Ser Glu Glu Thr Met Val Leu Glu Ala His Asp
            35                  40                  45 gcg caa ggg gat gtt cca gtc act gtt act gtc cac gac ttc cca ggc     192
Ala Gln Gly Asp Val Pro Val Thr Val Thr Val His Asp Phe Pro Gly
50                  55                  60 aaa aaa cta gtg ctg tcc agt gag aag act gtg ctg acc cct gcc acc     240
Lys Lys Leu Val Leu Ser Ser Glu Lys Thr Val Leu Thr Pro Ala Thr
65                  70                  75                  80 aac cac atg ggc aac gtc acc ttc acg atc cca gcc aac agg gag ttc     288
Asn His Met Gly Asn Val Thr Phe Thr Ile Pro Ala Asn Arg Glu Phe
                85                  90                  95 aag tca gaa aag ggg cgc aac aag ttc gtg acc gtg cag gcc acc ttc     336
Lys Ser Glu Lys Gly Arg Asn Lys Phe Val Thr Val Gln Ala Thr Phe
            100                 105                 110 ggg acc caa gtg gtg gag aag gtg gtg ctg gtc agc ctg cag agc ggg     384
Gly Thr Gln Val Val Glu Lys Val Val Leu Val Ser Leu Gln Ser Gly
        115                 120                 125 tac ctc ttc atc cag aca gac aag acc atc tac acc cct ggc tcc aca     432
Tyr Leu Phe Ile Gln Thr Asp Lys Thr Ile Tyr Thr Pro Gly Ser Thr
    130                 135                 140 gtt ctc tat cgg atc ttc acc gtc aac cac aag ctg cta ccc gtg ggc     480
Val Leu Tyr Arg Ile Phe Thr Val Asn His Lys Leu Leu Pro Val Gly
145                 150                 155                 160 cgg acg gtc atg gtc aac att gag aac ccg gaa ggc atc ccg gtc aag     528
Arg Thr Val Met Val Asn Ile Glu Asn Pro Glu Gly Ile Pro Val Lys
                165                 170                 175 cag gac tcc ttg tct tct cag aac cag ctt ggc gtc ttg ccc ttg tct     576
Gln Asp Ser Leu Ser Ser Gln Asn Gln Leu Gly Val Leu Pro Leu Ser
            180                 185                 190 tgg gac att ccg gaa ctc gtc aac atg ggc cag tgg aag atc cga gcc     624
Trp Asp Ile Pro Glu Leu Val Asn Met Gly Gln Trp Lys Ile Arg Ala
        195                 200                 205 tac tat gaa aac tca cca cag cag gtc ttc tcc act gag ttt gag gtg     672
Tyr Tyr Glu Asn Ser Pro Gln Gln Val Phe Ser Thr Glu Phe Glu Val
    210                 215                 220 aag gag tac gtg ctg ccc agt ttc gag gtc ata gtg gag cct aca gag     720
Lys Glu Tyr Val Leu Pro Ser Phe Glu Val Ile Val Glu Pro Thr Glu
225                 230                 235                 240 aaa ttc tac tac atc tat aac gag aag ggc ctg gag gtc acc atc acc     768
Lys Phe Tyr Tyr Ile Tyr Asn Glu Lys Gly Leu Glu Val Thr Ile Thr
                245                 250                 255 gcc agg ttc ctc tac ggg aag aaa gtg gag gga act gcc ttt gtc atc     816
Ala Arg Phe Leu Tyr Gly Lys Lys Val Glu Gly Thr Ala Phe Val Ile
            260                 265                 270 ttc ggg atc cag gat ggc gaa cag agg att tcc ctg cct gaa tcc ctc     864
Phe Gly Ile Gln Asp Gly Glu Gln Arg Ile Ser Leu Pro Glu Ser Leu
        275                 280                 285 aag cgc att ccg att gag gat ggc tcg ggg gag gtt gtg ctg agc cgg     912
Lys Arg Ile Pro Ile Glu Asp Gly Ser Gly Glu Val Val Leu Ser Arg
    290                 295                 300 aag gta ctg ctg gac ggg gtg cag aac ctc cga gca gaa gac ctg gtg     960
Lys Val Leu Leu Asp Gly Val Gln Asn Leu Arg Ala Glu Asp Leu Val
305                 310                 315                 320 ggg aag tct ttg tac gtg tct gcc acc gtc atc ttg cac tca ggc agt    1008
Gly Lys Ser Leu Tyr Val Ser Ala Thr Val Ile Leu His Ser Gly Ser
                325                 330                 335
```

```
gac atg gtg cag gca gag cgc agc ggg atc ccc atc gtg acc tct ccc    1056
Asp Met Val Gln Ala Glu Arg Ser Gly Ile Pro Ile Val Thr Ser Pro
            340                 345                 350 tac cag atc cac ttc acc aag aca ccc aag tac ttc aaa cca gga atg    1104
Tyr Gln Ile His Phe Thr Lys Thr Pro Lys Tyr Phe Lys Pro Gly Met
        355                 360                 365 ccc ttt gac ctc atg gtg ttc gtg acg aac cct gat ggc tct cca gcc    1152
Pro Phe Asp Leu Met Val Phe Val Thr Asn Pro Asp Gly Ser Pro Ala
370                 375                 380 tac cga gtc ccc gtg gca gtc cag ggc gag gac act gtg cag tct cta    1200
Tyr Arg Val Pro Val Ala Val Gln Gly Glu Asp Thr Val Gln Ser Leu
385                 390                 395                 400 acc cag gga gat ggc gtg gcc aaa ctc agc atc aac aca cac ccc agc    1248
Thr Gln Gly Asp Gly Val Ala Lys Leu Ser Ile Asn Thr His Pro Ser
                405                 410                 415 cag aag ccc ttg agc atc acg gtg cgc acg aag aag cag gag ctc tcg    1296
Gln Lys Pro Leu Ser Ile Thr Val Arg Thr Lys Lys Gln Glu Leu Ser
            420                 425                 430 gag gca gag cag gct acc agg acc atg cag gct ctg ccc tac agc acc    1344
Glu Ala Glu Gln Ala Thr Arg Thr Met Gln Ala Leu Pro Tyr Ser Thr
        435                 440                 445 gtg ggc aac tcc aac aat tac ctg cat ctc tca gtg cta cgt aca gag    1392
Val Gly Asn Ser Asn Asn Tyr Leu His Leu Ser Val Leu Arg Thr Glu
450                 455                 460 ctc aga ccc ggg gag acc ctc aac gtc aac ttc ctc ctg cga atg gac    1440
Leu Arg Pro Gly Glu Thr Leu Asn Val Asn Phe Leu Leu Arg Met Asp
465                 470                 475                 480 cgc gcc cac gag gcc aag atc cgc tac tac acc tac ctg atc atg aac    1488
Arg Ala His Glu Ala Lys Ile Arg Tyr Tyr Thr Tyr Leu Ile Met Asn
                485                 490                 495 aag ggc agg ctg ttg aag gcg gga cgc cag gtg cga gag ccc ggc cag    1536
Lys Gly Arg Leu Leu Lys Ala Gly Arg Gln Val Arg Glu Pro Gly Gln
            500                 505                 510 gac ctg gtg gtg ctg ccc ctg tcc atc acc acc gac ttc atc cct tcc    1584
Asp Leu Val Val Leu Pro Leu Ser Ile Thr Thr Asp Phe Ile Pro Ser
        515                 520                 525 ttc cgc ctg gtg gcg tac tac acg ctg atc ggt gcc agc ggc cag agg    1632
Phe Arg Leu Val Ala Tyr Tyr Thr Leu Ile Gly Ala Ser Gly Gln Arg
530                 535                 540 gag gtg gtg gcc gac tcc gtg tgg gtg gac gtc aag gac tcc tgc gtg    1680
Glu Val Val Ala Asp Ser Val Trp Val Asp Val Lys Asp Ser Cys Val
545                 550                 555                 560 ggc tcg ctg gtg gta aaa agc ggc cag tca gaa gac cgg cag cct gta    1728
Gly Ser Leu Val Val Lys Ser Gly Gln Ser Glu Asp Arg Gln Pro Val
                565                 570                 575 cct ggg cag cag atg acc ctg aag ata gag ggt gac cac ggg gcc cgg    1776
Pro Gly Gln Gln Met Thr Leu Lys Ile Glu Gly Asp His Gly Ala Arg
            580                 585                 590 gtg gta ctg gtg gcc gtg gac aag ggc gtg ttc gtg ctg aat aag aag    1824
Val Val Leu Val Ala Val Asp Lys Gly Val Phe Val Leu Asn Lys Lys
        595                 600                 605 aac aaa ctg acg cag agt aag atc tgg gac gtg gtg gag aag gca gac    1872
Asn Lys Leu Thr Gln Ser Lys Ile Trp Asp Val Val Glu Lys Ala Asp
610                 615                 620 atc ggc tgc acc ccg ggc agt ggg aag gat tac gcc ggt gtc ttc tcc    1920
Ile Gly Cys Thr Pro Gly Ser Gly Lys Asp Tyr Ala Gly Val Phe Ser
625                 630                 635                 640 gac gca ggg ctg acc ttc acg agc agc agt ggc cag cag acc gcc cag    1968
Asp Ala Gly Leu Thr Phe Thr Ser Ser Ser Gly Gln Gln Thr Ala Gln
```

-continued

```
                       645                 650                 655
agg gca gaa ctt cag tgc ccg cag cca gcc gcc cga cgc cgt tcc      2016
Arg Ala Glu Leu Gln Cys Pro Gln Pro Ala Ala Arg Arg Arg Ser
            660                 665                 670 gtg cag ctc acg gag aag cga atg gac aaa gtc ggc aag tac ccc aag  2064
Val Gln Leu Thr Glu Lys Arg Met Asp Lys Val Gly Lys Tyr Pro Lys
        675                 680                 685 gag ctg cgc aag tgc tgc gag gac ggc atg cgg gag aac ccc atg agg  2112
Glu Leu Arg Lys Cys Cys Glu Asp Gly Met Arg Glu Asn Pro Met Arg
    690                 695                 700 ttc tcg tgc cag cgc cgg acc cgt ttc atc tcc ctg ggc gag gcg tgc  2160
Phe Ser Cys Gln Arg Arg Thr Arg Phe Ile Ser Leu Gly Glu Ala Cys
705                 710                 715                 720 aag aag gtc ttc ctg gac tgc tgc aac tac atc aca gag ctg cgg cgg  2208
Lys Lys Val Phe Leu Asp Cys Cys Asn Tyr Ile Thr Glu Leu Arg Arg
                725                 730                 735 cag cac gcg cgg gcc agc cac ctg ggc ctg gcc agg agt aac ctg gat  2256
Gln His Ala Arg Ala Ser His Leu Gly Leu Ala Arg Ser Asn Leu Asp
            740                 745                 750 gag gac atc att gca gaa gag aac atc gtt tcc cga agt gag ttc cca  2304
Glu Asp Ile Ile Ala Glu Glu Asn Ile Val Ser Arg Ser Glu Phe Pro
        755                 760                 765 gag agc tgg ctg tgg aac gtt gag gac ttg aaa gag cca ccg aaa aat  2352
Glu Ser Trp Leu Trp Asn Val Glu Asp Leu Lys Glu Pro Pro Lys Asn
    770                 775                 780 gga atc tct acg aag ctc atg aat ata ttt ttg aaa gac tcc atc acc  2400
Gly Ile Ser Thr Lys Leu Met Asn Ile Phe Leu Lys Asp Ser Ile Thr
785                 790                 795                 800 acg tgg gag att ctg gct gtc agc atg tcg gac aag aaa ggg atc tgt  2448
Thr Trp Glu Ile Leu Ala Val Ser Met Ser Asp Lys Lys Gly Ile Cys
                805                 810                 815 gtg gca gac ccc ttc gag gtc aca gta atg cag gac ttc ttc atc gac  2496
Val Ala Asp Pro Phe Glu Val Thr Val Met Gln Asp Phe Phe Ile Asp
            820                 825                 830 ctg cgg cta ccc tac tct gtt gtt cga aac gag cag gtg gaa atc cga  2544
Leu Arg Leu Pro Tyr Ser Val Val Arg Asn Glu Gln Val Glu Ile Arg
        835                 840                 845 gcc gtt ctc tac aat tac cgg cag aac caa gag ctc aag gtg agg gtg  2592
Ala Val Leu Tyr Asn Tyr Arg Gln Asn Gln Glu Leu Lys Val Arg Val
    850                 855                 860 gaa cta ctc cac aat cca gcc ttc tgc agc ctg gcc acc acc aag agg  2640
Glu Leu Leu His Asn Pro Ala Phe Cys Ser Leu Ala Thr Thr Lys Arg
865                 870                 875                 880 cgt cac cag cag acc gta acc atc ccc ccc aag tcc tcg ttg tcc gtt  2688
Arg His Gln Gln Thr Val Thr Ile Pro Pro Lys Ser Ser Leu Ser Val
                885                 890                 895 cca tat gtc atc gtg ccg cta aag acc ggc ctg cag gaa gtg gaa gtc  2736
Pro Tyr Val Ile Val Pro Leu Lys Thr Gly Leu Gln Glu Val Glu Val
            900                 905                 910 aag gct gcc gtc tac cat cat ttc atc agt gac ggt gtc agg aag tcc  2784
Lys Ala Ala Val Tyr His His Phe Ile Ser Asp Gly Val Arg Lys Ser
        915                 920                 925 ctg aag gtc gtg ccg gaa gga atc aga atg aac aaa act gtg gct gtt  2832
Leu Lys Val Val Pro Glu Gly Ile Arg Met Asn Lys Thr Val Ala Val
    930                 935                 940 cgc acc ctg gat cca gaa cgc ctg ggc cgt gaa gga gtg cag aaa gag  2880
Arg Thr Leu Asp Pro Glu Arg Leu Gly Arg Glu Gly Val Gln Lys Glu
945                 950                 955                 960 gac atc cca cct gca gac ctc agt gac caa gtc ccg gac acc gag tct  2928
```

```
                Asp Ile Pro Pro Ala Asp Leu Ser Asp Gln Val Pro Asp Thr Glu Ser
                                965                 970                 975 gag acc aga att ctc ctg caa ggg acc cca gtg gcc cag atg aca gag           2976
Glu Thr Arg Ile Leu Leu Gln Gly Thr Pro Val Ala Gln Met Thr Glu
                980                 985                 990 gat gcc gtc gac gcg gaa cgg ctg aag cac ctc att gtg acc ccc tcg           3024
Asp Ala Val Asp Ala Glu Arg Leu Lys His Leu Ile Val Thr Pro Ser
        995                 1000                1005 ggc tgc ggg gaa cag aac atg atc ggc atg acg ccc acg gtc atc               3069
Gly Cys Gly Glu Gln Asn Met Ile Gly Met Thr Pro Thr Val Ile
    1010                1015                1020 gct gtg cat tac ctg gat gaa acg gag cag tgg gag aag ttc ggc               3114
Ala Val His Tyr Leu Asp Glu Thr Glu Gln Trp Glu Lys Phe Gly
    1025                1030                1035 cta gag aag cgg cag ggg gcc ttg gag ctc atc aag aag ggg tac               3159
Leu Glu Lys Arg Gln Gly Ala Leu Glu Leu Ile Lys Lys Gly Tyr
    1040                1045                1050 acc cag cag ctg gcc ttc aga caa ccc agc tct gcc ttt gcg gcc               3204
Thr Gln Gln Leu Ala Phe Arg Gln Pro Ser Ser Ala Phe Ala Ala
    1055                1060                1065 ttc gtg aaa cgg gca ccc agc acc tgg ctg acc gcc tac gtg gtc               3249
Phe Val Lys Arg Ala Pro Ser Thr Trp Leu Thr Ala Tyr Val Val
    1070                1075                1080 aag gtc ttc tct ctg gct gtc aac ctc atc gcc atc gac tcc caa               3294
Lys Val Phe Ser Leu Ala Val Asn Leu Ile Ala Ile Asp Ser Gln
    1085                1090                1095 gtc ctc tgc ggg gct gtt aaa tgg ctg atc ctg gag aag cag aag               3339
Val Leu Cys Gly Ala Val Lys Trp Leu Ile Leu Glu Lys Gln Lys
    1100                1105                1110 ccc gac ggg gtc ttc cag gag gat gcg ccc gtg ata cac caa gaa               3384
Pro Asp Gly Val Phe Gln Glu Asp Ala Pro Val Ile His Gln Glu
    1115                1120                1125 atg att ggt gga tta cgg aac aac aac gag aaa gac atg gcc ctc               3429
Met Ile Gly Gly Leu Arg Asn Asn Asn Glu Lys Asp Met Ala Leu
    1130                1135                1140 acg gcc ttt gtt ctc atc tcg ctg cag gag gct aaa gat att tgc               3474
Thr Ala Phe Val Leu Ile Ser Leu Gln Glu Ala Lys Asp Ile Cys
    1145                1150                1155 gag gag cag gtc aac agc ctg cca ggc agc atc act aaa gca gga               3519
Glu Glu Gln Val Asn Ser Leu Pro Gly Ser Ile Thr Lys Ala Gly
    1160                1165                1170 gac ttc ctt gaa gcc aac tac atg aac cta cag aga tcc tac act               3564
Asp Phe Leu Glu Ala Asn Tyr Met Asn Leu Gln Arg Ser Tyr Thr
    1175                1180                1185 gtg gcc att gct ggc tat gct ctg gcc cag atg ggc agg ctg aag               3609
Val Ala Ile Ala Gly Tyr Ala Leu Ala Gln Met Gly Arg Leu Lys
    1190                1195                1200 ggg cct ctt ctt aac aaa ttt ctg acc aca gcc aaa gat aag aac               3654
Gly Pro Leu Leu Asn Lys Phe Leu Thr Thr Ala Lys Asp Lys Asn
    1205                1210                1215 cgc tgg gag gac cct ggt aag cag ctc tac aac gtg gag gcc aca               3699
Arg Trp Glu Asp Pro Gly Lys Gln Leu Tyr Asn Val Glu Ala Thr
    1220                1225                1230 tcc tat gcc ctc ttg gcc cta ctg cag cta aaa gac ttt gac ttt               3744
Ser Tyr Ala Leu Leu Ala Leu Leu Gln Leu Lys Asp Phe Asp Phe
    1235                1240                1245 gtg cct ccc gtc gtg cgt tgg ctc aat gaa cag aga tac tac ggt               3789
Val Pro Pro Val Val Arg Trp Leu Asn Glu Gln Arg Tyr Tyr Gly
    1250                1255                1260
```

```
ggt ggc tat ggc tct acc cag gcc acc ttc atg gtg ttc caa gcc    3834
Gly Gly Tyr Gly Ser Thr Gln Ala Thr Phe Met Val Phe Gln Ala
1265                1270                1275 ttg gct caa tac caa aag gac gcc cct gac cac cag gaa ctg aac    3879
Leu Ala Gln Tyr Gln Lys Asp Ala Pro Asp His Gln Glu Leu Asn
    1280                1285                1290 ctt gat gtg tcc ctc caa ctg ccc agc cgc agc tcc aag atc acc    3924
Leu Asp Val Ser Leu Gln Leu Pro Ser Arg Ser Ser Lys Ile Thr
1295                1300                1305 cac cgt atc cac tgg gaa tct gcc agc ctc ctg cga tca gaa gag    3969
His Arg Ile His Trp Glu Ser Ala Ser Leu Leu Arg Ser Glu Glu
1310                1315                1320 acc aag gaa aat gag ggt ttc aca gtc aca gct gaa gga aaa ggc    4014
Thr Lys Glu Asn Glu Gly Phe Thr Val Thr Ala Glu Gly Lys Gly
1325                1330                1335 caa ggc acc ttg tcg gtg gtg aca atg tac cat gct aag gcc aaa    4059
Gln Gly Thr Leu Ser Val Val Thr Met Tyr His Ala Lys Ala Lys
1340                1345                1350 gat caa ctc acc tgt aat aaa ttc gac ctc aag gtc acc ata aaa    4104
Asp Gln Leu Thr Cys Asn Lys Phe Asp Leu Lys Val Thr Ile Lys
    1355                1360                1365 cca gca ccg gaa aca gaa aag agg cct cag gat gcc aag aac act    4149
Pro Ala Pro Glu Thr Glu Lys Arg Pro Gln Asp Ala Lys Asn Thr
1370                1375                1380 atg atc ctt gag atc tgc aca agg tat ctg gga gaa gtt gat tct    4194
Met Ile Leu Glu Ile Cys Thr Arg Tyr Leu Gly Glu Val Asp Ser
1385                1390                1395 aca atg aca ata att gat att tct atg ctg act ggt ttt ctc cct    4239
Thr Met Thr Ile Ile Asp Ile Ser Met Leu Thr Gly Phe Leu Pro
1400                1405                1410 gat gct gaa gac ctt aca agg ctt tct aaa gga gtg gac aga tac    4284
Asp Ala Glu Asp Leu Thr Arg Leu Ser Lys Gly Val Asp Arg Tyr
1415                1420                1425 atc tcc aga tat gaa gtt gac aat aat atg gct cag aaa gta gct    4329
Ile Ser Arg Tyr Glu Val Asp Asn Asn Met Ala Gln Lys Val Ala
1430                1435                1440 gtt atc att tac tta aac aag gtc tcc cac tct gaa gat gaa tgc    4374
Val Ile Ile Tyr Leu Asn Lys Val Ser His Ser Glu Asp Glu Cys
1445                1450                1455 ctg cac ttt aag att ctc aag cat ttt gaa gtt ggc ttc att cag    4419
Leu His Phe Lys Ile Leu Lys His Phe Glu Val Gly Phe Ile Gln
1460                1465                1470 cca gga tca gtc aag gtg tac agc tac tac aat cta gat gaa aaa    4464
Pro Gly Ser Val Lys Val Tyr Ser Tyr Tyr Asn Leu Asp Glu Lys
1475                1480                1485 tgt acc aag ttc tac cat cca gat aaa gga aca ggc ctt ctc aat    4509
Cys Thr Lys Phe Tyr His Pro Asp Lys Gly Thr Gly Leu Leu Asn
1490                1495                1500 aag ata tgt att ggt aac gtt tgc cga tgt gca gga gaa acc tgt    4554
Lys Ile Cys Ile Gly Asn Val Cys Arg Cys Ala Gly Glu Thr Cys
1505                1510                1515 tcc tcg ctc aac cat cag gaa agg att gat gtt cca tta caa att    4599
Ser Ser Leu Asn His Gln Glu Arg Ile Asp Val Pro Leu Gln Ile
1520                1525                1530 gaa aaa gcc tgc gag acg aat gtg gat tat gtc tac aaa acc aag    4644
Glu Lys Ala Cys Glu Thr Asn Val Asp Tyr Val Tyr Lys Thr Lys
1535                1540                1545 ctg ctt cga ata gaa gaa caa gat ggt aat gat atc tat gtc atg    4689
Leu Leu Arg Ile Glu Glu Gln Asp Gly Asn Asp Ile Tyr Val Met
1550                1555                1560
```

```
gat gtt tta gaa gtt att aaa caa ggt act gac gaa aat cca cga        4734
Asp Val Leu Glu Val Ile Lys Gln Gly Thr Asp Glu Asn Pro Arg
    1565                1570                1575 gca aag acc cac cag tac ata agt caa agg aaa tgc cag gag gct        4779
Ala Lys Thr His Gln Tyr Ile Ser Gln Arg Lys Cys Gln Glu Ala
1580                1585                1590 ctg aat ctg aag gtg aat gat gat tat ctg atc tgg ggt tcc agg        4824
Leu Asn Leu Lys Val Asn Asp Asp Tyr Leu Ile Trp Gly Ser Arg
    1595                1600                1605 agt gac ctg ttg ccc acg aaa gat aaa att tcc tac atc att aca        4869
Ser Asp Leu Leu Pro Thr Lys Asp Lys Ile Ser Tyr Ile Ile Thr
1610                1615                1620 aag aac aca tgg att gag aga tgg cca cat gaa gac gaa tgt cag        4914
Lys Asn Thr Trp Ile Glu Arg Trp Pro His Glu Asp Glu Cys Gln
    1625                1630                1635 gaa gaa gaa ttc caa aag ttg tgt gat gac ttt gct cag ttt agc        4959
Glu Glu Glu Phe Gln Lys Leu Cys Asp Asp Phe Ala Gln Phe Ser
1640                1645                1650 tac aca ttg act gag ttt ggc tgc cct act taa                         4992
Tyr Thr Leu Thr Glu Phe Gly Cys Pro Thr
    1655                1660

<210> SEQ ID NO 10
<211> LENGTH: 1663
<212> TYPE: PRT
<213> ORGANISM: Artificial Sequence
<220> FEATURE:
<223> OTHER INFORMATION: Recombinant Human C3

<400> SEQUENCE: 10

Met Gly Pro Thr Ser Gly Pro Ser Leu Leu Leu Leu Leu Thr His
1               5                   10                  15

Leu Pro Leu Ala Leu Gly Ser Pro Met Tyr Ser Ile Ile Thr Pro Asn
                20                  25                  30

Ile Leu Arg Leu Glu Ser Glu Glu Thr Met Val Leu Glu Ala His Asp
            35                  40                  45

Ala Gln Gly Asp Val Pro Val Thr Val Thr Val His Asp Phe Pro Gly
        50                  55                  60

Lys Lys Leu Val Leu Ser Ser Glu Lys Thr Val Leu Thr Pro Ala Thr
65                  70                  75                  80

Asn His Met Gly Asn Val Thr Phe Thr Ile Pro Ala Asn Arg Glu Phe
                85                  90                  95

Lys Ser Glu Lys Gly Arg Asn Lys Phe Val Thr Val Gln Ala Thr Phe
            100                 105                 110

Gly Thr Gln Val Val Glu Lys Val Val Leu Val Ser Leu Gln Ser Gly
        115                 120                 125

Tyr Leu Phe Ile Gln Thr Asp Lys Thr Ile Tyr Thr Pro Gly Ser Thr
    130                 135                 140

Val Leu Tyr Arg Ile Phe Thr Val Asn His Lys Leu Leu Pro Val Gly
145                 150                 155                 160

Arg Thr Val Met Val Asn Ile Glu Asn Pro Glu Gly Ile Pro Val Lys
                165                 170                 175

Gln Asp Ser Leu Ser Ser Gln Asn Gln Leu Gly Val Leu Pro Leu Ser
            180                 185                 190

Trp Asp Ile Pro Glu Leu Val Asn Met Gly Gln Trp Lys Ile Arg Ala
        195                 200                 205

Tyr Tyr Glu Asn Ser Pro Gln Gln Val Phe Ser Thr Glu Phe Glu Val
```

-continued

```
                210                 215                 220
Lys Glu Tyr Val Leu Pro Ser Phe Glu Val Ile Glu Pro Thr Glu
225                 230                 235                 240

Lys Phe Tyr Tyr Ile Tyr Asn Glu Lys Gly Leu Glu Val Thr Ile Thr
                245                 250                 255

Ala Arg Phe Leu Tyr Gly Lys Lys Val Glu Gly Thr Ala Phe Val Ile
                260                 265                 270

Phe Gly Ile Gln Asp Gly Glu Gln Arg Ile Ser Leu Pro Glu Ser Leu
                275                 280                 285

Lys Arg Ile Pro Ile Glu Asp Gly Ser Gly Val Val Leu Ser Arg
290                 295                 300

Lys Val Leu Leu Asp Gly Val Gln Asn Leu Arg Ala Glu Asp Leu Val
305                 310                 315                 320

Gly Lys Ser Leu Tyr Val Ser Ala Thr Val Ile Leu His Ser Gly Ser
                325                 330                 335

Asp Met Val Gln Ala Glu Arg Ser Gly Ile Pro Ile Val Thr Ser Pro
                340                 345                 350

Tyr Gln Ile His Phe Thr Lys Thr Pro Lys Tyr Phe Lys Pro Gly Met
                355                 360                 365

Pro Phe Asp Leu Met Val Phe Val Thr Asn Pro Asp Gly Ser Pro Ala
370                 375                 380

Tyr Arg Val Pro Val Ala Val Gln Gly Glu Asp Thr Val Gln Ser Leu
385                 390                 395                 400

Thr Gln Gly Asp Gly Val Ala Lys Leu Ser Ile Asn Thr His Pro Ser
                405                 410                 415

Gln Lys Pro Leu Ser Ile Thr Val Arg Thr Lys Lys Gln Glu Leu Ser
                420                 425                 430

Glu Ala Glu Gln Ala Thr Arg Thr Met Gln Ala Leu Pro Tyr Ser Thr
                435                 440                 445

Val Gly Asn Ser Asn Asn Tyr Leu His Leu Ser Val Leu Arg Thr Glu
                450                 455                 460

Leu Arg Pro Gly Glu Thr Leu Asn Val Asn Phe Leu Leu Arg Met Asp
465                 470                 475                 480

Arg Ala His Glu Ala Lys Ile Arg Tyr Tyr Thr Tyr Leu Ile Met Asn
                485                 490                 495

Lys Gly Arg Leu Leu Lys Ala Gly Arg Gln Val Arg Glu Pro Gly Gln
                500                 505                 510

Asp Leu Val Val Leu Pro Leu Ser Ile Thr Thr Asp Phe Ile Pro Ser
                515                 520                 525

Phe Arg Leu Val Ala Tyr Tyr Thr Leu Ile Gly Ala Ser Gly Gln Arg
530                 535                 540

Glu Val Val Ala Asp Ser Val Trp Val Asp Val Lys Asp Ser Cys Val
545                 550                 555                 560

Gly Ser Leu Val Val Lys Ser Gly Gln Ser Glu Asp Arg Gln Pro Val
                565                 570                 575

Pro Gly Gln Gln Met Thr Leu Lys Ile Glu Gly Asp His Gly Ala Arg
                580                 585                 590

Val Val Leu Val Ala Val Asp Lys Gly Val Phe Val Leu Asn Lys Lys
                595                 600                 605

Asn Lys Leu Thr Gln Ser Lys Ile Trp Asp Val Val Glu Lys Ala Asp
                610                 615                 620

Ile Gly Cys Thr Pro Gly Ser Gly Lys Asp Tyr Ala Gly Val Phe Ser
625                 630                 635                 640
```

-continued

Asp Ala Gly Leu Thr Phe Thr Ser Ser Gly Gln Gln Thr Ala Gln
            645                 650                 655

Arg Ala Glu Leu Gln Cys Pro Gln Pro Ala Arg Arg Arg Ser
        660                 665                 670

Val Gln Leu Thr Glu Lys Arg Met Asp Lys Val Gly Lys Tyr Pro Lys
        675                 680                 685

Glu Leu Arg Lys Cys Cys Glu Asp Gly Met Arg Glu Asn Pro Met Arg
    690                 695                 700

Phe Ser Cys Gln Arg Arg Thr Arg Phe Ile Ser Leu Gly Glu Ala Cys
705                 710                 715                 720

Lys Lys Val Phe Leu Asp Cys Cys Asn Tyr Ile Thr Glu Leu Arg Arg
                725                 730                 735

Gln His Ala Arg Ala Ser His Leu Gly Leu Ala Arg Ser Asn Leu Asp
                740                 745                 750

Glu Asp Ile Ile Ala Glu Glu Asn Ile Val Ser Arg Ser Glu Phe Pro
            755                 760                 765

Glu Ser Trp Leu Trp Asn Val Glu Asp Leu Lys Glu Pro Pro Lys Asn
    770                 775                 780

Gly Ile Ser Thr Lys Leu Met Asn Ile Phe Leu Lys Asp Ser Ile Thr
785                 790                 795                 800

Thr Trp Glu Ile Leu Ala Val Ser Met Ser Asp Lys Lys Gly Ile Cys
                805                 810                 815

Val Ala Asp Pro Phe Glu Val Thr Val Met Gln Asp Phe Phe Ile Asp
                820                 825                 830

Leu Arg Leu Pro Tyr Ser Val Arg Asn Glu Gln Val Glu Ile Arg
                835                 840                 845

Ala Val Leu Tyr Asn Tyr Arg Gln Asn Gln Glu Leu Lys Val Arg Val
            850                 855                 860

Glu Leu Leu His Asn Pro Ala Phe Cys Ser Leu Ala Thr Thr Lys Arg
865                 870                 875                 880

Arg His Gln Gln Thr Val Thr Ile Pro Pro Lys Ser Ser Leu Ser Val
                885                 890                 895

Pro Tyr Val Ile Val Pro Leu Lys Thr Gly Leu Gln Glu Val Glu Val
            900                 905                 910

Lys Ala Ala Val Tyr His His Phe Ile Ser Asp Gly Val Arg Lys Ser
        915                 920                 925

Leu Lys Val Val Pro Glu Gly Ile Arg Met Asn Lys Thr Val Ala Val
        930                 935                 940

Arg Thr Leu Asp Pro Glu Arg Leu Gly Arg Glu Gly Val Gln Lys Glu
945                 950                 955                 960

Asp Ile Pro Pro Ala Asp Leu Ser Asp Gln Val Pro Asp Thr Glu Ser
                965                 970                 975

Glu Thr Arg Ile Leu Leu Gln Gly Thr Pro Val Ala Gln Met Thr Glu
                980                 985                 990

Asp Ala Val Asp Ala Glu Arg Leu Lys His Leu Ile Val Thr Pro Ser
            995                 1000                1005

Gly Cys Gly Glu Gln Asn Met Ile Gly Met Thr Pro Thr Val Ile
    1010                1015                1020

Ala Val His Tyr Leu Asp Glu Thr Glu Gln Trp Glu Lys Phe Gly
    1025                1030                1035

Leu Glu Lys Arg Gln Gly Ala Leu Glu Leu Ile Lys Lys Gly Tyr
    1040                1045                1050

-continued

```
Thr Gln Gln Leu Ala Phe Arg Gln Pro Ser Ser Ala Phe Ala Ala
    1055                1060                1065

Phe Val Lys Arg Ala Pro Ser Thr Trp Leu Thr Ala Tyr Val Val
    1070                1075                1080

Lys Val Phe Ser Leu Ala Val Asn Leu Ile Ala Ile Asp Ser Gln
    1085                1090                1095

Val Leu Cys Gly Ala Val Lys Trp Leu Ile Leu Glu Lys Gln Lys
    1100                1105                1110

Pro Asp Gly Val Phe Gln Glu Asp Ala Pro Val Ile His Gln Glu
    1115                1120                1125

Met Ile Gly Gly Leu Arg Asn Asn Asn Glu Lys Asp Met Ala Leu
    1130                1135                1140

Thr Ala Phe Val Leu Ile Ser Leu Gln Glu Ala Lys Asp Ile Cys
    1145                1150                1155

Glu Glu Gln Val Asn Ser Leu Pro Gly Ser Ile Thr Lys Ala Gly
    1160                1165                1170

Asp Phe Leu Glu Ala Asn Tyr Met Asn Leu Gln Arg Ser Tyr Thr
    1175                1180                1185

Val Ala Ile Ala Gly Tyr Ala Leu Ala Gln Met Gly Arg Leu Lys
    1190                1195                1200

Gly Pro Leu Leu Asn Lys Phe Leu Thr Thr Ala Lys Asp Lys Asn
    1205                1210                1215

Arg Trp Glu Asp Pro Gly Lys Gln Leu Tyr Asn Val Glu Ala Thr
    1220                1225                1230

Ser Tyr Ala Leu Leu Ala Leu Leu Gln Leu Lys Asp Phe Asp Phe
    1235                1240                1245

Val Pro Pro Val Val Arg Trp Leu Asn Glu Gln Arg Tyr Tyr Gly
    1250                1255                1260

Gly Gly Tyr Gly Ser Thr Gln Ala Thr Phe Met Val Phe Gln Ala
    1265                1270                1275

Leu Ala Gln Tyr Gln Lys Asp Ala Pro Asp His Gln Glu Leu Asn
    1280                1285                1290

Leu Asp Val Ser Leu Gln Leu Pro Ser Arg Ser Ser Lys Ile Thr
    1295                1300                1305

His Arg Ile His Trp Glu Ser Ala Ser Leu Leu Arg Ser Glu Glu
    1310                1315                1320

Thr Lys Glu Asn Glu Gly Phe Thr Val Thr Ala Glu Gly Lys Gly
    1325                1330                1335

Gln Gly Thr Leu Ser Val Val Thr Met Tyr His Ala Lys Ala Lys
    1340                1345                1350

Asp Gln Leu Thr Cys Asn Lys Phe Asp Leu Lys Val Thr Ile Lys
    1355                1360                1365

Pro Ala Pro Glu Thr Glu Lys Arg Pro Gln Asp Ala Lys Asn Thr
    1370                1375                1380

Met Ile Leu Glu Ile Cys Thr Arg Tyr Leu Gly Glu Val Asp Ser
    1385                1390                1395

Thr Met Thr Ile Ile Asp Ile Ser Met Leu Thr Gly Phe Leu Pro
    1400                1405                1410

Asp Ala Glu Asp Leu Thr Arg Leu Ser Lys Gly Val Asp Arg Tyr
    1415                1420                1425

Ile Ser Arg Tyr Glu Val Asp Asn Asn Met Ala Gln Lys Val Ala
    1430                1435                1440

Val Ile Ile Tyr Leu Asn Lys Val Ser His Ser Glu Asp Glu Cys
```

-continued

```
                 1445                1450                1455

Leu His Phe Lys Ile Leu Lys His Phe Glu Val Gly Phe Ile Gln
    1460                1465                1470

Pro Gly Ser Val Lys Val Tyr Ser Tyr Tyr Asn Leu Asp Glu Lys
    1475                1480                1485

Cys Thr Lys Phe Tyr His Pro Asp Lys Gly Thr Gly Leu Leu Asn
    1490                1495                1500

Lys Ile Cys Ile Gly Asn Val Cys Arg Cys Ala Gly Glu Thr Cys
    1505                1510                1515

Ser Ser Leu Asn His Gln Glu Arg Ile Asp Val Pro Leu Gln Ile
    1520                1525                1530

Glu Lys Ala Cys Glu Thr Asn Val Asp Tyr Val Tyr Lys Thr Lys
    1535                1540                1545

Leu Leu Arg Ile Glu Glu Gln Asp Gly Asn Asp Ile Tyr Val Met
    1550                1555                1560

Asp Val Leu Glu Val Ile Lys Gln Gly Thr Asp Glu Asn Pro Arg
    1565                1570                1575

Ala Lys Thr His Gln Tyr Ile Ser Gln Arg Lys Cys Gln Glu Ala
    1580                1585                1590

Leu Asn Leu Lys Val Asn Asp Asp Tyr Leu Ile Trp Gly Ser Arg
    1595                1600                1605

Ser Asp Leu Leu Pro Thr Lys Asp Lys Ile Ser Tyr Ile Ile Thr
    1610                1615                1620

Lys Asn Thr Trp Ile Glu Arg Trp Pro His Glu Asp Glu Cys Gln
    1625                1630                1635

Glu Glu Glu Phe Gln Lys Leu Cys Asp Asp Phe Ala Gln Phe Ser
    1640                1645                1650

Tyr Thr Leu Thr Glu Phe Gly Cys Pro Thr
    1655                1660

<210> SEQ ID NO 11
<211> LENGTH: 4914
<212> TYPE: DNA
<213> ORGANISM: Artificial Sequence
<220> FEATURE:
<223> OTHER INFORMATION: Hybrid protein
<220> FEATURE:
<221> NAME/KEY: CDS
<222> LOCATION: (1)..(4914)
<223> OTHER INFORMATION: Construct H6 truncated

<400> SEQUENCE: 11 atg gga ccc acc tca ggt ccc agc ctg ctg ctc ctg cta cta acc cac      48
Met Gly Pro Thr Ser Gly Pro Ser Leu Leu Leu Leu Leu Leu Thr His
1               5                   10                  15 ctc ccc ctg gct ctg ggg agt ccc atg tac tct atc atc acc ccc aac      96
Leu Pro Leu Ala Leu Gly Ser Pro Met Tyr Ser Ile Ile Thr Pro Asn
            20                  25                  30 atc ttg cgg ctg gag agc gag gag acc atg gtg ctg gag gcc cac gac     144
Ile Leu Arg Leu Glu Ser Glu Glu Thr Met Val Leu Glu Ala His Asp
        35                  40                  45 gcg caa ggg gat gtt cca gtc act gtt act gtc cac gac ttc cca ggc     192
Ala Gln Gly Asp Val Pro Val Thr Val Thr Val His Asp Phe Pro Gly
    50                  55                  60 aaa aaa cta gtg ctg tcc agt gag aag act gtg ctg acc cct gcc acc     240
Lys Lys Leu Val Leu Ser Ser Glu Lys Thr Val Leu Thr Pro Ala Thr
65                  70                  75                  80 aac cac atg ggc aac gtc acc ttc acg atc cca gcc aac agg gag ttc     288
```

-continued

```
            Asn His Met Gly Asn Val Thr Phe Thr Ile Pro Ala Asn Arg Glu Phe
                            85                  90                  95 aag tca gaa aag ggg cgc aac aag ttc gtg acc gtg cag gcc acc ttc          336
Lys Ser Glu Lys Gly Arg Asn Lys Phe Val Thr Val Gln Ala Thr Phe
            100                 105                 110 ggg acc caa gtg gtg gag aag gtg gtg ctg gtc agc ctg cag agc ggg          384
Gly Thr Gln Val Val Glu Lys Val Val Leu Val Ser Leu Gln Ser Gly
            115                 120                 125 tac ctc ttc atc cag aca gac aag acc atc tac acc cct ggc tcc aca          432
Tyr Leu Phe Ile Gln Thr Asp Lys Thr Ile Tyr Thr Pro Gly Ser Thr
    130                 135                 140 gtt ctc tat cgg atc ttc acc gtc aac cac aag ctg cta ccc gtg ggc          480
Val Leu Tyr Arg Ile Phe Thr Val Asn His Lys Leu Leu Pro Val Gly
145                 150                 155                 160 cgg acg gtc atg gtc aac att gag aac ccg gaa ggc atc ccg gtc aag          528
Arg Thr Val Met Val Asn Ile Glu Asn Pro Glu Gly Ile Pro Val Lys
                165                 170                 175 cag gac tcc ttg tct tct cag aac cag ctt ggc gtc ttg ccc ttg tct          576
Gln Asp Ser Leu Ser Ser Gln Asn Gln Leu Gly Val Leu Pro Leu Ser
            180                 185                 190 tgg gac att ccg gaa ctc gtc aac atg ggc cag tgg aag atc cga gcc          624
Trp Asp Ile Pro Glu Leu Val Asn Met Gly Gln Trp Lys Ile Arg Ala
            195                 200                 205 tac tat gaa aac tca cca cag cag gtc ttc tcc act gag ttt gag gtg          672
Tyr Tyr Glu Asn Ser Pro Gln Gln Val Phe Ser Thr Glu Phe Glu Val
    210                 215                 220 aag gag tac gtg ctg ccc agt ttc gag gtc ata gtg gag cct aca gag          720
Lys Glu Tyr Val Leu Pro Ser Phe Glu Val Ile Val Glu Pro Thr Glu
225                 230                 235                 240 aaa ttc tac tac atc tat aac gag aag ggc ctg gag gtc acc atc acc          768
Lys Phe Tyr Tyr Ile Tyr Asn Glu Lys Gly Leu Glu Val Thr Ile Thr
                245                 250                 255 gcc agg ttc ctc tac ggg aag aaa gtg gag gga act gcc ttt gtc atc          816
Ala Arg Phe Leu Tyr Gly Lys Lys Val Glu Gly Thr Ala Phe Val Ile
            260                 265                 270 ttc ggg atc cag gat ggc gaa cag agg att tcc ctg cct gaa tcc ctc          864
Phe Gly Ile Gln Asp Gly Glu Gln Arg Ile Ser Leu Pro Glu Ser Leu
            275                 280                 285 aag cgc att ccg att gag gat ggc tcg ggg gag gtt gtg ctg agc cgg          912
Lys Arg Ile Pro Ile Glu Asp Gly Ser Gly Glu Val Val Leu Ser Arg
    290                 295                 300 aag gta ctg ctg gac ggg gtg cag aac ctc cga gca gaa gac ctg gtg          960
Lys Val Leu Leu Asp Gly Val Gln Asn Leu Arg Ala Glu Asp Leu Val
305                 310                 315                 320 ggg aag tct ttg tac gtg tct gcc acc gtc atc ttg cac tca ggc agt         1008
Gly Lys Ser Leu Tyr Val Ser Ala Thr Val Ile Leu His Ser Gly Ser
                325                 330                 335 gac atg gtg cag gca gag cgc agc ggg atc ccc atc gtg acc tct ccc         1056
Asp Met Val Gln Ala Glu Arg Ser Gly Ile Pro Ile Val Thr Ser Pro
            340                 345                 350 tac cag atc cac ttc acc aag aca ccc aag tac ttc aaa cca gga atg         1104
Tyr Gln Ile His Phe Thr Lys Thr Pro Lys Tyr Phe Lys Pro Gly Met
            355                 360                 365 ccc ttt gac ctc atg gtg ttc gtg acg aac cct gat ggc tct cca gcc         1152
Pro Phe Asp Leu Met Val Phe Val Thr Asn Pro Asp Gly Ser Pro Ala
    370                 375                 380 tac cga gtc ccc gtg gca gtc cag ggc gag gac act gtg cag tct cta         1200
Tyr Arg Val Pro Val Ala Val Gln Gly Glu Asp Thr Val Gln Ser Leu
385                 390                 395                 400
```

```
                                            -continued
acc cag gga gat ggc gtg gcc aaa ctc agc atc aac aca cac ccc agc    1248
Thr Gln Gly Asp Gly Val Ala Lys Leu Ser Ile Asn Thr His Pro Ser
                405                 410                 415 cag aag ccc ttg agc atc acg gtg cgc acg aag aag cag gag ctc tcg    1296
Gln Lys Pro Leu Ser Ile Thr Val Arg Thr Lys Lys Gln Glu Leu Ser
            420                 425                 430 gag gca gag cag gct acc agg acc atg cag gct ctg ccc tac agc acc    1344
Glu Ala Glu Gln Ala Thr Arg Thr Met Gln Ala Leu Pro Tyr Ser Thr
        435                 440                 445 gtg ggc aac tcc aac aat tac ctg cat ctc tca gtg cta cgt aca gag    1392
Val Gly Asn Ser Asn Asn Tyr Leu His Leu Ser Val Leu Arg Thr Glu
    450                 455                 460 ctc aga ccc ggg gag acc ctc aac gtc aac ttc ctc ctg cga atg gac    1440
Leu Arg Pro Gly Glu Thr Leu Asn Val Asn Phe Leu Leu Arg Met Asp
465                 470                 475                 480 cgc gcc cac gag gcc aag atc cgc tac tac acc tac ctg atc atg aac    1488
Arg Ala His Glu Ala Lys Ile Arg Tyr Tyr Thr Tyr Leu Ile Met Asn
                485                 490                 495 aag ggc agg ctg ttg aag gcg gga cgc cag gtg cga gag ccc ggc cag    1536
Lys Gly Arg Leu Leu Lys Ala Gly Arg Gln Val Arg Glu Pro Gly Gln
            500                 505                 510 gac ctg gtg gtg ctg ccc ctg tcc atc acc acc gac ttc atc cct tcc    1584
Asp Leu Val Val Leu Pro Leu Ser Ile Thr Thr Asp Phe Ile Pro Ser
        515                 520                 525 ttc cgc ctg gtg gcg tac tac acg ctg atc ggt gcc agc ggc cag agg    1632
Phe Arg Leu Val Ala Tyr Tyr Thr Leu Ile Gly Ala Ser Gly Gln Arg
    530                 535                 540 gag gtg gtg gcc gac tcc gtg tgg gtg gac gtc aag gac tcc tgc gtg    1680
Glu Val Val Ala Asp Ser Val Trp Val Asp Val Lys Asp Ser Cys Val
545                 550                 555                 560 ggc tcg ctg gtg gta aaa agc ggc cag tca gaa gac cgg cag cct gta    1728
Gly Ser Leu Val Val Lys Ser Gly Gln Ser Glu Asp Arg Gln Pro Val
                565                 570                 575 cct ggg cag cag atg acc ctg aag ata gag ggt gac cac ggg gcc cgg    1776
Pro Gly Gln Gln Met Thr Leu Lys Ile Glu Gly Asp His Gly Ala Arg
            580                 585                 590 gtg gta ctg gtg gcc gtg gac aag ggc gtg ttc gtg ctg aat aag aag    1824
Val Val Leu Val Ala Val Asp Lys Gly Val Phe Val Leu Asn Lys Lys
        595                 600                 605 aac aaa ctg acg cag agt aag atc tgg gac gtg gtg gag aag gca gac    1872
Asn Lys Leu Thr Gln Ser Lys Ile Trp Asp Val Val Glu Lys Ala Asp
    610                 615                 620 atc ggc tgc acc ccg ggc agt ggg aag gat tac gcc ggt gtc ttc tcc    1920
Ile Gly Cys Thr Pro Gly Ser Gly Lys Asp Tyr Ala Gly Val Phe Ser
625                 630                 635                 640 gac gca ggg ctg acc ttc acg agc agc agt ggc cag cag acc gcc cag    1968
Asp Ala Gly Leu Thr Phe Thr Ser Ser Ser Gly Gln Gln Thr Ala Gln
                645                 650                 655 agg gca gaa ctt cag tgc ccg cag cca gcc gcc cgc cga cgc cgt tcc    2016
Arg Ala Glu Leu Gln Cys Pro Gln Pro Ala Ala Arg Arg Arg Arg Ser
            660                 665                 670 gtg cag ctc acg gag aag cga atg gac aaa gtc ggc aag tac ccc aag    2064
Val Gln Leu Thr Glu Lys Arg Met Asp Lys Val Gly Lys Tyr Pro Lys
        675                 680                 685 gag ctg cgc aag tgc tgc gag gac ggc atg cgg gag aac ccc atg agg    2112
Glu Leu Arg Lys Cys Cys Glu Asp Gly Met Arg Glu Asn Pro Met Arg
    690                 695                 700 ttc tcg tgc cag cgc cgg acc cgt ttc atc tcc ctg ggc gag gcg tgc    2160
Phe Ser Cys Gln Arg Arg Thr Arg Phe Ile Ser Leu Gly Glu Ala Cys
705                 710                 715                 720
```

-continued

| | |
|---|---|
| aag aag gtc ttc ctg gac tgc tgc aac tac atc aca gag ctg cgg cgg<br>Lys Lys Val Phe Leu Asp Cys Cys Asn Tyr Ile Thr Glu Leu Arg Arg<br>                725                        730                     735 | 2208 |
| cag cac gcg cgg gcc agc cac ctg ggc ctg gcc agg agt aac ctg gat<br>Gln His Ala Arg Ala Ser His Leu Gly Leu Ala Arg Ser Asn Leu Asp<br>        740                           745                         750 | 2256 |
| gag gac atc att gca gaa gag aac atc gtt tcc cga agt gag ttc cca<br>Glu Asp Ile Ile Ala Glu Glu Asn Ile Val Ser Arg Ser Glu Phe Pro<br>755                          760                       765 | 2304 |
| gag agc tgg ctg tgg aac gtt gag gac ttg aaa gag cca ccg aaa aat<br>Glu Ser Trp Leu Trp Asn Val Glu Asp Leu Lys Glu Pro Pro Lys Asn<br>    770                       775                     780 | 2352 |
| gga atc tct acg aag ctc atg aat ata ttt ttg aaa gac tcc atc acc<br>Gly Ile Ser Thr Lys Leu Met Asn Ile Phe Leu Lys Asp Ser Ile Thr<br>785                       790                     795                   800 | 2400 |
| acg tgg gag att ctg gct gtc agc atg tcg gac aag aaa ggg atc tgt<br>Thr Trp Glu Ile Leu Ala Val Ser Met Ser Asp Lys Lys Gly Ile Cys<br>                805                       810                     815 | 2448 |
| gtg gca gac ccc ttc gag gtc aca gta atg cag gac ttc ttc atc gac<br>Val Ala Asp Pro Phe Glu Val Thr Val Met Gln Asp Phe Phe Ile Asp<br>        820                         825                       830 | 2496 |
| ctg cgg cta ccc tac tct gtt gtt cga aac gag cag gtg gaa atc cga<br>Leu Arg Leu Pro Tyr Ser Val Val Arg Asn Glu Gln Val Glu Ile Arg<br>            835                       840                     845 | 2544 |
| gcc gtt ctc tac aat tac cgg cag aac caa gag ctc aag gtg agg gtg<br>Ala Val Leu Tyr Asn Tyr Arg Gln Asn Gln Glu Leu Lys Val Arg Val<br>850                       855                     860 | 2592 |
| gaa cta ctc cac aat cca gcc ttc tgc agc ctg gcc acc acc aag agg<br>Glu Leu Leu His Asn Pro Ala Phe Cys Ser Leu Ala Thr Thr Lys Arg<br>865                       870                     875                   880 | 2640 |
| cgt cac cag cag acc gta acc atc ccc ccc aag tcc tcg ttg tcc gtt<br>Arg His Gln Gln Thr Val Thr Ile Pro Pro Lys Ser Ser Leu Ser Val<br>                885                       890                     895 | 2688 |
| cca tat gtc atc gtg ccg cta aag acc ggc ctg cag gaa gtg gaa gtc<br>Pro Tyr Val Ile Val Pro Leu Lys Thr Gly Leu Gln Glu Val Glu Val<br>        900                         905                     910 | 2736 |
| aag gct gcc gtc tac cat cat ttc atc agt gac ggt gtc agg aag tcc<br>Lys Ala Ala Val Tyr His His Phe Ile Ser Asp Gly Val Arg Lys Ser<br>            915                       920                     925 | 2784 |
| ctg aag gtc gtg ccg gaa gga atc aga atg aac aaa act gtg gct gtt<br>Leu Lys Val Val Pro Glu Gly Ile Arg Met Asn Lys Thr Val Ala Val<br>930                       935                     940 | 2832 |
| cgc acc ctg gat cca gaa cgc ctg ggc cgt gaa gga gtg cag aaa gag<br>Arg Thr Leu Asp Pro Glu Arg Leu Gly Arg Glu Gly Val Gln Lys Glu<br>945                       950                     955                   960 | 2880 |
| gac atc cca cct gca gac ctc agt gac caa gtc ccg gac acc gag tct<br>Asp Ile Pro Pro Ala Asp Leu Ser Asp Gln Val Pro Asp Thr Glu Ser<br>                965                       970                     975 | 2928 |
| gag acc aga att ctc ctg caa ggg acc cca gtg gcc cag atg aca gag<br>Glu Thr Arg Ile Leu Leu Gln Gly Thr Pro Val Ala Gln Met Thr Glu<br>            980                       985                     990 | 2976 |
| gat gcc gtc gac gcg gaa cgg ctg  aag cac ctc att gtg  acc ccc tcg<br>Asp Ala Val Asp Ala Glu Arg Leu  Lys His Leu Ile Val  Thr Pro Ser<br>    995                     1000                     1005 | 3024 |
| ggc tgc  ggg gaa cag aac atg  atc ggc atg acg ccc  acg gtc atc<br>Gly Cys  Gly Glu Gln Asn Met  Ile Gly Met Thr Pro  Thr Val Ile<br>    1010                   1015                     1020 | 3069 |
| gct gtg  cat tac ctg gat gaa  acg gag cag tgg gag  aag ttc ggc<br>Ala Val  His Tyr Leu Asp Glu  Thr Glu Gln Trp Glu  Lys Phe Gly | 3114 |

-continued

| | | | | | | | | | | | |
|---|---|---|---|---|---|---|---|---|---|---|---|
| | | 1025 | | | 1030 | | | 1035 | | | |
| cta | gag | aag | cgg | cag | ggg | gcc | ttg | gag | ctc | atc | aag | aag | ggg | tac | 3159 |
| Leu | Glu | Lys | Arg | Gln | Gly | Ala | Leu | Glu | Leu | Ile | Lys | Lys | Gly | Tyr | |
| | 1040 | | | | 1045 | | | | 1050 | | | | | | |
| acc | cag | cag | ctg | gcc | ttc | aga | caa | ccc | agc | tct | gcc | ttt | gcg | gcc | 3204 |
| Thr | Gln | Gln | Leu | Ala | Phe | Arg | Gln | Pro | Ser | Ser | Ala | Phe | Ala | Ala | |
| 1055 | | | | | 1060 | | | | | 1065 | | | | | |
| ttc | gtg | aaa | cgg | gca | ccc | agc | acc | tgg | ctg | acc | gcc | tac | gtg | gtc | 3249 |
| Phe | Val | Lys | Arg | Ala | Pro | Ser | Thr | Trp | Leu | Thr | Ala | Tyr | Val | Val | |
| 1070 | | | | | 1075 | | | | | 1080 | | | | | |
| aag | gtc | ttc | tct | ctg | gct | gtc | aac | ctc | atc | gcc | atc | gac | tcc | caa | 3294 |
| Lys | Val | Phe | Ser | Leu | Ala | Val | Asn | Leu | Ile | Ala | Ile | Asp | Ser | Gln | |
| 1085 | | | | | 1090 | | | | | 1095 | | | | | |
| gtc | ctc | tgc | ggg | gct | gtt | aaa | tgg | ctg | atc | ctg | gag | aag | cag | aag | 3339 |
| Val | Leu | Cys | Gly | Ala | Val | Lys | Trp | Leu | Ile | Leu | Glu | Lys | Gln | Lys | |
| 1100 | | | | | 1105 | | | | | 1110 | | | | | |
| ccc | gac | ggg | gtc | ttc | cag | gag | gat | gcg | ccc | gtg | ata | cac | caa | gaa | 3384 |
| Pro | Asp | Gly | Val | Phe | Gln | Glu | Asp | Ala | Pro | Val | Ile | His | Gln | Glu | |
| 1115 | | | | | 1120 | | | | | 1125 | | | | | |
| atg | att | ggt | gga | tta | cgg | aac | aac | aac | gag | aaa | gac | atg | gcc | ctc | 3429 |
| Met | Ile | Gly | Gly | Leu | Arg | Asn | Asn | Asn | Glu | Lys | Asp | Met | Ala | Leu | |
| 1130 | | | | | 1135 | | | | | 1140 | | | | | |
| acg | gcc | ttt | gtt | ctc | atc | tcg | ctg | cag | gag | gct | aaa | gat | att | tgc | 3474 |
| Thr | Ala | Phe | Val | Leu | Ile | Ser | Leu | Gln | Glu | Ala | Lys | Asp | Ile | Cys | |
| 1145 | | | | | 1150 | | | | | 1155 | | | | | |
| gag | gag | cag | gtc | aac | agc | ctg | cca | ggc | agc | atc | act | aaa | gca | gga | 3519 |
| Glu | Glu | Gln | Val | Asn | Ser | Leu | Pro | Gly | Ser | Ile | Thr | Lys | Ala | Gly | |
| 1160 | | | | | 1165 | | | | | 1170 | | | | | |
| gac | ttc | ctt | gaa | gcc | aac | tac | atg | aac | cta | cag | aga | tcc | tac | act | 3564 |
| Asp | Phe | Leu | Glu | Ala | Asn | Tyr | Met | Asn | Leu | Gln | Arg | Ser | Tyr | Thr | |
| 1175 | | | | | 1180 | | | | | 1185 | | | | | |
| gtg | gcc | att | gct | ggc | tat | gct | ctg | gcc | cag | atg | ggc | agg | ctg | aag | 3609 |
| Val | Ala | Ile | Ala | Gly | Tyr | Ala | Leu | Ala | Gln | Met | Gly | Arg | Leu | Lys | |
| 1190 | | | | | 1195 | | | | | 1200 | | | | | |
| ggg | cct | ctt | ctt | aac | aaa | ttt | ctg | acc | aca | gcc | aaa | gat | aag | aac | 3654 |
| Gly | Pro | Leu | Leu | Asn | Lys | Phe | Leu | Thr | Thr | Ala | Lys | Asp | Lys | Asn | |
| 1205 | | | | | 1210 | | | | | 1215 | | | | | |
| cgc | tgg | gag | gac | cct | ggt | aag | cag | ctc | tac | aac | gtg | gag | gcc | aca | 3699 |
| Arg | Trp | Glu | Asp | Pro | Gly | Lys | Gln | Leu | Tyr | Asn | Val | Glu | Ala | Thr | |
| 1220 | | | | | 1225 | | | | | 1230 | | | | | |
| tcc | tat | gcc | ctc | ttg | gcc | cta | ctg | cag | cta | aaa | gac | ttt | gac | ttt | 3744 |
| Ser | Tyr | Ala | Leu | Leu | Ala | Leu | Leu | Gln | Leu | Lys | Asp | Phe | Asp | Phe | |
| 1235 | | | | | 1240 | | | | | 1245 | | | | | |
| gtg | cct | ccc | gtc | gtg | cgt | tgg | ctc | aat | gaa | cag | aga | tac | tac | ggt | 3789 |
| Val | Pro | Pro | Val | Val | Arg | Trp | Leu | Asn | Glu | Gln | Arg | Tyr | Tyr | Gly | |
| 1250 | | | | | 1255 | | | | | 1260 | | | | | |
| ggt | ggc | tat | ggc | tct | acc | cag | gcc | acc | ttc | atg | gtg | ttc | caa | gcc | 3834 |
| Gly | Gly | Tyr | Gly | Ser | Thr | Gln | Ala | Thr | Phe | Met | Val | Phe | Gln | Ala | |
| 1265 | | | | | 1270 | | | | | 1275 | | | | | |
| ttg | gct | caa | tac | caa | aag | gac | gcc | cct | gac | cac | cag | gaa | ctg | aac | 3879 |
| Leu | Ala | Gln | Tyr | Gln | Lys | Asp | Ala | Pro | Asp | His | Gln | Glu | Leu | Asn | |
| 1280 | | | | | 1285 | | | | | 1290 | | | | | |
| ctt | gat | gtg | tcc | ctc | caa | ctg | ccc | agc | cgc | agc | tcc | aag | atc | acc | 3924 |
| Leu | Asp | Val | Ser | Leu | Gln | Leu | Pro | Ser | Arg | Ser | Ser | Lys | Ile | Thr | |
| 1295 | | | | | 1300 | | | | | 1305 | | | | | |
| cac | cgt | atc | cac | tgg | gaa | tct | gcc | agc | ctc | ctg | cga | tca | gaa | gag | 3969 |
| His | Arg | Ile | His | Trp | Glu | Ser | Ala | Ser | Leu | Leu | Arg | Ser | Glu | Glu | |
| 1310 | | | | | 1315 | | | | | 1320 | | | | | |
| acc | aag | gaa | aat | gag | ggt | ttc | aca | gtc | aca | gct | gaa | gga | aaa | ggc | 4014 |

```
              Thr Lys Glu Asn Glu Gly Phe Thr Val Thr Ala Glu Gly Lys Gly
                  1325            1330                1335 caa ggc acc ttg tcg gtg gtg aca atg tac cat gct aag gcc aaa                    4059
Gln Gly Thr Leu Ser Val Val Thr Met Tyr His Ala Lys Ala Lys
    1340            1345                1350 gat caa ctc acc tgt aat aaa ttc gac ctc aag gtc acc ata aaa                    4104
Asp Gln Leu Thr Cys Asn Lys Phe Asp Leu Lys Val Thr Ile Lys
    1355            1360                1365 cca gca ccg gaa aca gaa aag agg cct cag gat gcc aag aac act                    4149
Pro Ala Pro Glu Thr Glu Lys Arg Pro Gln Asp Ala Lys Asn Thr
    1370            1375                1380 atg atc ctt gag atc tgc aca agg tat ctg gga gaa gtt gat tct                    4194
Met Ile Leu Glu Ile Cys Thr Arg Tyr Leu Gly Glu Val Asp Ser
    1385            1390                1395 aca atg aca ata att gat att tct atg ctg act ggt ttt ctc cct                    4239
Thr Met Thr Ile Ile Asp Ile Ser Met Leu Thr Gly Phe Leu Pro
    1400            1405                1410 gat gct gaa gac ctt aca agg ctt tct aaa gga gtg gac aga tac                    4284
Asp Ala Glu Asp Leu Thr Arg Leu Ser Lys Gly Val Asp Arg Tyr
    1415            1420                1425 atc tcc aga tat gaa gtt gac aat aat atg gct cag aaa gta gct                    4329
Ile Ser Arg Tyr Glu Val Asp Asn Asn Met Ala Gln Lys Val Ala
    1430            1435                1440 gtt atc att tac tta aac aag gtc tcc cac tct gaa gat gaa tgc                    4374
Val Ile Ile Tyr Leu Asn Lys Val Ser His Ser Glu Asp Glu Cys
    1445            1450                1455 ctg cac ttt aag att ctc aag cat ttt gaa gtt ggc ttc att cag                    4419
Leu His Phe Lys Ile Leu Lys His Phe Glu Val Gly Phe Ile Gln
    1460            1465                1470 cca gga tca gtc aag gtg tac agc tac tac aat cta gat gaa aaa                    4464
Pro Gly Ser Val Lys Val Tyr Ser Tyr Tyr Asn Leu Asp Glu Lys
    1475            1480                1485 tgt acc aag ttc tac cat cca gat aaa gga aca ggc ctt ctc aat                    4509
Cys Thr Lys Phe Tyr His Pro Asp Lys Gly Thr Gly Leu Leu Asn
    1490            1495                1500 aag ata tgt att ggt aac gtt tgc cga tgt gca gga gaa acc tgt                    4554
Lys Ile Cys Ile Gly Asn Val Cys Arg Cys Ala Gly Glu Thr Cys
    1505            1510                1515 tcc tcg ctc aac cat cag gaa agg att gat gtt cca tta caa att                    4599
Ser Ser Leu Asn His Gln Glu Arg Ile Asp Val Pro Leu Gln Ile
    1520            1525                1530 gaa aaa gcc tgc gag acg aat gtg gat tat gtc tac aaa acc aag                    4644
Glu Lys Ala Cys Glu Thr Asn Val Asp Tyr Val Tyr Lys Thr Lys
    1535            1540                1545 ctg ctt cga ata gaa gaa caa gat ggt aat gat atc tat gtc atg                    4689
Leu Leu Arg Ile Glu Glu Gln Asp Gly Asn Asp Ile Tyr Val Met
    1550            1555                1560 gat gtt tta gaa gtt att aaa caa ggt act gac gaa aat cca cga                    4734
Asp Val Leu Glu Val Ile Lys Gln Gly Thr Asp Glu Asn Pro Arg
    1565            1570                1575 gca aag acc cac cag tac ata agt caa agg aaa tgc cag gag gct                    4779
Ala Lys Thr His Gln Tyr Ile Ser Gln Arg Lys Cys Gln Glu Ala
    1580            1585                1590 ctg aat ctg aag gtg aat gat gat tat ctg atc tgg ggt tcc agg                    4824
Leu Asn Leu Lys Val Asn Asp Asp Tyr Leu Ile Trp Gly Ser Arg
    1595            1600                1605 agt gac ctg ttg ccc acg aaa gat aaa att tcc tac atc att aca                    4869
Ser Asp Leu Leu Pro Thr Lys Asp Lys Ile Ser Tyr Ile Ile Thr
    1610            1615                1620
```

```
                                                                         -continued aag  aac  aca  tgg  att  gag  aga  tgg  cca  cat  gaa  gac  gaa  tgt  cag       4914
Lys  Asn  Thr  Trp  Ile  Glu  Arg  Trp  Pro  His  Glu  Asp  Glu  Cys  Gln
     1625                1630                     1635
```

<210> SEQ ID NO 12
<211> LENGTH: 1638
<212> TYPE: PRT
<213> ORGANISM: Artificial Sequence
<220> FEATURE:
<223> OTHER INFORMATION: Hybrid protein

<400> SEQUENCE: 12

```
Met Gly Pro Thr Ser Gly Pro Ser Leu Leu Leu Leu Leu Thr His
1               5                   10                  15

Leu Pro Leu Ala Leu Gly Ser Pro Met Tyr Ser Ile Ile Thr Pro Asn
            20                  25                  30

Ile Leu Arg Leu Glu Ser Glu Glu Thr Met Val Leu Glu Ala His Asp
        35                  40                  45

Ala Gln Gly Asp Val Pro Val Thr Val Thr Val His Asp Phe Pro Gly
    50                  55                  60

Lys Lys Leu Val Leu Ser Ser Glu Lys Thr Val Leu Thr Pro Ala Thr
65                  70                  75                  80

Asn His Met Gly Asn Val Thr Phe Thr Ile Pro Ala Asn Arg Glu Phe
                85                  90                  95

Lys Ser Glu Lys Gly Arg Asn Lys Phe Val Thr Val Gln Ala Thr Phe
            100                 105                 110

Gly Thr Gln Val Val Glu Lys Val Val Leu Val Ser Leu Gln Ser Gly
        115                 120                 125

Tyr Leu Phe Ile Gln Thr Asp Lys Thr Ile Tyr Thr Pro Gly Ser Thr
    130                 135                 140

Val Leu Tyr Arg Ile Phe Thr Val Asn His Lys Leu Leu Pro Val Gly
145                 150                 155                 160

Arg Thr Val Met Val Asn Ile Glu Asn Pro Glu Gly Ile Pro Val Lys
                165                 170                 175

Gln Asp Ser Leu Ser Ser Gln Asn Gln Leu Gly Val Leu Pro Leu Ser
            180                 185                 190

Trp Asp Ile Pro Glu Leu Val Asn Met Gly Gln Trp Lys Ile Arg Ala
        195                 200                 205

Tyr Tyr Glu Asn Ser Pro Gln Gln Val Phe Ser Thr Glu Phe Glu Val
    210                 215                 220

Lys Glu Tyr Val Leu Pro Ser Phe Glu Val Ile Val Glu Pro Thr Glu
225                 230                 235                 240

Lys Phe Tyr Tyr Ile Tyr Asn Glu Lys Gly Leu Glu Val Thr Ile Thr
                245                 250                 255

Ala Arg Phe Leu Tyr Gly Lys Lys Val Glu Gly Thr Ala Phe Val Ile
            260                 265                 270

Phe Gly Ile Gln Asp Gly Glu Gln Arg Ile Ser Leu Pro Glu Ser Leu
        275                 280                 285

Lys Arg Ile Pro Ile Glu Asp Gly Ser Gly Glu Val Val Leu Ser Arg
    290                 295                 300

Lys Val Leu Leu Asp Gly Val Gln Asn Leu Arg Ala Glu Asp Leu Val
305                 310                 315                 320

Gly Lys Ser Leu Tyr Val Ser Ala Thr Val Ile Leu His Ser Gly Ser
                325                 330                 335

Asp Met Val Gln Ala Glu Arg Ser Gly Ile Pro Ile Val Thr Ser Pro
            340                 345                 350
```

-continued

Tyr Gln Ile His Phe Thr Lys Thr Pro Lys Tyr Phe Lys Pro Gly Met
        355                 360                 365

Pro Phe Asp Leu Met Val Phe Val Thr Asn Pro Asp Gly Ser Pro Ala
    370                 375                 380

Tyr Arg Val Pro Val Ala Val Gln Gly Glu Asp Thr Val Gln Ser Leu
385                 390                 395                 400

Thr Gln Gly Asp Gly Val Ala Lys Leu Ser Ile Asn Thr His Pro Ser
                405                 410                 415

Gln Lys Pro Leu Ser Ile Thr Val Arg Thr Lys Lys Gln Glu Leu Ser
            420                 425                 430

Glu Ala Glu Gln Ala Thr Arg Thr Met Gln Ala Leu Pro Tyr Ser Thr
        435                 440                 445

Val Gly Asn Ser Asn Asn Tyr Leu His Leu Ser Val Leu Arg Thr Glu
    450                 455                 460

Leu Arg Pro Gly Glu Thr Leu Asn Val Asn Phe Leu Leu Arg Met Asp
465                 470                 475                 480

Arg Ala His Glu Ala Lys Ile Arg Tyr Tyr Thr Tyr Leu Ile Met Asn
                485                 490                 495

Lys Gly Arg Leu Leu Lys Ala Gly Arg Gln Val Arg Glu Pro Gly Gln
            500                 505                 510

Asp Leu Val Val Leu Pro Leu Ser Ile Thr Thr Asp Phe Ile Pro Ser
        515                 520                 525

Phe Arg Leu Val Ala Tyr Tyr Thr Leu Ile Gly Ala Ser Gly Gln Arg
    530                 535                 540

Glu Val Val Ala Asp Ser Val Trp Val Asp Val Lys Asp Ser Cys Val
545                 550                 555                 560

Gly Ser Leu Val Val Lys Ser Gly Gln Ser Glu Asp Arg Gln Pro Val
                565                 570                 575

Pro Gly Gln Gln Met Thr Leu Lys Ile Glu Gly Asp His Gly Ala Arg
            580                 585                 590

Val Val Leu Val Ala Val Asp Lys Gly Val Phe Val Leu Asn Lys Lys
        595                 600                 605

Asn Lys Leu Thr Gln Ser Lys Ile Trp Asp Val Val Glu Lys Ala Asp
    610                 615                 620

Ile Gly Cys Thr Pro Gly Ser Gly Lys Asp Tyr Ala Gly Val Phe Ser
625                 630                 635                 640

Asp Ala Gly Leu Thr Phe Thr Ser Ser Ser Gly Gln Gln Thr Ala Gln
                645                 650                 655

Arg Ala Glu Leu Gln Cys Pro Gln Pro Ala Ala Arg Arg Arg Arg Ser
            660                 665                 670

Val Gln Leu Thr Glu Lys Arg Met Asp Lys Val Gly Lys Tyr Pro Lys
        675                 680                 685

Glu Leu Arg Lys Cys Cys Glu Asp Gly Met Arg Glu Asn Pro Met Arg
    690                 695                 700

Phe Ser Cys Gln Arg Arg Thr Arg Phe Ile Ser Leu Gly Glu Ala Cys
705                 710                 715                 720

Lys Lys Val Phe Leu Asp Cys Cys Asn Tyr Ile Thr Glu Leu Arg Arg
                725                 730                 735

Gln His Ala Arg Ala Ser His Leu Gly Leu Ala Arg Ser Asn Leu Asp
            740                 745                 750

Glu Asp Ile Ile Ala Glu Glu Asn Ile Val Ser Arg Ser Glu Phe Pro
        755                 760                 765

-continued

Glu Ser Trp Leu Trp Asn Val Glu Asp Leu Lys Glu Pro Pro Lys Asn
770                 775                 780

Gly Ile Ser Thr Lys Leu Met Asn Ile Phe Leu Lys Asp Ser Ile Thr
785                 790                 795                 800

Thr Trp Glu Ile Leu Ala Val Ser Met Ser Asp Lys Lys Gly Ile Cys
            805                 810                 815

Val Ala Asp Pro Phe Glu Val Thr Val Met Gln Asp Phe Phe Ile Asp
            820                 825                 830

Leu Arg Leu Pro Tyr Ser Val Arg Asn Glu Gln Val Glu Ile Arg
            835                 840                 845

Ala Val Leu Tyr Asn Tyr Arg Gln Asn Gln Glu Leu Lys Val Arg Val
850                 855                 860

Glu Leu Leu His Asn Pro Ala Phe Cys Ser Leu Ala Thr Thr Lys Arg
865                 870                 875                 880

Arg His Gln Gln Thr Val Thr Ile Pro Pro Lys Ser Ser Leu Ser Val
                885                 890                 895

Pro Tyr Val Ile Val Pro Leu Lys Thr Gly Leu Gln Glu Val Glu Val
            900                 905                 910

Lys Ala Ala Val Tyr His His Phe Ile Ser Asp Gly Val Arg Lys Ser
            915                 920                 925

Leu Lys Val Val Pro Glu Gly Ile Arg Met Asn Lys Thr Val Ala Val
930                 935                 940

Arg Thr Leu Asp Pro Glu Arg Leu Gly Arg Glu Gly Val Gln Lys Glu
945                 950                 955                 960

Asp Ile Pro Pro Ala Asp Leu Ser Asp Gln Val Pro Asp Thr Glu Ser
                965                 970                 975

Glu Thr Arg Ile Leu Leu Gln Gly Thr Pro Val Ala Gln Met Thr Glu
            980                 985                 990

Asp Ala Val Asp Ala Glu Arg Leu Lys His Leu Ile Val Thr Pro Ser
995                 1000                1005

Gly Cys Gly Glu Gln Asn Met Ile Gly Met Thr Pro Thr Val Ile
    1010                1015                1020

Ala Val His Tyr Leu Asp Glu Thr Glu Gln Trp Glu Lys Phe Gly
    1025                1030                1035

Leu Glu Lys Arg Gln Gly Ala Leu Glu Leu Ile Lys Lys Gly Tyr
    1040                1045                1050

Thr Gln Gln Leu Ala Phe Arg Gln Pro Ser Ser Ala Phe Ala Ala
    1055                1060                1065

Phe Val Lys Arg Ala Pro Ser Thr Trp Leu Thr Ala Tyr Val Val
    1070                1075                1080

Lys Val Phe Ser Leu Ala Val Asn Leu Ile Ala Ile Asp Ser Gln
    1085                1090                1095

Val Leu Cys Gly Ala Val Lys Trp Leu Ile Leu Glu Lys Gln Lys
    1100                1105                1110

Pro Asp Gly Val Phe Gln Glu Asp Ala Pro Val Ile His Gln Glu
    1115                1120                1125

Met Ile Gly Gly Leu Arg Asn Asn Asn Glu Lys Asp Met Ala Leu
    1130                1135                1140

Thr Ala Phe Val Leu Ile Ser Leu Gln Glu Ala Lys Asp Ile Cys
    1145                1150                1155

Glu Glu Gln Val Asn Ser Leu Pro Gly Ser Ile Thr Lys Ala Gly
    1160                1165                1170

Asp Phe Leu Glu Ala Asn Tyr Met Asn Leu Gln Arg Ser Tyr Thr

-continued

```
                1175                1180                1185

Val Ala Ile Ala Gly Tyr Ala Leu Ala Gln Met Gly Arg Leu Lys
     1190                1195                1200

Gly Pro Leu Leu Asn Lys Phe Leu Thr Thr Ala Lys Asp Lys Asn
     1205                1210                1215

Arg Trp Glu Asp Pro Gly Lys Gln Leu Tyr Asn Val Glu Ala Thr
     1220                1225                1230

Ser Tyr Ala Leu Leu Ala Leu Leu Gln Leu Lys Asp Phe Asp Phe
     1235                1240                1245

Val Pro Pro Val Val Arg Trp Leu Asn Glu Gln Arg Tyr Tyr Gly
     1250                1255                1260

Gly Gly Tyr Gly Ser Thr Gln Ala Thr Phe Met Val Phe Gln Ala
     1265                1270                1275

Leu Ala Gln Tyr Gln Lys Asp Ala Pro Asp His Gln Glu Leu Asn
     1280                1285                1290

Leu Asp Val Ser Leu Gln Leu Pro Ser Arg Ser Ser Lys Ile Thr
     1295                1300                1305

His Arg Ile His Trp Glu Ser Ala Ser Leu Leu Arg Ser Glu Glu
     1310                1315                1320

Thr Lys Glu Asn Glu Gly Phe Thr Val Thr Ala Glu Gly Lys Gly
     1325                1330                1335

Gln Gly Thr Leu Ser Val Val Thr Met Tyr His Ala Lys Ala Lys
     1340                1345                1350

Asp Gln Leu Thr Cys Asn Lys Phe Asp Leu Lys Val Thr Ile Lys
     1355                1360                1365

Pro Ala Pro Glu Thr Glu Lys Arg Pro Gln Asp Ala Lys Asn Thr
     1370                1375                1380

Met Ile Leu Glu Ile Cys Thr Arg Tyr Leu Gly Glu Val Asp Ser
     1385                1390                1395

Thr Met Thr Ile Ile Asp Ile Ser Met Leu Thr Gly Phe Leu Pro
     1400                1405                1410

Asp Ala Glu Asp Leu Thr Arg Leu Ser Lys Gly Val Asp Arg Tyr
     1415                1420                1425

Ile Ser Arg Tyr Glu Val Asp Asn Asn Met Ala Gln Lys Val Ala
     1430                1435                1440

Val Ile Ile Tyr Leu Asn Lys Val Ser His Ser Glu Asp Glu Cys
     1445                1450                1455

Leu His Phe Lys Ile Leu Lys His Phe Glu Val Gly Phe Ile Gln
     1460                1465                1470

Pro Gly Ser Val Lys Val Tyr Ser Tyr Tyr Asn Leu Asp Glu Lys
     1475                1480                1485

Cys Thr Lys Phe Tyr His Pro Asp Lys Gly Thr Gly Leu Leu Asn
     1490                1495                1500

Lys Ile Cys Ile Gly Asn Val Cys Arg Cys Ala Gly Glu Thr Cys
     1505                1510                1515

Ser Ser Leu Asn His Gln Glu Arg Ile Asp Val Pro Leu Gln Ile
     1520                1525                1530

Glu Lys Ala Cys Glu Thr Asn Val Asp Tyr Val Tyr Lys Thr Lys
     1535                1540                1545

Leu Leu Arg Ile Glu Glu Gln Asp Gly Asn Asp Ile Tyr Val Met
     1550                1555                1560

Asp Val Leu Glu Val Ile Lys Gln Gly Thr Asp Glu Asn Pro Arg
     1565                1570                1575
```

```
Ala Lys Thr His Gln Tyr Ile Ser Gln Arg Lys Cys Gln Glu Ala
    1580                1585                1590

Leu Asn Leu Lys Val Asn Asp Asp Tyr Leu Ile Trp Gly Ser Arg
    1595                1600                1605

Ser Asp Leu Leu Pro Thr Lys Asp Lys Ile Ser Tyr Ile Ile Thr
    1610                1615                1620

Lys Asn Thr Trp Ile Glu Arg Trp Pro His Glu Asp Glu Cys Gln
    1625                1630                1635

<210> SEQ ID NO 13
<211> LENGTH: 21
<212> TYPE: DNA
<213> ORGANISM: Artificial Sequence
<220> FEATURE:
<223> OTHER INFORMATION: Oligonucleotide

<400> SEQUENCE: 13
ggatccaggt gctcgggttg g                                         21

<210> SEQ ID NO 14
<211> LENGTH: 27
<212> TYPE: DNA
<213> ORGANISM: Artificial Sequence
<220> FEATURE:
<223> OTHER INFORMATION: Oligonucleotide

<400> SEQUENCE: 14
agtaccttcc ggctcagcac aacctcc                                   27

<210> SEQ ID NO 15
<211> LENGTH: 31
<212> TYPE: DNA
<213> ORGANISM: Artificial Sequence
<220> FEATURE:
<223> OTHER INFORMATION: Oligonucleotide

<400> SEQUENCE: 15
cggaggtacc atgagagga tggctctcta t                               31

<210> SEQ ID NO 16
<211> LENGTH: 28
<212> TYPE: DNA
<213> ORGANISM: Artificial Sequence
<220> FEATURE:
<223> OTHER INFORMATION: Oligonucleotide

<400> SEQUENCE: 16
gatagacacg tggaaatttt cattgccg                                  28

<210> SEQ ID NO 17
<211> LENGTH: 48
<212> TYPE: DNA
<213> ORGANISM: Artificial Sequence
<220> FEATURE:
<223> OTHER INFORMATION: Oligonucleotide

<400> SEQUENCE: 17 gtcttttcg aactgcgggt ggctccaccc atgagaagac cctggaaa              48

<210> SEQ ID NO 18
<211> LENGTH: 55
<212> TYPE: DNA
<213> ORGANISM: Artificial Sequence
<220> FEATURE:
```

```
<223> OTHER INFORMATION: Oligonucleotide

<400> SEQUENCE: 18
acccgcagtt cgaaaaagac gatgacgata aagctctcta caccctcatc acccc        55

<210> SEQ ID NO 19
<211> LENGTH: 39
<212> TYPE: DNA
<213> ORGANISM: Artificial Sequence
<220> FEATURE:
<223> OTHER INFORMATION: Oligonucleotide

<400> SEQUENCE: 19
tcgaactgcg ggtggctcca ccccagagcc aggggagg                           39

<210> SEQ ID NO 20
<211> LENGTH: 56
<212> TYPE: DNA
<213> ORGANISM: Artificial Sequence
<220> FEATURE:
<223> OTHER INFORMATION: Oligonucleotide

<400> SEQUENCE: 20
acccgcagtt cgaaaaagac gatgacgata aaagtcccat gtactctatc atcacc       56

<210> SEQ ID NO 21
<211> LENGTH: 26
<212> TYPE: DNA
<213> ORGANISM: Artificial Sequence
<220> FEATURE:
<223> OTHER INFORMATION: Oligonucleotide

<400> SEQUENCE: 21
tatgtgtaca aaaccaagct gcttcg                                        26

<210> SEQ ID NO 22
<211> LENGTH: 34
<212> TYPE: DNA
<213> ORGANISM: Artificial Sequence
<220> FEATURE:
<223> OTHER INFORMATION: Oligonucleotide

<400> SEQUENCE: 22
ttcttctaga ttaagtaggg cagccaaact cagt                               34

<210> SEQ ID NO 23
<211> LENGTH: 37
<212> TYPE: DNA
<213> ORGANISM: Artificial Sequence
<220> FEATURE:
<223> OTHER INFORMATION: Oligonucleotide

<400> SEQUENCE: 23
atgatgatga tgatgatgcc ccagagccag ggggagg                            37

<210> SEQ ID NO 24
<211> LENGTH: 41
<212> TYPE: DNA
<213> ORGANISM: Artificial Sequence
<220> FEATURE:
<223> OTHER INFORMATION: Oligonucleotide

<400> SEQUENCE: 24
catcatcatc atcatcatga cgatgacgat aaaagtccca t                       41
```

COMPLEMENT DEPLETION USING RECOMBINANT HUMAN C3-DERIVATIVES

This application is based on, and claims the benefit of, U.S. Provisional Application No. 60/484,797, filed Jul. 3, 2003, and entitled Complement Depletion using recombinant Human C3-Derivatives, and which is incorporated herein by reference

BACKGROUND OF THE INVENTION

The activation of the complement system can be achieved by three different pathways, the classical antibody-dependent activation pathway, the alternative activation pathway and the lectin-activation pathway. The alternative activation pathway as well as the lectin-pathway were shown not to be dependent on antibodies. All pathways share a similar cascade-like organization, wherein a protease acts on zymogenes of a subsequent protease. This cascade results in an amplification of the initiation signals. The central step of the complement cascade resides in the formation of a C3-convertase, which cleaves C3 to C3b and C3a (FIG. 1). Subsequently, the resulting C3b can act as a part of a C5-convertase, which cleaves C5 in C5b and C5a. In the terminal pathway, the gradual accumulation of C6, C7, C8 and several molecules C9 results in the formation of the membrane attack complex which is capable of forming a pore in the membrane of the target cells, thereby effecting lysis of the cells.

The complement protein C3 is the central component of all activation pathways. It is predominantly expressed in the liver as a 1663 amino acid precursor protein (Alper et al., 1969). After the 22 amino acid signal sequence has been cleaved off, the precursor protein is proteolytically cleaved into two chains by removal of four arginine residues. The resulting α-chain has a molecular weight of 115 kDa and the β-chain has a molecular weight of 73 kDa (DeBruijn and Fey, 1985). The chains are linked by a disulfide bridge and by non-covalent interactions (Dolmer and Sottrup-Jensen, 1993; Janatova, 1986). Furthermore, the resulting 188 kDa protein carries a carbohydrate chain on each chain, which consists of 5 to 9 mannose residues and two N-acetylglucosamine residues (Hirani et al., 1986).

C3 is cleaved between the amino acids $Arg^{726}$ and $Ser^{727}$ by the C3-convertases. The 9 kDa C3a, which results from the cleavage, is an anaphylatoxin and causes an increase in chemotaxis as well as an increase in the permeability of the blood capillaries. By cleavage of the 179 kDa-C3b between the amino acid $Cys^{988}$ and $Glu^{991}$ a highly reactive thioester is released, by the use of which C3b binds on the cell surfaces via transacetylation (Tack et al., 1980). Furthermore, several binding sites for different complement proteins are exposed by the cleavage, which explains the various interactions of the C3,-b molecule. Several regulatory complement proteins interact with C3b, which comprises binding sites for CR1 or Factor H, which act as co-factors for the cleavage by Factor I. Factor I cleaves C3b between $Arg^{1281}$ and $Ser^{1282}$, and $Arg^{1298}$ and $Ser^{1299}$, whereby the fragments C3f and C3bi emerge, the latter of which is inactive and unable to bind Factor B and C5 (Lachmann et al., 1982; Davis et al., 1982). C3bi, however, is capable to remain on the surface of pathogens, where it is recognized by CR3, which occurs on macrophages and killer cells. Subsequently, CR3 mediates the destruction of pathogens (Newman et al., 1984). In case CR1 acts as a co-factor for the protease, Factor I can additionally cleave between amino acids $Arg^{932}$ and $Glu^{933}$, thereby forming C3dg and C3c (Ross et al., 1982). C3dg is also capable to remain on the surface and is recognized by CR2 (CD21), which is expressed on B-lymphocytes and dendritic cells (Law and Dodds, 1997). The binding of C3dg to the complement receptor CR2 leads to the activation of B cells (Bohnsack and Cooper, 1988).

After the degradation of C3 by a protease from the venom of the cobra *Naja siamensis* the fragment C3o is formed, which no longer contains the amino acids 730-739. However, C3o is capable of binding Factor B (O'Keefe et al., 1988). In contrast, the cleavage product of the Factor I proteolysis C3c cannot form a convertase. Based on the comparison of C3c and C3o, one region in C3o of the amino acid sequence $^{933}$EGVQKEDIPP appeared to be responsible for binding to Factor B. In further studies, the amino acids $^{937}$KED were mutated to alanine. However, no changes in the binding characteristics of Factor B to C3b could be shown (Taniguchi-Sidle und Isenman, 1994).

Activated complement proteins cannot distinguish between external substances and substances which occur naturally in the body. Thereby, it is ensured that for example self-reactive B-cells can be eliminated. Thus, a plurality of regulatory mechanisms is necessary for protecting healthy cells which occur naturally in the body.

The regulation is effected by short half life of the activated complement proteins on the one hand and by plasma proteins such as the C1-Inhibitor (C1-Inh), Factor H and Factor I, as well as membrane-bound proteins such as the Decay-Accelerating-Factor (DAF, CD55), the Membrane-Cofactor-Protein (MCP, CD46) and the Complement Receptor 1 (CR1, CD35) on the other hand, which regulate the complement cascade on specific levels.

C1-Inh controls the activation of C1 by binding to activated C1r and C1s which results in the dissociation of C1q. The time period for the cleavage of C2 and C4 by activated C1 is restricted to a few minutes by C1-Inh (Mollnes und Lachmann, 1988). The C4-binding protein (C4bp) binds to C4b and separates it from C2b. Additionally, it acts as a co-factor for the cleavage of C4b and C3b by Factor I (Scharfstein et al., 1978). The C3-convertase of the classical pathway is inactivated in the same manner by DAF, which exists on all peripheral cells of the blood, epithet and endothel (Lublin and Atkinson, 1989, Lublin and Atkinson, 1990).

C3b represents the central component of all three activation pathways. C3b is regulated by Factor H, CR1, DAF as well as by MCP. Here, Bb is competitively displaced by CR1, Factor H and DAF from the complex of the C3-convertase C3bBb (Makrides et al., 1992). Subsequently, C3b is cleaved by Factor I and inactivated (Pangburn and Müller-Eberhard, 1984). MCP directly attacks C3b and is also a co-factor for the cleavage by Factor I. Protectin (CD95) is a further membrane-bound regulatory protein. It inhibits the polymerization of C9 by binding to C8 and C9 (Mollnes and Lachmann, 1988).

Besides the regulation for the activation, an additional transcriptional control of the complement genes exists. For example, several genes of the complement proteins are upregulated by cytokine and IFNγ-activated transcription factors after damaging a tissue (Volanakis, 1995).

The strict regulatory mechanisms prevent an attack of the complement system on cells which occur naturally in the body. However, body tissue can be damaged by unregulated activation triggered by diverse diseases. In this situation, the activation of the complement is not the primary reason for disease. However, the resulting damaging of the tissue is mediated by the complement. Diseases which are connected with the activation of the complement can be divided into three groups: Chronical diseases, acute diseases and incompatibility towards biomaterials. The group of acute diseases comprise for example asthma (Regal et al., 1993; Regal and Fraser, 1996), sepsis (Hack et al., 1989; Hack et al., 1992), hyperacute rejection in connection with transplantations or xenotransplantations (Bach et al., 1995; Baldwin et al., 1995), pneumonia (Eppinger et al., 1997) and cardiac infarction (Kilgore et al., 1997), as well as a massive C3a-accumulation, which occurs in connection with the cardiopulmonale bypass-operation (Kirklin et al., 1983; Homeister et al., 1992). The chronical diseases comprise, for example, systemic lupus erythematodes (SLE) (Belmont et al., 1986; Buyon et al., 1992), glomerulonephritis (Couser et al., 1985; Couser et al., 1995), rheumatoide arthritis (Kemp et al., 1992; Wang et al., 1995), Alzheimer's disease (Rogers et al., 1992; Morgan et al., 1997), myastenia gravis (Lennon et al., 1978; Piddlesden et al., 1996) and multiple sclerosis (Piddlesden et al., 1994; Williams et al., 1994) as well as organ rejection after transplantations or xenotransplantations (Baldwin et al., 1995; Dalmasso, 1997). The group of incompatibilities towards biomaterials was described in connection with operation material at a cardiopulmonal bypass (Craddock et al., 1977; Mollnes, 1997), with depositions of blood platelets (Gyongyossy-Issa et al., 1994) and with conducting hemodialysis (Cheung et al., 1994; Mollnes, 1997).

A reduced protein concentration of a complement protein or mutations which lead to a total loss of the protein are the reason for many complement-associated diseases. Factor I-deficiency results in a very small content of C3 and other complement proteins of the cascade in the blood. This leads to diverse diseases, such as a monthly occuring meningitis which is associated with menstruation (Gonzales-Rubio et al., 2001). Factor H-deficiency by gene mutation is associated with the hemolytic-uremic syndrom (Zipfel et al., 2001). An unrestricted activity in the classical activation by depletion of C1, C2 or C4 leads for example to a higher disposition towards systemic lupus erythematodes (Morgan and Walport, 1991). A depletion of a component from the alternative activation such as Factor B or Factor D leads to a higher susceptibility towards infections (Morgan and Walport, 1991).

Complement-associated diseases occur both with an increased and decreased complement activation. In case the regulation is disturbed or the activation is prevented, effetive complement modulators are needed.

The group of complement inhibitors for therapeutic use comprises proteins such as the C1-Inhibitor and the soluble complement regulators sCR1 (soluble CR1), sMCP or sDAF, antibodies against C5 or C3 and smaller molecules such as the peptide Compstatin or RNA-aptamers. Several complement inhibitors are tested in clinical phases I, II or III, such as the C5-Inhibitor Pexelizumab, a monoclonal antibody for use at cardiopulmonal bypass (Whiss, 2002) or the soluble complement receptor sCR1 (Zimmerman et al., 2000).

The C1-Inhibitor is the only plasma protein which has been tested in in vivo-studies (Struber et al., 1999; Horstick, 2002). The serine protease is a suicide inhibitor of the serpine family which inhibits activated C1s and C1q by binding to the active site (Sim et al., 1979). The disadvantages of these molecules relate to the sole inhibition of the classical activation pathways as well as in the susceptibility of the protein towards the inactivation by elastase. For this reason, elastase-resistent C1-Inhibitor mutants were generated (Eldering et al., 1993).

The recombinant complement inhibitors embrace soluble regulators such as sCR1, sMCP and sDAF (Christiansen et al., 1996). The soluble complement receptor sCR1 acts as C3- and C5-convertase-inhibitor and has been tested successfully in diverse animal models such as for myasthenia gravis (Piddlesden et al., 1996), multiple sclerosis (Piddlesden et al., 1994) or asthma (Regal et al., 1993). By altering the conditions of expression, it was possible to increase the short half-life of approx. 8 h in vivo up to 70 h. It is proposed that a different glycosylation pattern is responsible for the increased half-life (Weismann et al., 1990; Zimmerman et al., 2000).

The complement receptors MCP and DAF act as complement inhibitors both in vitro and in vivo, for example in the model of reverse passive Arthus-reaction (Moran et al., 1992; Christiansen et al., 1996). sDAF accellerates the decomposition of both the classical and the alternative C3- and C5-convertases. However, sDAF does not act as a co-factor for the cleavage of Factor I (Kinoshita et al., 1985). In contrast, sMCP acts as co-factor for the cleavage of C3b and C4b by Factor I. However, it does not act on the convertases (Liszewski and Atkinson, 1992).

Protectin (CD59) is a further membrane protein which protects naturally occuring cells of the body from MAC-mediated damage. It binds to C5b-8 and prevents the formation of a pore in the membrane by binding of C9 (Davies, 1996). Its soluble counter-part, sCD59, showed inhibition in vitro (Sugita et al., 1994).

A further group of complement inhibitors consists of antibodies, wherein C5 in particular represents an attractive target protein, since its concentration in the serum is clearly lower than the one of C3. Monoclonal antibodies combine the advantage of specifity and high affinity with a relatively long half-life and the ease of production in large amounts. One prerequisite for the therapeutic application is the human origin of the antibodies which prevents an immune response, for example the human anti-mouse-antibody-response. Several antibodies against C3 (Kemp et al., 1994), C3a (Burger et al., 1988; Elsner et al., 1994) or against C5a (Ames et al., 1994; Park et al., 1999) have been developed. Some have been tested in different animal models, for example for nephritis (Wang et al., 1996), collagen-induced arthritis (Wang et al., 1995), myocardial ischemia und reperfusion (Vakeva et al., 1998).

Anaphylatoxin-receptor-antagonists (Konteatis et al., 1994; Pellas et al., 1998; Heller et al., 1999) and RNA-aptamers, which inhibit the C5-cleavage (Biesecker et al., 1999) belong to the group of complement inhibitors with low molecular weight. Compstatin, a C3-Inhibitor, binds to native C3 and prevents its cleavage in C3b. By application of Compstatin, the hyperacute rejection of transplants in an ex-vivo pig-to-human-liver-transplantation was prevented (Fiane et al., 1999a; Fiane et al., 1999b).

Cobra Venom Factor (CVF) is a potent complement modulator of natural origin. CVF is a 149 kDa-glycoprotein from the venom of the cobra species Naja, Ophiophagus and Hemachatus (Müller-Eberhard and Fjellström, 1971). The non-toxic protein consists of three chains, the 68 kDa α-chain, the 48 kDa β-chain and the 32 kDa γ-chain which are linked by disulfide bridges. Additional intramolecular disulfide bridges exist both in the α- and β-chain (one in the α-chain and six in the β-chain; Vogel et al., 1996). The γ-chain can exhibit different sizes due to different processing on the C-terminus (Vogel and Müller-Eberhard, 1984). Two carbohydrate residues are attached to the α-chain and one to the β-chain in form of complex, N-bound oligosaccharide chains (Vogel and Müller-Eberhard, 1984; Grier et al., 1987).

The percentual composition of the secondary structure of CVF was determined by circular dichroism. The composition shows a high analogy to the composition of the secondary structures of the human three-chain C3-derivate C3c. For CVF 11% helices, 47% β-sheets and 18% β-loops were determined. The C3c-molecule also has 11% helices and 47% β-sheets. In contrast, human C3 consists of 24% helices and 32% β-sheets (Vogel et al., 1984). In the primary structure of the pre-pro-CVF the α-chain is encoded first, followed by the γ-chain and subsequently by the β-chain. On the C-terminus of the α-chain 4 arginine residues are located, followed by aC3a-homologous region. Subsequent to the γ-chain, a C3d-homologous region is located. Both the signal peptide and the arginine residues and the C3a- and C3d-homologous regions are removed post-translationally, thereby generating the three-chain structure. The venom protease, which is thought to be responsible for the modification also cleaves C3 in a CVF-similar structure (O'Keefe et al., 1988).

CVF shares an identity of 85% and a similarity of 92% on the protein level with cobra C3 (coC3). With human C3 the identity amounts to 51% and the similarity to 70% (Fritzinger et al., 1992; Fritzinger et al., 1994; Vogel et al., 1996). Moreover, both proteins have a chain structure of the same kind.

This high similarity is also reflected by the fact that CVF—as C3b— can bind to Factor B and forms a convertase by the Factor D-initiated cleavage of B in Bb and Ba. In contrast to C3Bb, the CVF-dependent convertase CVFBb is a C3- and C5-convertase. By the resistence of CVFBb towards Factor H and Factor I, a convertase is formed with a much higher half-life of 7 h (Vogel and Müller-Eberhard, 1982) under physiological conditions. In comparison, C3bBb has a half-life of 1.5 min (Medicus et al., 1976).

In addition to the increased stability, the CVF-dependent convertase CVFBb cleaves C3 and C5 also in fluid phase, whereas the dependent convertase C3bBb is only active when bound to the cell surface (Vogel et al., 1996). CVF unifies all the above characteristics and leads to a permanent activation of the complement system and to decomplementation resulting thereof.

The decomplementing characteristic of CVF offers a variety of applications. After decomplementation the synthesis of complement protein takes approx. 7 days; during this time e.g. the function of the complement system in the immune response in vivo as well as in the pathogenesis of diseases can be studied (Cochrane et al., 1970; Ryan et al., 1986).

In various xenotransplantation models, such as liver transplantation from guinea pigs to rats, heart transplantations from hamsters to mice as well as islet cell transplantations from rats to mice, CVF was successfully employed (Chrupcala et al., 1994; Chrupcala et al., 1996; Lin et al., 2000; Oberholzer et al., 1999) In all these cases, hyperacute rejection of transplant could be prevented by CVF. Different studies demonstrate that also for diseases like arthritis (Lens et al., 1984), arteriosclerosis (Pang and Minta, 1980) and encephalomyelitis (Morariu and Dalmasso, 1978) CVF can be therapeutically employed.

The problem with therapeutic applications of CVF, however, predominantly resides in the strong immunogenic character of CVF. CVF contains a foreign peptide structure and complex, N-bound oligosaccharide chains with terminal galactosyl residues, which have a significant immunogenic potential (Taniguchi et al., 1996). Consequently, CVF is not suitable for repetitive application. With a relative high portion of carbohydrate structures (7.4%, Vogel and Müller-Eberhardt, 1984) CVF differs clearly from human C3 which only has 1.7% (Hirani et al., 1986). Activity analyses in complement consumption-assays and bystander lysis-assays of CVF deglycosylated by n-glycanase showed that the oligosaccharide chains of CVF are not necessary for both C3-convertase and C5-convertase activity. A reduction of the immunogenicity, however, cannot be achieved by deglycosylation since deglycosylated CVF is still strongly immunogenic due to its foreign amino acid composition.

In an attempt to reduce the immunogenicity of CVF, the CVF α-chain was replaced by the corresponding human C3-β-chain (Kölln et al., 2001). The resulting hybrid protein, however, is still strongly immunogenic and thus inappropriate for therapeutic uses.

From these published results, no information is available which could aid in designing a human C3-derivative i) capable of forming a stable C3-convertase comparable to CVFBb, ii) and suitable for therapeutic applications. Furthermore, published CVF/cobra C3 hybrids (Wehrhahn, 2000) are not suitable to provide any valuable data with regard to the tertiary structure of a C3-derivative required for effective binding of Factor B and for increasing the half life of the resulting C3-convertase.

The identity of cobra C3 with human C3 is too low to allow any specific structural conclusions.

Accordingly, there exists a need to identify polypeptides that exhibit complement-depleting activity and to develop methods of preparing these compounds recombinantly as therapeutics. There also exists a need to identify polypeptides having reduced or eliminated immunogenicity, which polypeptides can be used therapeutically for treating complement-associated disorders and disorders affected by complement activation, respectively.

The present invention satisfies this need, and provides related advantages as well.

SUMMARY OF THE INVENTION

The invention provides isolated polypeptides having complement-modulating activity. Specifically, the invention resides in the provision of isolated polypeptides having complement-depleting properties, i.e. that effect an efficient consumption of complement in human serum. Thus, the invention provides molecules capable of effectively inhibiting the complement system by depletion.

More specifically, the invention relates to polypeptides which are derivatives of the human complement component C3 (referred to herein as 'human C3', or 'C3', respectively), where the carboxy terminal (C terminal) part of the polypeptide is replaced by a carboxyterminal part or fragment of Cobra Venom Factor (CVF). The amino acid sequences of human C3 and CVF are depicted as SEQ ID NO:2 and SEQ ID NO:4, respectively.

The number of amino acids of CVF which replace the C terminal C3 fragment is either equal or less than the number of amino acids which have been 'removed' in relation to the native human C3 sequence. The polypeptides of the invention, which are in some respect hybrid polypeptides of C3 and CVF or chimeric proteins, respectively, require at least the presence of amino acids 1575 to 1617 of the CVF sequence shown as SEQ ID NO:4, inorder to retain complement depleting activity.

In addition, without departing from the spirit of the invention, it may be desired for specific purposes, however, to attach additional non-C3 and non-CVF amino acids to the carboxy terminus of the hybrid proteins.

The polypeptides of the invention being at least 70% identical to the sequence of human C3 are less immunogenic than CVF (SEQ ID NO:4) or CVF in which the α-chain is replaced by the corresponding human C3 β-chain.

Also provided are methods of modulating or depleting complement in a human subject and methods of therapeutical treatment, respectively, by administering to the human an effective amount of a C3-derivative of the invention.

A further embodiment is a pharmaceutical composition comprising a protein of the invention.

The invention also provides nucleic acid molecules encoding novel C3-derivatives.

Vectors comprising nucleic acid molecules encoding novel C3-derivatives and isolated host cells transfected with said vectors are provided as well.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 shows an alignment of the amino acid sequences of human complement component C3 (C3) and of Cobra Venom Factor (CVF). ('*' indicates identical amino acids; ':' indicates conservative amino acid replacements; '.' indicates semi-conservative amino acid replacements according to ClustalW).

FIGS. 2A and 2B show schematic representations of C3 preCVF, of construct H2 according to Kölln et al. (2001) and of various C3-derivatives according to the present invention, CVF and CVF part within hybrid constructs are shown in white, C3 and C3 part are dark coloured. The AA values above constructs H5, H6, H6 truncated, respectively, indicate the number of CVF amino acids contained in the expressed hybrid proteins. For two further constructs (H7 and H7 truncated), the C3 part has been extended to the 3' end, thus encoding for 50 additional C3 amino acids, whereas different lengths are used for the CVF part. The construct H7 truncated represents a specific embodiment of the invention, where the hybrid protein comprises the minimum number of 43 CVF amino acids (amino acids 1575 to 1617 of SEQ ID NO:4).

Figure 3:
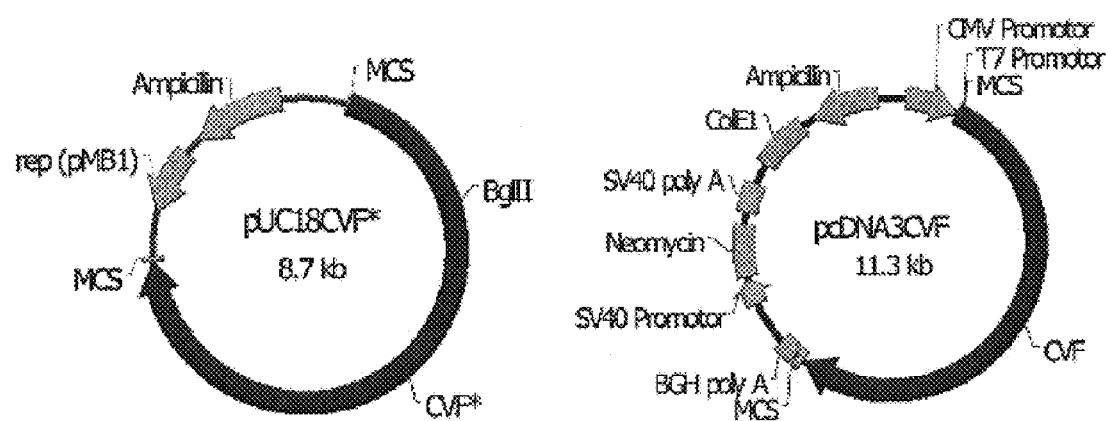
FIG. 3 shows a simplified map of pUC18CVF* and pcDNACVF.

(A) Activation of purified human factor B. Purified hC3 (lane 1), CVF (lane 3) and H5 (lane 6) were incubated for 2 h in the presence of factor D, factor B, and Mg$^{2+}$. Inhibition of convertase formation by EDTA (hC3: lane 2; nCVF: lane 4) and incubation of factor B with factor D and Mg$^{2+}$ (lane 5) were performed as controls. After separation of the reaction mixture by 10% SDS-PAGE under non-reducing conditions, generation of the cleavage products Bb and Ba was analyzed by western blotting using anti-factor B antibodies.

Figure 9:
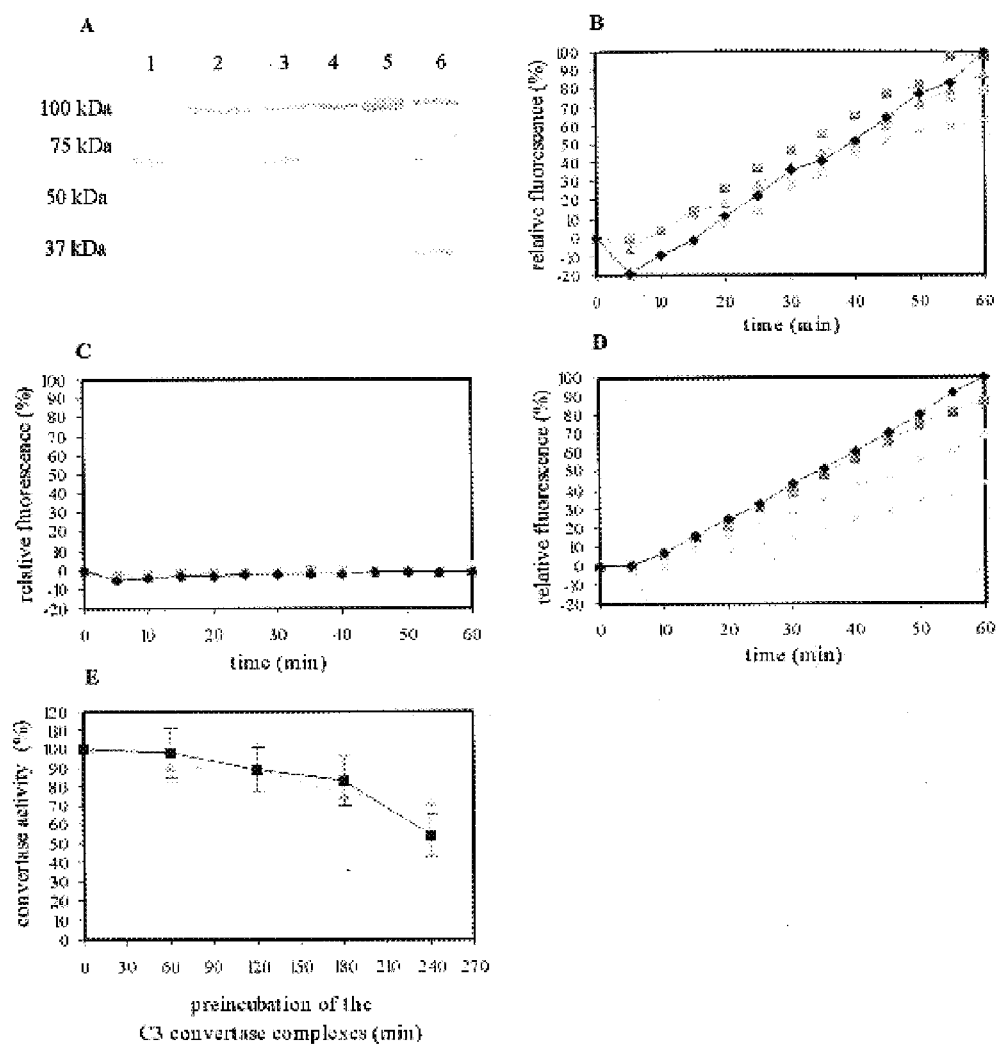
FIG. 9 shows functional characteristics of the H5-dependent C3 convertase.

(B-D) Catalytic activity of nCVFBb, hC3Bb, and H5Bb complexes. Shown is the time-dependent generation of fluorescent amido-methylcoumarin (AMC) from Boc-Leu-Gly-Arg-AMC by the different C3 convertases (B: nCVFBb; C: hC3Bb; D: H5Bb) after preincubation at 37° C. for 60 min (squares), 120 min (triangles), 180 min (dots), and 240 min (crosses) in the absence of the fluorogenic substrate. New formation of convertase complexes was inhibited by addition of EDTA prior to preincubation. Convertase activity of complexes without preincubation (diamonds) was used as control. After addition of the fluorogenic peptide to the samples, the timedependent release of AMC was followed by measuring fluorescence at 465 nm. (E) Stability of nCVFBb and H5Bb complexes. Based on the slopes in FIG. 9B, D, the catalytic activity of both C3 convertases (nCVFBb: gray triangles; H5Bb: black squares) was determined. Shown are mean values±s.d. obtained from at least three independent experiments.

FIG. 10 shows a comparison of the amino acid residues of human C3 and CVF at the C-terminal regions. The restriction sites for the cloning of H5 (BglII) and H6 (Bsp1407I) are indicated. (* identical amino acids, : conservative amino acid exchange,. semi-conservative amino acid exchange; classification according to ClustalW).

FIGS. 11 A and 11 B shows a schematic representation of the construct H6. A: Chain structures of C3 and praCVF. B: Structure of H6, cDNA.

Figure 12:
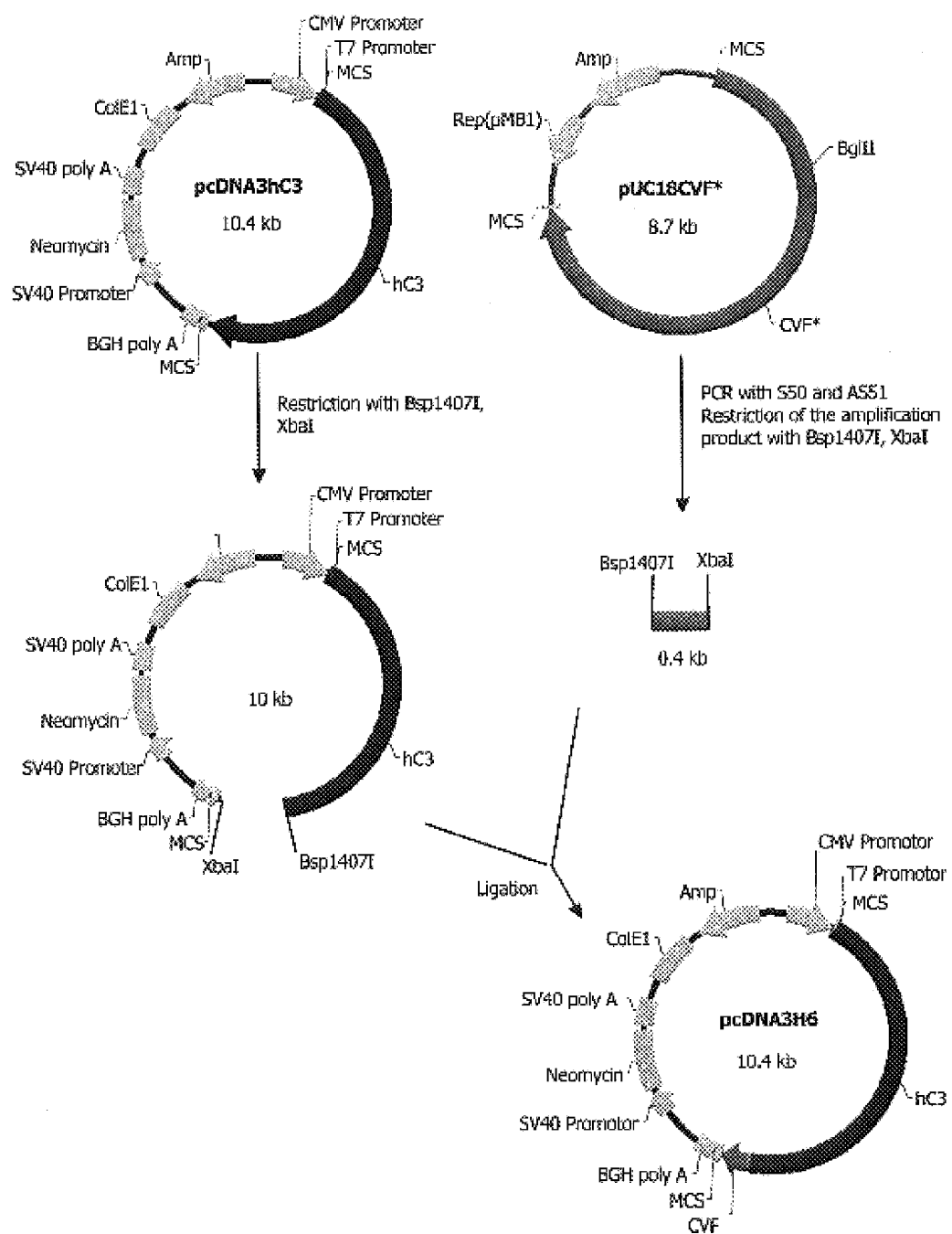

FIG. 12 shows a schematic representation of the cloning strategy for H6.

Figure 13:
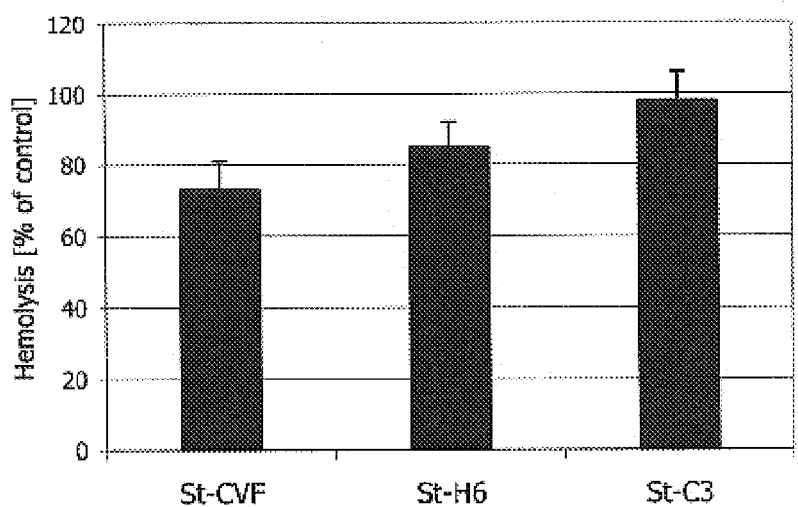

FIG. 13 shows a solid phase-assay with St-H6, St-CVF and St-C3. The recombinant proteins were bound toStrep-Tactin which in turn was immobilized on the ELISA plate. Then, a solid phase-assay was performed in the ELISA plate. The samples were incubated with human serum at 37° C. in an incubation shaker at 150 rpm for 3 h. Subsequently, the reaction mixtureswere transferred to 2 ml reaction tubes. 100 μl GVBS$^{++}$ and 30 μl sensitized sheep-erythrocytes ($5 \times 10^8$ cells/ml) were added. Then, the mixture was incubated in a thermomixer until the serum controls reached a hemolysis of approx. 80% compared to the control with ddH$_2$O. After addition of 850 μl GVBS$^{++}$ the mixture was centrifuged (4° C., 2000 xg, 2 min) and the supernatants were measured at 412 nm. The figure shows the mean values±standard deviation of at leastthree independent experiments.

Figure 14:
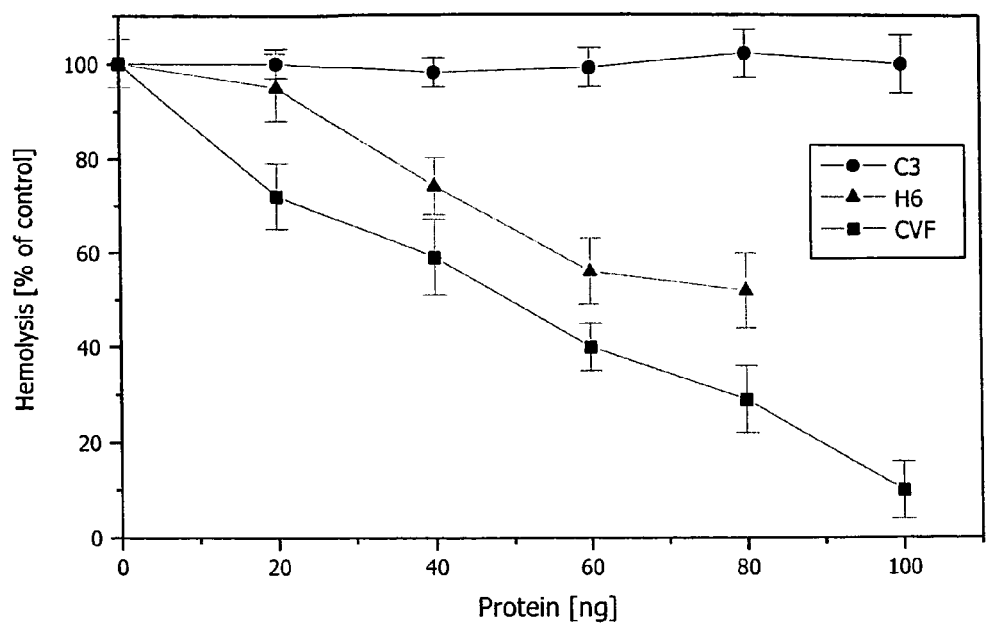

FIG. 14 shows a complement-consumption-assay with CVF, His-H6 and C3. The samples (40 μl) were incubated with human serum (approx. 10 μl) at 37° C. in a thermomixer under agitation for 3 h. Subsequently, 100 μl GVBS$^{++}$ and 30 μl sensitized sheep-erythrocytes ($5 \times 10^8$ cells/ml) were added and the mixture was further incubated in a thermomixer until the serum controls reached a hemolysis of approx. 80% compared to the control with ddH$_2$O. After addition of 850 µl GVBS$^{++}$ the mixture was centrifuged (4° C., 2000 xg, 2 min) and the supernatants were measured at 412 nm. The figure shows the mean values±standard deviation of at least three independent experiments.

Figure 15:
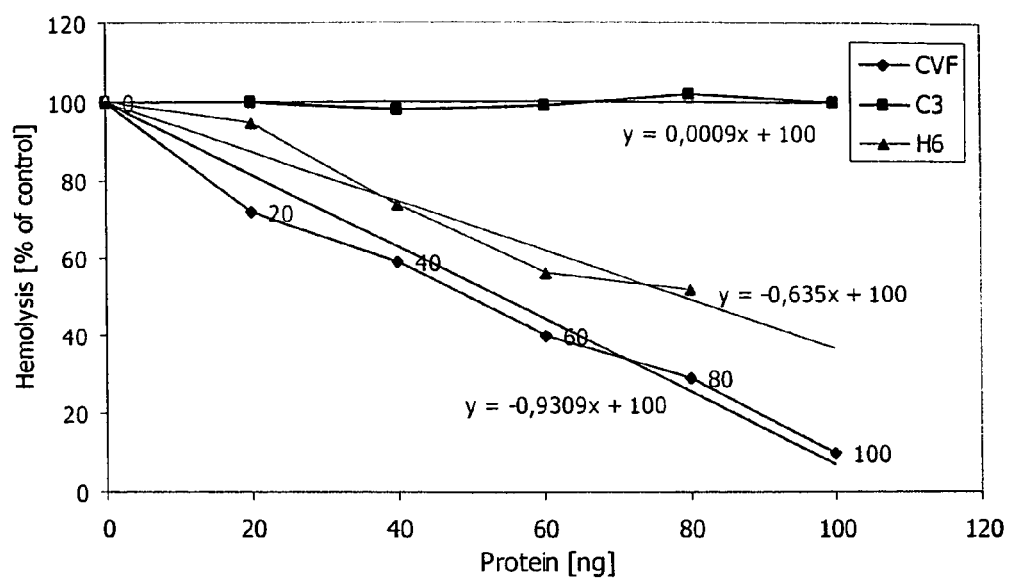

FIG. 15 shows the evaluation of the complement-consuming activity of CVF, His-H6 and C3 by linear regression analysis.

Figure 16:
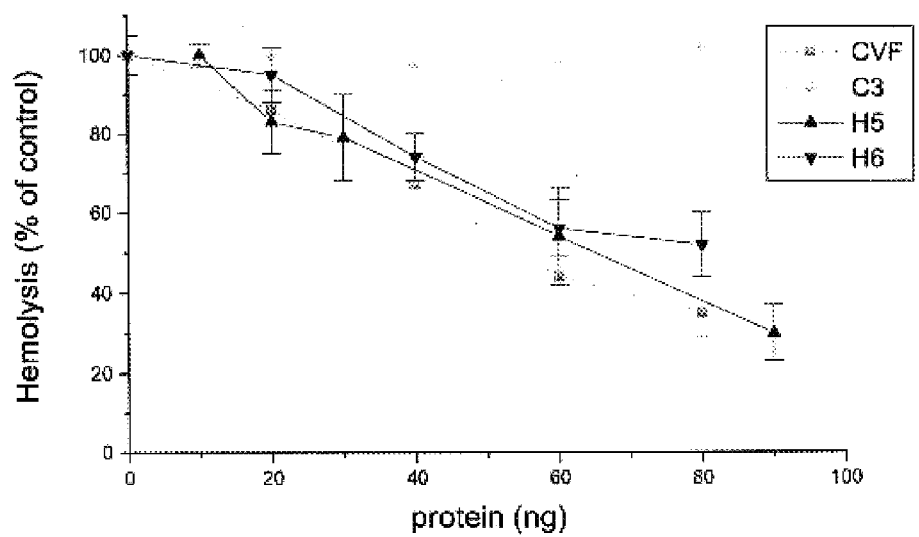

FIG. 16 shows the results of a complement consumption assay with hybrids H5 and H6, CVF, and human C3. The samples (40 µl) were incubated with human serum (approx. 10 µl) at 37° C. in a thermomixer under agitation for 3 h. Subsequently, 100 µl GVBS$^{++}$ and 30 µl sensitized sheep-erythrocytes (5×10$^8$ cells/ml) were added and the mixture was further incubated in a thermomixer until the serum controls reached a hemolysis of approx. 80% compared to the control with ddH$_2$O. After addition of 850 µl GVBS$^{++}$ the mixture was centrifuged (4° C., 2000 xg, 2 min) and the supernatants were measured at 412 nm. The figure shows the mean values±standard deviation of at least three independent experiments.

DETAILED DESCRIPTION OF THE INVENTION

The invention provides isolated polypeptides or proteins, respectively, that are biologically active derivatives of human complement component C3, that are able to continuously activate human complement system in human serum and thus to temporarily achieve inactivation of the complement system.

As used herein, the term "human complement component C3" ('human C3' or 'C3', respectively) refers to a polypeptide comprising the amino acid sequence of human complement component C3 shown in FIG. 1 (SEQ ID NO:2).

As used herein, the term 'CVF' refers to a polypeptide comprising the amino acid sequence of Cobra Venom Factor as shown in FIG. 1 (SEQ ID NO:4).

As used herein, the terms "comprising," "having," "encoding," and "containing," and derivatives of these terms, are intended to be open-ended. "consisting" is intended to be closed-ended.

The invention specifically relates to a polypeptide or protein having a length of 1638 to 1663 amino acids, which is a derivative of human complement component C3 (human C3), the amino acid sequence of which is shown in SEQ ID NO:2, wherein the carboxy terminal part of at least 68 amino acid residues of human C3 is replaced by a partial sequence of Cobra Venom Factor (CVF), the amino acid sequence of which is shown in SEQ ID NO:4, which partial sequence comprises at least the 68 carboxy terminal amino acid residues of CVF or a fragment thereof lacking 1 to 25 carboxy terminal amino acids, wherein said protein has at least 70% identity to human C3 or a fragment thereof, the fragment comprising at least amino acids 1 to 1638 of SEQ ID NO:2. Thus, the invention provides a protein comprising a derivative of human complement component C3 (human C3), the human C3 having an amino acid sequence set forth as SEQ ID NO: 2, wherein the carboxy terminal part of at least 68amino acids of said human C3 is replaced by a partial sequence of Cobra Venom Factor (CVF), the CVF having an amino acid sequence set forth as SEQ ID NO: 4, wherein the partial sequence of CVF comprises at least at least 68 carboxy terminal amino acids ofCVF or a fragment thereof, said fragment lacking 1 to 25 carboxy terminal amino acids, and wherein said protein has at least 70 percent identity to said human C3 or a fragment of said human C3 comprising at least amino acids 1 to 1638 of the amino acid sequence set forth as SEQ ID NO: 2. An alignment of the C3 and CVF sequences is shown in FIG. 1.

In addition, without departing from the spirit of the invention, it may be desired for specific purposes, however, to attach additional non-C3 and non-CVF amino acids to the carboxy terminus of the hybrid proteins.

Decomplementing activity of C3/CVF hybrid proteins is observed with polypeptides where the C3 α-chain was replaced by the corresponding carboxy terminal amino acids of the CVF chain (including the γ- and the β-chain of CVF). However, due to the high immunogenicity of such polypeptides, a higher degree of humanization is desired. Thus, according to a preferred embodiment, the polypeptides of the invention comprise an amino terminal C3 fragment containing the amino acids forming the β-chain (amino acids 23 to 667 of SEQ ID NO:2) as well as additional amino acids of the C3 chain following at the carboxy terminal end of the β-chain, i.e. from amino acid 668 towards the carboxy terminus of the peptide. At least 68 amino acids of the C3 sequence are replaced by amino acids of the corresponding CVF sequence. Reference is made in this respect to FIG. 1, showing the alignment of the C3 and CVF sequences. The requirement that the amino acid sequence of the polypeptides of the invention have at least 70% identity to the amino acid sequence of human C3 is intended to ensure that immunogenicity of the hybrid proteins is kept at a relatively low level. The 70% value thus also determines the minimum sequence stretch of the C3 sequence which is required for being combined with the amino acids of the CVF sequence which replace the corresponding carboxy terminal C3 amino acids. It is desired to provide polypeptides where the identity with the human C3 sequence is at least 80%, or preferably at least 90% and most preferably at least 95%.

According to a preferred embodiment of the invention, the protein or polypeptide, which is a derivative of human complement component C3 (human C3), has an amino acid sequence, which is selected from the group consisting of:
 a) the sequence shown in SEQ ID NO:6;
 b) the sequence shown in SEQ ID NO:8;
 c) the sequence shown in SEQ ID NO:10; and
 d) the sequence shown in SEQ ID NO:12.

The most preferred constructs represented by SEQ ID NO:6 and SEQ ID NO:8 are hereinafter also termed 'H5' and 'H6', respectively. The identity of the amino acid sequences with human C3 amino acid sequence is approx. 90.7% (91%) for H5, and 96.3% (96%) for H6. Reference is made in this regard to FIG. 2 showing various embodiments of the invention, including hybrids H5 and H6.

In order to retain decomplementing activity, the proteins require the presence of at least a stretch of 43 CVF amino acids in the carboxy terminal region, namely amino acids 1575 to 1617 of SEQ ID NO:3, which replace amino acids 1596 to 1638 of the C3 sequence (cf. FIG. 2, H7 truncated). The 43 amino acid stretch may either directly form the carboxy terminus of the hybrid protein or may be embedded within a larger sequence part comprising, for example, up to 118 CVF amino acids as is the case for H6 (i.e. replacing amino acids 1546 to 1663 of the C3 sequence), or up to 275 CVF amino acids as is the case for H5 (i.e. replacing amino acids 1389 to 1663 of the C3 sequence). In the latter cases, the 43 amino acidsare embedded within a larger CVF fragment having amino acid stretches of various lengths at both ends of the 43 amino acid stretch. In the case of H5 and H6, the proteins additionally comprise the 25 carboxy terminal amino acids of the CVF sequence part (ie. amino acids 1618 to 1642 of SEQ ID NO:3), resulting in a total length of 1663 amino acids for H5 and H6. As already outlined above, in the hybrid proteins of the invention some or all of these 25 carboxy terminal amino acids of CVF may be lacking, resulting in a polypeptide of the invention having a length of between 1638 and less than 1663 amino acids.

The invention also relates to anucleic acid encoding a protein having a length of 1638 to 1663 amino acids, which is a derivative of human complement component C3 (human C3), the amino acid sequence of which is shown in SEQ ID NO:2, wherein the carboxy terminal part of at least 68 amino acids of human C3 is replaced by a partial sequence of Cobra Venom Factor (CVF), the amino acid sequence of which is shown in SEQ ID NO:4, which partial sequence comprises at least the 68 carboxy terminal amino acids of CVF or a fragment thereof lacking 1 to 25 carboxy terminal amino acids, wherein said protein has at least 70% identity to human C3 or a fragment thereof, the fragment comprising at least aminoacids 1 to 1638 of SEQ ID NO:2.

According to a preferred embodiment, the nucleic acid is a nucleic acid encoding a protein having the amino acid sequence shown in SEQ ID NO:6. Preferably, the nucleic acid has the nucleotide sequence shown in SEQ ID NO:5.

According to another embodiment, the nucleic acid is a nucleic acid encoding a protein having the amino acid sequence shown in SEQ ID NO:8. Preferably, the nucleic acid has the nucleotide sequence shown in SEQ ID NO:7.

According to a further embodiment, the nucleic acid is a nucleic acid encoding a protein having the amino acid sequence shown in SEQ ID NO:10. Preferably, the nucleic acid has the nucleotide sequence shown in SEQ ID NO:9.

Further provided is a nucleic acid encoding a protein having the amino acid sequence shown in SEQ ID NO:12. Preferably, the nucleic acid has the nucleotide sequence shown in SEQ ID NO:11.

As used herein, the term "nucleic acid molecule" refers to a polynucleotide of natural or synthetic origin, which can be single- or double stranded, can correspond to genomic DNA, cDNA or RNA, and can represent either the sense or antisense strand or both.

The term "nucleic acid molecule" is intended to include nucleic acid molecules that contain one or more non-natural nucleotides, such as nucleotides having modifications to the base, the sugar, or the phosphate portion, or having one or more non-natural linkages, such as phosphothioate linkages. Such modifications can be advantageous in increasing the stability of the nucleic acid molecule, particularly when used in hybridization applications.

Furthermore, the term "nucleic acid molecule" is intended to include nucleic acid molecules modified to contain a detectable moiety, such as a radiolabel, a fluorochrome, a ferromagnetic substance, or a detectable binding agent such as biotin. Nucleic acid molecules containing such moieties are useful as probes for detecting the presence or expression of C3-derivative nucleic acid molecule.

The invention is also directed to expression of the protein in suitable host cells. In this context, a vector is provided which comprises a nucleic acid, which nucleic acid encodes a protein having a length of 1638 to 1663 amino acids, which is a derivative of human complement component C3 (human C3), the amino acid sequence of which is shown in SEQ ID NO:2, wherein the carboxy terminal part of at least 68 amino acids of human C3 is replaced by a partial sequence of Cobra Venom Factor (CVF), the amino acid sequence of which is shown in SEQ ID NO:4, which partial sequence comprises at least the 68 carboxy terminal amino acids of CVF or a fragment thereof lacking 1 to 25 carboxy terminal amino acids, wherein said protein has at least 70% identity to human C3 or a fragment thereof, thefragment comprising at least amino acids 1 to 1638 of SEQ ID NO:2.

Preferably, the vector comprisesa nucleic acid, which nucleic acid encodes a protein having an amino acid sequence, which amino acid is selected from the group consisting of:
 a) the amino acid sequence shown in SEQ ID NO:6;
 b) the amino acid sequence shown in SEQ ID NO:8;
 c) the amino acid sequence shown in SEQ ID NO:10; and
 d) the amino acid sequence shown in SEQ ID NO:12.

According to a preferred embodiment, the vector comprises a nucleic acid, which nucleic acid has a nucleotide sequence selected from the group consisting of:
 a) the nucleotide sequence shown in SEQ ID NO:5;
 b) the nucleotide sequence shown in SEQ ID NO:7;
 c) the nucleotide sequence shown in SEQ ID NO:9; and
 d) the nucleotide sequence shown inSEQ ID NO:11.

The constructs represented by SEQ ID NO:5 and SEQ ID NO:7 are hereinafter also termed 'H5' and 'H6', respectively.

In the afore mentioned expression vectors, the nucleic acid molecules are operatively linked to a promoter of gene expression. As used herein, the term "operatively linked" is intended to mean that the nucleic acid molecule is positioned with respect to either the endogenous promoter, or a heterologous promoter, in such a manner that the promoter will direct the transcription ofRNA using the nucleic acid molecule as a template. The invention provides nucleic acid molecules which are operatively linked to said promoter as well as vectors comprising said promoter driven nucleic acid molecules.

Methods for operatively linking a nucleic acid to a heterologous promoter are well known in the art and include, for example, cloning the nucleic acid into a vector containing the desired promoter, or appending the promoter to a nucleic acid sequence using polymerase chain reaction (PCR). A nucleic acid molecule operatively linked to a promoter of RNA transcription can be used to express C3-derivative transcripts and polypeptides in a desired host cell or in vitro transcription-translation system. The choice of promoter to operatively link to an invention nucleic acid molecule will depend on the intended application, and can be determined by those skilled in the art. Exemplary promoters suitable for mammalian cell systems include, for example, the SV40 early promoter, the cytomegalovirus (CMV) promoter, the mouse mammary tumor virus (MMTV) steroid-inducible promoter, and the Moloney murine leukemia virus (MMLV) promoter. Exemplary promoters suitable for bacterial cell systems include, for example, T7, T3, SP6 and lac promoters.

Exemplary vectors of the invention include vectors derived from a virus, such as a bacteriophage, a baculovirus or a retrovirus, and vectors derived from bacteria or a combination of bacterial sequences and sequences from other organisms, such as a cosmid or a plasmid. The vectors of the invention will generally contain elements such as an origin of replication compatible with the intended hast cells; transcription termination and RNA processing signals; one or more selectable markers compatible with the intended host cells;and one or more multiple cloning sites. Optionally, the vector will further contain sequences encoding tag sequences, such as GST tags, and/or a protease cleavage site, such as a Factor Xa site, which facilitate expression and purification of the encoded polypeptide.

The choice of particular elements to include in a vector will depend on factors such as the intended host cells; the insert size; whether expression of the inserted sequence is desired; the desired copy number of the vector; the desired selection system, and the like. The factors involved in ensuring compatibility between a host cell and a vector for different applications are well known in the art.

Also provided are cells containing an isolated nucleic acid molecule encoding a C3-derivative of the invention. The isolated nucleic acid molecule will generally be contained within a vector. The cells of the invention can be used, for example, for molecular biology applications such as expansion, subcloning or modification of the isolated nucleic acid molecule. For such applications, bacterial cells, such as laboratory strains of E. coli, are useful, and expression of the encoded polypeptide is not required. The cells of the invention can also advantageously be used to recombinantly express and isolate the encoded polypeptide. For such applications, bacterial cells (e.g. E. coli), insect cells (e.g. Drosophila), yeast cells (e.g. S. cerevisiae), and vertebrate cells (e.g. mammalian primary cells and established cell lines; and amphibian cells, such as Xenopus embryos and oocytes), can be utilized.

The polypeptides described herein, which are referred to, for example, as C3-derivatives or hybrid proteins, are therapeutic compounds that can be administered to individuals, in particular to human subjects, for decomplementation.

According to a preferred embodiment, the invention provides the use of said polypeptides in a method fortreating a patient suffering from complement-associated disorders or disorders affected by complement activation, comprising administering an effective amount of said protein or polypeptide, respectively. Specifically, the complement-associated disorder includes but is not limited to asthma, systemic lupus erythematodes, glomerulonephritis, rheumatoid arthritis, Alzheimer's disease, multiple sclerosis, myocardial ischemia, reperfusion, sepsis, hyperacute rejection, transplant rejection), cardiopulmonary bypass, myocardial infarction, angioplasty, nephritis, dermatomyositis, pemphigoid, spinal cord injury, and Parkinson's disease The invention thus relates to the use of the polypeptides or proteins of the invention for preparing a pharmaceutical composition for decomplementation, for treating a patient suffering from complement-associated disorders or disorders affected by complement activation (see above).

The invention further provides a pharmaceutical composition comprising the protein or polypeptide of the invention. Specifically, a pharmaceutical composition of the invention comprises an effective amount of a protein having an amino acid sequence, said amino acid sequence being selected from the group consisting of:
 a) the amino acid sequence shown in SEQ ID NO:6;
 b) the amino acid sequence shown in SEQ ID NO:8;
 c) the amino acid sequence shown in SEQ ID NO:10; and
 d) the amino acid sequenceshown in SEQ ID NO:12.

The therapeutic compounds can be administered to a mammal or human, respectively, by routes known in the art including, for example, intravenously, intramuscularly, subcutaneously, intraorbitally, intracapsularly, intraperitoneally, intracisternally, intra-articularly, intracerebrally, rectally, topically, intranasally, or transdermally. Preferred routes for human administration are intravenous administration. The pharmaceutical compositions of the invention are thus formulated forsaid administration routes, and, according to a preferred embodiment, comprise the compound and a pharmaceutically acceptable carrier depending on the route of administration of the compound and on its particular physical and chemical characteristics. Pharmaceutically acceptable carriers are well known in the art and include sterile aqueous solvents such as physiologically buffered saline, and other solvents or vehicles such as glycols, glycerol, oils such as olive oil and injectable organic esters. A pharmaceutically acceptable carrier can further contain physiologically acceptable compounds that stabilize the compound, increase its solubility, or increase its absorption. Such physiologically acceptable compounds include carbohydrates such as glucose, sucrose or dextrans; antioxidants, such as ascorbic acid or glutathione; chelating agents; and low molecular weight proteins.

The following examples are intended to illustrate but not limit the present invention.

EXAMPLE I

1 Materials and Methods
 1.1 Materials
 1.1.1 Chemicals
 General chemicals were purchased from Sigma (Taufkirchen, Germany), Merck (Darmstadt, Germany), Fluka (Buchs, Switzerland), Invitrogen (Leek, Netherlands), Biomol Feinchemikalien (Hamburg, Germany), Gibco BRL (Eggenstein, Germany), Applichem (Darmstadt, Germany), Roth (Karlsruhe, Germany), Millipore (Eschborn, Germany), Calbiochem (Schwalbach, Germany) and Peqlab (Erlangen, Germany).
 1.1.2 Enzymes, Proteins and Antibodies
 Restriction enzymes, Mung Bean nuclease, T4-Ligase, Calf intestinal alkaline phosphatase (CIAP) and the respective buffers were purchased from MBI Fermentas (St. Leon-Rot, Germany) and at NEB (Frankfurt, Germany). Thermus aquaticus DNA-polymerase was purchased from AGS (Heidelberg, Germany) or Roche (Mannheim, Germany). Lysozyme was also purchased from Roche (Mannheim, Germany). RNase was purchased from Sigma (Taufkirchen, Germany). CVF, C3 and Factor B are commercially available from Calbiochem (Schwalbach, Germany).

Antisera with specificity for CVF, C3 and Factor B can be generated following standard immunization procedures. Factor D was purchased from Sigma (Taufkirchen, Germany). Strep-Tactin was purchased from IBA (Göttingen, Germany). Antiserum against C3 from goat was purchased from Cappel (Eschwege, Germany). A monoclonal antibody against C3d was purchased from Quidel (Heidelberg, Germany). The monoclonal anti-Strep-tagII antibody was purchased from IBA (Göttingen, Germany). The secondary antibody anti-rabbit, anti-mouse or anti-goat, conjugated with alkaline phosphatase or peroxidase was also purchased from Sigma (Taufkirchen, Germany) or Cappel (Eschwege, Germany).
 1.1.3 Affinity Matrix and Particles
 Ni-NTA-agarose was purchased from Qiagen (Hilden, Germany). Strep-Tactin-Sepharose was purchased from IBA (Göttingen, Germany) and protein A/G-agarose was purchased from Santa Cruz Biotechnology (Santa Cruz, Calif., USA).
 1.1.4 Bacteria and Yeast Strains
 The bacteria strain E. coli DH5α(Promega, Mannheim, Germany) was used for amplification of plasmids. In Table 1, the genotypes of the strains are listed.

TABLE 1

| Genotypes of the bacteria strains used. |
|---|
| DH5α    F$^-$, endA1, gryA96, thi-1 hsdR17 (r$_K^-$,m$_K^+$), supE44, relA1. Φ80ΔlacZΔM15, Δ (lacZYA-argF), U169 |

1.1.5 Vectors

Figure 4:
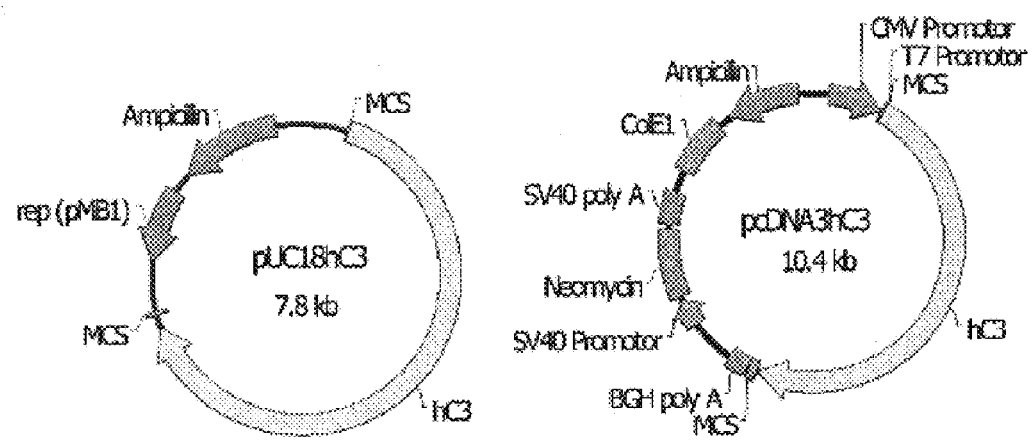
FIG. 4 shows a simplified map of pUC18hC3 and pcDNA3hC3.
Figure 5:
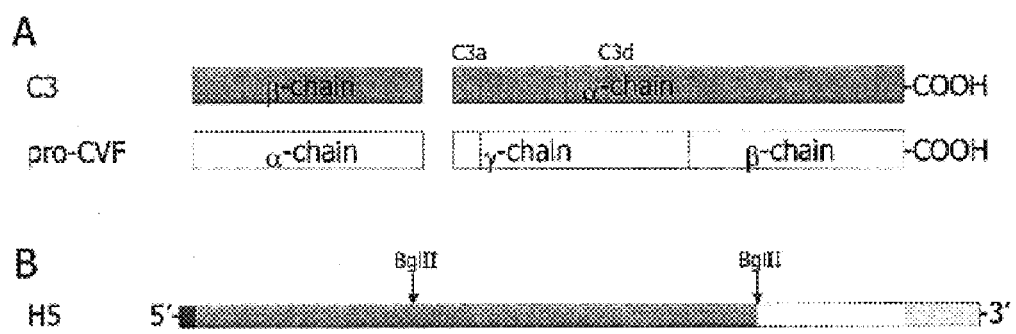
FIGS. 5A and 5B show a schematic representation of the Construct H5 encoding a hybrid protein of approx. 91% identity with human C3 A: Chain structures of C3 and praCVF. B: Structure of the cDNA of H5. The dark part of the nucleic acid from the 5' end up to the BglII cleavage site represents part of the molecule comprising C3 nucleic acids, the white part downstream of the BglII site comprises CVF nucleic acids.

The commercially available vectors which were used are listed. The vectors which are not commercially available are depicted in FIGS. 3 and 4.

pUC18

Vector pUC18 (MBI Fermentas, St. Leon-Rot, Germany) was used for cloning.

pEGFP-N1

Vector pEGFP-N1 (Clontech, Heidelberg, Germany) was used for transfection of mammalian cell lines in order to determine the transfection efficiency.

pcDNA3

Vector pcDNA3 (Invitrogen, Leek, Netherlands) was used for eukaryotic expression of proteins.

**pUC18CVF*/pCDNA3CVF**

Plasmids pUC18CVF* and pcDNA3CVF contain the cDNA of CVF (Genebank Accession No. U09969). In pUC18CVF*, a BglII-restriction site was introduced in Position 1793 (Mutation A1797C) and a HindIII-restriction site was deleted in Position 2380 (A2380T, G2381C). Plasmid pcDNA3CVF is shown in FIG. 3.

pUC18hC3/pcDNA3hC3

The plasmids contain the cDNA of human C3 (FIG. 4).

1.1.6 Cell Lines and Culture

GMEM medium, DMEM medium, penicillin G, streptomycin, geneticin and trypsin/EDTA were purchased from Gibco BRL (Eggenstein, Germany). Adenosine, guanosine, cytosine, uracil, thymidine, L-aspartic acid, and L-glutamic acid were purchased from Sigma-Aldrich (Steinheim, Germany). Culture flasks were purchased from Greiner (Frickenhausen, Germany), Nunc (Wiesbaden, Germany) or Sarstedt (Numbrecht, Germany). Fetal calf serum was purchased from Biochrom (Berlin, Germany).

Cell lines CHO, COS-7 and HEK293 were used for expression. CHO-cells were cultured in GMEM with 10% FCS and other additives. HEK293 and COS-7-cells were cultured in DMEM with 10% FCS.

1.1.7 Solutions

| | | |
|---|---|---|
| BCIP-stock solution | 0.5% (w/v) | BCIP in DMF |
| CAPS-buffer | 20 mM | CAPS, pH 11.0 |
| | 10% | methanol |
| citrate buffer | 50 mM | citric acid, pH 4.0 |
| Coomassie-destainer | 45% (v/v) | methanol |
| | 10% (v/v) | glacial acidic acid |
| Coomassie- | 0.25% (w/v) | Coomassie Brillant Blue R-250 |
| staining solution | 45% (v/v) | methanol |
| | 10% (v/v) | glacial acidic acid |
| detection buffer | 0.1 M | Tris-HCl |
| (for AP) | 4 mM | $MgCl_2$ |
| | pH 9.5 | |
| detection buffer | 3.3 mg ABTS | |
| (for POD) | 15 ml | citrate buffer, pH 4.0 |
| | 26.5 μl | $H_2O_2$ |
| developer | 0.26 M | sodium carbonate |
| (silver staining) | 0.6% (v/v) | formaldehyde (37%) |
| staining solution | 6 mM | silver nitrate |
| (silver staining) | 0.6% (v/v) | formaldehyde (37%) |
| fixing solution | 30% (v/v) | ethanol |
| (silver solution) | 10% (v/v) | glacial acidic acid |
| FCS | 30 min heat-inactivated at 56° C., storage in 50 ml aliquots at −20° C. | |
| G418-stock solution (40 mg/ml) | 0.4% (w/v) | G418 in HEPES (100 mM), pH 7.4 filter sterile, storage at −20° C. |
| G + A | 600 mg | L-Aspartamic acid |
| | 600 mg | L-Glutamic acid |
| | ad 100 ml dd$H_2O$ | |
| | filter sterile, storage at 4° C. | |
| $GVBS^{++}$ | 0.1% | gelatine |
| | in $VBS^{++}$, dissolve at 50° C., storage at 4° C. | |
| incubation solution | 25% (v/v) | ethanol |
| (silver staining) | 14 mM | sodium thiosulfate |
| | 0.5 M | sodium acetate |
| | 0.5% (v/v) | glutardialdehyde (25%) |
| incubation buffer | 0.1 M | $NaHCO_3$, pH 9.5 |
| loading dye (6×) | 20% (w/v) | Ficoll 400 |
| | 100 mM | EDTA |
| | 0.025% (w/v) | bromphenol-blue |
| | 0.025% (w/v) | xylen xyanol FF |
| Solution I | 50 mM | glucose |
| | 25 mM | Tris-HCl, pH 8.0 |
| | 10 mM | EDTA |
| | autoclave, storage at 4° C. | |
| Solution II | 0.2 M | NaOH |
| | 1% | SDS |
| Solution III | 3 M | potassium acetate |
| | 11.5% | acidic acid |
| | autoclave, storage at 4° C. | |
| NBT-stock solution | 0.1% (w/v) | NBT in 0.1 M Tris-HCl, pH 9.5 |
| nucleoside | 175 mg | adenosine |
| | 175 mg | guanosine |
| | 175 mg | cytosine |
| | 175 mg | uracil |
| | 60 mg | thymidine |
| | ad 500 ml d$H_2O$ | |
| | filter sterile | |
| PBS (5×) | 68.4 mM | NaCl |
| | 13.4 mM | KCl |
| | 7.3 mM | $KH_2PO_4$ |
| | 40 mM | $NaH_2PO_4$, pH 7.4 |
| phenol/chloroform | 50% (v/v) | phenol (Tris saturated) |
| | 50% (v/v) | chloroform |
| sample buffer (4×) | 250 mM | Tris-HCl, pH 6.8 |
| | 8% (w/v) | SDS |
| | 40% (v/v) | glycerin |
| | 0.004% (w/v) | bromphenol-blue |
| stacking gel | 0.5 M | Tris-HCl |
| buffer (4×) | 0.4% | SDS |
| | pH 6.8 | |
| SDS-stock solution | 10% (w/v) | SDS |
| stop solution | 50 mM | EDTA |
| (silver staining) | | |
| TAE-buffer (50×) | 2 M | Tris-acetate |
| | 20% | 0.5 M EDTA |
| | pH 8.0 | |
| tank buffer (1×) | 25 mM | Tris-HCl |
| | 192 mM | glycin |
| | 0.1% | SDS |
| TBS (5×) | 100 mM | Tris |
| | 250 mM | sodium chloride |
| | pH 7.5 | |
| TBST | 0.05% (v/v) | Tween 20 in TBS |
| separation gel | 150 mM | Tris-HCl |
| buffer (4×) | 0.4% | SDS |
| | pH 8.8 | |
| Tris-HCl pH 9.5 | 100 mM | Tris |
| | 4 mM | $MgCl_2$ |
| | pH 9.5 | |
| VBS | 2.5 mM | sodium-5,5-diethylbarbituric acid |
| | 143 mM | NaCl |
| | pH 7.4 | |
| $VBS^{++}$ | 0.15 mM | $CaCl_2$ |
| | 0.75 mM | $MgCl_2$ |
| | in VBS, pH 7.4 | |
| washing buffer | 0.1% (v/v) | Tween 20 in PBS |

1.1.8 Media

| | | |
|---|---|---|
| GMEM-medium | 50 ml | BHK21 medium 10 × (Glasgow MEM) |
| (without FCS) | 18.1 ml | sodium bicarbonate, 7.5% |
| | 5 ml | G + A |

-continued

| | | |
|---|---|---|
| | 10 ml | nucleoside |
| | 5 ml | sodium pyruvate, 100 mM |
| | 5 ml | NEAA (Non-essential amino acids, 100×) |
| | 450 ml | ddH$_2$O |
| | filter sterile (0.2 µm, Surfactant-free cellulose acetate-filter units, Nunc, Wiesbaden, Germany) | |
| GMEM-medium (with FCS) | 50 ml | BHK21 medium 10× |
| | 18.1 ml | sodium bicarbonate, 7.5% |
| | 5 ml | G + A |
| | 10 ml | nucleoside |
| | 5 ml | sodium pyruvate, 100 mM |
| | 5 ml | penicillin-streptomycin-solution |
| | 5 ml | NEAA (100×) |
| | 400 ml | ddH$_2$O |
| | 50 ml | FCS |
| | filter sterile (0.2 µm, Surfactant-free cellulose acetate-filter units, Nunc, Wiesbaden, Germany) | |
| LB-medium | 10 g | NaCl |
| | 5 g | yeast-Extract |
| | 10 g | bacto-trypton |
| | ad 1 l ddH$_2$O, autoclave | |
| LB-agar | 10 g | NaCl |
| | 5 g | yeast-extract |
| | 10 g | bacto-trypton |
| | 15 g | agar |
| | ad 1 l ddH$_2$O, autoclave | |
| TSS-solution | 85% (v/v) | LB-medium |
| | 10% (w/v) | PEG 8000 |
| | 5% (v/v) | DMSO |
| | 50 mM | MgCl$_2$, pH 6.5 |
| | autoclave | |

1.1.9 Oligonucleotides

The oligonucleotides which were used were synthesized by Metabion (Martinsried, Germany) (Table 2).

TABLE 2

List of the oligonucleotides used.

| Name | Sequence 5'-3' |
|---|---|
| AJS01 | GGATCCAGGTGCTCGGGTTGG |
| AS03 | AGTACCTTCCGGCTCAGCACAACCTCC |
| S23StrepI | CGGAGGTACCATGGAGAGGATGGCTCTCTAT |
| AS26StrepIV | GATAGACACGTGGAAATTTTCATTGCCG |
| AS34StrepV | GTCTTTTTCGAACTGCGGGTGGCTCCACCCATGAAGACCCTGGAAA |
| S35StrepVI | ACCCGCAGTTCGAAAAAGACGATGACGATAAAGCTCTCTACACCCTCATCACCCC |
| AS36StrepVhC3 | TCGAACTGCGGGTGGCTCCACCCCAGAGCCAGGGGAGG |
| S37StrepVIhC3 | ACCCGCAGTTCGAAAAAGACGATGACGATAAAAGTCCCATGTACTCTATCATCACC |
| S50H8for | TATGTGTACAAAACCAAGCTGCTTCG |
| AS51H8Back | TTCTTCTAGATTAAGTAGGGCAGCCAAACTCAGT |
| AS61His5'hC3 | ATGATGATGATGATGCCCCAGAGCCAGGGGAGG |
| S62his5'hC3 | CATCATCATCATCATGACGATGACGATAAAAGTCCCAT |

1.2 Methods 1.2.1 Densitometric determination of concentration

For densitometric determination of the concentration, 45 dilutions of known concentration of native CVF or human C3 (depending on the sample) were applied in addition to different volumina of the protein containing sample to be determined. The concentrations of the proteins of the calibration serious was chosen so that they were located in the range of the protein amount which was expected in the sample. The gel was subjected to wet-blotting or semidry-blotting procedures and the proteins were subsequently stained using immuno-printing. Then, the membrane was scanned and the concentration of the sample was determined using the program Imagemaster 1D Elite Version 2.01 (Amersham Pharmacia Biotech, Freiburg, Germany)

1.2.2 ELISA

ELISA was performed in order to detect proteins in supernatant. For this purpose, 1 µg of a protein, which was diluted in 100 µl incubation solution were immobilized on the well of an ELISA plate overnight at 4° C. Subsequently, the wells of the plate were washed three times with washing buffer (200 µl). Then, the wells were blocked with 200 µl 5% milk powder in PBS for 5 hours at room temperature. After washing three times, 200 µl of the supernatant of transient expression or purified diluted proteins in PBS, respectively, were introduced into the wells and incubated overnight under agitation at 4° C. After this, the samples were washed three times with washing buffer and incubated with 100 µl of a 1:1000 dilution of the respective antibody in 2,5% milk powder in PBS at room temperature. Subsequently, the samples were washed three times and incubated for one hour with 100 µl of a 1:1000 dilution of an respective peroxidase-conjugate in a 2,5% milk powder in PBS at room temperature. Finally, the samples were washed three times, and then 100 µl detection buffer (for POD) were added. After staining the wells, extinction at 405 nm was measured with a micro titer plate-photometer (ELISA-Reader, SLT-Instruments, Grödingen, Austria, Easy Reader EAR 400AT).

1.2.3 Expression of CVF, C3 and the hybrids in mammalia

For expression of recombinant CVF, C3 and of the hybrids of the invention, different cell lines were available.

COS-7-cells were originally obtained from kidney of monkeys and contain the SV-40 origin of replication. They express the large T-antigen of the SV-40 virus, which facilitates efficient replication. As a consequence, these plasmids show high copy numbers in the cell. Thus, the cells are suitable for transient expression. CHO-cells from the ovaria of Chinese hamster contain an RNA polymerase gene having a nucleus localisation signal. Therefore, they can be used for preparation of stably tranfected cell lines. HEK293-cells are human embryonic kidney cells and can be used for transient or stable expression. The HEK.EBNA-cells which were employed constitutively express the Epstein-Barr-Virus (EBV) Nuclear Antigen 1 (EBNA-1, EBV nuclear antigen 1). EBNA-1 was identified as the gene which is mainly responsible for immortalization of cells by the EBV (Lupton and Levine, 1985). For expression, vector pcDNA3 was available, which facilitates an efficient expression in mammalia via the CMV-promotor. The neomycin gene is available as resistence for the expression under selection pressure. The expression wasperformed as desribed in 1.2.9.

1.2.4 Partial purification of the recombinant CVF from the supernatant of the transient expression For separation of the low molecular components of the culture supernatants or column fractions, these supernatants or fractions were transferred into a dialysis tube (SpectraPor CE 100, MWCO 100 kDa, Roth, Karlsruhe, Germany) and dialysed overnight against PBS.

The concentration of dialysed samples was performed with Centricon-units (MWCO 100 kDa, Millipore, Eschborn, Germany). For this purpose, centrifugation was performed at 1,000 xg (4° C.) until the desired final volume was reached.

For partial purification and for separation of interfering components, respectively, as well as of low molecular components, column chromatographic methods were employed. The supernatant (2.5 ml) from transient expression was loaded onto a PD10-column according to the manufacturer's instructions (Amersham Pharmacia Biotech, Freiburg, Germany). PBS was used as a running buffer. The fractions were examined for recombinant protein by Western blotting and subsequent immunoprinting. For partial purification, 2 ml supernatant of the transient expression were loaded onto a 1 ml EconoPac-column (Biorad, Munich, Germany) using a Trisbuffer (50 mM, pH 7.5). The same buffer with 500 mM NaCl added thereto was used for elution. The fractions were also examined for protein content and dialysed against PBS.

For control purposes, the identic procedure was employed with the supernatant of non-transfected cells.

1.2.5 Purification and detection of proteins using the Strep-tag system 1.2.5.1 The Strep-tag system For purification and immobilization of the recombinant proteins, CVF, C3 and the hybrids consisting of CVF and C3 were supplied with a Strep-tag-fusion peptide. The Strep-tag is a synthetic peptide consisting of 9 amino acids (AWRHPQFGG), which binds to streptavidin with an affinity of $2.7 \times 10^4$ (Schmidt et al., 1996). It uses the binding pocket for biotin. As C-terminal fusion partner for proteins, it can be used for purification and detection. An N-terminal fusion is also possible since the system has been improved. The resulting Strep-tagII (WSHPQFEK) binds with a lower affinity to Streptavidin (Schmidtet al., 1996), however, a derivate was found by a selection round with randomly mutated Streptavidin, which in turn has a sufficient high affinity (Skerra and Schmidt, 2000). With a dissociation constant of 1 µM, the agarose-immobilized Streptavidin-derivate Strep-Tactin can be used for purification. Strep-tactin-conjugates or anti-Strep-tagII antibodies can be utilized for detection in immunoprinting or in ELISA analysis.

1.2.5.2 Detection of strep-tag fusionproteins

For detection of strep-tagII-fusion proteins in supernatant of transient expression, an ELISA was conducted. For this purpose, 3 µg strep-tactin (diluted in 40 µl incubation solution) were immobilized overnight at 4° C. on the surface on the wells of an ELISA plate (Greiner, Frickenhausen, Gemany). Subsequently, the procedure described above in connection with the ELISA was performed.

1.2.6 Purification of hydrid H5

Supernatant (500 ml) obtained from stably transfected cells was adjusted to pH 7.5, passed trough a 0.45 µm cellulose acetate membrane and loaded onto a Poros HQ/M anion exchange column equilibrated with 50 mM Tris, pH 7.5 using ÄKTA purifier (Amersham Bioscience, Freiburg, Germany). The recombinant protein was eluted using a linear (0-500 mM) NaCl gradient. Fractions (2 ml) were analyzed using 7.5% SDS-PAGE and western blotting, pooled and dialyzed against phosphate buffered saline (PBS). The pooled sample was diluted (1:9) in 50 mM sodium phosphate, 0.55 M sodium sulfate buffer, pH 7.0, filtered (0.2 µm) and applied to a thiophilic resin (1.5 ml, BD Bioscience, Heidelberg, Germany) equilibrated with 50 mM sodium phosphate, 0.5 M sodium sulfate buffer, pH 7.0. After extensive washing of non-adsorbed proteins with the equilibration buffer (>30 column volumes), elution was performed using 50 mM sodium phosphate buffer, pH 7.0. Fractions (1.5 ml) were analyzed by 7.5% SDS-PAGE and western blotting. Fractions containing H5 were pooled, dialyzed against 100 mM Tris, 150 mM NaCl, pH 8.0 (buffer W), loaded onto Strep-Tactin sepharose (2 ml, IBA, Göttingen, Germany) equilibrated with buffer W, washed with 10 ml buffer W, and eluted with buffer W containing 2.5 mM desthiobiotin. Protein concentration and purity of the fractions were analyzed by 7.5% SDS-PAGE. Pooled fractions were dialyzed against PBS and employed for further characterization.

1.2.7 Purification of hybrid His-H6

For purification of His-H6 using IMAC, imidazol was added to 50 ml stable supernatant and incubated over night on a shaking unit. The matrix was then centrifuged (700 xg, 10 min, 4° C.), the supernatant removed, and the matrix was resuspended in 50 ml PBS. Following centrifugation (700 xg, 10 min, 4° C.), the matrix was again resuspended in 5 ml PBS and loaded onto a flowthrough column. Subsequently, bound proteins were eluted from the column in 1 ml portions using 3 ml 300 mM imidazole in PBS. Then, protein content was determined in the fractions by SDSPAGE followed by subsequent Western blot and immunoprinting. Suitable fractions were combined, dialysed against PBS and used for further analysis.

1.2.8 Complement methods 1.2.8.1 Preparation of sensitized sheep erythrocytes

Sheep whole blood (1 ml, Behringwerke, Marburg) was resuspended in 13 ml cold GVBS$^{++}$ and centrifuged (10 min, 1,000 xg, 4° C.). Supernatant was removed, and the erythrocytes were again resuspended in 14 ml GVBS$^{++}$. This procedure was repeated until supernatant became clear. Subsequently, the erythrocytes were resuspenden in approx. 5 ml GVBS$^{++}$. Erythrocytes were adjusted by diluting with GVBS$^{++}$ to give an absorption of 1.9 ($5 \times 10^8$ cells(ml) at 412 nm for 30 µl erythrocyte suspension in 1 ml ddH$_2$O. 2 µl antiserum against sheep erythrocytes (anti sheep red blood cell stroma, Sigma, Taufkirchen) were added to each of 1 ml of the adjusted erythrocytes. Sensitizing was performed for 1 h in a water bath at 37° C., while inverting the reaction tube regularly after 10 min. The sensitized erythrocytes were washed 3 times with 2 ml GVBS$^{++}$ and centrifuged (3 min, 1,000 xg, 4° C.). The erythrocytes could be stored up to three days. Prior to each use, OD$_{412}$ was adjusted to 1.9.

1.2.8.2 Isolation of guinea pig-erythrocytes

Guinea pig-erythrocytes were isolated from whole blood, which was obtained from isofluoran-narcotized guinea pigs by punction of the eyes. Approximately 1 ml blood was taken and immediately transferred into a tube containing 1 ml ice-cold ACD solution. The ACD solution serves as anti-coagulant. The erythrocytes were separated by centrifugation (1,000 xg, 4 min, 4° C.), resuspended in 14 ml GVBS$^{++}$ and again centrifuged (1,000 xg, 4 min., 4° C.). This procedure was repeated 3 to 4 times until the supernatant remained clear. Finally, the erythrocytes were resuspended in approximately 5 ml GVBS$^{++}$. The erythrocytes were diluted with GVBS$^{++}$ until 30 µl of the erythrocyte suspension in 1 ml ddH$_2$O gave an absorption of 1.9 ($5 \times 10^8$ cells/ml) at 412 nm.

1.2.8.3 Complement consumption assay

This test is based on the complement consuming effect of CVF. If a CVF containing sample is incubated with human serum, the complement proteins are consumed depending on the CVF activity (Ballow and Cochrane, 1969; Cochrane et. al., 1970). The remaining complement activity of the serum can be detected subsequently using sensitized sheep erythrocytes.

First, quantification of human serum was performed by serum titration, which led to hemolysis of sheep erythrocytes by 70-90%. For this purpose, different serum concentrations (serum value) were provided in 2 ml reaction tubes (double measurements) and filled up to 40 µl with GVBS$^{++}$. Additionally, controls were prepared, which contained 40 µl GVBS$^{++}$ (buffer-control) only, or 40 µl ddH$_2$O (complete lysis) only, respectively. All reactions were incubated for 30 min at 37° C. under agitation (Thermomixer 5437, Eppendorf, Hamburg, Germany). Then, 100 µl cold GVBS$^{++}$ or 100 µl ddH$_2$O (upon complete lysis), respectively, and 30 µl sensitized sheep erythrocytes were added. Further incubation took place for 30 min, as described above. Subsequently, the samples were kept on ice. 850 µl cold VBS$^{++}$ or 850 µl ddH$_2$O (upon complete lysis), were added, respectively. The supernatants were transferred into cuvettes, and optical density was measured at 412 nm. Hemolysis was subsequently calculated according to the following formula:

$$\% \text{ hemolysis} = \frac{OD_{412} \text{ serum value} - OD_{412} \text{ buffer control}}{OD_{412} \text{ complete lysis} - OD_{412} \text{ buffer control}} \times 100\%$$

For complement consumption assay, the amount of serum determined in prior tests and the samples (max. 20 µl) were provided in a 2 ml reaction tube (double measurements) and supplemented with GVBS$^{++}$ to give 40 µl. Additionally, reaction mixes of the following controls were prepared: determined amount of serum, supplemented with GVBS$^{++}$ to give 40 µl (serum control, 4 to 5 samples); 40 µl GVBS$^{++}$ (buffer control) and 40 µl ddH$_2$O (complete lysis). All reaction mixes were incubated for 3 hours at 37° C. under agitation. Then, 100 µl cold GVBS$^{++}$ or 100 µl ddH$_2$O upon complete lysis, respectively, and 30 µl adjusted sensitized sheep erythrocytes were added, and incubation took place for 30-40 min, as described above. After 15 min, serum control as well as a reaction mix of the complete lysis were measured according to the following principle. The samples were kept on ice, 850 µl cold VBS$^{++}$ or 850 µl ddH$_2$O at complete lysis, respectively, were added and centrifuged (4° C., 2,000 xg, 2 min.). Supernatants were transferred into cuvettes, and the optical density was measured at 412 nm. Lysis was calculated according to the following formula:

$$\% \text{ hemolysis} = \frac{OD_{412} \text{ serum control} - OD_{412} \text{ buffer control}}{OD_{412} \text{ complete lysis} - OD_{412} \text{ buffer control}} \times 100\%$$

In case the value for the serum control was clearly below 80% of the complete lysis value, a second serum control was taken after 10 further minutes of incubation and measured as described above. Once a value of 70-80% hemolysis was obtained, all reaction mixes were measured and evaluated according to the same principle In order to facilitate comparison of different series of measurements, values were referred to the corresponding serum control.

1.2.8.4 Solid Phase Complement Consumption Assay

For characterization of complement consuming activity of the recombinant strep-tagII-C3/CVF hybrids, a solid phase assay was performed. Here, proteins were bound via their strep-tag to an ELISA plate, which was covered with streptactin. Subsequently, activity can be determined by adding serum. For this purpose, 3 µg strep-tactin (diluted in 40 µl incubation solution) were immobilized overnight at 4° C. on the surface of the wells of an ELISA plate (Greiner, Frickenhausen, Germany). Then, the wells were washed 3 times with 200 µl washing buffer and subsequently blocked with 200 µl 3% BSA in PBS for 5 hours at room temperature. After washing the wells again (3 times), different volumes of the supernatants or of the samples were provided in the wells. Protein concentration in the supernatants was previously determined densitometrically. After over night incubation at 4° C. under agitation, the wells were washed 3 times with washing buffer. Subsequently, GVBS$^{++}$ and the amounts of serum determined in serum titration were added, giving a volume of 60 µl. The ELISA plate was sealed with paraffin and fixed to the bottom of an incubation shaker. Subsequently, incubation took place for 3 hours at 37° C., 150 rpm. Supernatants were transferred into 2 ml reaction tubes, and following addition of 100 µl GVBS$^{++}$ and 30 µl sensitized erythrocytes the camplement consumption assay was conducted as described.

1.2.8.5 Bystander lysis-assay

This test for detecting hemolytic activity is based on fluid C5-activation and can be determined by lysis of non-sensitized guinea pig erythrocytes (Vogel, 1985). In this method, the extent of complement activation is determined by photometric measurement of released hemoglobin. Different amounts of the protein to be analyzed were diluted in 20 µl GVBS$^{++}$ mixed with 20 µl guinea pig serum (Sigma, Taufkirchen, Germany) and 20 µl guinea pig erythrocytes (5×108 cells/ml) in a 2 ml reaction tube and incubated for 3 hours at 37° C. under agitation (Thermomixer 5436, Eppendorf, Hamburg, Germany). The reaction was stopped by adding 1 ml icecold VBS++-buffer. The erythrocytes were centrifuged (2,000 xg, 4° C., 2 min) and released hemoglobin in the supernatant was determined by measurement of extinction at 412 nm. Reaction mixes with 20 µl erythrocytes and 40 µl ddH2O (complete lysis) or 20 µl guinea pig serum, 20 µl erythrocytes and 20 µl GVBS++ (serum control), respectively, served as controls.

1.2.8.6 Determination of the stability of C3 convertases 500 ng of each native CVF (nCVF), hC3, and the derivative H5 were mixed with 950 ng of factor B and 8 ng of factor D in a volume of 60 µl VBS (2.5 mM Na-5,5-diethyl-barbituric acid, 143 mM NaCl, pH 7.4). After addition of MgCl$_2$ to a final concentration of 10 mM, the samples were incubated for 2 h at 37° C. to allow for convertase formation. Subsequently, all samples were supplemented with EDTA to a final concentration of 10 mM to inhibit further formation of convertases. Thereafter, the samples were incubated at 37° C. and after different periods of incubation 20 µl aliquots were added to 150 µM Boc-Leu-Gly-Arg-7-amido-4-methylcoumarin acetate (Sigma, Taufkirchen, Germany) in 180 µl VBS. The timecourse of fluorophore release was determined in black FIAPlates (96 K, Greiner Bio-One, Frickenhausen, Germany) using an excitation filter of 370 nm and an emission filter of 465 nm in amicroplate reader (Genios, Tecan, Creilsheim, Germany). Values after 60 min of fluorophore release were defined as 100%. The slope of the graph was used to determine the enzymatic activity of the sample.

1.2.9 Tissue culture and expression methods 1.2.9.1 Culturing and passaging of COS-7 and HEK293 cells COS-7 cells or HEK293 cells were cultured in an incubator (Heraeus Instruments Begasungsbrutschrank 6060) in a water saturated atmosphere (5% CO$_2$) at 37° C. Growth was performed in DMEM medium (Gibco/BRL, Eggenstein, Germany) which was supplemented with 10% FCS (Biochrom, Berlin, Germany). As soon as cells grew confluently in the tissue culture flasks (75 cm$^3$, Cellstar, Greiner Labortechnik, Frickenhausen, Germany), they were passaged into a new culture flask (approximately every 3 days). Cell supernatant was removed and the cells were washed with PBS. 4 µl trpysin/EDTA (Gibco BRL, Eggenstein, Germany) were added, and the cells were incubated for 5 min in an incubator. Detachment of the cells from the bottom was suported by gentile knocking and was controlled under the microscope.

When the cells were almost completely detached, the procedure was stopped by adding 8 ml serum-containing medium. The suspension was transferred into a 15 ml-reaction tube, and the cells were sedimented by centrifugation (5 min, 1,000 xg, RT). The supernatant was removed, the pellet was resuspended in 10 ml serum-containing medium and 1 to 3 ml of the cell suspension were transferred into a new tissue culture flask and supplemented with serum containing medium to give a final volume of 13 ml.

1.2.9.2 Culturing and passaging CHO-cells

Growth of cells was performed in serum-containing GMEM-medium (10% FCS). Culturing and passaging of CHO-cells was performed in an analogous manner as described for COS-7-cells.

1.2.9.3 Transfection

For expression in mammalian systems, expression vector pcDNA3 (Invitrogen, Leek, the Netherlands) comprising the corresponding genes was introduced into the cells by the GenePorter reagent (PeqLab, Erlangen).

DNA (1 to 4 µg) and 10 to 15 µl GenePorter transfection reagent were diluted in 500 µl serum-free medium and pooled. The reaction mix was incubated for 45 min at room temperature. At the same time, the cells which were passaged in a 6well plate approx. 24 hours earlier (300-500 µl of cell suspension with 2 ml serum containing medium per well; TC-plate, 6-well, Greiner Labortechnik, Frickenhausen, Germany), were washed with PBS. Then, the DNA GenePorter mix was carefully added drop-wise to the cells, and the 6-well plate was placed in the incubator. After 3 hours, the medium was replaced against 2 ml serum-containing medium, and the cells were kept for 2 to 3 days in the incubator for cell growth.

When using Nutridoma HU (100×; Roche Diagnostics, Mannheim, Germany), the cells were added to Nutridoma HU after transfection in serum-free medium and kept growing in the incubator for 2 to 3 days.

A reaction mix without DNA was prepared as negative control. If applicable, a reaction mix with 1 µg pEGFP-N1 was prepared as positive control. Plasmid pEGFP-N1 encodes the green fluorescence protein (GFP) and can be used for determining transfection efficiency since the GFP expressing cells can be detected using a fluorescence microscope. The supernatant of the pEGFPN1 transfected cells was already removed after 24 hours, cells were washed with 2 ml PBS, and 500 µl trypsin/EDTA were added. Detachment of cells was performed for 5 min in the incubator. Then, 2 ml PBS were added and the cell suspension was transferred into a 50 ml reaction tube for centrifugation (5 min., 1,000 xg, RT). The supernatant was removed and the cell pellet was resuspended in 2 ml PBS. 10 µl thereof were provided in a Neubauer-counting chamber, and the number of fluorescencing cells and the total number of all cells were counted in the outer four squares.

Calculation of the cell number/ml:

$$\text{Cells/ml} = \frac{\text{Number of cells of all squares}}{4} \times 10^4$$

Calculation of transfection efficiency:

$$\text{Efficiency (\%)} = \frac{\text{number of fluorescent cells}}{\text{number of cells of all squares}} \times 100\%$$

1.2.9.4 Expression under selection pressure

In order to increase yields, generation of stably expressing lines was desired, wherein the reaction mixes from transient expression were kept in culture by adding an antibiotic and by sub culturing. Depending on resistance, 10 µl/ml culture medium were added to an antibiotic stock solution (G418), or 5 µl/ml culture medium were added to zeocine.

1.2.9.5 Expression in serum or protein-free medium

For culturing in serum-free or protein-free medium, cells were step-wise adapted with SCF30- or Mampf3-medium (Promocell, Heidelberg, Germany) with 1 mM L-glutamine. The percentual portion of the serum-free or protein-free medium was increased by 25% in every second passage. Otherwise, passaging took place as described.

1.2.9.6 Monoclonalization

In order to obtain a homogeneous cell population, monoclonalization was conducted, wherein the different cells were monoclonalized, expanded and subsequently examined with respect to their expression level by Western blotting and immuno printing.

For this purpose, all cells were incubated for 3 to 4 passages after transfection under selection pressure in order to guarantee that a large portion of cells contained the resistance and therefore expressed the target protein. This procedure allows to equate the cell number per ml, which is counted thereafter using a Neubauer-counting-chamber, with the number of cells, which express the target protein. Subsequently, cell density was set to 1 cell per 100 µl medium with 10% FCS, and 100 µl of this dilution were introduced into each of the 48-96 wells of the 96 well plates (Greiner Labortechnik, Frickenhausen, Germany). After approximately one week, the medium was removed, and 100 µl medium with 10% FCS were added. After approximately 2 weeks, the wells were examined under the microscope for one colony per well. Some were selected, and the cells were detached with 25 µl trypsine for 5 min at 37° C. and completely transferred into the well of a 24-well-plate (Greiner Labortechnik, Frickenhausen, Germany), which was completely filled with 500 µl medium containing 10% FCS. After one week, this precedure was repeated with 100 µl trypsine, and all cells were placed into a well of a 6-wellplate. After another 3 to 4 days, 100 µl supernatant per well were taken and examined by Western blotting andsubsequent immuno printing. The cell population, which finally showed the strongest band, was further expressed under selection pressure and cryoconserved, if applicable.

EXAMPLE II

Concept and establishment of a solid phase assay (cf. Example I, 1.2.8.4)

The assay comprises immobilizing the hybrids as Strep-tagII fusion proteins to Strep-Tactin, which is bound to the surface of ELISA plates. The subsequent addition of buffer and serum should facilitate the conduction of the complement-consumption-assays in the ELISA plate.

For immobilization, a Strep-tagII was selected, which is a peptide consisting of 8 amino acids (WSHPQFEK). With a dissociation constant of 1 µM to Strep-Tactin, the Strep-tag is suitable for directed immobilization as well as for protein purification and detection purposes.

Fusion of an affinity tag to CVF and C3

The presence of the affinity tag is essential for the performance of the developed solid-phase-assay. The proteins which shall be analyzed need a fusion tag; therefore, an enterokinase-cleavage site was inserted into the cDNA of CVF and C3 between the signal sequence and the N-terminus of the Strep-tagII which allows the cleavage of the affinity tags lateron.

Using the CVF-cDNA two amplification products were generated in two PCR reactions using the oligonucleotides S35 and AS26 and the oligonucleotides S23 and AS34. The amplification products were hybridized using PCR. The amplification product was digested using the restriction enzymes KpnI and Eco72I and ligated into a pcDNA3CVF-vector which was digested analogously. The cDNA of human C3 was treated in an analogous manner. Using the oligonucleotides S01 and AS36 and S37 and AS03, amplification products were generated and hybridized. For insertion, the restriction sites NotI and Bpu1102I were used.

Alternatively, His tags were used as affinity tags, which—in analogy to the Strep-tags—were inserted between the signal sequence and the N-terminus.

Briefly, for H6, two amplification products were generated using St-hC3 with the oligonucleotides S01 and AS61 and with the oligonucleotides S62 and AS03. The amplification products were hybridized by PCR. Then, the amplification product was inserted via the restriction sites NotI and Bpu1102I in an analogously digested vector. The successful transient expression of the hybrid HisH6 was verified in a sandwich-ELISA and in an immunoblot. The densitometric quantification which was performed on the basis of the immunoblot resulted in yields of 1-2 mg/l.

Subsequently, St-CVF, St-C3 or the hybrids His-H6 or St-H6 hybrids, respectively, were successfully expressed in CHO-cells. A densitometric quantification was performed on the basis of an immunoblot and resulted in yields, which are comparable to the respective yields of wildtype proteins.

Evaluation of assay conditions

For establishing this solid-phase-assay which should offer the possibility of directly characterizing proteins after transient expression, an evaluation of the conditions was performed. The basis for evaluation is the adaption of the complement consumption assay to a solid phase-format. In order to determine the most suitable conditions, native CVF was used in a complement consumption assay in an ELISA plate under variation of different parameters.

For incubating the samples in the ELISA plate agitation at 37° C., a common incubation shaker was used. For optimizing the conditions, the reaction mixtures were measured at different rotation velocities for ensuring sufficient admixture of the samples, which is necessary for the assay. Further reaction mixtures were analyzed with different pre-incubation periods for obtaining representative values for the expected protein concentration range of 20-200 ng protein.

The best results were obtained at a rotation velocity of 150 rpm and a pre-incubation time of 3 hours, since the samples with different protein concentrations represent significant distinguishable values.

Activity studies of the Strep-tag-Fusion Proteins

A prerequesite for the solid phase assay is the accessibility of the Strep-tag-fusion protein, which was examined in an ELISA analysis. The fusion proteins St-CVF and St-C3 were selectively immobilized to Strep-Tactin on the surface on an ELISA plate. Detection of the target proteins was performed using polyclonal sera. Both proteins could be immobilized and detected, thus demonstrating the accessibility of the Strep-tag.

The concentration of the two proteins in the supernatant of the transient expression was quantified densitometrically on the basis of immunoblot. Polyclonal sera against C3 and CVF were used. The quantified recombinant proteins were then immobilized in comparable concentrations to Strep-Tactin and utilized in a complement consumption assay under evaluated conditions.

The activity of the recombinant CVF expressed in mammalia could be demonstrated through significant reduction of hemolysis compared to human C3.

The positive results which were achieved also confirm that the established solid phase complement consumption assay is an effective method for characterizing hybrids consisting of CVF and human C3.

Discussion

The solid phase-assay enables the binding of CVF and of the hybrids via an affinity tag to a protein immobilized on a suitable surface. In this manner, the interfering components could be separated and a subsequent complement consumption assay with the immobilized proteins enables the characterization of the hybrids.

The Strep-tagII was introduced via oligonucleotides between the signal sequence and the N-terminus of the CVF and C3, respectively. Additionally, an enterokinase-restriction site was inserted which allows the cleavage of the Strep-tagII lateron.

All fusion proteins were successfully expressed in CHO-cells, and the accessibility of the fusion peptide was confirmed by ELISA analysis. The fusion of the Strep-tag did neither influence secretion nor expression yield, as shown by densitometric quantification.

The performing of the complement-consumption-assay in a solid-phase-system requires an adaption of the assay conditions. For this reason, an evaluation of different parameters was performed. Different concentrations of nCVF were subjected to complement-consumption-assays under different conditions in an ELISA plate. Both the rotation velocity as well as the time period of the pre-incubation was varied. Subsequent studies under optimized conditions (150 rpm, 3 h pre-incubation with St-CVF) confirmed the general feasability of this assay system. A significant complement-consuming activity was demonstrated for St-CVF. In contrast, the control protein St-C3 did not show an activity.

The establishing of solid-phase-assays therefore allows for the first time the efficient characterization of transiently expressed proteins comprising a Strep-tag-fusion peptide. The successful characterization of the recombinant CVF confirmed that a further processing of the two-chain CVF is not required for activity.

EXAMPLE III

Generation and Expression of H5

Cloning and Expression of Construct H5

A hybrid was constructed, which contains th human β-chain and additionally the humanized Factor B- and Factor H-binding sites as well as the cleavage sites for Protease Factor I. In order to generate the construct, BglII restriction sites were used. Construct H5 is shown in FIG. 5. In addition tothe α-chain, the γ-chain as well as the C3a and the C3d regions were humanized.

For cloning of construct H5, a fragment consisting of pUC18 and the 3'terminus of CVF was obtained from pUC18CVF* utilizing Ecl136I and BglII restriction. Subsequently, said fragment was ligated with a fragment obtained from pcDNA3hC3 by EcoRI restriction, followed by mung bean nuclease digestion and BglII restriction. The latter fragment had a size of 1870 bp contained the 5' terminus of C3 cDNA. The vector ligated in this way (referred to as H2Δ2307bp) contained 1800 bp of the C3 5' terminus and 1000 bp of the CVF 3' terminus.

Figure 6A:
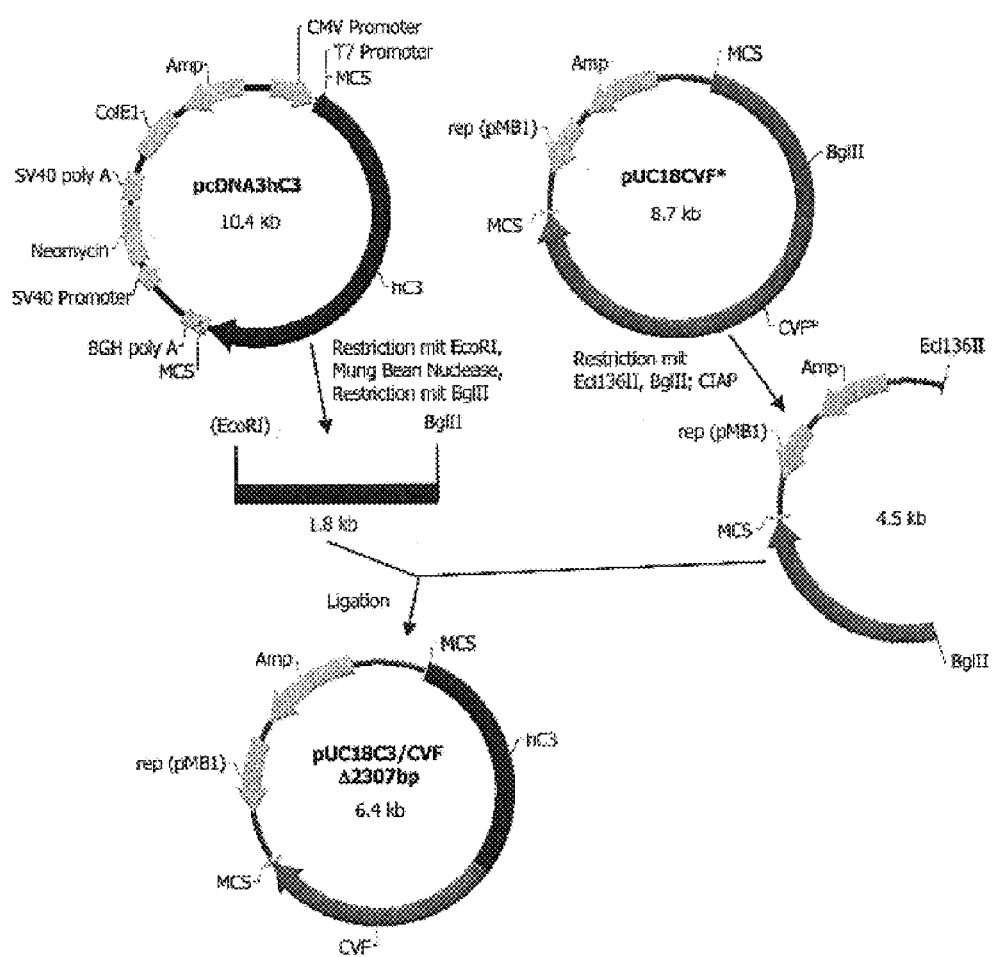
FIGS. 6 (A+B) shows the cloning strategy used for generating construct H5 expressing a hybrid protein of 1663 amino acids in length, which amino terminally comprises amino acids 1 to 1388 of C3 followed by amino acids 1368 to 1642 of CVF at the carboxy terminus.
Figure 6B:
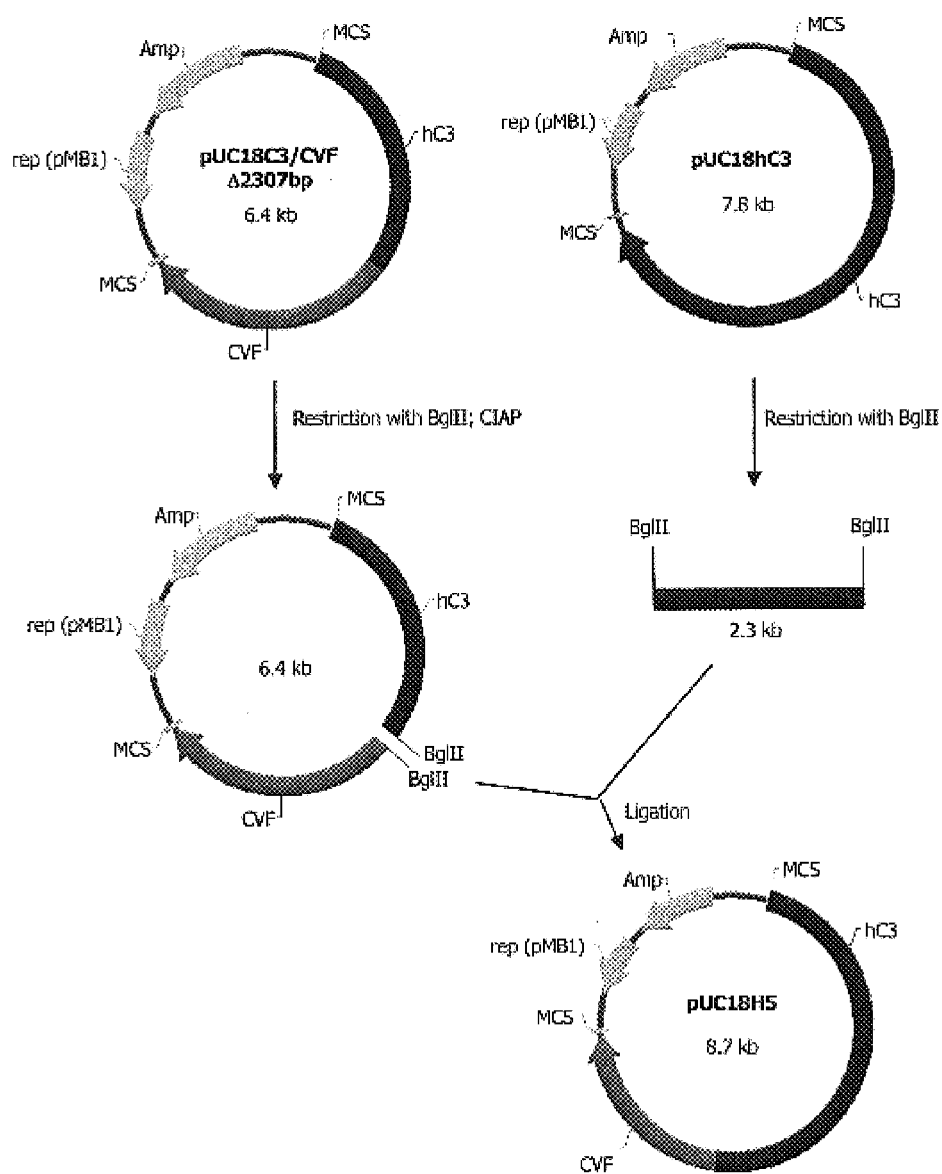

In order to complete construct H5, vector H2Δ2307bp was digested with BglII. The middle region of the C3cDNA was isolated from plasmid pUC18hC3 via its BglII restriction sites and inserted into the vector. The resulting construct H5 was then inserted into an analogously digested pcDNA3-vector via the EagI-restriction sites (FIGS. 6; A+B). Subsequently, a Strep-tag was inserted between the signal sequence and the N-terminus.

Expression in CHO-cells was confirmed in an ELISA via Strep-Tactin and in an immunoblot. Quantification which was performed on the basis of an immunoblot resulted in yields of 1-2 mg/l, wherein the polyclonal serum was employed against C3. Since hybrid H5 has 90% identity compared to human C3, it can be presumed that the polyclonal serum detects both proteins with a variance that is lower than the one of densitometric quantification.

Determination of the densitometric concentration was confirmed by a sandwich ELISA. Here, a monoclonal C3d-antibody and the antibody fragment C3-1, respectively, were immobilized on the surface of an ELISA plate and then incubated with the recombinant proteins. The detection was performed using a polyclonal C3-antiserum. In addition to the samples, various concentrations of human C3 were employed. The evaluation of the ELISA analysis confirmed the concentrations obtained from the densitometric quantification.

Characterization of Hybrid H5

Figure 7:
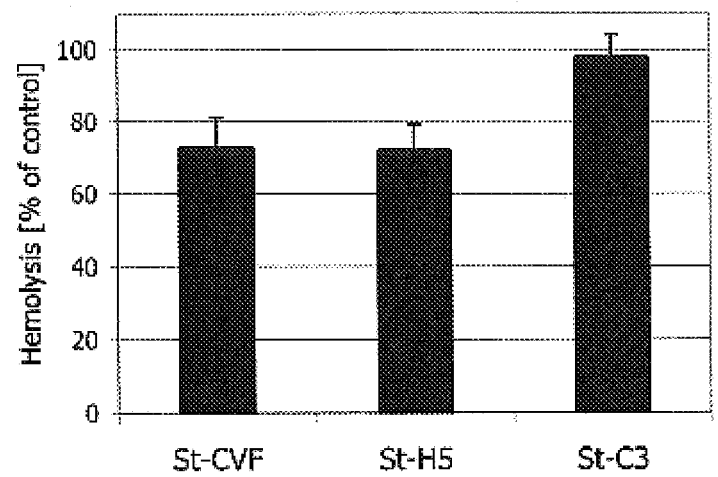
FIG. 7 shows a solid phase assay with St-H5, St-CVF and St-C3. The complement-consumption-assay was conducted in an ELISA plate. The proteins which were immobilized to Strep-Tactin were incubated with human serum at 37° C. in an incubation shaker at 150 rpm for 3 h. Subsequently, the reaction mixtures were transferred to 2 ml reaction tubes. 100 μl GVBS$^{++}$ and 30 μl sensitized sheep erythrocytes ($5 \times 10^8$ cells/ml) were added to the mixture. Then, the mixture was further incubated in a thermomixer until the samples with serum alone reached a hemolysis of approx. 80% compared to the controls with ddH$_2$O. After addition of 850 μl GVBS$^{++}$ the mixture was centrifuged (4° C., 2000 xg, 2 min) and the supernatants were measured at 412 nm. The Figure shows the mean values±standard deviation of at leastthree independent experiments.
Figure 8:
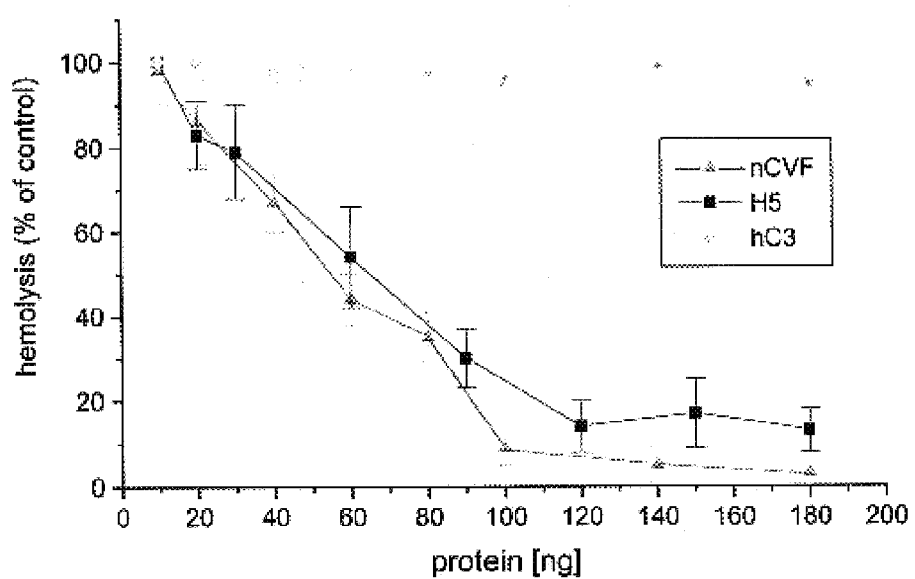
FIG. 8 shows the complement-consuming activity of CVF, St-H5 and C3. The samples (40 μl) were incubated with human serum (approx. 10 μl) at 37° C. in a thermomixer under agitation for 3 h. Subsequently, 100 μl GVBS$^{++}$ and 30 μl sensitized sheep-erythrocytes ($5 \times 10^8$ cells/ml) were added and the mixture was further incubatedin a thermomixer until the serum controls reached hemolysis of approx. 80% compared to the control with ddH$_2$O. After addition of 850 μl GVBS$^{++}$ the mixture was centrifuged (4° C., 2000 xg, 2 min) and the supernatants were measured at 412 nm. The figure shows the mean values±standard deviation of at least three independent experiments.

Following successful transient expression, hybrid H5 was used in a solid phase-assay, where CVF and human C3 served as controls (FIG. 7).

Hybrid H5 clearly showed complement-consuming activity which is comparable to CVF. Despite of ist degree of 90% humanization, hybrid H5 completely retains complement-consuming activity.

To analyze the functional activity of derivative H5 more in detail, we established a stably transfected CHO cell line and purified the protein using thiophilic and strep-tactin resins (for details see Example I, 1.2.6). A detailed analysis of the complement-consuming activity of H5 over a broad concentration range confirmed the CVF-like activity observed in analyses of transiently expressed H5. As evident from FIG. 8, H5 exhibits approx. 85% of the complement-consuming activity of purified native CVF.

Furthermore, we analyzed the formation and stability of the convertase generated by the derivative H5 (for details see Example I, 1.2.8.6). As shown in FIG. 9A, the recombinant protein activates factor B by producing Bb and Ba in the presence of factor D and $Mg^{2+}$ in an identical manner as C3(H2O) and CVF. The time dependent reduction in the release of 7-amido-4-methylcoumarin from a fluorogenic substrate analogue by the action of the convertase (FIGS. 9B-D) revealed a half-life of the H5-dependent convertase of approx. 5-6 hours (FIG. 9E), which is close to the reported 7 hour half-life of the CVF-dependent convertase (Vogel und Müller-Eberhard, 1982). In contrast, the C3bBb convertase complex exhibited no activity, thereby confirming the extremely short half-life in the range of 1 to 2 minutes (Medicus et al., 1976).

These results confirm the fact that, in addition to the CVF-α-chain, also the CVF-γ-chain as well as the C3a- and C3d-homologous regions can be substituted against human C3 without loss of complement-consuming activity.

EXAMPLE IV

Expression and Characterisation of Hybrid H6

Cloning and Expression of Hybrid H6

Due to the fact that the complement-consuming activity of the hybrid H5 was successfully detected, a further minimizing of the CVF-region was envisaged. If the C-termini of CVF and human C3 are compared, it is obvious that in the depicted region upstream of the Bsp1407I-restriction sites the identify between human C3 and CVF is 56%, whereas the C-termini of the two proteins merely exhibits in an identity of 44% (FIG. 10).

For the construction of the new hybrid H6, the Bsp1407I-restriction site was used. The C-terminal region of CVF was selected, whereas the region upstream of the Bsp1407I-restriction site was humanized. Hybrid H6 has 96.3% identity to human C3 (FIG. 11).

For the cloning of construct H6, a 350 bp-fragment from pUC18CVF* was amplified by PCR using the oligonucleotides S50 and AS51. This fragment contains the 3'-terminus of CVF. The amplification product and the vector pcDNASt-hC3 were digested with Bsp1407I and XbaI and ligated (FIG. 12).

Expression of hybrid H6 was successfully confirmed in an ELISA via Strep-Tactin and in an immunoblot.

The concentration of hybrid H6 in the supernatant of the transient expression was quantified densitometrically on the basis of an immunoblot, wherein polyclonal serum against C3 was employed. This yielded concentrations of approx.1-2 mg/l supernatant.

Characerization of Hybrid H6

In addition to densitometric determination, a sandwich ELISA was performed for quantifying recombinant C3 and hybrid H6. The quantification resulted in identical concentrations. Then, hybrid H6 was examined in a solid phase-assay for complement-consuming activity (FIG. 13).

The activity of hybrid H6 was shown in the solid phase-assay. Humanization of the CVF-molecule was successfully performed, whereby the complement-consuming activity was retained. H6 was purified for further characterization.

Cloning and Expression of Hybrid His-H6

For a detailed characterization of hybrid H6, purification was performed according to established techniques using affinity-chromatographical methods on the basis of the Histag-system. For this purpose, the insertion of the His-tag was performed in analogy to the insertion of Strep-tag between signal sequence and N-terminus.

Briefly, two amplification products were generated using St-hC3 with the oligonucleotides S01 and AS61 and with the oligonucleotides S62 and AS03. The amplification products were hybridized by PCR. Then, the amplification product was inserted via the restriction sites NotI and Bpu1102I in an analogously digested vector. The successful transient expression of the hybrid His-H6 was verified in a sandwich-ELISA and in an immunoblot. The densitometric quantification which was performed on the basis of the immunoblot resulted in yields of 1-2 mg/l.

Purification and Characterisation of Hybrid H6

For the purification of the hybrid, stable expressing CHO-cells were monoclonalized and expanded. Subsequently, imidazole was added to the supernatant of the CHO-cells in a final concentration of 20 mM and the mixture was incubated with Ni-NTA-matrix. The elution fractions were then analyzed in an immunoblot. The fractions were pooled, dialyzed and quantified in a Sandwich-ELISA using a monoclonal antibody. Densitometric determination was performed on the basis of an immunoblot and it confirmed the quantification achieved with the ELISA. Protein concentrations of 3-4 µg/ml were obtained. For determining purity, the samples were separated by SD-SPAGE, and the gel was subjected to silver staining. It was determined that the purification procedure via the His-tag resulted in a restricted purification, since a part of the protein did not bind to the matrix. Furthermore, the fractions contained a strong protein background. For subsequent studies, however, sufficient concentrations of the hybrids were obtained.

For further characterization of hybrid H6, first the C3-convertase activity was determined in a complement consumption assay in solution (FIG. 14), where the activity of hybrid H6 can be correlated to the activity of CVF. The activities of the proteins were reflected by a significant reduction in hemolysis. The evaluation resulted in a 68% complement-consuming activity in compared to the activity of CVF (FIG. 15).

In a Bystander Lysis-test it was determined whether hybrid H6 also has the ability (compared to CVF) to activate the complement system via a C5-convertase-activity in fluid phase. The guinea pig serum employed is activated by CVF and the guinea pig erythrocytes are lysed by subsequent formation of the membrane attack complex. Subsequently, the released hemoglobin can be measured in the supernatant at 412 nm. It was demonstrated that hybrid H6 does not exert significant fluid phase C5-convertase activity.

Discussion

Recombinant CVF was detected in the supernatant of all three mammalian cell lines (CHO, COS-7 and HEK293). The densitometrically quantified yields were approx. 0.5-3 mg/l.

The recombinant CVF with an apparent molecular weight of 210 kDa had the structure of two chains. Here, theCVF-α-chain as in the native protein is a singular chain, whereas the γ and the β-chain are expressed together with regions which are homologous to the C3-fragments C3d and C3a as one chain. The processing is analogous to the processing of the two-chain human C3; only 4 arginine residues are removed in the two proteins. Further processing of CVF in the cobra by a venom protease (O'Keefe et al., 1988) does not occur in mammalian and insect cells. However, the recombinant two-chain CVF from insect cells exhibits a comparable activity to native CVF (Kock, 1996).

The modification of CVF by the generation and characterization of different hybrids from CVF and human C3 led to the expression of hybrids, the majority of which consists of human C3. In order to analyze in how far the expression systems are also suitable for such hybrids, human C3 was expressed in addition to CVF in CHO—, HEK293- and COS-7-cells. The recombinant protein was also detected in the cell supernatant. Recombinant C3 showed an apparent molecular weight of 210 kDa and expression yields ranged from 1-3 mg/l, which is in compliance with literature values (Fecke et al., 1998). For the secretory expression of the proteins, the native signal sequences of CVF and human C3 were used.

Due to the fact that CHO-cells allow for stable integration and further exhibit higher yields compared to HEK293-cells, CHO-cells were selected for further studies.

Successful expression of CVF and human C3 in mammalian cells can be considered as a useful basis for further expression of hybrids of CVF and human C3.

Following successful expression of CVF and human C3, it was possible to establish mammalian cells as expression systems for these hybrids. Subsequently, a method had to be developed for analyzing the complement-consuming activity of the hybrids. For this purpose, recombinant CVF in the supernatants of transient expression was studied with regard to its decomplementing activity in complement-consumption-assays. However, no difference to control supernatants without CVF could be detected. Neither by a transient expression with the serum replacement substance Nutridoma nor by culturing the cells in serum-free medium or by culturing in protein-free medium an activity of the recombinat CVF could be detected. The densitometrically quantified yields of expression with different replacment substances ranged from 0.3-1.5 mg/l. Thus, they were slightly lower compared to the yields obtained by use of serum containing medium. The results indicated that direct characterization of rCVF in supernatants of transient expression is not feasable. Consequently, further strategies where analyzed to characterize CVF and diverse hybrids after transient expression without the need to apply time- and cost-consuming purification procedures for increasing the concentration of C3/CVF-hybrid molecules. Different techniques for concentrating and purification were examined in order to achieve a separation of the components which prevent characterization of rCVF in supernatants. Subsequent analyses of the samples in complement consumption assays, however, did not reveal any success of the applied strategies. The decomplementing activity in the samples did not differ significantly from corresponding controls, but the results pointed to the presence of high molecular weight compounds in the samples interfering with the complement consumption assays. Based on these data, solid-phase assays were developed for complement consumption analyses. One strategy employed a Strep-tag fused to the N-terminus of the recombinant proteins.

Hybrid H5 only comprises the functional relevant β-chain of CVF and shares identity with human C3 of 90.7%. Based on the data available for human C3, it comprises the Factor B and Factor H-binding sites as well as the cleavage sites for Factor I.

The hybrid was generated, fused with a Strep-tag and was successfully expressed in CHO-cells.

Subsequently, complement consuming activity was characterized in a solid phase-assay. It was confirmed that H5 has an activity comparable to CVF.

For the first time, a C3/CVF hybrid protein was provided where the CVF-portion could be reduced to 9% while retaining a CVF-like activity. The hybrid only comprises the CVF-β-chain and exhibits decomplementing activity.

Up to now, the C3-region, which is homologous to the CVF-β-chain has only insufficiently been studied. Therefore, only a few binding sites are identified. A known binding site for the complement receptor CR3 is located in the region of amino acids 1361-1381 (Wright et al., 1987). CR3, which is present on macrophages and killer cells, binds to C3bi which has bound on the surface of pathogenes and mediates the destruction of the pathogene (Newman et al., 1984). In the conducted in vitro-assay, the binding of CR3 does not have any influence. In the vicinity of the CR3-region, the binding site for properdin with the amino acids 1424-1432 is in the analogous C3-region (Daoudaki et al., 1988. properdin binds and stabilizes the alternative C3-convertase C3bBb (Fearon et al., 1975). A binding site is also postulated in the CVF-molecule. The identity of the binding sites of C3 and CVF amounts to 70%, which is clearly higher than the identity of the whole proteins (Fritzinger et al., 1994). However, even an identity of 70% is in accordance with crucial structural differences in the CVF-β-chain and the C3-region homologous to the CVF-β-chain.

Considering the available data for human C3, H5 should be inactive. It comprises the human cleavage sites for Factor I and an additional cleavage site for Factor H. Furthermore, the increased stability of the CVF-dependent convertase as a result of the stronger binding of CVF to Factor B, should be lost by humanization in H5 since all postulated binding regions for Factor B are located in regions replaced by C3-sequences. However, since no loss of activity was observed, it is possible that structural differences between H5 and C3 protect the hybrid H5 from a regulation by Factor H and Factor I. Further, it would be conceivable that an additional region which is located in the region of the CVF-β-chain is responsible for the stronger binding to Factor B.

Quantification of hybrid H5 by antibody-based procedures did not pose any problems. Since the identity with C3 amounts to approx. 91%, it can be assumed that the polyclonal serum against C3 recognizes the hybrid H5 with a comparable reactivity. Therefore, quantification based on densitometric immunoblot analysis or ELISA with polyclonal anti-C3 sera was considered to provide reliable results.

This new molecule is of therapeutic relevance since it should clearly exhibit a lower immunogenicity compared to CVF or CVF in which the α-chain is replaced by the corresponding human C3-β-chain. Nevertheless, it shows the same complement-consuming activity. It should be possible to apply this molecule in low concentrations.

After having demonstrated that hybrid H5 exerts complement-activating activity, the analogous region of the human C3-cDNA was compared to the homologous regions of the CVF-cDNA. After analyzing the identities of CVF and human C3 in the analogous terminal regions, a further construct was generated, H6. Hybrid H6 corresponds to human C3 in the first 1527 amino acids; the C-terminus of the protein is CVF-sequence and exhibits an identity of 96.3% to human C3.

After cloning, the hybrid was transiently expressed in CHO-cells and yields of 1-2 mg/l were obtained. Subsequent analysis of the activity of the hybrid H6 in a solid phase-assay demonstrated a substantial complement-consuming activity.

Upon quantification, activity decreased only by 50% when utilizing comparable amounts of H6 and CVF in the solid phase-assay.

With hybrids H5 and H6, two humanized CVF-molecules were generated, which can be used in a therapeutic application. The hybrid H5 exhibits a complement-consuming activity comparable to that of CVF. Hybrid H6 shows 96% identity to human C3 and, most probably, this molecule is not immunogenic. However, H6 shows a loss of approx. 50% in activity compared to the CVF-molecule.

Since hybrid H6 could also be identified as a C3-derivative containing less than 4% foreign amino acid residues, further data were collected. First, a His-tag fusion protein was generated. Hybrid H6 was provided with a His-tag using oligonucleotides as already done for the cloning of the Strep-tag. The His-tag fusion protein was successfully expressed in CHO-cells given yields of 1-3 mg/l. After generating a stable cell-line, hybrid His-H6 was enriched using IMAC. However, the majority of the protein could not be immobilized and was detected in the flow-through. Additionally, the elution fractions were contaminated by a strong protein background. Nevertheless, sufficient amounts of the protein were obtained for further analyses.

The protein was densitometrically determined in the immunoblot and quantification was confirmed using immobilized anti-C3 antibodies in a Sandwich-ELISA. Concentrations of 3-4 mg/l were determined. In a subsequent complement-consumption-assay, in which up to 80 ng protein was employed, a loss of activity of only 32% compared to CVF was demonstrated. The results show that thegenerated molecule exhibits a clear complement-consuming activity despite its 96% humanization. Therefore, the requirements of low dose applications are fulfilled. Therefore, CVF is an attractive complement modulator.

Additionally, the purified protein wa employed in a Bystander Lysis-Assay for the determination of fluid-phase-C5-convertase activity. In contrast to CVF, hybrid H6 did not exert significant fluid phase-C5-convertase activity. The Bystander Lysis-activity of CVF leads to a fast and massive accumulation of C5a, which can cause severe tissue damages (Till et al., 1982; Schmid et al., 1997). Therefore, a loss in C5-convertase activity caused by humanizing seems to represent an advantage.

SUMMARY

Using cassette mutagenetic C3-derivatives were generated which are capable of forming stable C3-convertases. Specific sequences of CVF were utilized for the replacement of corresponding C3-regions (cf. alignment in FIG. 1).

All C3/CVF hybrids as well as CVF and human C3 as such were utilized in parallel complement consumption assays.

The assays confirmed that the complement-consuming activity of both CVF and H5, the latter of which has 90.7% identity to human C3, are comparable. The activity of H6 having 96% identity to human C3 was slightly decreased incomparison to CVF (FIG. 16).

The therapeutic application of a complement modulator or inhibitor is attractive for treating several complement-associated diseases or diseases affected by complement activation such as asthma (Regal et al. 1993), systemic lupus erythematodes (Belmont et al., 1996), glomerulonephritis (Couser et al, 1985), rheumatoid arthritis (Kemp et al., 1992), Alzheimer's disease (Rogers et al., 1992), multiple sclerosis (Piddlesden et al., 1996), sepsis (Hack et al., 1989), hyperacute rejection and transplant rejection (Bach et al., 1995, Baldwin et al., 1995), cardiopulmonary bypass, myocardial infarction, angioplasty, nephritis, dermatomyositis, pemphigoid, spinal cord injury, and Parkinson's disease.

Comparison of complement inhibitors with respect to production costs and dosage requirements for therapeutic applications indicates a preference for the C3/CVF hybrid proteins. The generated C3-derivatives are, as enzymes, superior to other complement inhibitors. The 32% activity loss observed for H6 can be compensated by a higher application dose of approx. 400 μg/kg. However, this dose is still low compared to other inhibitors known in the art which require up to 80fold higher doses to be applied. The current invention provides human C3-derivatives that are capable of forming C3-convertases exerting an extended CVF, Bb-like half-life of several hours, compared to 1.5 minutes of the naturally occurring C3-convertase, thus escaping the physiological degradation mechanisms. The high degrees of identity to human C3 should allow repetitive therapeutic applications of the polypeptides of the invention.

List of Abbreviations
A Adenine
ABTS 2,2'-Azino-bis(2-ethylbenzthiazoline-6-sulfonic acid)
Amp Ampicillin resistance gene
AP Alkaline phosphatase
APS Ammonium persulfate
BCIP 5-Bromo-4-chloro-3-indolylphosphate
bp Base pairs
BSA Bovine serum albumin
C Cytosine
C1-Inh C1 inhibitor
C4bp C4 binding protein
C3 Third complement protein
CAPS 3-Cyclohexyl amine-1-propane sulfonic acid
cDNA Complementary DNA
CHO Chinese hamster ovary
CIAP Calf intestinal alkaline phosphatase
CMV Cytomegalovirus
coC3 Cobra C3
CR Complement receptor
CVF Cobra Venom Factor
DAF Decay accelerating factor
ddH$_2$O Double destilled water
DMEM Dulbecco's Modified Eagle Medium
DMF Dimethyl formamide
DMSO Dimethyl sulfoxide
DNA Deoxyribonucleic acid
dNTP 2'-Deoxyribonucleic acid
DTT Dithiothreitol
EBV Epstein-Barr virus
EDTA Ethylene diamine tetraacetate
ELISA Enzyme-linked immunosorbent assay
EK Enterokinase
FCS Fetal calf serum
G Guanine
G418 Geneticin 418
GFP Green fluorescent protein
GMEM Glasgow Modified Eagle Medium
GVBS$^{++}$ Veronal buffer with gelatin
hC3 Human complement factor C3
HEK Human embryonic kidney
HEPES N-2-hydroxyethylpiperazine-N-2-ethylsulfonic acid
His Histidine
IMAC Immobilized metal ion affinity chromatography
kb Kilo bases
kDa Kilo dalton
LB Luria-Bertani
MAC Membrane attack complex
MASP MBL-associated serine protease
MBL Mannose-binding lectin
MCP Membrane cofactor protein
MCS Multiple cloning site
NaAc Sodium acetate
NBT Nitroblue tetrazolium chloride
NEAA Non-essential amino acids
NHS Normal human serum
OD Optical density
ori Origin of replication
PAGE Polyacrylamide gel electrophoresis
PBS Phosphate buffered saline
PCR Polymerase chain reaction
Penstrep Penicillin/streptomycin
POD Peroxidase
PVDF Polyvinylidene difluoride
RNA Ribonucleic acid
RNase Ribonuclease
rpm Rotations per minute
RT Room temperature
SDS Sodium dodecyl sulfate
St Strep-tagII
T Thymine
TAE Tris-acetate-EDTA buffer
Taq Thermus aquaticus
TBS Tris buffered saline
TEMED N,N,N',N'-Tetraethylmethylene diamine
TES Tris EDTA sucrose
TPBS PBS with Tween
Tris Tris-(hydroxymethyl)-aminomethane
TSS Transformation and storage solution
Tween Polyoxyethylene sorbitane monolaurate
U Unit
VBS Veronal buffered saline
VBS$^{++}$ Veronal buffered saline with MgCl$_2$ and CaCl$_2$
v/v Volume per volume
w/v Weight per volume
xg multiple of gravitation List of References
Alper, C. A.; Johnson, A. M.; Birtch, A. G. and Moore, F. D. (1969) Human C'3: evidence for the liver as the primary site of synthesis. *Science,* 163, 286-288.
Ames, R. S.; Li,Y.; Sarau, H. M.; Nuthulaganti, P.; Foley, J. J.; Ellis, C.; Zeng, Z.; Su, K.; Jurewicz, A. J.; Hertzberg, R. P.; Bergsma, D. J. and Kumar, C. (1996) Molecular cloning and characterization of the human anaphylatoxin C3a receptor. *J Biol Chem,* 271, 20231-20234.
Bach, F. H.; Robson, S. C.; Winkler, H.; Ferran, C.; Stuhlmeier, K. M.; Wrighton, C. J. and Hancock, W. W. (1995) Barriers to xenotransplantation. *Nat Med,* 1, 869-873.
Baldwin, W. M., 3rd; Pruitt, S. K.; Brauer, R. B.; Daha, M. R. and Sanfilippo, F. (1995) Complement in organ transplantation. Contributions to inflammation, injury, and rejection. *Transplantation,* 59, 797-808.
Ballow, M. and Cochrane, C. G. (1969) Two anticomplementary factors in cobra venom: hemolysis of guinea pig erythrocytes by one of them. *J Immunol,* 103, 944-952.
Belmont, H. M.; Hopkins, P.; Edelson, H. S.; Kaplan, H. B.; Ludewig, R.; Weissmann, G. and Abramson, S. (1986) Complement activation during systemic lupus erythematosus. C3a and C5a anaphylatoxins circulate during exacerbations of disease. *Arthritis Rheum,* 29, 1085-1089.
Biesecker, G.; Dihel, L.; Enney, K. and Bendele, R. A. (1999) Derivation of RNA aptamer inhibitors of human complement C5. *Immunopharmacology,* 42, 219-230.
Bohnsack, J. F. and Cooper, N. R. (1988) CR2 ligands modulate human B cell activation. *J Immunol,* 141, 2569-2576.
Burger, R.; Zilow, G.; Bader, A.; Friedlein, A. and Naser, W. (1988) The C terminus of the anaphylatoxin C3a generated upon complement activation represents a neoantigenic determinant with diagnostic potential. *J Immunol,* 141, 553-558.
Busch, K.; Piehler, J. and Fromm, H. (2000) Plant succinic semialdehyde dehydrogenase: dissection of nucleotide binding by surface plasmon resonance and fluorescence spectroscopy. *Biochemistry,* 39, 10110-10117.
Buyon, J. P.; Tamerius, J.; Ordorica, S.; Young, B. and Abramson, S. B. (1992) Activation of the alternative complement pathway accompanies disease flares in systemic lupus erythematosus during pregnancy. *Arthritis Rheum,* 35, 55-61.
Cheung, A. K.; Parker, C. J. and Hohnholt, M. (1994) Soluble complement receptor type 1 inhibits complement activation induced by hemodialysis membranes in vitro. *Kidney Int,* 46, 1680-1687.

Christiansen, D.; Milland, J.; Thorley, B. R.; McKenzie, I. F. and Loveland, B. E. (1996) A functional analysis of recombinant soluble CD46 in vivo and a comparison with recombinant soluble forms of CD55 and CD35 in vitro. *Eur J Immunol*, 26, 578-585.

Chrupcala, M.; Pomer, S.; Staehler, G.; Waldherr, R. and Kirschfink, C. (1994) Prolongation of discordant renal xenograft survival by depletion of complement. Comparative effects of systemically administered cobra venom factor and soluble complement receptor type 1 in a guinea-pig to rat model. *Transpl Int*, 7 Suppl 1, S650-653.

Chrupcala, M.; Pomer, S.; Waldherr, R.; Staehler, G. and Kirschfink, M. (1996) [Effect of complement modulation with the soluble complement receptor sCR1 on survival and function of kidney xenotransplant. An experimental study with a new guinea pig to rate transplant model]. *Urologe A*, 35, 478-484.

Cochrane, C. G.; Müller-Eberhard, H. J. and Aikin, B. S. (1970) Depletion of plasma complement in vivo by a protein of cobra venom: its effect on various immunologic reactions. *J Immunol*, 105, 55-69.

Cooper, P. D. (1985) Complement and cancer: activation of the alternative pathway as a theoretical base for immunotherapy. *Adv Immun Cancer Ther*, 1, 125-166.

Cooper, P. D. and Sim, R. B. (1984) Substances that can trigger activation of the alternative pathway of complement have anti-melanoma activity in mice. *Int J Cancer*, 33, 683-687.

Couser, W. G.; Baker, P. J. and Adler, S. (1985) Complement and the direct mediation of immune glomerular injury: a new perspective. *Kidney Int*, 28, 879-890.

Couser, W. G.; Johnson, R. J.; Young, B. A.; Yeh, C. G.; Toth, C. A. and Rudolph, A. R. (1995) The effects of soluble recombinant complement receptor 1 on complement-mediated experimental glomerulonephritis. *J Am Soc Nephrol*, 5, 1888-1894.

Craddock, P. R.; Fehr, J.; Dalmasso, A. P; Brighan, K. L. and Jacob, H. S. (1977) Hemodialysis leukopenia. Pulmonary vascular leukostasis resulting from complement activation by dialyzer cellophane membranes. *J Clin Invest*, 59, 879-888.

Dalmasso, A. P. (1997) Role of complement in xenografts rejection, in *Xenotransplantation: The Transplantation of Organs and Tissues Between Species*, Vol. 2nd ed (Cooper, D. K.; Kemp, E.; Platt, J. L. and White, D. J., eds), pp 33-60. Springer, Berlin.

Daoudaki, M. E.; Becherer, J. D. and Lambris, J. D. (1988) A 3-4 amino acid peptide of the third component of complement mediates properdin binding. *J Immunol*, 140, 1577-1580.

Davies, A. (1996) Policing the membrane: cell surface proteins which regulate complement. *Res Immunol*, 147, 82-87.

Davis, A. E., 3rd and Harrison, R. A. (1982) Structural characterization of factor I mediated cleavage of the third component of complement. *Biochemistry*, 21, 5745-5749.

DeBruijn, M. H. L. and Fey., G. H (1985) Human complement component C3: cDNA coding sequence and derived primary structure. *Proc. Natl. Acad. Sci. USA*, 708-712.

Dolmer, K. and Sottrup-Jensen, L. (1993) Disulfide bridges in human complement component C3b. *FEBS Lett*, 315, 85-90.

Eldering, E.; Huijbregts, C. C.; Nuijens, J. H.; Verhoeven, A. J. and Hack, C. E. (1993) Recombinant C1 inhibitor P5/P3 variants display resistance to catalytic inactivation by stimulated neutrophils. *J Clin Invest*, 91, 1035-1043.

Elsner, J.; Oppermann, M.; Czech, W.; Dobos, G.; Schopf, E.; Norgauer, J. and Kapp, A. (1994) C3a activates reactive oxygen radical species production and intracellular calcium transients in human eosinophils. *Eur J Immunol*, 24, 518-522.

Eppinger, M. J.; Deeb, G. M.; Bolling, S. F. and Ward, P. A. (1997) Mediators of ischemia-reperfusion injury of rat lung. *Am J Pathol*, 150, 1773-1784.

Fearon, D. T. and Austen, K. F. (1975) Properdin: binding to C3b and stabilization of the C3b-dependent C3-convertase. *J Exp Med*, 142, 856-863.

Fecke, W.; Farries, T. C.; D'Cruz, L. G.; Napper, C. M. and Harrison, R. A. (1998) Expression of factor I-resistant mutants of the human complement component C3 in heterologous systems. *Xenotransplantation*, 5, 29-34.

Fiane, A. E.; Mollnes, T. E.; Videm, V.; Hovig, T.; Hogasen, K.; Mellbye, O. J.; Spruce, L.; Moore, W. T.; Sahu, A. and Lambris, J. D. (1999a) Prolongation of ex vivo-perfused pig xenograft survival by the complement inhibitor Compstatin. *Transplant Proc*, 31, 934-935.

Fiane, A. E.; Mollnes, T. E.; Videm, V.; Hovig, T.; Hogasen, K.; Mellbye, O. J.; Spruce, L.; Moore, W. T.; Sahu,A. and Lambris, J. D. (1999b) Compstatin, a peptide inhibitor of C3, prolongs survival of ex vivo perfused pig xenografts. *Xenotransplantation*, 6, 52-65.

Fishelson, Z. (1991) Complement C3: a molecular mosaic of binding sites. *Mol Immunol*, 28, 545-552.

Fritzinger, D. C.; Bredehorst, R. and Vogel, C. W. (1994) Molecular cloning and derived primary structure of cobra venom factor. *Proc Natl Acad Sci USA*, 91, 12775-12779.

Fritzinger, D. C.; Petrella, E. C.; Connelly, M. B.; Bredehorst, R. and Vogel, C. W. (1992) Primary structure of cobra complement component C3. *J Immunol*, 149, 3554-3562.

Gonzalez-Rubio, C.; Ferreira-Cerdan, A.; Ponce, I. M.; Arpa, J.; Fontan, G. and Lopez-Trascasa, M. (2001) Complement factor I deficiency associated with recurrent meningitis coinciding with menstruation. *Arch Neurol*, 58, 1923-1928.

Gowda, D. C.; Petrella, E. C.; Raj, T. T.; Bredehorst, R. and Vogel, C. W. (1994) Immunoreactivity and function of oligosaccharides in cobra venom factor. *J Immunol*, 152, 2977-2986.

Grier, A. H. and Vogel, C. W. (1989) The oligosaccharide chains of cobra venom factor are required for complement activation. *Mol Immunol*, 26, 563-574.

Grier, A. H.; Schultz, M. and Vogel, C. W. (1987) Cobra venom factor and human C3 share carbohydrate antigenicdeterminants. *J Immunol*, 139, 1245-1252.

Griffiths, A. D.; Williams, S. C.; Hartley, O.; Tomlinson, I. M.; Waterhouse, P.; Crosby, W. L.; Kontermann, R. E.; Jones, P. T.; Low, N. M.; Allison, T. J. and et al. (1994) Isolation of high affinity human antibodies directly from large synthetic repertoires. *Embo J*, 13, 3245-3260.

Gyongyossy-Issa, M. I.; McLeod, E. and Devine, D. V. (1994) Complement activation in platelet concentrates is surface-dependent and modulated by the platelets. *J Lab Clin Med*, 123, 859-868.

Hack, C. E.; Nuijens, J. H.; Felt-Bersma, R. J.; Schreuder, W. O.; Eerenberg-Belmer, A. J.; Paardekooper, J.; Bronsveld, W. and Thijs, L. G. (1989) Elevated plasma levels of the anaphylatoxins C3a and C4a are associated with a fatal outcome in sepsis. *Am J Med*, 86, 20-26. Hack, C. E.; Voerman, H. J.; Eisele, B.; Keinecke, H. O.; Nuijens, J. H.; Eerenberg, A. J.; Ogilvie, A.; Strack van Schijndel, R. J.; Delvos, U. and Thijs, L. G. (1992) C1-esterase inhibitor substitution in sepsis. *Lancet*, 339, 378.

Heller, T.; Hennecke, M.; Baumann, U.; Gessner, J. E.; zu Vilsendorf, A. M.; Baensch, M.; Boulay, F.; Kola, A.; Klos, A.; Bautsch, W. and Kohl, J. (1999) Selection of a C5a receptor antagonist from phage libraries attenuating the inflammatory response inimmune complex disease and ischemia/reperfusion injury. *J Immunol,* 163, 985-994.

Higgins, P. J.; Ko, J. L.; Lobell, R.; Sardonini, C.; Alessi, M. K. and Yeh, C. G. (1997) A soluble chimeric complement inhibitory protein that possesses both decay-accelerating and factor I cofactor activities. *J Immunol,* 158, 2872-2881.

Hirani, S.; Lambris, J. D. and Müller-Eberhard, H. J. (1986) Structural analysis of the asparagine-linked oligosaccharides of human complement component C3. *Biochem J,* 233, 613-616.

Homeister, J. W.; Satoh, P. and Lucchesi, B. R. (1992) Effects of complement activation in the isolated heart. Role of the terminal complement components. *Circ Res,* 71, 303-319.

Horstick, G. (2002) C1-esterase inhibitor in ischemia and reperfusion. *Immunobiology,* 205, 552-562.

Kahnberg, K. E.; Lindhe, J. and Attstrom, R. (1976) The role of complement in initial gingivitis. I. The effect of decomplementation by cobra venom factor. *J Periodontal Res,* 11, 269-278.

Kemp, E.; Dieperink, H.; Leth, P.; Jensenius, J. C.; Nielsen, B.; Lillevang, S. T.; Salomon, S.; Steinbruchel, D.; Larsen, S.; Koch, C. and et al. (1994) Monoclonal antibodies to complement C3 prolong survival of discordant xenografts: guinea pig heart to rat transplantation. *Transplant Proc,* 26, 1011-1015.

Kemp, P. A.; Spragg, J. H.; Brown, J. C.; Morgan, B. P.; Gunn, C. A. and Taylor, P. W. (1992) Immunohistochemical determination of complement activation in joint tissues of patients with rheumatoid arthritis and osteoarthritis using neoantigen-specific monoclonal antibodies. *J Clin Lab Immunol,* 37, 147-162.

Kilgore, K. S.; Friedrichs, G. S.; Homeister, J. W. and Lucchesi, B. R. (1994) The complement system in myocardial ischaemia/reperfusion injury. *Cardiovasc Res,* 28, 437-444.

Kinoshita, T.; Medof, M. E.; Silber, R. and Nussenzweig, V. (1985) Distribution of decay-accelerating factor in the peripheral blood of normal individuals and patients with paroxysmal nocturnal hemoglobinuria. *J Exp Med,* 162, 75-92.

Kirklin, J. K.; Westaby, S.; Blackstone, E. H.; Kirklin, J. W.; Chenoweth, D. E. and Pacifico, A. D. (1983) Complement and the damaging effects of cardiopulmonary bypass. *J Thorac Cardiovasc Surg,* 86, 845-857.

Kock, M. A. (1996) Expression and characterization of recombinant cobra venom factor, Dissertation, Fachbereich Chemie. Universität Hamburg, Hamburg.

Kölln, J. Ziegelmüller, P.; Klensang, K.; Schneider, I.; Bredehorst, R. and Andrä, J. (2001) Transient expression of active Cobra Venom Factor (CVF) and CVF/C3 chimeras in mammalian cells. *Biol Chem,* 382, 164.

Konteatis, Z. D.; Siciliano, S. J.; Van Riper, G.; Molineaux, C. J.; Pandya, S.; Fischer, P.; Rosen, H.; Mumford, R. A. and Springer, M. S. (1994) Development of C5a receptor antagonists. Differential loss of functional responses. *J Immunol,* 153, 4200-4205.

Lachmann, P. J.; Pangburn, M. K. and Oldroyd, R. G. (1982) Breakdown of C3 after complement activation. Identification of a new fragment C3g, using monoclonal antibodies. *J Exp Med,* 156, 205-216.

Laemmli, U. K. (1970) Cleavage of structural proteins during the assembly of the head of bacteriophage T4. *Nature,* 227, 680-685.

Law, S. K. and Dodds, A. W. (1997) The internal thioester and the covalent binding properties of the complement proteins C3 and C4. *Protein Sci,* 6, 263-274.

Lennon, V. A.; Seybold, M. E.; Lindstrom, J. M.; Cochrane, C. and Ulevitch, R. (1978) Role of complement in the pathogenesis of experimental autoimmune myasthenia gravis. *J Exp Med,* 147, 973-983.

Lens, J. W.; van den Berg, W. B.; van de Putte, L. B.; Berden, J H. and Lems, S. P. (1984) Flare-up of antigen-induced arthritis in mice after challenge with intravenous antigen: effects of pretreatment with cobra venom factor and anti-lymphocyte serum. *Clin Exp Immunol,* 57, 520-528.

Lin, Y.; Soares, M. P.; Sato, K.; Csizmadia, E.; Robson, S. C.; Smith, N. and Bach, F. H. (2000) Long-term survival of hamster hearts in presensitized rats. *J Immunol,* 164, 4883-4892.

Liszewski, M. K. and Atkinson, J. P. (1992) Membrane cofactor protein. *Curr Top Microbiol Immunol,* 178, 45-60.

Lublin, D. M. and Atkinson, J. P. (1989) Decay-accelerating factor: biochemistry, molecular biology, and function. *Annu Rev Immunol,* 7, 35-58.

Lublin, D. M. and Atkinson, J. P. (1990) Decay-accelerating factor and membrane cofactor protein. *Curr Top Microbiol Immunol,* 153, 123-145.

Lupton, S. and Levine, A. J. (1985) Mapping genetic elements of Epstein-Barr virus that facilitate extrachromosomal persistence of Epstein-Barr virus-derived plasmids in human cells. *Mol Cell Biol,* 5, 2533-2542.

Makrides, S. C.; Scesney, S. M.; Ford, P. J.; Evans, K. S.; Carson, G. R. and Marsh, H. C., Jr. (1992) Cell surface expression of the C3b/C4b receptor (CR1) protects Chinese hamster ovary cells from lysis by human complement. *J Biol Chem,* 267, 24754-24761.

Medicus, R. G.; Götze, O. and Müller-Eberhard, H. J. (1976) Alternative pathway of complement: recruitment of precursor properdin by the labile C3/C5 convertase and the potentiation of the pathways. *J Exp Med,* 144, 1076-1093.

Mollnes, T. E. (1997) Biocompatibility: complement as mediator of tissue damage and as indicator of incompatibility. *Exp Clin Immunogenet,* 14, 24-29.

Mollnes, T. E. and Lachmann, P. J. (1988) Regulation of complement. *Scand J Immunol,* 27, 127-142.

Moran, P.; Beasley, H.; Gorrell, A.; Martin, E.; Gribling, P.; Fuchs, H.; Gillett, N.; Burton, L. E. and Caras, I. W. (1992) Human recombinant soluble decay accelerating factor inhibits complement activation in vitro and in vivo. *J Immunol,* 149, 1736-1743.

Morariu, M. A. and Dalmasso, A. P. (1978) Experimental allergic encephalomyelitis in cobra venom factor-treated and C4-deficient guinea pigs. *Ann Neurol,* 4, 427-430.

Morgan, B. P. and Walport, M. J. (1991) Complement deficiency and disease. *Immunol Today,* 12, 301-306.

Morgan, B. P.; Gasque, P.; Singhrao, S. K. and Piddlesden, S. J. (1997) Role of complement in inflammation and injury in the nervous system. *Exp Clin Immunogenet,* 14, 19-23.

Müller-Eberhard, H. J. and Fjellstrom, K. E. (1971) Isolation of the anticomplementary protein from cobra venom and its mode of action on C3. *J Immunol,* 107, 1666-1672.

Newman, S. L.; Devery-Pocius, J. E.; Ross, G. D. and Henson, P. M. (1984) Phagocytosis by human monocyte-derived macrophages. Independent function of receptors for C3b (CR1) and iC3b (CR3). *Complement,* 1, 213-227.

Oberholzer, J.; Yu, D.; Triponez, F.; Cretin, N.; Andereggen, E.; Mentha, G.; White, D.; Buehler, L.; Morel, P. and Lou, J. (1999) Decomplementation with cobra venom factor prolongs survival of xenografted islets in a rat to mouse-model. *Immunology,* 97, 173-180.

O'Keefe, M. C.; Caporale, L. H. and Vogel, C. W. (1988) A novel cleavage product of human complement component C3 with structural and functional properties of cobra venom factor. *J Biol Chem*, 263, 12690-12697.

Oran, A. E. and Isenman, D. E. (1999) Identification of residues within the 727-767 segment of human complement component C3 important for its interaction with factor H and with complement receptor 1 (CR1, CD35). *J Biol Chem*, 274, 5120-5130.

Pang, A. S. and Minta, J. O. (1980) Inhibition of vitamin D2-induced arteriosclerosis in rats by depletion of complement with cobra venom factor. *Artery*, 7, 109-122.

Pangburn, M. K. and Müller-Eberhard, H. J. (1984) The alternative pathway of complement. *Springer Semin Immunopathol*, 7, 163-192.

Park, K. W.; Tofukuji, M.; Metais, C.; Comunale, M. E.; Dai, H. B.; Simons, M.; Stahl, G. L.; Agah, A. and Sellke, F. W. (1999) Attenuation of endothelium-dependent dilation of pig pulmonary arterioles after cardiopulmonary bypass is prevented by monoclonal antibody to complement C5a. *Anesth Analg*, 89, 42-48.

Pellas, T. C.; Boyar, W.; van Oostrum, J.; Wasvary, J.; Fryer, L. R.; Pastor, G.; Sills, M.; Braunwalder, A.; Yarwood, D. R.; Kramer, R.; Kimble, E.; Hadala, J.; Haston, W.; MoreiraLudewig, R.; Uziel-Fusi, S.; Peters, P.; Bill, K. and Wennogle, L. P. (1998) Novel C5a receptor antagonists regulate neutrophil functions in vitro and in vivo. *J Immunol*, 160, 5616-5621.

Piddlesden, S. J.; Jiang, S.; Levin, J. L.; Vincent, A. and Morgan, B. P. (1996) Soluble complement receptor 1 (sCR1) protects against experimental autoimmune myasthenia gravis. *J Neuroimmunol*, 71, 173-177.

Piddlesden, S. J.; Storch, M. K.; Hibbs, M.; Freeman, A. M.; Lassmann, H. and Morgan, B. P. (1994) Soluble recombinant complement receptor 1 inhibits inflammation and demyelination in antibody mediated demyelinating experimental allergic encephalomyelitisi. *J Immunol*, 152, 5477-5484.

Pinter, C.; Siccardi, A. G.; Lopalco, L.; Longhi, R. and Clivio, A. (1995) HIV glycoprotein 41 and complement factor H interact with each other and share functional as well as antigenic homology. *AIDS Res Hum Retroviruses*, 11, 971-980.

Regal, J. F. and Fraser, D. G. (1996) Systemic complement system depletion does not inhibit cellular accumulation in antihistamine pretreated allergic guinea pig lung. *Int Arch Allergy Immunol*, 109, 150-160.

Regal, J. F.; Fraser, D. G. and Toth, C. A. (1993) Role of the complement system in antigen-induced bronchoconstriction and changes in blood pressure in the guinea pig. *J Pharmacol Exp Ther*, 267, 979-988.

Rogers, J.; Cooper, N. R.; Webster, S.; Schultz, J.; McGeer, P. L.; Styren, S. D.; Civin, W. H.; Brachova, L.; Bradt, B.; Ward, P. and et al. (1992) Complement activation by beta-amyloid in Alzheimer disease. *Proc Natl Acad Sci USA*, 89, 10016-10020.

Ross, S. C. and Densen, P. (1984) Complement deficiency states and infection: epidemiology, pathogenesis and consequences of neisserial and other infections in an immune deficiency. *Medicine (Baltimore)*, 63, 243-273.

Saiki, R. K.; Gelfand, D. H.; Stoffel, S.; Scharf, S. J.; Higuchi, R.; Horn, G. T.; Mullis, K. B. and Erlich, H. A. (1988) Primer-directed enzymatic amplification of DNA with a thermostable DNA polymerase. *Science*, 239, 487-491.

Scharfstein, J.; Ferreira, A.; Gigli, I. and Nussenzweig, V. (1978) Human C4-binding protein. I. Isolation and characterization. *J Exp Med*, 148, 207-222.

Schmid, E.; Warner, R. L.; Crouch, L. D.; Friedl, H. P.; Till, G. O.; Hugli, T. E. and Ward, P. A. (1997) Neutrophilchemotactic activity and C5a following systemic activation of complement in rats. *Inflammation*, 21, 325-333.

Schmidt, T. G.; Koepke, J.; Frank, R. and Skerra, A. (1996) Molecular interaction between the Strep-tag affinity peptide and its cognate target, streptavidin. *J Mol Biol*, 255, 753-766.

Sim, R. B.; Reboul, A.; Arlaud, G. J.; Villiers, C. L. and Colomb, M. G. (1979) Interaction of 125I-labelled complement subcomponents C-1r and C-1s with protease inhibitors in plasma. *FEBS Lett*, 97, 111-115.

Skerra, A. and Schmidt, T. G. (2000) Use of the Strep-Tag and streptavidin for detection and purification of recombinant proteins. *Methods Enzymol*, 326, 271-304.

Smyth, N.; Odenthal, U.; Merkl, B. and Paulsson, M. (2000) Eukaryotic expression and purification of recombinant extracellular matrix proteins carrying the Strep II tag. *Methods Mol Biol*, 139, 49-57.

Spillner, E. (2002) Selektion und Expression von rekombinanten Antikörpern für analytische und therapeutische Applikationen, in *Fachbereich Chemie*. Universität Hamburg, Hamburg.

Stoiber, H.; Schneider, R.; Janatova, J. and Dierich, M. P. (1995) Human complement proteins C3b, C4b, factor H and properdin react with specific sites in gp120 and gp41, the envelope proteins of HIV-1. *Immunobiology*, 193, 98-113.

Struber, M.; Hagl, C.; Hirt, S. W.; Cremer, J.; Harringer, W. and Haverich, A. (1999) C1-esterase inhibitor in graft failure after lung transplantation. *Intensive Care Med*, 25, 1315-1318.

Sugita, Y.; Ito, K.; Shiozuka, K.; Suzuki, H.; Gushima, H.; Tomita M. and Masuho, Y. (1994) Recombinant soluble CD59 inhibits reactive hemolysis with complement. *Immunology*, 82, 34-41.

Tack, B. F.; Harrison, R. A.; Janatova, J.; Thomas, M. L. and Prahl, J. W. (1980) Evidence for presence of an internal thiolester bondin third component of human complement. *Proc Natl Acad Sci USA*, 77, 5764-5768.

Taniguchi, S.; Kobayashi, T.; Neethling, F. A.; Ye, Y.; Niekrasz, M.; White, D. J. and Cooper, D. K. (1996) Cobra venom factor stimulates anti-alpha-galactose antibody production in baboons. Implications for pig-to-human xenotransplantation. *Transplantation*, 62, 678-681.

Taniguchi-Sidle, A. and Isenman, D. E. (1994) Interactions of human complement component C3 with factor B and with complement receptors type 1 (CR1, CD35) and type 3 (CR3, CD11 b/CD18) involve an acidic sequence at the N-terminus of C3 alpha'-chain. *J Immunol*, 153, 5285-5302.

Till, G. O.; Johnson, K. J.; Kunkel, R. and Ward, P. A. (1982) Intravascular activation of complement and acute lung injury. Dependency on neutrophils and toxic oxygen metabolites. *J Clin Invest*, 69, 1126-1135.

Vakeva, A. P.; Agah, A.; Rollins, S. A.; Matis, L. A.; Li, L. and Stahl, G. L. (1998) Myocardial infarction and apoptosis after myocardial ischemia and reperfusion: role of the terminal complement components and inhibition by anti-C5 therapy. *Circulation*, 97, 2259-2267.

Vogel, C. W. (1985) Untersuchungen zur Strukturhomologie von Kobrafaktor mit dem menschlichen Komplementprotein C3 sowie Synthese kovalenter Hybridproteine aus Kobrafaktor und monoklonalen Antikörpern als selektivzytolytisches Prinzip, Dissertation, Fachbereich Chemie. Universität Hamburg, Hamburg.

Vogel, C. W. and Müller-Eberhard, H. J. (1982) The cobra venom factor-dependent C3-convertase of human complement. A kinetic and thermodynamic analysis of a protease acting on its natural high molecular weight substrate. *J Biol Chem*, 257, 8292-8299.

Vogel, C. W. and Müller-Eberhard, H. J. (1984) Cobra venom factor: improved method for purification and biochemical characterization. *J Immunol Methods*, 73, 203-220.

Vogel, C. W.; Smith, C. A. and Müller-Eberhard, H. J. (1984) Cobra venom factor: structural homology with the third component of human complement. *J Immunol*, 133, 3235-3241.

Vogel, C. W.; Wilkie, S. D. and Morgan, A. C. (1985) In vivo studies with covalent conjugates of cobra venom factor and monoclonal antibodies to human tumors. *Haematol Blood Transfus*, 29, 514-517.

Vogel, C. W.; Bredehorst, R.; Fritzinger, D. C.; Grunwald, T.; ZiegelMüller, P. and Kock, M. A. (1996) Structure and function of cobra venom factor, the complement-activating protein in cobra venom. *Adv Exp Med Biol*, 391, 97-114.

Volanakis, J. E. (1995) Transcriptional regulation of complement genes. *Annu Rev Immunol*, 13, 277-305.

Wang, Y.; Rollins, S. A.; Madri, J. A. and Matis, L. A. (1995) Anti-C5 monoclonal antibody therapy prevents collagen-induced arthritis and ameliorates established disease. *Proc Natl Acad Sci USA*, 92, 8955-8959.

Wang, Y.; Hu, Q.; Madri, J. A.; Rollins, S. A.; Chodera, A and Matis, L. A. (1996) Amelioration of lupus-like autoimmune disease in NZB/WF1 mice after treatment with a blocking monoclonal antibody specific for complement component C5. *Proc Natl Acad Sci USA*, 93, 8563-8568.

Wehrhahn, D. (2000) Untersuchungen zur Struktur-Funktionsbeziehungen von Kobra Venom Faktor-Konstruktion und rekombinante Expression von Kobra Venom Faktor/Kobra C3 Hybriden, Dissertation, Fachbereich Chemie. Universität Hamburg, Hamburg.

Weisman, H. F.; Bartow, T.; Leppo, M. K.; Marsh, H.C., Jr.; Carson, G. R.; Concino, M. F.; Boyle, M. P.; Roux, K. H.; Weisfeldt, M. L. and Fearon, D. T. (1990) Soluble human complement receptor type 1: in vivo inhibitor of complement suppressing post-ischemic myocardial inflammation and necrosis. *Science*, 249, 146-151.

Whiss, P. A. (2002) Pexelizumab Alexion. *Curr Opin Investig Drugs*, 3, 870-877.

Williams, K. C.; Ulvestad, E. and Hickey, W. F. (1994) Immunology of multiple sclerosis. *Clin Neurosci*, 2, 229-245.

Wright, S. D.; Reddy, P. D.; Jong, M. T. and Erickson, B. W. (1987) C3bi receptor (complement receptor type 3) recognizes a region of complement protein C3 containing sequence Arg-Gly-Asp. *Proc Natl Acad Sci USA*, 84, 1965-8.

Zimmerman, J. L.; Dellinger, R. P.; Straube, R. C. and Levin, J. L. (2000) Phase I trial of the recombinant soluble complement receptor 1 in acute lung injury and acute respiratory distress syndrome. *Crit Care Med*, 28, 3149-3154.

Zipfel, P. F.; Skerka, C.; Caprioli, J.; Manuelian, T.; Neumann, H. H.; Noris, M. and Remuzzi, G. (p2001) Complement factor H and hemolytic uremic syndrome. *Int Immunopharmacol*, 1, 461-468.

We claim:

1. A hybrid protein comprising a partial sequence of human complement component C3 (human C3), the human C3 having the amino acid sequence set forth as SEQ ID NO: 2, and a partial sequence of Cobra Venom Factor (CVF), the CVF having the amino acid sequence set forth as SEQ ID NO: 4, wherein the carboxy terminal part of at least 68 amino acids of said human C3 is replaced by the partial sequence of CVF; wherein the partial sequence of CVF comprises at least 68 carboxy terminal amino acids of CVF, and wherein said protein has at least 90 percent identity to said human C3; and wherein said protein is capable of forming a stable C3 convertase.

2. A pharmaceutical composition comprising the hybrid protein of claim 1.

3. The protein of claim 1 wherein the hybrid protein has at least 95 percent identity to said human C3.

4. The hybrid protein of claim 1 having an amino acid sequence selected from the group consisting of SEQ ID Nos: 6, 8, 10, and 12.

* * * * *